US011124460B2

(12) United States Patent
Thompson et al.

(10) Patent No.: US 11,124,460 B2
(45) Date of Patent: Sep. 21, 2021

(54) METHODS FOR PROMOTING PLANT HEALTH USING FREE ENZYMES AND MICROORGANISMS THAT OVEREXPRESS ENZYMES

(71) Applicant: Spogen Biotech Inc., St. Louis, MO (US)

(72) Inventors: Brian M. Thompson, Creve Coeur, MO (US); Jorg Augustin, Chesterfield, MO (US)

(73) Assignee: Spogen Biotech Inc., St. Louis ( * ) Notice: Subject to any disclaimer, the term of this patent is extended or adjusted under 35 U.S.C. 154(b) by 0 days.

(21) Appl. No.: 15/460,468

(22) Filed: Mar. 16, 2017

(65) Prior Publication Data

US 2017/0356002 A1 Dec. 14, 2017

Related U.S. Application Data

(60) Provisional application No. 62/309,426, filed on Mar. 16, 2016.

(51) Int. Cl.

| | |
|---|---|
| ***C05F 11/08*** | (2006.01) |
| ***C05B 15/00*** | (2006.01) |
| ***C12N 9/78*** | (2006.01) |
| ***C05G 3/60*** | (2020.01) |
| ***A01N 63/50*** | (2020.01) |
| ***C05F 17/20*** | (2020.01) |
| ***C05C 9/00*** | (2006.01) |
| ***C07K 14/415*** | (2006.01) |
| ***C12N 1/20*** | (2006.01) |
| ***C12N 15/82*** | (2006.01) |
| *A01H 5/00* | (2018.01) |

(52) U.S. Cl.

CPC .............. *C05F 11/08* (2013.01); *A01N 63/50* (2020.01); *C05B 15/00* (2013.01); *C05C 9/00* (2013.01); *C05F 17/20* (2020.01); *C05G 3/60* (2020.02); *C07K 14/415* (2013.01); *C12N 1/20* (2013.01); *C12N 9/78* (2013.01); *C12N 15/8237* (2013.01); *C12N 15/8249* (2013.01); *C12N 15/8279* (2013.01); *C12Y 302/01* (2013.01); *C12Y 305/99007* (2013.01); *C12Y 402/0202* (2013.01); *A01H 5/00* (2013.01); *Y02A 40/22* (2018.01); *Y02P 60/21* (2015.11)

(58) Field of Classification Search

None

See application file for complete search history.

(56) References Cited

U.S. PATENT DOCUMENTS

| | | | | |
|---|---|---|---|---|
| 5,348,743 | A * | 9/1994 | Ryals | A01N 63/00 424/94.61 |
| 5,631,007 | A | 5/1997 | Ryals et al. | |
| 5,776,448 | A | 7/1998 | Suslow et al. | |
| 5,958,104 | A | 9/1999 | Nonomura et al. | |
| 6,184,440 | B1 | 2/2001 | Shoseyov et al. | |
| 6,346,131 | B1 * | 2/2002 | Bergevin | C05B 7/00 71/32 |
| 6,548,743 | B1 | 4/2003 | Sheen et al. | |
| 6,566,114 | B1 | 5/2003 | Kauppinen et al. | |
| 6,630,340 | B2 * | 10/2003 | Wilting | C11D 3/38636 435/183 |
| 7,417,181 | B2 * | 8/2008 | Wang | C12N 9/16 435/320.1 |
| 7,432,097 | B2 * | 10/2008 | Short | A21D 8/042 424/94.6 |
| 7,504,120 | B2 * | 3/2009 | Steer | C12N 9/2434 426/63 |
| 7,615,681 | B2 * | 11/2009 | Georges | C12N 9/16 435/183 |
| 7,919,678 | B2 | 4/2011 | Mironov | |
| 7,960,148 | B2 * | 6/2011 | Steer | C12N 9/2405 435/97 |
| 8,097,769 | B2 * | 1/2012 | Sarria-Millan | C12N 9/88 435/320.1 |

(Continued)

FOREIGN PATENT DOCUMENTS

| | | | |
|---|---|---|---|
| CN | 103086784 | A | 5/2013 |
| CN | 104945164 | A | 9/2015 |
| EP | 1 359 134 | A1 | 5/2003 |
| EP | 0 901 527 | B1 | 8/2005 |
| EP | 1 590 466 | B1 | 9/2010 |
| EP | 2 561 760 | A2 | 2/2013 |
| EP | 2 069 504 | B1 | 6/2015 |
| EP | 2 658 961 | B1 | 8/2015 |
| JP | 253870 | A | 9/2000 |
| RU | 2503721 | C2 | 3/2009 |
| RU | 2529949 | C2 | 11/2009 |
| RU | 2012129907 | A | 6/2011 |

(Continued)

OTHER PUBLICATIONS

Yang et al. A Novel β-mannanase with High Specific Activity from Bacillus circulans CGMCC1554: Gene Cloning, Expression and Enzymatic Characterization. Appl Biochem Biotechnol (2009) 159:85-94. (Year: 2009).*

(Continued)

*Primary Examiner* — Cynthia E Collins

(74) *Attorney, Agent, or Firm* — Dentons US LLP

(57) ABSTRACT

Methods for stimulating plant growth and/or promoting plant health using free enzymes or recombinant microorganisms that overexpress enzymes are provided. Plant seeds coated with free enzymes or recombinant microorganisms that overexpress enzymes are also provided. Compositions comprising a fertilizer and an enzyme or a recombinant microorganism that overexpresses an enzyme are provided. Modified enzymes having ACC deaminase activity, recombinant microorganisms expressing the modified enzymes, plant seeds treated with the modified enzymes or recombinant microorganisms, and methods for stimulating plant growth and/or promoting plant health using the modified enzymes or recombinant microorganisms are also provided.

42 Claims, No Drawings

Specification includes a Sequence Listing.

(56) References Cited

U.S. PATENT DOCUMENTS

| | | | |
|---|---|---|---|
| 9,068,189 B2 | 6/2015 | Mishra et al. | |
| 9,068,194 B2 | 6/2015 | Unkefer et al. | |
| 9,125,419 B2 * | 9/2015 | Asolkar | C12R 1/07 |
| 9,132,175 B2 | 9/2015 | Stewart et al. | |
| 9,476,058 B2 * | 10/2016 | Lim | C12N 15/8245 |
| 9,540,633 B2 * | 1/2017 | Brinch-Pedersen | A01H 5/10 |
| 9,573,980 B2 | 2/2017 | Thompson et al. | |
| 9,826,743 B2 * | 11/2017 | Curtis | A01N 63/00 |
| 9,845,342 B2 | 12/2017 | Thompson et al. | |
| 9,850,289 B2 | 12/2017 | Thompson et al. | |
| 9,932,275 B2 * | 4/2018 | Puah | C05B 15/00 |
| 10,173,938 B2 * | 1/2019 | Rosas Gajardo | C05F 17/964 |
| 2008/0233175 A1 | 9/2008 | Steer et al. | |
| 2009/0099079 A1 * | 4/2009 | Emalfarb | C07H 21/00 514/1.2 |
| 2010/0205690 A1 | 8/2010 | Blasing et al. | |
| 2011/0321197 A1 | 12/2011 | Schon et al. | |
| 2012/0227134 A1 | 9/2012 | Schon et al. | |
| 2012/0266327 A1 | 10/2012 | Sanz Molinero et al. | |
| 2013/0116124 A1 | 5/2013 | Baroja Fernandez et al. | |
| 2013/0216653 A1 | 8/2013 | Perkins et al. | |
| 2014/0031576 A1 | 1/2014 | Toriumi | |
| 2014/0259225 A1 | 9/2014 | Frank et al. | |
| 2014/0274707 A1 | 9/2014 | Thompson et al. | |
| 2014/0308748 A1 | 10/2014 | Mishra et al. | |
| 2014/0342905 A1 * | 11/2014 | Bullis | A01N 63/00 504/100 |
| 2015/0274605 A1 * | 10/2015 | Waldron | C05F 5/008 71/8 |
| 2016/0031948 A1 | 2/2016 | Thompson et al. | |
| 2016/0073640 A1 | 3/2016 | Curtis et al. | |
| 2016/0108096 A1 | 4/2016 | Thompson et al. | |
| 2016/0236996 A1 * | 8/2016 | Chaudhry | C05C 11/00 |
| 2016/0340658 A1 * | 11/2016 | Lessl | C12N 9/16 |
| 2017/0135353 A1 | 5/2017 | Thompson et al. | |
| 2017/0283472 A1 | 10/2017 | Curtis et al. | |
| 2017/0290339 A1 | 10/2017 | Curtis et al. | |
| 2017/0295785 A1 | 10/2017 | Curtis et al. | |
| 2017/0295797 A1 | 10/2017 | Curtis et al. | |
| 2017/0295798 A1 | 10/2017 | Curtis et al. | |
| 2017/0318808 A1 | 11/2017 | Curtis et al. | |

FOREIGN PATENT DOCUMENTS

| | | |
|---|---|---|
| WO | 02/00232 A2 | 1/2002 |
| WO | 03/066846 A1 | 8/2003 |
| WO | 2005/028654 A1 | 3/2005 |
| WO | 2006/012366 A2 | 2/2006 |
| WO | 2007/078127 A1 | 7/2007 |
| WO | 2008/017483 A2 | 2/2008 |
| WO | 2009/037329 A2 | 3/2009 |
| WO | 2010/046221 A1 | 4/2010 |
| WO | 2011/106794 A1 | 9/2011 |
| WO | 2013/102934 A1 | 7/2013 |
| WO | 2014/004487 A1 | 1/2014 |
| WO | 2014/145964 A1 | 9/2014 |
| WO | 2015/118516 A1 | 8/2015 |
| WO | 2016/044661 A1 | 3/2016 |

OTHER PUBLICATIONS

Vasil et al. Herbicide Resistant Fertile Transgenic Wheat Plants Obtained by Microprojectile Bombardment of Regenerable Embryogenic Callus Bio/Technology vol. 10, pp. 667-674 (1992). (Year: 1992).*

UniProtKB Accession No. C4PKL1, Purple acid phosphatase, Jul. 7, 2009 (Year: 2009).*

Murashige, T. and Skoog, F. (1962) A Revised Medium for Rapid Growth and Bioassays with Tobacco Tissue Cultures. Physiologia Plantarum, 15, 473-497 (Year: 1962).*

Brandt Steric P DS Water Soluble Fertilizer Product Description, Brandt Consolidated, Inc., Springfield, IL, May 2013. (Year: 2013).*

UniProtKB Accession No. P23903, Glucan endo-1,3-beta-glucosidase A1, Nov. 1, 1991. (Year: 1991).*

UniProtKB Accession No. O52864, Phosphatidyl-degrading phospholipase C, Jun. 1, 1998. (Year: 1998).*

Ahemad, M., et al., "Mechanisms and Applications of Plant Growth Promoting Rhizobacteria: Current Perspective," Journal of King Saud University—Science, 2014, pp. 1-20, vol. 26.

Bae, C., et al., "Multiple Classes of Immune-Related Proteases Associated with the Cell Death Response in Pepper Plants," PLoS One, May 2013, pp. 1-11, vol. 8, Issue 5, e63533.

Berlemont, R., et al., "Phylogenetic Distribution of Potential Cellulases in Bacteria," Applied and Environmental Microbiology, Mar. 2013, pp. 1545-1554, vol. 79, No. 5.

Chakraborty, U., et al., "Plant Growth Promotion and Induction of Resistance in Camellia sinensis by Bacillus megaterium," Journal of Basic Microbiology, 2006, pp. 186-195, vol. 46, No. 3.

Chapman, K. D., "Phospholipase Activity During Plant Growth and Development and in Response to Environmental Stress," Trends in Plant Science, Nov. 1998, pp. 419-426, vol. 3, No. 11.

Choudhary, D. K., et al., "Interactions of *Bacillus* spp. and Plants—With Special Reference to Induced Systemic Resistance (ISR)," Microbiological Research, 2009, pp. 493-513, vol. 164, No. 5.

Corbineau, F., et al., "Improvement of Germination of Terminalia Ivorensis Seeds," Forest Genetic Resources Information No. 21, http://www.fao.org/docrep/006/v3030e/V3030E10.htm, 7 pages.

De Freitas, J. R., et al., "Phosphate-Solubilizing Rhizobacteria Enhance the Growth and Yield but not Phosphorus Uptake of Canola (*Brassica napus* L.)," Biology and Fertility of Soils, 1997, pp. 358-364, vol. 24, Issue 4.

Dong, Y.-H., et al., "Identification of Quorum-Quenching N-Acyll Homoserine Lactonases from *Bacillus* Species," Applied and Environmental Microbiology, Apr. 2002, pp. 1754-1759, vol. 68, No. 4.

Dourado, M. N., et al., "Biotechnological and Agronomic Potential of Endophytic Pink-Pigmented Methylotrophic *Methylobacterium* spp.," BioMed Research International, 2015, 19 pages, Article ID 909016, vol. 2015, Hindawi Publishing Corporation.

Dowd, P. E., et al., "The Emerging Roles of Phospholipase C in Plant Growth and Development," Lipid Signaling in Plants, Plant Cell Monographs 16, 2010, pp. 23-37.

Faria, D. C., et al., "Endophytic Bacteria Isolated From Orchid and Their Potential to Promote Plant Growth," World Journal of Microbiology and Biotechnology, Feb. 2013, pp. 217-221, vol. 29, Issue 2.

Gamalero, E., et al., "Bacterial Modulation of Plant Ethylene Levels," Plant Physiology, Sep. 2015, pp. 13-22, vol. 169.

Glick, B. R., "Modulation of Plant Ethylene Levels by the Bacterial Enzyme ACC Deaminase," FEMS Microbiology Letters, 2005, pp. 1-7, vol. 251.

Gnanaraj, M., et al., "Isolation and Gene Expression Analysis of Phospholipase C in Response to Abiotic Stresses from *Vigna radiata* (L.) Wilczek," Indian Journal of Experimental Biology, Jun. 2015, pp. 335-341, vol. 53.

Goldberg, L. J., et al., "A Bacterial Spore Demonstrating Rapid Larvicidal Activity Against Anopheles Sergentii, Uranotaenia Unguiculata, Culex Univitattus, Aedes Aegypti and Culex Pipiens," Mosquito News, Sep. 1977, pp. 355-358, vol. 37, No. 3.

Guerchicoff, A., et al., "Identification and Characterization of a Previously Undescribed cyt Gene in *Bacillus thuringiensis* subsp. israelensis," Applied and Environmental Microbiology, Jul. 1997, pp. 2716-2721, vol. 63, No. 7.

Gujar, P. D., et al., "Effect of Phytase from Aspergillus niger on Plant Growth and Mineral Assimilation in Wheat (Triticum aestivum Linn.) and its Potential for Use as a Soil Amendment," Journal of the Science and Food Agriculture, 2013, pp. 2242-2247, vol. 93, No. 9.

Hafeez, F. Y., et al., "PGPR: Versatile Tool to Combat Soil Borne Pathogens and Improve Plant Health," Aspects of Applied Biology, Crop Protection in Southern Britain, 2011, pp. 241-245, vol. 106.

Han, W., et al., "The Application of Exogenous Cellulase to Improve Soil Fertility and Plant Growth Due to Acceleration of Straw Decomposition," Bioresource Technology, 2010, pp. 3724-3731, vol. 101.

(56) References Cited

OTHER PUBLICATIONS

Hartati, S., et al., "Overexpression of Poplar Cellulase Accelerates Growth and Disturbs the Closing Movements of Leaves in Sengon," Plant Physiology, Jun. 2008, pp. 552-561, vol. 147.
Hong, Y., et al., "Phospholipases in Plant Response to Nitrogen and Phosphorus Availability," Phospholipases in Plant Signaling, Signaling and Communication in Plants, 2014, pp. 159-180, vol. 20, Springer, Berlin, Heidelberg.
Hontzeas, N., et al., "Changes in Gene Expression in Canola Roots Induced by ACC-Deaminase-Containing Plant-Growth-Promoting Bacteria," Molecular Plant-Microbe Interactions, Aug. 2004, pp. 865-871, vol. 17, No. 8.
Howard, G., et al., "Effects of Cellulolytic Ruminol Bacteria and of Cell Extracts on Germination of *Euonymus americanus* L. Seeds," Applied and Environmental Microbiology, Jan. 1988, pp. 218-224, vol. 54, No. 1.
Idriss, E. E., et al., "Extracellular Phytase Activity of Bacillus amyloliquefaciens FZB45 Contributes to its Plant-Growth-Promoting Effect," Microbiology, 2002, pp. 2097-2109, vol. 148.
International Search Report issued for PCT/US2017/022662 dated Jun. 5, 2017, 5 pages.
Islam, M. R., et al., "Characterization of Plant Growth-Promoting Traits of Free-Living Diazotrophic Bacteria and Their Inoculation Effects on Growth and Nitrogen Uptake of Crop Plants," Journal of Microbiology and Biotechnology, Oct. 2009, pp. 1213-1222, vol. 19, No. 10.
Jackson, W. T., "Effect of Pectinase and Cellulase Preparations on the Growth and Development of Root Hairs," Physiologia Plantarum, 1959, pp. 502-510, vol. 12.
Jeong, H., et al., "Draft Genome Sequence of the Paenibacillus polymyxa Type Strain (ATCC 842T), A Plant Growth-Promoting Bacterium," Journal of Bacteriology, 2011, pp. 5026-5027, vol. 193, No. 18.
Kim, J. F., et al., "Genome Sequence of the Polymyxin-Producing Plant-Probiotic Rhizobacterium Paenibacillus polymyxa E681," Journal of Bacteriology, 2010, pp. 6103-6104, vol. 192, No. 22.
Kong, Z., et al., "Effects of 1-aminocyclopropane-1-carboxylate (ACC) Deaminase-Overproducing Sinorhizobium-meliloti on Plant Growth and Copper Tolerance of Medicago lupulina," Plant and Soil, Jun. 2015, pp. 383-398, vol. 391, Issue 1 (Abstract only, 7 pages).
Leite, H. A., et al., "Bacillus subtilis and Enterobacter cloacae endophytes from healthy *Theobroma cacao* L. Trees can systemically colonize seedlings and promote growth," Applied Microbiology and Biotechnology, Dec. 2012, pp. 2639-2651, vol. 97, No. 6.
Li, J., et al., "An ACC Deaminase Minus Mutant of Enterobacter cloacae UW4 No Longer Promotes Root Elongation," Current Microbiology, Aug. 2000, pp. 101-105, vol. 41, No. 2.
Li, W., et al., "Cloning of the Thermostable Cellulose Gene from the Newly Isolated Bacillus subtillus and its Expression in *Excherichia coli*," Molecular Biotechnology, 2008, pp. 195-201, vol. 40, Issue 2.
Li, Z., et al., "A Colorimetric Assay of 1-aminocyclopropane-1-carboxylate (ACC) Based on Ninhydrin Reaction for Rapid Screening of Bacteria Containing ACC Deaminase," Letters in Applied Microbiology, 2011, pp. 178-185, vol. 53.
Lin, Z., et al., "Recent Advances in Ethylene Research," Journal of Experimental Botany, 2009, pp. 3311-3336, vol. 60, Issue 12.
Liu, J. L., et al., "Effects of Two Plant Growth-Promoting Rhizobacteria Containing 1-aminocyclopropane-1-carboxylate Deaminase on Oat Growth in Petroleum-Contaminated Soil," International Journal of Environmental Science and Technology, Dec. 2015, pp. 3887-3894, vol. 12, Issue 12 (Abstract only, 6 pages).
Liu, W., et al., "THIS1 is a Putative Lipase that Regulates Tillering, Plant Height, and Spikelet Fertility in Rice," Journal of Experimental Botany, 2013, pp. 1-14, vol. 64, No. 14.
Medie, F., et al., "Genome Analyses Highlight the Different Biological Roles of Cellulases," Nature Reviews, Microbiology, Mar. 2012, pp. 227-234, vol. 10.
Meldau, D. G., et al., "A Native Plant Growth Promoting Bacterium, *Bacillus* sp.B55, Rescues Growth Performance of an Ethylene-Insensitive Plant Genotype in Nature," Frontiers in Plant Science, Jun. 2012, pp. 1-13, vol. 3, Article 112.
Mercado, J. A., et al., "Expression of the B-1,3-Glucanase Gene bgn13.1 From Trichoderma harzianum in Strawberry Increases Tolerance to Crown Rot Diseases But Interferes with Plant Growth," Transgenic Research, 2015, 11 pages, vol. 24, No. 6.
Ngamau, C., "Endophytic bacteria associated with bananas (*Musi* spp.) in Kenya and their potential as biological fertilizers," A thesis submitted in fulfillment for the degree of Doctor of Philosophy in Plant Science in the Jomo Kenyatta University of Agriculture and Technology, 2013, 191 pages.
Oh, T.-K., et al., "Expression of Aspergillus nidulans phy Gene in Nicotiana benthamiana Produces Active Phytase with Broad Specificities," International Journal of Molecular Sciences, 2014, pp. 15571-15591, vol. 15, No. 9.
Penrose, D. M., et al., "Levels of ACC and Related Compounds in Exudate and Extracts of Canola Seeds Treated with ACC Deaminase-Containing Plant Growth-Promoting Bacteria," Canadian Journal of Microbiology, Apr. 2001, pp. 368-372, vol. 47, No. 4.
Phitsuwan, P., et al., "Present and Potential Applications of Cellulases in Agriculture, Biotechnology, and Bioenergy," Folia Microbiology, 2013, pp. 163-176, vol. 58.
Pilar-Izquierdo, M. D., et al., "Barley Seed Coating with Free and Immobilized Alkaline Phosphatase to Improve P Uptake and Plant Growth," Crops and Soils Research Paper, Journal of Agricultural Science, 2012, pp. 691-701, vol. 150.
Ping, R., et al., "Effect of Cellulase on Germination of Pinus tabulaeformis Seeds and Grow Seedlings," Journal of Northwest Forestry College, 2005, pp. 78-79, vol. 20, No. 1 (Abstract, 1 page).
Reetha, S., et al., "Screening of Cellulase and Pectinase by Using Pseudomonas fluorescence and Bacillus subtilis," International Letters of Natural Sciences, 2014, pp. 75-80, vol. 8, No. 2.
Saleh, S., et al., "Involvement of gacS and rpoS in Enhancement of the Plant Growth-Promoting Capabilities of Enterobacter cloacae CAL2 and UW4," Canadian Journal of Microbiology, Aug. 2001, pp. 698-705, vol. 47, No. 8.
Sales, J., et al. "Coffee (*Coffea arabica* L.) Seeds Germination After Treatment With Different Concentrations and Embedding Times in Cellulase," Ciencia e Agrotecnologia [online], 2003, pp. 557-564, vol. 27, No. 3, ISSN 1413-7054. http://dx.doi.org/10.1590/S1413-70542003000300009, (Abstract only, 1 page).
U.S. Appl. No. 15/414,050, filed Jan. 24, 2017.
U.S. Appl. No. 15/842,062, filed Dec. 14, 2017.
U.S. Appl. No. 15/846,487, filed Dec. 19, 2017.
U.S. Appl. No. 62/560,876, filed Sep. 20, 2017.
U.S. Appl. No. 15/511,839, filed Mar. 16, 2017.
U.S. Appl. No. 15/511,822, filed Mar. 16, 2017.
U.S. Appl. No. 15/511,854, filed Mar. 16, 2017.
U.S. Appl. No. 15/511,835, filed Mar. 16, 2017.
U.S. Appl. No. 15/511,864, filed Mar. 16, 2017.
U.S. Appl. No. 15/511,844, filed Mar. 16, 2017.
Shahid, M., et al., "Root Colonization and Growth Promotion of Sunflower (*Helianthus annuus* L.) by Phosphate Solubilizing *enterobacter* sp. Fs-11," World Journal of Microbiology and Biotechnology, 2012, pp. 2749-2758, vol. 28, Issue 8.
Shani, Z., et al., "Expression of Endo-1,4-B-Glucanase (cel1) in *Arabidopsis thaliana* is Associated with Plant Growth, Xylem Development and Cell Wall Thickening," Plant Cell Reports, 2006, pp. 1067-1074, vol. 25, No. 10.
Shankar, M., et al., "Root Colonization of a Rice Growth Promoting Strain of Enterobacter cloacae," Journal of Basic Microbiology, 2011, pp. 523-530, vol. 51, No. 5.
Shao, J., et al., "Contribution of Indole-3-acetic Acid in the Plant Growth Promotion by the Rhizospheric Strain Bacillus amyloliquefaciens SQR9," Biology and Fertility of Soils, Apr. 2015, pp. 321-330, vol. 51, Issue 3.
Shen, M., et al., "Effect of Plant Growth-Promoting Rhizobacteria (PGPRs) on Plant Growth, Yield, and Quality of Tomato (*Lycopersicon esculentum* Mill.) Under Simulated Seawater Irrigation," The Journal of General and Applied Microbiology, 2012, pp. 253-262, vol. 58, No. 4.
Siddikee, Md. A., et al., "Halotolerant Bacteria with ACC Deaminase Activity Alleviate Salt Stress Effect in Canola Seed Germination,"

(56) References Cited

OTHER PUBLICATIONS

Journal of the Korean Society for Applied Biological Chemistry, Apr. 2015, pp. 237-241, vol. 58, Issue 2.
Singh, B., et al., "Microbial Phytases in Phosphorus Acquisition and Plant Growth Promotion," Physiology and Molecular Biology of Plants, Apr.-Jun. 2011, pp. 93-103, vol. 17, Issue 2.
Singh, B., et al., "Plant Growth Promotion by an Extracellular HAP-Phytase of a Thermophilic Mold Sporotrichum thermophile," Applied Biochemistry and Biotechnology, Mar. 2010, pp. 1267-1276, vol. 160, Issue 5.
Smirnova, I., et al., "The Effect of Inoculation by Cellulolytic Bacteria Bacillus cytaseus on Wheat Productivity," Plant Growth-Promoting Rhizobacteria (PGPR) for Substainable Agriculture, Proceedings of the 2nd Asian PGPR Conference, Aug. 21-24, 2011, pp. 185-191, Beijing, P.R. China.
Stearns, J., C., et al., "Effects of Bacterial ACC Deaminase on *Brassica napus* Gene Expression," Molecular Plant-Microbe Interactions, 2012, pp. 668-676, vol. 25, No. 5.
Trivedi, P., et al., "Plant Growth Promotion Abilities and Formulation of Bacillus megaterium Strain B 388 (MTCC6521) Isolated from a Temperate Himalayan Location," Indian Journal of Microbiology, 2008, pp. 342-347, vol. 48, Issue 3.
Vendan, R. T., et al., "Diversity of Endophytic Bacteria in Ginseng and Their Potential for Plant Growth Promotion," The Journal of Microbiology, 2010, pp. 559-565, vol. 48, Issue 5.
Wang, X., et al., "PLD: Phospholipase Ds in Plant Signaling," Phospholipases in Plant Signaling, 2013, pp. 3-26.
Written Opinion issued for PCT/US2017/022662 dated Jun. 5, 2017, 6 pages.
Yadav, S., et al., "Diversity and Phylogeny of Plant Growth-Promoting Bacilli from Moderately Acidic Soil," Journal of Basic Microbiology, Feb. 2011, pp. 98-106, vol. 51, Issue 1.
Zeigler, D. R., "Bacillus Thuringiensis Bacillus Cereus," Bacillus Genetic Stock Center Catalog of Strains, 1999, Seventh Edition, vol. 2, 58 pages.
Siddikee, Md. A., et al., "Regulation of Ethylene Biosynthesis Under Salt Stress in Red Pepper (*Capsicum annuum* L.) by 1-Aminocyclopropane-1-Carboxylic Acid (ACC) Deaminase-Producing Halotolerant Bacteria," Journal of Plant Growth Regulation, 2012, pp. 265-272, vol. 31, Issue 2.
Fan, L., et al., "Antisense Suppression of Phospholipase D(alpha) Retards Abscisic Acid- and Ethylene-Promoted Senescence of Post-harvest *Arabidopsis* Leaves," The Plant Cell, Dec. 1997, pp. 2183-2196, vol. 9.
Glass, M., et al., "Endo-(beta)-1,4-Glucanases Impact Plant Cell Wall Development by Influencing Cellulose Crystallization," Journal of Integrative Plant Biology, Apr. 2015, pp. 396-410, vol. 57, Issue 4.
Hong, Y., et al., "Phospholipase D(alpha)3 Is Involved in the Hyperormotic Response in *Arabidopsis*," The Plant Cell, Mar. 2008, pp. 803-816, vol. 20.
Li, M., et al., Overexpression of Patatin-Related Phospholipase AIII(delta) Altered Plant Growth and Increased Seed Oil Content in Camelina, Plant Biotechnology Journal, 2015, pp. 766-778, vol. 13.
Shani, Z., et al., "Growth Enhancement of Transgenic Poplar Plants by Overexpression of *Arabidopsis thaliana* Endo-1,4-beta-Glucanase (cel1)," Molecular Breeding, 2004, pp. 321-330, vol. 14.
Bewley, J. D., "Breaking Down the Walls—A Role for Endo-beta-mannanase in Release from Seed Dormancy?," Trends in Plant Science, Dec. 1997, pp. S1360-S1385, vol. 2, No. 12.
Leviatov, S., et al., "Involvement of Endomannanase in the Control of Tomato Seed Germination Under Low Temperature Conditions," Annals of Botany, 1995, pp. 1-6, vol. 76.
Partial Supplementary European Search Report issued for EP17767505.5 dated Feb. 26, 2020, 5 pages.
Rodriguez-Gacio, M. C., et a., "Softening-up Mannan-rich Cell Walls," Journal of Experimental Botany, 2012, pp. 3975-3988, vol. 63, No. 11.
Yang, P., et al., "A Novel Beta-Mannanase with High Specific Activity from Bacillus circulans CGMCC1554: Gene Cloning, Expression and Enzymatic Characterization," Applied Biochemistry and Biotechnology, 2009, pp. 85-94, vol. 159, No. 1.
Sadowski, M. I., et al., "The Sequence-Structure Relationship and Protein Function Prediction," Current Opinion in Structural Biology, 2009, pp. 357-362, vol. 19, No. 3.
Seffernick, J. L., et al., "Melamine Deaminase and Atrazine Chlorohydrolase: 98 Percent Identical but Functionally Different," Journal of Bacteriology, Apr. 2001, pp. 2405-2410, vol. 183, No. 8.
Sloma, A., et al., "Cloning and Characterization of the Gene for an Additional Extracellular Serine Protease of Bacillus subtilis," Journal of Bacteriology, Nov. 1991, pp. 6889-6895, vol. 173, No. 21.
Tang, S., et al., "Identification of Dehalobacter Reductive Dehalogenases that Catalyse Dechlorination of Chloroform, 1,1,1-Trichloroethane and 1,1-Dichloroethane," Philosophical Transactions of the Royal Society, 2013, pp. 1-10, vol. 368, No. 1616.
Thallinger, B., et al., "Antimicrobial Enzymes: An Emerging Strategy to Fight Microbes and Microbial Biofilms," Biotechnology Journal, 2013, pp. 97-109, vol. 8, No. 1.
Valbuzzi, A., et al., "A Novel Member of the Subtilisin-like Protease Family from Bacillus subtilis," Microbiology, 1999, pp. 3121-3127, vol. 145, Part 11.
Akinrinlola, et al., "Evaluation of Bacillus Strains for Plant Growth Promotion and Predictability of Efficacy by In Vitro Physiological Traits", Intl. Journal of Microbiology vol. 2008 Article ID 5686874, 11 pages.
Benfield, et al., "Structural Studies Examining the Substrate Specificity Profiles of PC-PLCBc Proteins Variants" (2007) vol. 460, No. 1, pp. 41-47.
Cheng, "Purification and Characterization of a Thermostable β-Mannanase from Bacillus Subtilis BE-91: Potential Application in Inflammatory Diseases" BioMed Research International (2016) vol. 2016, Article ID 6380147, pp. 1-7.
UniProtKB Accession No. W7KRH1, Intracellular Serine Protease, Apr. 16, 2014, 2 pages.
UniProtKB Accession No. A0A380XNG8, Intracellular Serine Protease, Nov. 7, 2018, 1 page.
Di Benedetto, et al., "Isolation, Screening, and Characterization of Plant-Growth-Promoting Bacteria from Durum Wheat Rhizosphere to Improve N and P Nutrient Use Efficiency", Microorganisms (2019) vol. 7, No. 541, pp. 1-18.
Dowd and Gilroy, "The Emerging Roles of Phospholipase C in Plant Growth and Development", Plant Cell Monographs (2009) vol. 16, pp. 23-27.
Dunne, C., et al., "Overproduction of an Inducible Extracellular Serine Protease Improves Biological Control of Pythium ultimum by Stenotrophomonas maltophilia Strain W81," Microbiology, (2000) vol. 146, Part 8, pp. 2069-2078.
Emi, et al., "Crystallization and Some Properties of Mannanase" Agricultural and Biological Chemistry (1972) vol. 36, No. 6, pp. 991-1001.
Geng et al., "A Novel Serine Protease, Sep1 from Bacillus Firmus DS-1 Has Nematicidal Activity and Degrades Multiple Intestinal-Associated Nematode Proteins", Scientific Reports, (2016) vol. 6, pp. 1-12.
Khan, N., et al., "Antifungal Activity of Bacillus Species Against Fusarium and Analysis of the Potential Mechanisms Used in Biocontrol," Frontiers in Microbiology (2018) vol. 9, Article 2363, pp. 1-12.
Li, et al., "Structure Prediction and Enzymatic Properties of Phytase PhyS", Advances in Enzyme Research (2019) vol. 7, pp. 57-65.
Quan, et al., "Purification and Properties of a Phytase from Candida Krusei WZ-001", Journal of Bioscience (2002) vol. 34, No. 5, pp. 419-425.
Quecine, et al. "Sugarcane Growth Promotion by the Endophytic Bacterium Pantoea Agglomerans 33.1", Applied and Environmental Microbiology (2012) vol. 78, No. 21, pp. 7511-7518.
Raddadi, et al., "Screening of Plant Growth Promoting Traits of Bacillus Thuringiensis" Annals of Microbiology (2008) vol. 58, No. 1, pp. 47-52.
Van Pouderoyen, et al., "Structural Insights Into the Processivity of Endopolygalacturonase I from Aspergillus niger," FEBS Letters (2003) vol. 554, No. 3 pp. 462-466.

(56) References Cited

OTHER PUBLICATIONS

Yen, Y.-H., et al., "An Antifungal Protease Produced by Pseudomonas aeruginosa M-1001 with Shrimp and Crab Shell Powder as a Carbon Source," Enzyme and Microbial Technology (2006) vol. 39, pp. 311-317.
K. Jetiyanon et al., "Film Coating of Seeds with Bacillus Cereus RS87 Spores for Early Plant Growth Enhancement", Canadian Journal of Microbiology (2008) vol. 54, pp. 861-867.
S. Shah, et al., "Isolation and Characterization of ACC Deaminase Genes From Two Different Plant Growth-Promoting Rhizobacteria" Canadian Journal of Microbiology (1998) vol. 44, pp. 833-843.

* cited by examiner

SEQUENCE LISTING

<160> NUMBER OF SEQ ID NOS: 147

<210> SEQ ID NO 1
<211> LENGTH: 996
<212> TYPE: DNA
<213> ORGANISM: Bacillus thuringiensis

<400> SEQUENCE: 1

```
atgaatttag ctaaattccc gagaaaaaaa tatacagaat catatacacc aattgaaaag      60

ttaaacaact tttctgaagc acttggtggg ccgactattt attttaaacg agatgattta     120

cttggtttaa cagctggtgg taataagacg agaaagttag agtttctagt tgcggatgca     180

gaggcaaaag gtgcagatac gttaattaca gctggtggta ttcagtcaaa ccattgccgt     240

ctaacactgg cagctgcggt aaaagaaaaa atgaaatgta tccttgtatt agaagaaggg     300

cttgaaccag aagagaagcc agactttaac ggaaactatt tcttatatca tttactaggt     360

gctgaaaatg taattgttgt accaaacggg gcagatctta tggaagagat gcataaagta     420

gcgaaagaag ttagtgaaaa aggtaataca ccatatgtca taccagttgg tggatcaaat     480

cctactggtg caatgggata cgttgcttgt gcgcaagaaa ttatggcaca atcatttgac     540

caaggaattg atttcagtac agtcgtttgc gtaagcggta gcgctggtat gcacgctggt     600

ttaattactg gttttgctgg aacacaaagc cacattcctg taattggaat caacgtaagt     660

agaggaaaag ctgagcaaga agagaaagta gcaaaacttg tagatgaaac ttcagcacac     720

gttggtattc caaactttat cccgcgtgac gctgttacgt gctttgatga atatgtaggg     780

ccaggatatg cgttaccaac gccggaaatg gtagaggcag ttcagttact tgcgaaaaca     840

gaaggtattt tacttgatcc agtgtataca ggtaaagcgg tagcgggatt aatcgactta     900

attaaaaaag gtacatttaa taaagaagac aacattttat tcgtacattc aggtggttca     960

ccagctttat atgcgaatac ttctttattt gcgtaa                              996
```

<210> SEQ ID NO 2
<211> LENGTH: 996
<212> TYPE: DNA
<213> ORGANISM: Bacillus pseudomycoides

<400> SEQUENCE: 2

```
atgaatttag cgaagtttcc tagaaagaaa tacacagaat catatacgcc aatcgaaaaa      60

ttaaatcact tttctgaagt cctaggagga ccttctattt actttaaacg agatgattta     120

cttggtttaa cagctggcgg aaataaaaca agaaaattag aattccttgt ggcggatgca     180

caggcgaaag gtgtagatac gttaattact gctggtggta ttcagtcaaa tcattgccga     240

ttaacattag cggctgcggt aaaagagaaa atgaaatgca ttcttgtatt agaagaagga     300

cttgaaccag aagaaaaacc agactttaat gggaattact tcttatatca tttattaggt     360

gctgaaaatg taatcgttgt gccaaacgga actgacctta tggatgagat gcaaaaagtg     420

gccaaagaag taactgaaaa agggcataca ccatacgtca ttccagttgg aggatccaat     480
```

```
cctaccggtg caatgggata tattgcatgt gcagaggaaa ttatggctca atcgtttgag    540

caagggatag atttcaatgc ggttgtttgt gtaagtggta gcggtggcat gcatgctggt    600

ttgattactg gattttatgg aagacaaaca gggatcccga taatcggaat gaatgtgagc    660

cgcggaaaag ctgaacaaga agaaaaagta tgtaagcttg tgcaagaaac ttcagcgcat    720

gttggtattc caaacagtat tccgcgtgag gctgtgacat gttttgatga atacgttggg    780

ccaggatacg ctttaccaac acctgaaatg gtagaagctg ttcaactttt agcaaaaaca    840

gaaggaattt tactggatcc agtatataca gggaaagcag tagctggact gatcgacata    900

attcgaaaag gtacatttaa gaaagaagat aacatcctat ttgtacattc aggtggttct    960

ccggcgttat atgcgaatac atcactattt tcctaa                              996
```

<210> SEQ ID NO 3
<211> LENGTH: 996
<212> TYPE: DNA
<213> ORGANISM: Bacillus thuringiensis

<400> SEQUENCE: 3

```
atgaatttag ctaaattccc gagaaaaaaa tatacagagt catatacacc aattgaaaaa     60

ttaaacaatt tttctgaagt acttggtggg ccgactattt attttaaacg agatgattta    120

cttggtttaa cagctggtgg taataagacg agaaagttag agtttctagt tgcggatgca    180

caggcaaaag gtgcagatac gttaattaca gctggtggta ttcagtcaaa ccattgccgt    240

ctaacactgg cagctgcggt aaaagaaaaa atgaaatgta tccttgtatt agaagaaggg    300

cttgaaccag aagagaagcc agactttaac ggaaactatt tcttatatca cttattaggt    360

gctgaaaatg tcattgttgt accaaacgga gcagacctga tggaagaaat gcataaagta    420

gcaaaagaag taagtgaaaa agggaataca ccatatgtaa ttccagttgg tggatcaaac    480

cctacgggcg ctatgggata cgttgcttgt gcgcaagaaa ttatggcgca atcatttgag    540

caaggaattg atttcagttc agttgtttgt gtaagtggta gcggcggtat gcatgctggt    600

ttaattactg gttttgctgg aacacaaagc cacattcctg taattggaat caacgtaagt    660

agaggaaaag ctgagcaaga agagaaagta gcaaaacttg tagatgaaac ttcagcacac    720

gttggtattc caaactttat ctcgcgcgac gctgttacgt gctttgatca atatgtagga    780

ccaggctatg cgttaccaac gcaggaaatg gtagaggcag ttcagttact tgcgaaaaca    840

gaaggtattt tacttgatcc agtgtataca ggtaaagcgg tagcgggatt aatcgactta    900

attaaaaaag ggacatttaa taaagaagac aacattttat tcgtacattc aggtggttca    960

ccagctttat atgcgaatac ttctttattt gcgtaa                              996
```

<210> SEQ ID NO 4
<211> LENGTH: 996
<212> TYPE: DNA
<213> ORGANISM: Bacillus thuringiensis

<400> SEQUENCE: 4

```
atgaatttag ctaaattccc gagaaaaaaa tatacagaat catatacacc aattgaaaag     60

ttaaacaact tttctgaagc acttggtggg ccgactattt attttaaacg agatgattta    120

cttggtttaa cagctggtgg taataagacg agaaagttag agtttctagt tgcggatgca    180

gaggcaaaag gtgcagatac gttaattaca gctggtggta ttcagtcaaa ccattgccgt    240

ctaacactgg cagctgcggt aaaagaaaaa atgaaatgta tccttgtatt agaagaaggg    300

cttgaaccag aagagaagcc agactttaac ggaaactatt tcttatatca tttactaggt    360
```

gctgaaaatg taattgttgt accaaacggg gcagatctta tggaagagat gcataaagta 420
gcgaaagaag ttagtgaaaa aggtaataca ccatatgtca taccagttgg tggatcaaat 480
cctactggtg caatgggata cgttgcttgt gcgcaagaaa ttatggcaca atcatttgac 540
caaggaattg atttcagtac agtcgtttgc gtaagcggta gcgctggtat gcacgctggt 600
ttaattactg gttttgctgg aacacaaagc cacattcctg taattggaat caacgtaagt 660
agaggaaaag ctgagcaaga agagaaagta gcaaaacttg tagatgaaac ttcagcacac 720
gttggtattc caaactttat cccgcgtgac gctgttacgt gctttgatga atatgtaggg 780
ccaggatatg cgttaccaac gccggaaatg gtagaggcag ttcagttact tgcgaaaaca 840
gaaggtattt tacttgatcc agtgtatgaa ggtaaagcgg tagcgggatt aatcgactta 900
attaaaaaag gtacatttaa taaagaagac aacattttat tcgtacattt aggtggttca 960
ccagctttat atgcgaatac ttctttattt gcgtaa 996

<210> SEQ ID NO 5
<211> LENGTH: 996
<212> TYPE: DNA
<213> ORGANISM: Bacillus pseudomycoides

<400> SEQUENCE: 5
atgaatttag cgaagtttcc tagaaagaaa tacacagaat catatacgcc aatcgaaaaa 60
ttaaatcact tttctgaagt cctaggagga ccttctattt actttaaacg agatgattta 120
cttggtttaa cagctggcgg aaataaaaca agaaaattag aattccttgt ggcggatgca 180
caggcgaaag gtgtagatac gttaattact gctggtggta ttcagtcaaa tcattgccga 240
ttaacattag cggctgcggt aaaagagaaa atgaaatgca ttcttgtatt agaagaagga 300
cttgaaccag aagaaaaacc agactttaat gggaattact tcttatatca tttattaggt 360
gctgaaaatg taatcgttgt gccaaacgga actgacctta tggatgagat gcaaaaagtg 420
gccaaagaag taactgaaaa agggcataca ccatacgtca ttccagttgg aggatccaat 480
cctaccggtg caatgggata tattgcatgt gcagaggaaa ttatggctca atcgtttgag 540
caagggatag atttcaatgc ggttgtttgt gtaagtggta gcggtggcat gcatgctggt 600
ttgattactg gattttatgg aagacaaaca gggatcccga taatcggaat gaatgtgagc 660
cgcggaaaag ctgaacaaga agaaaaagta tgtaagcttg tgcaagaaac ttcagcgcat 720
gttggtattc caaacagtat tccgcgtgag gctgtgacat gttttgatga atacgttggg 780
ccaggatacg ctttaccaac acctgaaatg gtagaagctg ttcaactttt agcaaaaaca 840
gaaggaattt tactggatcc agtatatgaa gggaaagcag tagctggact gatcgacata 900
attcgaaaag gtacatttaa gaaagaagat aacatcctat ttgtacattt aggtggttct 960
ccggcgttat atgcgaatac atcactattt tcctaa 996

<210> SEQ ID NO 6
<211> LENGTH: 996
<212> TYPE: DNA
<213> ORGANISM: Bacillus thuringiensis

<400> SEQUENCE: 6
atgaatttag ctaaattccc gagaaaaaaa tatacagagt catatacacc aattgaaaaa 60
ttaaacaatt tttctgaagt acttggtggg ccgactattt attttaaacg agatgattta 120
cttggtttaa cagctggtgg taataagacg agaaagttag agtttctagt tgcggatgca 180

```
caggcaaaag gtgcagatac gttaattaca gctggtggta ttcagtcaaa ccattgccgt    240
ctaacactgg cagctgcggt aaaagaaaaa atgaaatgta tccttgtatt agaagaaggg    300
cttgaaccag aagagaagcc agactttaac ggaaactatt tcttatatca cttattaggt    360
gctgaaaatg tcattgttgt accaaacgga gcagacctga tggaagaaat gcataaagta    420
gcaaaagaag taagtgaaaa agggaataca ccatatgtaa ttccagttgg tggatcaaac    480
cctacgggcg ctatgggata cgttgcttgt gcgcaagaaa ttatggcgca atcatttgag    540
caaggaattg atttcagttc agttgtttgt gtaagtggta gcggcggtat gcatgctggt    600
ttaattactg gttttgctgg aacacaaagc cacattcctg taattggaat caacgtaagt    660
agaggaaaag ctgagcaaga agagaaagta gcaaaacttg tagatgaaac ttcagcacac    720
gttggtattc caaactttat ctcgcgcgac gctgttacgt gctttgatca atatgtagga    780
ccaggctatg cgttaccaac gcaggaaatg gtagaggcag ttcagttact tgcgaaaaca    840
gaaggtattt tacttgatcc agtgtatgaa ggtaaagcgg tagcgggatt aatcgactta    900
attaaaaaag ggacatttaa taaagaagac aacattttat tcgtacattt aggtggttca    960
ccagctttat atgcgaatac ttctttattt gcgtaa                              996
```

<210> SEQ ID NO 7
<211> LENGTH: 331
<212> TYPE: PRT
<213> ORGANISM: Bacillus thuringiensis

<400> SEQUENCE: 7

```
Met Asn Leu Ala Lys Phe Pro Arg Lys Lys Tyr Thr Glu Ser Tyr Thr
1               5                   10                  15

Pro Ile Glu Lys Leu Asn Asn Phe Ser Glu Ala Leu Gly Gly Pro Thr
            20                  25                  30

Ile Tyr Phe Lys Arg Asp Asp Leu Leu Gly Leu Thr Ala Gly Gly Asn
        35                  40                  45

Lys Thr Arg Lys Leu Glu Phe Leu Val Ala Asp Ala Glu Ala Lys Gly
    50                  55                  60

Ala Asp Thr Leu Ile Thr Ala Gly Gly Ile Gln Ser Asn His Cys Arg
65                  70                  75                  80

Leu Thr Leu Ala Ala Ala Val Lys Glu Lys Met Lys Cys Ile Leu Val
                85                  90                  95

Leu Glu Glu Gly Leu Glu Pro Glu Glu Lys Pro Asp Phe Asn Gly Asn
            100                 105                 110

Tyr Phe Leu Tyr His Leu Leu Gly Ala Glu Asn Val Ile Val Val Pro
        115                 120                 125

Asn Gly Ala Asp Leu Met Glu Glu Met His Lys Val Ala Lys Glu Val
    130                 135                 140

Ser Glu Lys Gly Asn Thr Pro Tyr Val Ile Pro Val Gly Gly Ser Asn
145                 150                 155                 160

Pro Thr Gly Ala Met Gly Tyr Val Ala Cys Ala Gln Glu Ile Met Ala
                165                 170                 175

Gln Ser Phe Asp Gln Gly Ile Asp Phe Ser Thr Val Val Cys Val Ser
            180                 185                 190

Gly Ser Ala Gly Met His Ala Gly Leu Ile Thr Gly Phe Ala Gly Thr
        195                 200                 205

Gln Ser His Ile Pro Val Ile Gly Ile Asn Val Ser Arg Gly Lys Ala
    210                 215                 220

Glu Gln Glu Glu Lys Val Ala Lys Leu Val Asp Glu Thr Ser Ala His
```

```
225                 230                 235                 240

Val Gly Ile Pro Asn Phe Ile Pro Arg Asp Ala Val Thr Cys Phe Asp
                245                 250                 255

Glu Tyr Val Gly Pro Gly Tyr Ala Leu Pro Thr Pro Glu Met Val Glu
            260                 265                 270

Ala Val Gln Leu Leu Ala Lys Thr Glu Gly Ile Leu Leu Asp Pro Val
        275                 280                 285

Tyr Thr Gly Lys Ala Val Ala Gly Leu Ile Asp Leu Ile Lys Lys Gly
    290                 295                 300

Thr Phe Asn Lys Glu Asp Asn Ile Leu Phe Val His Ser Gly Gly Ser
305                 310                 315                 320

Pro Ala Leu Tyr Ala Asn Thr Ser Leu Phe Ala
                325                 330


<210> SEQ ID NO 8
<211> LENGTH: 331
<212> TYPE: PRT
<213> ORGANISM: Bacillus pseudomycoides

<400> SEQUENCE: 8

Met Asn Leu Ala Lys Phe Pro Arg Lys Lys Tyr Thr Glu Ser Tyr Thr
1               5                   10                  15

Pro Ile Glu Lys Leu Asn His Phe Ser Glu Val Leu Gly Gly Pro Ser
            20                  25                  30

Ile Tyr Phe Lys Arg Asp Asp Leu Leu Gly Leu Thr Ala Gly Gly Asn
        35                  40                  45

Lys Thr Arg Lys Leu Glu Phe Leu Val Ala Asp Ala Gln Ala Lys Gly
    50                  55                  60

Val Asp Thr Leu Ile Thr Ala Gly Gly Ile Gln Ser Asn His Cys Arg
65                  70                  75                  80

Leu Thr Leu Ala Ala Ala Val Lys Glu Lys Met Lys Cys Ile Leu Val
                85                  90                  95

Leu Glu Glu Gly Leu Glu Pro Glu Glu Lys Pro Asp Phe Asn Gly Asn
            100                 105                 110

Tyr Phe Leu Tyr His Leu Leu Gly Ala Glu Asn Val Ile Val Val Pro
        115                 120                 125

Asn Gly Thr Asp Leu Met Asp Glu Met Gln Lys Val Ala Lys Glu Val
    130                 135                 140

Thr Glu Lys Gly His Thr Pro Tyr Val Ile Pro Val Gly Gly Ser Asn
145                 150                 155                 160

Pro Thr Gly Ala Met Gly Tyr Ile Ala Cys Ala Glu Glu Ile Met Ala
                165                 170                 175

Gln Ser Phe Glu Gln Gly Ile Asp Phe Asn Ala Val Val Cys Val Ser
            180                 185                 190

Gly Ser Gly Gly Met His Ala Gly Leu Ile Thr Gly Phe Tyr Gly Arg
        195                 200                 205

Gln Thr Gly Ile Pro Ile Ile Gly Met Asn Val Ser Arg Gly Lys Ala
    210                 215                 220

Glu Gln Glu Glu Lys Val Cys Lys Leu Val Gln Glu Thr Ser Ala His
225                 230                 235                 240

Val Gly Ile Pro Asn Ser Ile Pro Arg Glu Ala Val Thr Cys Phe Asp
                245                 250                 255

Glu Tyr Val Gly Pro Gly Tyr Ala Leu Pro Thr Pro Glu Met Val Glu
            260                 265                 270
```

-continued

```
Ala Val Gln Leu Leu Ala Lys Thr Glu Gly Ile Leu Leu Asp Pro Val
        275                 280                 285

Tyr Thr Gly Lys Ala Val Ala Gly Leu Ile Asp Ile Ile Arg Lys Gly
    290                 295                 300

Thr Phe Lys Lys Glu Asp Asn Ile Leu Phe Val His Ser Gly Gly Ser
305                 310                 315                 320

Pro Ala Leu Tyr Ala Asn Thr Ser Leu Phe Ser
                325                 330


<210> SEQ ID NO 9
<211> LENGTH: 331
<212> TYPE: PRT
<213> ORGANISM: Bacillus thuringiensis

<400> SEQUENCE: 9

Met Asn Leu Ala Lys Phe Pro Arg Lys Lys Tyr Thr Glu Ser Tyr Thr
1               5                   10                  15

Pro Ile Glu Lys Leu Asn Asn Phe Ser Glu Val Leu Gly Gly Pro Thr
            20                  25                  30

Ile Tyr Phe Lys Arg Asp Asp Leu Leu Gly Leu Thr Ala Gly Gly Asn
        35                  40                  45

Lys Thr Arg Lys Leu Glu Phe Leu Val Ala Asp Ala Gln Ala Lys Gly
    50                  55                  60

Ala Asp Thr Leu Ile Thr Ala Gly Gly Ile Gln Ser Asn His Cys Arg
65                  70                  75                  80

Leu Thr Leu Ala Ala Ala Val Lys Glu Lys Met Lys Cys Ile Leu Val
                85                  90                  95

Leu Glu Glu Gly Leu Glu Pro Glu Glu Lys Pro Asp Phe Asn Gly Asn
            100                 105                 110

Tyr Phe Leu Tyr His Leu Leu Gly Ala Glu Asn Val Ile Val Val Pro
        115                 120                 125

Asn Gly Ala Asp Leu Met Glu Glu Met His Lys Val Ala Lys Glu Val
    130                 135                 140

Ser Glu Lys Gly Asn Thr Pro Tyr Val Ile Pro Val Gly Gly Ser Asn
145                 150                 155                 160

Pro Thr Gly Ala Met Gly Tyr Val Ala Cys Ala Gln Glu Ile Met Ala
                165                 170                 175

Gln Ser Phe Glu Gln Gly Ile Asp Phe Ser Ser Val Val Cys Val Ser
            180                 185                 190

Gly Ser Gly Gly Met His Ala Gly Leu Ile Thr Gly Phe Ala Gly Thr
        195                 200                 205

Gln Ser His Ile Pro Val Ile Gly Ile Asn Val Ser Arg Gly Lys Ala
    210                 215                 220

Glu Gln Glu Glu Lys Val Ala Lys Leu Val Asp Glu Thr Ser Ala His
225                 230                 235                 240

Val Gly Ile Pro Asn Phe Ile Ser Arg Asp Ala Val Thr Cys Phe Asp
                245                 250                 255

Gln Tyr Val Gly Pro Gly Tyr Ala Leu Pro Thr Gln Glu Met Val Glu
            260                 265                 270

Ala Val Gln Leu Leu Ala Lys Thr Glu Gly Ile Leu Leu Asp Pro Val
        275                 280                 285

Tyr Thr Gly Lys Ala Val Ala Gly Leu Ile Asp Leu Ile Lys Lys Gly
    290                 295                 300

Thr Phe Asn Lys Glu Asp Asn Ile Leu Phe Val His Ser Gly Gly Ser
305                 310                 315                 320
```

Pro Ala Leu Tyr Ala Asn Thr Ser Leu Phe Ala
325 330

<210> SEQ ID NO 10
<211> LENGTH: 331
<212> TYPE: PRT
<213> ORGANISM: Bacillus thuringiensis

<400> SEQUENCE: 10

Met Asn Leu Ala Lys Phe Pro Arg Lys Lys Tyr Thr Glu Ser Tyr Thr
1 5 10 15

Pro Ile Glu Lys Leu Asn Asn Phe Ser Glu Ala Leu Gly Gly Pro Thr
20 25 30

Ile Tyr Phe Lys Arg Asp Asp Leu Leu Gly Leu Thr Ala Gly Gly Asn
35 40 45

Lys Thr Arg Lys Leu Glu Phe Leu Val Ala Asp Ala Glu Ala Lys Gly
50 55 60

Ala Asp Thr Leu Ile Thr Ala Gly Gly Ile Gln Ser Asn His Cys Arg
65 70 75 80

Leu Thr Leu Ala Ala Ala Val Lys Glu Lys Met Lys Cys Ile Leu Val
85 90 95

Leu Glu Glu Gly Leu Glu Pro Glu Glu Lys Pro Asp Phe Asn Gly Asn
100 105 110

Tyr Phe Leu Tyr His Leu Leu Gly Ala Glu Asn Val Ile Val Val Pro
115 120 125

Asn Gly Ala Asp Leu Met Glu Glu Met His Lys Val Ala Lys Glu Val
130 135 140

Ser Glu Lys Gly Asn Thr Pro Tyr Val Ile Pro Val Gly Gly Ser Asn
145 150 155 160

Pro Thr Gly Ala Met Gly Tyr Val Ala Cys Ala Gln Glu Ile Met Ala
165 170 175

Gln Ser Phe Asp Gln Gly Ile Asp Phe Ser Thr Val Val Cys Val Ser
180 185 190

Gly Ser Ala Gly Met His Ala Gly Leu Ile Thr Gly Phe Ala Gly Thr
195 200 205

Gln Ser His Ile Pro Val Ile Gly Ile Asn Val Ser Arg Gly Lys Ala
210 215 220

Glu Gln Glu Glu Lys Val Ala Lys Leu Val Asp Glu Thr Ser Ala His
225 230 235 240

Val Gly Ile Pro Asn Phe Ile Pro Arg Asp Ala Val Thr Cys Phe Asp
245 250 255

Glu Tyr Val Gly Pro Gly Tyr Ala Leu Pro Thr Pro Glu Met Val Glu
260 265 270

Ala Val Gln Leu Leu Ala Lys Thr Glu Gly Ile Leu Leu Asp Pro Val
275 280 285

Tyr Glu Gly Lys Ala Val Ala Gly Leu Ile Asp Leu Ile Lys Lys Gly
290 295 300

Thr Phe Asn Lys Glu Asp Asn Ile Leu Phe Val His Leu Gly Gly Ser
305 310 315 320

Pro Ala Leu Tyr Ala Asn Thr Ser Leu Phe Ala
325 330

<210> SEQ ID NO 11
<211> LENGTH: 331
<212> TYPE: PRT

<213> ORGANISM: Bacillus pseudomycoides

<400> SEQUENCE: 11

Met Asn Leu Ala Lys Phe Pro Arg Lys Lys Tyr Thr Glu Ser Tyr Thr
1 5 10 15

Pro Ile Glu Lys Leu Asn His Phe Ser Glu Val Leu Gly Gly Pro Ser
20 25 30

Ile Tyr Phe Lys Arg Asp Asp Leu Leu Gly Leu Thr Ala Gly Gly Asn
35 40 45

Lys Thr Arg Lys Leu Glu Phe Leu Val Ala Asp Ala Gln Ala Lys Gly
50 55 60

Val Asp Thr Leu Ile Thr Ala Gly Gly Ile Gln Ser Asn His Cys Arg
65 70 75 80

Leu Thr Leu Ala Ala Ala Val Lys Glu Lys Met Lys Cys Ile Leu Val
85 90 95

Leu Glu Glu Gly Leu Glu Pro Glu Glu Lys Pro Asp Phe Asn Gly Asn
100 105 110

Tyr Phe Leu Tyr His Leu Leu Gly Ala Glu Asn Val Ile Val Val Pro
115 120 125

Asn Gly Thr Asp Leu Met Asp Glu Met Gln Lys Val Ala Lys Glu Val
130 135 140

Thr Glu Lys Gly His Thr Pro Tyr Val Ile Pro Val Gly Gly Ser Asn
145 150 155 160

Pro Thr Gly Ala Met Gly Tyr Ile Ala Cys Ala Glu Glu Ile Met Ala
165 170 175

Gln Ser Phe Glu Gln Gly Ile Asp Phe Asn Ala Val Val Cys Val Ser
180 185 190

Gly Ser Gly Gly Met His Ala Gly Leu Ile Thr Gly Phe Tyr Gly Arg
195 200 205

Gln Thr Gly Ile Pro Ile Ile Gly Met Asn Val Ser Arg Gly Lys Ala
210 215 220

Glu Gln Glu Glu Lys Val Cys Lys Leu Val Gln Glu Thr Ser Ala His
225 230 235 240

Val Gly Ile Pro Asn Ser Ile Pro Arg Glu Ala Val Thr Cys Phe Asp
245 250 255

Glu Tyr Val Gly Pro Gly Tyr Ala Leu Pro Thr Pro Glu Met Val Glu
260 265 270

Ala Val Gln Leu Leu Ala Lys Thr Glu Gly Ile Leu Leu Asp Pro Val
275 280 285

Tyr Glu Gly Lys Ala Val Ala Gly Leu Ile Asp Ile Ile Arg Lys Gly
290 295 300

Thr Phe Lys Lys Glu Asp Asn Ile Leu Phe Val His Leu Gly Gly Ser
305 310 315 320

Pro Ala Leu Tyr Ala Asn Thr Ser Leu Phe Ser
325 330

<210> SEQ ID NO 12
<211> LENGTH: 331
<212> TYPE: PRT
<213> ORGANISM: Bacillus thuringiensis

<400> SEQUENCE: 12

Met Asn Leu Ala Lys Phe Pro Arg Lys Lys Tyr Thr Glu Ser Tyr Thr
1 5 10 15

Pro Ile Glu Lys Leu Asn Asn Phe Ser Glu Val Leu Gly Gly Pro Thr

```
            20                  25                  30

Ile Tyr Phe Lys Arg Asp Asp Leu Leu Gly Leu Thr Ala Gly Gly Asn
        35                  40                  45

Lys Thr Arg Lys Leu Glu Phe Leu Val Ala Asp Ala Gln Ala Lys Gly
    50                  55                  60

Ala Asp Thr Leu Ile Thr Ala Gly Gly Ile Gln Ser Asn His Cys Arg
65                  70                  75                  80

Leu Thr Leu Ala Ala Ala Val Lys Glu Lys Met Lys Cys Ile Leu Val
                85                  90                  95

Leu Glu Glu Gly Leu Glu Pro Glu Glu Lys Pro Asp Phe Asn Gly Asn
            100                 105                 110

Tyr Phe Leu Tyr His Leu Leu Gly Ala Glu Asn Val Ile Val Val Pro
        115                 120                 125

Asn Gly Ala Asp Leu Met Glu Glu Met His Lys Val Ala Lys Glu Val
    130                 135                 140

Ser Glu Lys Gly Asn Thr Pro Tyr Val Ile Pro Val Gly Gly Ser Asn
145                 150                 155                 160

Pro Thr Gly Ala Met Gly Tyr Val Ala Cys Ala Gln Glu Ile Met Ala
                165                 170                 175

Gln Ser Phe Glu Gln Gly Ile Asp Phe Ser Ser Val Val Cys Val Ser
            180                 185                 190

Gly Ser Gly Gly Met His Ala Gly Leu Ile Thr Gly Phe Ala Gly Thr
        195                 200                 205

Gln Ser His Ile Pro Val Ile Gly Ile Asn Val Ser Arg Gly Lys Ala
    210                 215                 220

Glu Gln Glu Glu Lys Val Ala Lys Leu Val Asp Glu Thr Ser Ala His
225                 230                 235                 240

Val Gly Ile Pro Asn Phe Ile Ser Arg Asp Ala Val Thr Cys Phe Asp
                245                 250                 255

Gln Tyr Val Gly Pro Gly Tyr Ala Leu Pro Thr Gln Glu Met Val Glu
            260                 265                 270

Ala Val Gln Leu Leu Ala Lys Thr Glu Gly Ile Leu Leu Asp Pro Val
        275                 280                 285

Tyr Glu Gly Lys Ala Val Ala Gly Leu Ile Asp Leu Ile Lys Lys Gly
    290                 295                 300

Thr Phe Asn Lys Glu Asp Asn Ile Leu Phe Val His Leu Gly Gly Ser
305                 310                 315                 320

Pro Ala Leu Tyr Ala Asn Thr Ser Leu Phe Ala
                325                 330


<210> SEQ ID NO 13
<211> LENGTH: 259
<212> TYPE: PRT
<213> ORGANISM: Bacillus thuringiensis

<400> SEQUENCE: 13

His Glu Asn Asp Gly Gly Gln Arg Phe Gly Val Ile Pro Arg Trp Ser
1               5                   10                  15

Ala Glu Asp Lys His Lys Glu Gly Val Asn Ser His Leu Trp Ile Val
            20                  25                  30

Asn Arg Ala Ile Asp Ile Met Ser Arg Asn Thr Thr Leu Val Lys Gln
        35                  40                  45

Asp Arg Val Ala Leu Leu Asn Glu Trp Arg Thr Glu Leu Glu Asn Gly
    50                  55                  60
```

```
Ile Tyr Ala Ala Asp Tyr Glu Asn Pro Tyr Tyr Asp Asn Ser Thr Phe
65                  70                  75                  80

Ala Ser His Phe Tyr Asp Pro Asp Asn Gly Lys Thr Tyr Ile Pro Tyr
                85                  90                  95

Ala Lys Gln Ala Lys Glu Thr Gly Ala Lys Tyr Phe Lys Leu Ala Gly
            100                 105                 110

Glu Ser Tyr Lys Asn Lys Asp Met Gln Gln Ala Phe Phe Tyr Leu Gly
        115                 120                 125

Leu Ser Leu His Tyr Leu Gly Asp Val Asn Gln Pro Met His Ala Ala
    130                 135                 140

Asn Phe Thr Asn Leu Ser Tyr Pro Gln Gly Phe His Ser Lys Tyr Glu
145                 150                 155                 160

Asn Phe Val Asp Thr Ile Lys Asp Asn Tyr Lys Val Thr Asp Gly Asn
                165                 170                 175

Gly Tyr Trp Asn Trp Lys Gly Thr Asn Pro Glu Asp Trp Ile His Gly
            180                 185                 190

Ala Ala Val Val Ala Lys Gln Asp Tyr Ala Gly Ile Val Asn Asp Asn
        195                 200                 205

Thr Lys Asp Trp Phe Val Arg Ala Ala Val Ser Gln Glu Tyr Ala Asp
    210                 215                 220

Lys Trp Arg Ala Glu Val Thr Pro Met Thr Gly Lys Arg Leu Met Asp
225                 230                 235                 240

Ala Gln Arg Val Thr Ala Gly Tyr Ile Gln Leu Trp Phe Asp Thr Tyr
                245                 250                 255

Gly Asp Arg
```

```
<210> SEQ ID NO 14
<211> LENGTH: 259
<212> TYPE: PRT
<213> ORGANISM: Bacillus thuringiensis

<400> SEQUENCE: 14

His Glu Asn Asp Gly Gly Gln Arg Phe Gly Val Ile Pro Arg Trp Ser
1               5                   10                  15

Ala Glu Asp Lys His Lys Glu Gly Val Asn Ser His Leu Trp Ile Val
            20                  25                  30

Asn Arg Ala Ile Asp Ile Met Ser Arg Asn Thr Thr Leu Val Lys Gln
        35                  40                  45

Asp Arg Val Ala Leu Leu Asn Glu Trp Arg Thr Glu Leu Glu Asn Gly
    50                  55                  60

Ile Tyr Ala Ala Asp Tyr Glu Asn Pro Tyr Tyr Asp Asn Ser Thr Phe
65                  70                  75                  80

Ala Ser His Phe Tyr Asp Pro Asp Asn Gly Lys Thr Tyr Ile Pro Tyr
                85                  90                  95

Ala Lys Gln Ala Lys Glu Thr Gly Ala Lys Tyr Phe Lys Leu Ala Gly
            100                 105                 110

Glu Ser Tyr Lys Asn Lys Asp Met Gln Gln Ala Phe Phe Tyr Leu Gly
        115                 120                 125

Leu Ser Leu His Tyr Leu Gly Asp Val Asn Gln Pro Met His Ala Ala
    130                 135                 140

Asn Phe Thr Asn Leu Ser Tyr Pro Gln Gly Phe His Ser Lys Tyr Glu
145                 150                 155                 160

Asn Phe Val Asp Thr Ile Lys Asp Asn Tyr Lys Val Thr Asp Gly Asn
                165                 170                 175
```

```
Gly Tyr Trp Asn Trp Lys Gly Thr Asn Pro Glu Asp Trp Ile His Gly
            180                 185                 190

Ala Ala Val Val Ala Lys Gln Asp Tyr Ala Gly Ile Val Asn Asp Asn
        195                 200                 205

Thr Lys Asp Trp Phe Val Arg Ala Ala Val Ser Gln Glu Tyr Ala Asp
    210                 215                 220

Lys Trp Arg Ala Glu Val Thr Pro Met Thr Gly Lys Arg Leu Met Asp
225                 230                 235                 240

Ala Gln Arg Val Thr Ala Gly Tyr Ile Gln Leu Trp Phe Asp Thr Tyr
                245                 250                 255

Gly Asp Arg


<210> SEQ ID NO 15
<211> LENGTH: 259
<212> TYPE: PRT
<213> ORGANISM: Bacillus thuringiensis

<400> SEQUENCE: 15

His Glu Asn Asp Gly Gly Gln Arg Phe Gly Val Ile Pro Arg Trp Ser
1               5                   10                  15

Ala Glu Asp Lys His Lys Glu Gly Val Asn Ser His Leu Trp Ile Val
            20                  25                  30

Asn Arg Ala Ile Asp Ile Met Ser Arg Asn Thr Thr Leu Val Lys Gln
        35                  40                  45

Asp Arg Val Ala Leu Leu Asn Glu Trp Arg Thr Glu Leu Glu Asn Gly
    50                  55                  60

Ile Tyr Ala Ala Asp Tyr Glu Asn Pro Tyr Tyr Asp Asn Ser Thr Phe
65                  70                  75                  80

Ala Ser His Phe Tyr Asp Pro Asp Asn Gly Lys Thr Tyr Ile Pro Tyr
                85                  90                  95

Ala Lys Gln Ala Lys Glu Thr Gly Ala Lys Tyr Phe Lys Leu Ala Gly
            100                 105                 110

Glu Ser Tyr Lys Asn Lys Asp Met Lys Gln Ala Phe Phe Tyr Leu Gly
        115                 120                 125

Leu Ser Leu His Tyr Leu Gly Asp Val Asn Gln Pro Met His Ala Ala
    130                 135                 140

Asn Phe Thr Asn Leu Ser Tyr Pro Gln Gly Phe His Ser Lys Tyr Glu
145                 150                 155                 160

Asn Phe Val Asp Thr Ile Lys Asp Asn Tyr Lys Val Thr Asp Gly Asn
                165                 170                 175

Gly Tyr Trp Asn Trp Lys Gly Thr Asn Pro Glu Asp Trp Ile His Gly
            180                 185                 190

Ala Ala Val Val Ala Lys Gln Asp Tyr Ala Gly Ile Val Asn Asp Asn
        195                 200                 205

Thr Lys Asp Trp Phe Val Arg Ala Ala Val Ser Gln Glu Tyr Ala Asp
    210                 215                 220

Lys Trp Arg Ala Glu Val Thr Pro Met Thr Gly Lys Arg Leu Met Asp
225                 230                 235                 240

Ala Gln Arg Val Thr Ala Gly Tyr Ile Gln Leu Trp Phe Asp Thr Tyr
                245                 250                 255

Gly Asn Arg


<210> SEQ ID NO 16
<211> LENGTH: 305
<212> TYPE: PRT
```

<213> ORGANISM: Bacillus thuringiensis

<400> SEQUENCE: 16

Ala Ser Thr Asn Gln Asn Asp Thr Leu Lys Val Met Thr His Asn Val
1 5 10 15

Tyr Met Leu Ser Thr Asn Leu Tyr Pro Asn Trp Gly Gln Thr Glu Arg
20 25 30

Ala Asp Leu Ile Gly Ala Ala Asp Tyr Ile Lys Asn Gln Asp Val Val
35 40 45

Ile Leu Asn Glu Val Phe Asp Asn Ser Ala Ser Asp Arg Leu Leu Gly
50 55 60

Asn Leu Lys Lys Glu Tyr Pro Asn Gln Thr Ala Val Leu Gly Arg Ser
65 70 75 80

Ser Gly Ser Glu Trp Asp Lys Lys Leu Gly Asn Tyr Ser Ser Ser Thr
85 90 95

Pro Glu Asp Gly Gly Val Ala Ile Val Ser Lys Trp Pro Ile Ala Glu
100 105 110

Lys Ile Gln Tyr Val Phe Ala Lys Gly Cys Gly Pro Asp Asn Leu Ser
115 120 125

Asn Lys Gly Phe Val Tyr Thr Lys Ile Lys Lys Asn Asp Arg Phe Ile
130 135 140

His Val Ile Gly Thr His Leu Gln Ala Glu Asp Ser Met Cys Gly Lys
145 150 155 160

Thr Ser Pro Ala Ser Val Arg Thr Asn Gln Leu Lys Glu Ile Gln Asp
165 170 175

Phe Ile Lys Asn Lys Asn Ile Pro Asn Asn Glu Tyr Val Leu Ile Gly
180 185 190

Gly Asp Met Asn Val Asn Lys Ile Asn Ala Glu Asn Lys Asn Asp Ser
195 200 205

Glu Tyr Thr Ser Met Phe Lys Thr Leu Asn Ala Ser Val Pro Ser Tyr
210 215 220

Thr Gly His Thr Ala Thr Trp Asp Ala Thr Thr Asn Ser Ile Ala Lys
225 230 235 240

Tyr Asn Phe Pro Asp Ser Pro Ala Glu Tyr Leu Asp Tyr Ile Ile Ala
245 250 255

Ser Lys Asp His Ala Asn Pro Ser Tyr Ile Glu Asn Lys Val Leu Gln
260 265 270

Pro Lys Ser Pro Gln Trp Thr Val Thr Ser Trp Phe Gln Lys Tyr Thr
275 280 285

Tyr Asn Asp Tyr Ser Asp His Tyr Pro Val Glu Ala Thr Ile Ser Met
290 295 300

Lys
305

<210> SEQ ID NO 17
<211> LENGTH: 259
<212> TYPE: PRT
<213> ORGANISM: Bacillus cereus

<400> SEQUENCE: 17

His Glu Asn Asp Gly Gly Ser Lys Ile Lys Ile Val His Arg Trp Ser
1 5 10 15

Ala Glu Asp Lys His Lys Glu Gly Val Asn Ser His Leu Trp Ile Val
20 25 30

Asn Arg Ala Ile Asp Ile Met Ser Arg Asn Thr Thr Leu Val Lys Gln

```
        35                  40                  45

Asp Arg Val Ala Gln Leu Asn Glu Trp Arg Thr Glu Leu Glu Asn Gly
    50                  55                  60

Ile Tyr Ala Ala Asp Tyr Glu Asn Pro Tyr Tyr Asp Asn Ser Thr Phe
65                  70                  75                  80

Ala Ser His Phe Tyr Asp Pro Asp Asn Gly Lys Thr Tyr Ile Pro Phe
                85                  90                  95

Ala Lys Gln Ala Lys Glu Thr Gly Ala Lys Tyr Phe Lys Leu Ala Gly
            100                 105                 110

Glu Ser Tyr Lys Asn Lys Asp Met Lys Gln Ala Phe Phe Tyr Leu Gly
        115                 120                 125

Leu Ser Leu His Tyr Leu Gly Asp Val Asn Gln Pro Met His Ala Ala
    130                 135                 140

Asn Phe Thr Asn Leu Ser Tyr Pro Gln Gly Phe His Ser Lys Tyr Glu
145                 150                 155                 160

Asn Phe Val Asp Thr Ile Lys Asp Asn Tyr Lys Val Thr Asp Gly Asn
                165                 170                 175

Gly Tyr Trp Asn Trp Lys Gly Thr Asn Pro Glu Glu Trp Ile His Gly
            180                 185                 190

Ala Ala Val Val Ala Lys Gln Asp Tyr Ser Gly Ile Val Asn Asp Asn
        195                 200                 205

Thr Lys Asp Trp Phe Val Lys Ala Ala Val Ser Gln Glu Tyr Ala Asp
    210                 215                 220

Lys Trp Arg Ala Glu Val Thr Pro Met Thr Gly Lys Arg Leu Met Asp
225                 230                 235                 240

Ala Gln Arg Val Thr Ala Gly Tyr Ile Gln Leu Trp Phe Asp Thr Tyr
                245                 250                 255

Gly Asp Arg


<210> SEQ ID NO 18
<211> LENGTH: 369
<212> TYPE: PRT
<213> ORGANISM: Clostridium perfringens

<400> SEQUENCE: 18

Asp Gly Lys Ile Asp Gly Thr Gly Thr His Ala Met Ile Val Thr Gln
1               5                   10                  15

Gly Val Ser Ile Leu Glu Asn Asp Leu Ser Lys Asn Glu Pro Glu Ser
            20                  25                  30

Val Arg Lys Asn Leu Glu Ile Leu Lys Glu Asn Met His Glu Leu Gln
        35                  40                  45

Leu Gly Ser Thr Tyr Pro Asp Tyr Asp Lys Asn Ala Tyr Asp Leu Tyr
    50                  55                  60

Gln Asp His Phe Trp Asp Pro Asp Thr Asp Asn Asn Phe Ser Lys Asp
65                  70                  75                  80

Asn Ser Trp Tyr Leu Ala Tyr Ser Ile Pro Asp Thr Gly Glu Ser Gln
                85                  90                  95

Ile Arg Lys Phe Ser Ala Leu Ala Arg Tyr Glu Trp Gln Arg Gly Asn
            100                 105                 110

Tyr Lys Gln Ala Thr Phe Tyr Leu Gly Glu Ala Met His Tyr Phe Gly
        115                 120                 125

Asp Ile Asp Thr Pro Tyr His Pro Ala Asn Val Thr Ala Val Asp Ser
    130                 135                 140

Ala Gly His Val Lys Phe Glu Thr Phe Ala Glu Glu Arg Lys Glu Gln
```

-continued

```
145                 150                 155                 160

Tyr Lys Ile Asn Thr Ala Gly Cys Lys Thr Asn Glu Asp Phe Tyr Ala
                165                 170                 175

Asp Ile Leu Lys Asn Lys Asp Phe Asn Ala Trp Ser Lys Glu Tyr Ala
            180                 185                 190

Arg Gly Phe Ala Lys Thr Gly Lys Ser Ile Tyr Tyr Ser His Ala Ser
        195                 200                 205

Met Ser His Ser Trp Asp Asp Trp Asp Tyr Ala Ala Lys Val Thr Leu
    210                 215                 220

Ala Asn Ser Gln Lys Gly Thr Ala Gly Tyr Ile Tyr Arg Phe Leu His
225                 230                 235                 240

Asp Val Ser Glu Gly Asn Asp Pro Ser Val Gly Lys Asn Val Lys Glu
                245                 250                 255

Leu Val Ala Tyr Ile Ser Thr Ser Gly Glu Lys Asp Ala Gly Thr Asp
            260                 265                 270

Asp Tyr Met Tyr Phe Gly Ile Lys Thr Lys Asp Gly Lys Thr Gln Glu
        275                 280                 285

Trp Glu Met Asp Asn Pro Gly Asn Asp Phe Met Thr Gly Ser Lys Asp
    290                 295                 300

Thr Tyr Thr Phe Lys Leu Lys Asp Glu Asn Leu Lys Ile Asp Asp Ile
305                 310                 315                 320

Gln Asn Met Trp Ile Arg Lys Arg Lys Tyr Thr Ala Phe Pro Asp Ala
                325                 330                 335

Tyr Lys Pro Glu Asn Ile Lys Ile Ile Ala Asn Gly Lys Val Val Val
            340                 345                 350

Asp Lys Asp Ile Asn Glu Trp Ile Ser Gly Asn Ser Thr Tyr Asn Ile
        355                 360                 365

Lys


<210> SEQ ID NO 19
<211> LENGTH: 495
<212> TYPE: PRT
<213> ORGANISM: Streptomyces chromofuscus

<400> SEQUENCE: 19

Pro Leu Pro Asp Gly Val Leu Leu Trp Thr Arg Val Thr Pro Thr Ala
1               5                   10                  15

Asp Ala Thr Pro Gly Ser Gly Leu Gly Pro Asp Thr Glu Val Gly Trp
            20                  25                  30

Thr Val Ala Thr Asp Lys Ala Phe Thr Asn Val Val Ala Lys Gly Ser
        35                  40                  45

Thr Thr Ala Thr Ala Ala Ser Asp His Thr Val Lys Ala Asp Ile Arg
    50                  55                  60

Gly Leu Ala Pro Ala Thr Asp His Trp Phe Arg Phe Ser Ala Gly Gly
65                  70                  75                  80

Thr Asp Ser Pro Ala Gly Arg Ala Arg Thr Ala Pro Ala Ala Asp Ala
                85                  90                  95

Ala Val Ala Gly Leu Arg Phe Gly Val Val Ser Cys Ala Asn Trp Glu
            100                 105                 110

Ala Gly Tyr Phe Ala Ala Tyr Arg His Leu Ala Ala Arg Gly Asp Leu
        115                 120                 125

Asp Ala Trp Leu His Leu Gly Asp Tyr Ile Tyr Glu Tyr Gly Ala Gly
    130                 135                 140

Glu Tyr Gly Thr Arg Gly Thr Ser Val Arg Ser His Ala Pro Ala His
```

-continued

```
145                 150                 155                 160

Glu Ile Leu Thr Leu Ala Asp Tyr Arg Val Arg His Gly Arg Tyr Lys
                165                 170                 175

Thr Asp Pro Asp Leu Gln Ala Leu His Ala Ala Ala Pro Val Val Ala
            180                 185                 190

Ile Trp Asp Asp His Glu Ile Ala Asn Asp Thr Trp Ser Gly Gly Ala
        195                 200                 205

Glu Asn His Thr Glu Gly Val Glu Gly Ala Trp Ala Ala Arg Gln Ala
    210                 215                 220

Ala Ala Lys Gln Ala Tyr Phe Glu Trp Met Pro Val Arg Pro Ala Ile
225                 230                 235                 240

Ala Gly Thr Thr Tyr Arg Arg Leu Arg Phe Gly Lys Leu Ala Asp Leu
                245                 250                 255

Ser Leu Leu Asp Leu Arg Ser Phe Arg Ala Gln Gln Val Ser Leu Gly
            260                 265                 270

Asp Gly Asp Val Asp Asp Pro Asp Arg Thr Leu Thr Gly Arg Ala Gln
        275                 280                 285

Leu Asp Trp Leu Lys Ala Gly Leu Lys Ser Ser Asp Thr Thr Trp Arg
    290                 295                 300

Leu Val Gly Asn Ser Val Met Ile Ala Pro Phe Ala Ile Gly Ser Leu
305                 310                 315                 320

Ser Ala Glu Leu Leu Lys Pro Leu Ala Lys Leu Leu Gly Leu Pro Gln
                325                 330                 335

Glu Gly Leu Ala Val Asn Thr Asp Gln Trp Asp Gly Tyr Thr Asp Asp
            340                 345                 350

Arg Arg Glu Leu Leu Ala His Leu Arg Ser Asn Ala Ile Arg Asn Thr
        355                 360                 365

Val Phe Leu Thr Gly Asp Ile His Met Ala Trp Ala Asn Asp Val Pro
    370                 375                 380

Val Asn Ala Gly Thr Tyr Pro Leu Ser Ala Ser Ala Ala Thr Glu Phe
385                 390                 395                 400

Val Val Thr Ser Val Thr Ser Asp Asn Leu Asp Asp Leu Val Lys Val
                405                 410                 415

Pro Glu Gly Thr Val Ser Ala Leu Ala Ser Pro Val Ile Arg Ala Ala
            420                 425                 430

Asn Arg His Val His Trp Val Asp Thr Asp Arg His Gly Tyr Gly Val
        435                 440                 445

Leu Asp Ile Thr Ala Glu Arg Ala Gln Met Asp Tyr Tyr Val Leu Ser
    450                 455                 460

Asp Arg Thr Gln Ala Gly Ala Thr Ala Ser Trp Ser Arg Ser Tyr Arg
465                 470                 475                 480

Thr Arg Ser Gly Thr Gln Arg Val Glu Arg Thr Tyr Asp Pro Glu
                485                 490                 495


<210> SEQ ID NO 20
<211> LENGTH: 240
<212> TYPE: PRT
<213> ORGANISM: Bacillus thuringiensis

<400> SEQUENCE: 20

Met Arg Thr Pro Leu Ser Phe Asp Lys Asp Thr Ala Ile Leu Leu Ala
1               5                   10                  15

Ser Cys Cys Glu Leu Thr Tyr Glu Gln Tyr Lys Gln Asn Gly Ile Phe
            20                  25                  30
```

-continued

```
Glu Ile Pro Asp Gly Phe Gln Tyr Val Gln Gly Phe Gln Gly Lys Ala
        35                  40                  45

Ile Gln Thr Thr Glu Trp Phe Gly Phe Ile Leu Glu Ser Glu Asp Thr
    50                  55                  60

Ile Ile Val Ala Phe Arg Gly Thr Gln Thr Asp Pro Asp Trp Ile Ile
65                  70                  75                  80

Asp Ser Leu Val Asn Gln Lys Pro Tyr Pro Tyr Ala Leu Asn Gly Gly
                85                  90                  95

Asn Val His Asn Gly Phe Leu Ser Ile Tyr Glu Ser Cys Arg Asp Ser
            100                 105                 110

Ile Met Asp Met Leu Val Ser Leu Pro Ala His Lys Lys Leu Leu Ala
        115                 120                 125

Thr Gly His Ser Leu Gly Gly Ala Leu Ala Thr Leu His Ile Leu Asp
    130                 135                 140

Ala Arg Ile Asn Thr Ala Phe Ala Gln Tyr Gly Leu Tyr Ser Phe Ala
145                 150                 155                 160

Ser Pro Lys Val Gly Asp Ile Ala Phe Arg Asn Tyr Tyr Lys Leu Gln
                165                 170                 175

Val Ala Ser Ser Phe Arg Phe Val Asn Leu Phe Asp Val Val Pro Leu
            180                 185                 190

Leu Pro Pro Arg Asn Ile Asn Phe Asn Asp His Asp Trp Glu Tyr Ala
        195                 200                 205

His Val His His Asn Met Thr Phe Thr Lys Asn Thr Lys Ser Ile Thr
    210                 215                 220

Asn Asn His Ser Ile Thr Thr Tyr Lys Thr Cys Leu Thr Ser His Phe
225                 230                 235                 240


<210> SEQ ID NO 21
<211> LENGTH: 181
<212> TYPE: PRT
<213> ORGANISM: Bacillus subtilis

<400> SEQUENCE: 21

Ala Glu His Asn Pro Val Val Met Val His Gly Ile Gly Gly Ala Ser
1               5                   10                  15

Phe Asn Phe Ala Gly Ile Lys Ser Tyr Leu Val Ser Gln Gly Trp Ser
            20                  25                  30

Arg Asp Lys Leu Tyr Ala Val Asp Phe Trp Asp Lys Thr Gly Thr Asn
        35                  40                  45

Tyr Asn Asn Gly Pro Val Leu Ser Arg Phe Val Gln Lys Val Leu Asp
    50                  55                  60

Glu Thr Gly Ala Lys Lys Val Asp Ile Val Ala His Ser Met Gly Gly
65                  70                  75                  80

Ala Asn Thr Leu Tyr Tyr Ile Lys Asn Leu Asp Gly Gly Asn Lys Val
                85                  90                  95

Ala Asn Val Val Thr Leu Gly Gly Ala Asn Arg Leu Thr Thr Gly Lys
            100                 105                 110

Ala Leu Pro Gly Thr Asp Pro Asn Gln Lys Ile Leu Tyr Thr Ser Ile
        115                 120                 125

Tyr Ser Ser Ala Asp Met Ile Val Met Asn Tyr Leu Ser Arg Leu Asp
    130                 135                 140

Gly Ala Arg Asn Val Gln Ile His Gly Val Gly His Ile Gly Leu Leu
145                 150                 155                 160

Tyr Ser Ser Gln Val Asn Ser Leu Ile Lys Glu Gly Leu Asn Gly Gly
                165                 170                 175
```

Gly Gln Asn Thr Asn
180

<210> SEQ ID NO 22
<211> LENGTH: 309
<212> TYPE: PRT
<213> ORGANISM: Caldicellulosiruptor saccharolyticus

<400> SEQUENCE: 22

Lys Asp Leu Glu Gly Val His Arg Asp Ile Leu Leu Lys His Phe Asn
1 5 10 15

Ser Leu Thr Pro Glu Asn Ala Met Lys Phe Glu Asn Ile His Pro Glu
20 25 30

Glu Gln Arg Tyr Asn Phe Glu Glu Val Ala Arg Ile Lys Glu Phe Ala
35 40 45

Ile Lys Asn Asp Met Lys Leu Arg Gly His Thr Phe Val Trp His Asn
50 55 60

Gln Thr Pro Gly Trp Val Phe Leu Asp Lys Asn Gly Glu Glu Ala Ser
65 70 75 80

Lys Glu Leu Val Ile Glu Arg Leu Arg Glu His Ile Lys Thr Leu Cys
85 90 95

Glu Arg Tyr Lys Asp Val Val Tyr Ala Trp Asp Val Val Asn Glu Ala
100 105 110

Val Glu Asp Lys Thr Glu Lys Leu Leu Arg Glu Ser Asn Trp Arg Lys
115 120 125

Ile Ile Gly Asp Asp Tyr Ile Lys Ile Ala Phe Glu Ile Ala Arg Glu
130 135 140

Tyr Ala Gly Asp Ala Lys Leu Phe Tyr Asn Asp Tyr Asn Asn Glu Met
145 150 155 160

Pro Tyr Lys Leu Glu Lys Thr Tyr Lys Val Leu Lys Glu Leu Leu Glu
165 170 175

Arg Gly Thr Pro Ile Asp Gly Ile Gly Ile Gln Ala His Trp Asn Ile
180 185 190

Trp Asp Lys Asn Leu Val Ser Asn Leu Lys Lys Ala Ile Glu Val Tyr
195 200 205

Ala Ser Leu Gly Leu Glu Ile His Ile Thr Glu Leu Asp Ile Ser Val
210 215 220

Phe Glu Phe Glu Asp Lys Arg Thr Asp Leu Phe Glu Pro Thr Pro Glu
225 230 235 240

Met Leu Glu Leu Gln Ala Lys Val Tyr Glu Asp Val Phe Ala Val Phe
245 250 255

Arg Glu Tyr Lys Asp Val Ile Thr Ser Val Thr Leu Trp Gly Ile Ser
260 265 270

Asp Arg His Thr Trp Lys Asp Asn Phe Pro Val Lys Gly Arg Lys Asp
275 280 285

Trp Pro Leu Leu Phe Asp Val Asn Gly Lys Pro Lys Glu Ala Leu Tyr
290 295 300

Arg Ile Leu Arg Phe
305

<210> SEQ ID NO 23
<211> LENGTH: 185
<212> TYPE: PRT
<213> ORGANISM: Bacillus subtilis

<400> SEQUENCE: 23

```
Ala Ser Thr Asp Tyr Trp Gln Asn Trp Thr Asp Gly Gly Gly Ile Val
1               5                   10                  15

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
        35                  40                  45

Arg Thr Ile Asn Tyr Asn Ala Gly Val Trp Ala Pro Asn Gly Asn Gly
    50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Lys Ser Asp Gly Gly Thr Tyr Asp Ile Tyr Thr Thr Thr Arg
            100                 105                 110

Tyr Asn Ala Pro Ser Ile Asp Gly Asp Arg Thr Thr Phe Thr Gln Tyr
        115                 120                 125

Trp Ser Val Arg Gln Ser Lys Arg Pro Thr Gly Ser Asn Ala Thr Ile
    130                 135                 140

Thr Phe Ser Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185
```

<210> SEQ ID NO 24
<211> LENGTH: 487
<212> TYPE: PRT
<213> ORGANISM: Bacillus subtilis

<400> SEQUENCE: 24

```
Ala Thr Ser Thr Thr Ile Ala Lys His Ile Gly Asn Ser Asn Pro Leu
1               5                   10                  15

Ile Asp His His Leu Gly Ala Asp Pro Val Ala Leu Thr Tyr Asn Gly
            20                  25                  30

Arg Val Tyr Ile Tyr Met Ser Ser Asp Asp Tyr Glu Tyr Asn Ser Asn
        35                  40                  45

Gly Thr Ile Lys Asp Asn Ser Phe Ala Asn Leu Asn Arg Val Phe Val
    50                  55                  60

Ile Ser Ser Ala Asp Met Val Asn Trp Thr Asp His Gly Ala Ile Pro
65                  70                  75                  80

Val Ala Gly Ala Asn Gly Ala Asn Gly Gly Arg Gly Ile Ala Lys Trp
                85                  90                  95

Ala Gly Ala Ser Trp Ala Pro Ser Ile Ala Val Lys Lys Ile Asn Gly
            100                 105                 110

Lys Asp Lys Phe Phe Leu Tyr Phe Ala Asn Ser Gly Gly Gly Ile Gly
        115                 120                 125

Val Leu Thr Ala Asp Ser Pro Ile Gly Pro Trp Thr Asp Pro Ile Gly
    130                 135                 140

Lys Pro Leu Val Thr Pro Ser Thr Pro Gly Met Ser Gly Val Val Trp
145                 150                 155                 160

Leu Phe Asp Pro Ala Val Phe Val Asp Asp Asp Gly Thr Gly Tyr Leu
                165                 170                 175

Tyr Ala Gly Gly Gly Val Pro Gly Val Ser Asn Pro Thr Gln Gly Gln
```

```
            180                 185                 190

Trp Ala Asn Pro Lys Thr Ala Arg Val Ile Lys Leu Gly Pro Asp Met
        195                 200                 205

Thr Ser Val Val Gly Ser Ala Ser Thr Ile Asp Ala Pro Phe Met Phe
    210                 215                 220

Glu Asp Ser Gly Leu His Lys Tyr Asn Gly Thr Tyr Tyr Tyr Ser Tyr
225                 230                 235                 240

Cys Ile Asn Phe Gly Gly Thr His Pro Ala Asp Lys Pro Pro Gly Glu
                245                 250                 255

Ile Gly Tyr Met Thr Ser Ser Ser Pro Met Gly Pro Phe Thr Tyr Arg
            260                 265                 270

Gly His Phe Leu Lys Asn Pro Gly Ala Phe Phe Gly Gly Gly Gly Asn
        275                 280                 285

Asn His His Ala Val Phe Asn Phe Lys Asn Glu Trp Tyr Val Val Tyr
    290                 295                 300

His Ala Gln Thr Val Ser Ser Ala Leu Phe Gly Ala Gly Lys Gly Tyr
305                 310                 315                 320

Arg Ser Pro His Ile Asn Lys Leu Val His Asn Ala Asp Gly Ser Ile
                325                 330                 335

Gln Glu Val Ala Ala Asn Tyr Ala Gly Val Thr Gln Ile Ser Asn Leu
            340                 345                 350

Asn Pro Tyr Asn Arg Val Glu Ala Glu Thr Phe Ala Trp Asn Gly Arg
        355                 360                 365

Ile Leu Thr Glu Lys Ser Thr Ala Pro Gly Gly Pro Val Asn Asn Gln
    370                 375                 380

His Val Thr Ser Ile Gln Asn Gly Asp Trp Ile Ala Val Gly Asn Ala
385                 390                 395                 400

Asp Phe Gly Ala Gly Gly Ala Arg Ser Phe Lys Ala Asn Val Ala Ser
                405                 410                 415

Thr Leu Gly Gly Lys Ile Glu Val Arg Leu Asp Ser Ala Asp Gly Lys
            420                 425                 430

Leu Val Gly Thr Leu Asn Val Pro Ser Thr Gly Gly Ala Gln Thr Trp
        435                 440                 445

Arg Glu Ile Glu Thr Ala Val Ser Gly Ala Thr Gly Val His Lys Val
    450                 455                 460

Phe Phe Val Phe Thr Gly Thr Gly Thr Gly Asn Leu Phe Asn Phe Asp
465                 470                 475                 480

Tyr Trp Gln Phe Thr Gln Arg
                485


<210> SEQ ID NO 25
<211> LENGTH: 183
<212> TYPE: PRT
<213> ORGANISM: Bacillus stearothermophilus

<400> SEQUENCE: 25

Ala Thr Asp Tyr Trp Gln Tyr Trp Thr Asp Gly Gly Gly Met Val Asn
1               5                   10                  15

Ala Val Asn Gly Pro Gly Gly Asn Tyr Ser Val Thr Trp Gln Asn Thr
            20                  25                  30

Gly Asn Phe Val Val Gly Lys Gly Trp Thr Val Gly Ser Pro Asn Arg
        35                  40                  45

Val Ile Asn Tyr Asn Ala Gly Ile Trp Glu Pro Ser Gly Asn Gly Tyr
    50                  55                  60
```

-continued

```
Leu Thr Leu Tyr Gly Trp Thr Arg Asn Ala Leu Ile Glu Tyr Tyr Val
65                  70                  75                  80

Val Asp Ser Trp Gly Thr Tyr Arg Pro Thr Gly Asn Tyr Lys Gly Thr
                85                  90                  95

Val Asn Ser Asp Gly Gly Thr Tyr Asp Ile Tyr Thr Thr Met Arg Tyr
            100                 105                 110

Asn Ala Pro Ser Ile Asp Gly Thr Gln Thr Phe Gln Gln Phe Trp Ser
        115                 120                 125

Val Arg Gln Ser Lys Arg Pro Thr Gly Ser Asn Val Ser Ile Thr Phe
    130                 135                 140

Ser Asn His Val Asn Ala Trp Arg Ser Lys Gly Met Asn Leu Gly Ser
145                 150                 155                 160

Ser Trp Ala Tyr Gln Val Leu Ala Thr Glu Gly Tyr Gln Ser Ser Gly
                165                 170                 175

Arg Ser Asn Val Thr Val Trp
            180


<210> SEQ ID NO 26
<211> LENGTH: 488
<212> TYPE: PRT
<213> ORGANISM: Caldicellulosiruptor saccharolyticus

<400> SEQUENCE: 26

Met Glu Arg Arg Lys Ile Met Lys Ile Thr Ile Asn Tyr Gly Lys Arg
1               5                   10                  15

Leu Gly Lys Ile Asn Lys Phe Trp Ala Lys Cys Val Gly Ser Cys His
            20                  25                  30

Ala Thr Thr Ala Leu Arg Glu Asp Trp Arg Lys Gln Leu Lys Lys Cys
        35                  40                  45

Arg Asp Glu Leu Gly Phe Glu Tyr Ile Arg Phe His Gly Trp Leu Asn
    50                  55                  60

Asp Asp Met Ser Val Cys Phe Arg Asn Asp Asp Gly Leu Leu Ser Phe
65                  70                  75                  80

Ser Phe Phe Asn Ile Asp Ser Ile Ile Asp Phe Leu Leu Glu Ile Gly
                85                  90                  95

Met Lys Pro Phe Ile Glu Leu Ser Phe Met Pro Glu Ala Leu Ala Ser
            100                 105                 110

Gly Thr Lys Thr Val Phe His Tyr Lys Gly Asn Ile Thr Pro Pro Lys
        115                 120                 125

Ser Tyr Glu Glu Trp Gly Gln Leu Ile Glu Glu Leu Ala Arg His Leu
    130                 135                 140

Ile Ser Arg Tyr Gly Lys Asn Glu Val Arg Glu Trp Phe Phe Glu Val
145                 150                 155                 160

Trp Asn Glu Pro Asn Leu Lys Asp Phe Phe Trp Ala Gly Thr Met Glu
                165                 170                 175

Glu Tyr Phe Lys Leu Tyr Lys Tyr Ala Ala Phe Ala Ile Lys Lys Val
            180                 185                 190

Asp Ser Glu Leu Arg Val Gly Gly Pro Ala Thr Ala Ile Asp Ala Trp
        195                 200                 205

Ile Pro Glu Leu Lys Asp Phe Cys Thr Lys Asn Gly Val Pro Ile Asp
    210                 215                 220

Phe Ile Ser Thr His Gln Tyr Pro Thr Asp Leu Ala Phe Ser Thr Ser
225                 230                 235                 240

Ser Asn Met Glu Glu Ala Met Ala Lys Ala Lys Arg Gly Glu Leu Ala
                245                 250                 255
```

```
Glu Arg Val Lys Lys Ala Leu Glu Glu Ala Tyr Pro Leu Pro Val Tyr
            260                 265                 270

Tyr Thr Glu Trp Asn Asn Ser Pro Ser Pro Arg Asp Pro Tyr His Asp
        275                 280                 285

Ile Pro Tyr Asp Ala Ala Phe Ile Val Lys Thr Ile Ile Asp Ile Ile
    290                 295                 300

Asp Leu Pro Leu Gly Cys Tyr Ser Tyr Trp Thr Phe Thr Asp Ile Phe
305                 310                 315                 320

Glu Glu Cys Gly Gln Ser Ser Leu Pro Phe His Gly Gly Phe Gly Leu
                325                 330                 335

Leu Asn Ile His Gly Ile Pro Lys Pro Ser Tyr Arg Ala Phe Gln Ile
            340                 345                 350

Leu Asp Lys Leu Asn Gly Glu Arg Ile Glu Ile Glu Phe Glu Asp Lys
        355                 360                 365

Ser Pro Thr Ile Asp Cys Ile Ala Val Gln Asn Glu Arg Glu Ile Ile
    370                 375                 380

Leu Val Ile Ser Asn His Asn Val Pro Leu Ser Pro Ile Asp Thr Glu
385                 390                 395                 400

Asn Ile Lys Val Val Leu Lys Gly Ile Glu Asn Cys Arg Glu Val Phe
                405                 410                 415

Val Glu Arg Ile Asp Glu Tyr Asn Ala Asn Pro Lys Arg Val Trp Leu
            420                 425                 430

Glu Met Gly Ser Pro Ala Tyr Leu Asn Arg Glu Gln Ile Glu Glu Leu
        435                 440                 445

Ile Lys Ala Ser Glu Leu Lys Lys Glu Lys Val Ser Trp Gly Ile Val
    450                 455                 460

Asn Asn Asn Glu Ile Thr Phe Asp Leu Ser Val Leu Pro His Ser Val
465                 470                 475                 480

Val Ala Val Thr Ile Lys Asn Gly
                485


<210> SEQ ID NO 27
<211> LENGTH: 250
<212> TYPE: PRT
<213> ORGANISM: Bacillus thuringiensis

<400> SEQUENCE: 27

Met Thr Val Lys Lys Leu Tyr Phe Ile Pro Ala Gly Arg Cys Met Leu
1               5                   10                  15

Asp His Ser Ser Val Asn Ser Thr Leu Thr Pro Gly Asn Leu Leu Asn
            20                  25                  30

Leu Pro Val Trp Cys Tyr Leu Leu Glu Thr Glu Glu Gly Pro Ile Leu
        35                  40                  45

Val Asp Thr Gly Met Pro Glu Ile Ala Val Asn Asn Glu Gly Leu Phe
    50                  55                  60

Asn Gly Thr Phe Val Glu Gly Gln Ile Leu Pro Lys Met Thr Glu Glu
65                  70                  75                  80

Asp Arg Ile Ile Thr Ile Leu Lys Arg Ala Gly Tyr Glu Pro Asp Asp
                85                  90                  95

Leu Leu Tyr Ile Ile Ser Ser His Leu His Phe Asp His Ala Gly Gly
            100                 105                 110

Asn Gly Ala Phe Ser Asn Thr Pro Ile Ile Ile Gln Arg Ala Glu Tyr
        115                 120                 125

Glu Ala Ala Gln Tyr Arg Glu Glu Tyr Leu Lys Glu Cys Ile Leu Pro
```

-continued

```
    130                 135                 140

His Leu Asn Tyr Lys Ile Ile Glu Gly Asp Tyr Glu Val Val Pro Gly
145                 150                 155                 160

Val Arg Leu Leu Tyr Thr Pro Gly His Ser Pro Gly His Gln Ser Leu
                165                 170                 175

Leu Ile Glu Thr Glu Lys Ser Gly Pro Ile Leu Leu Thr Ile Asp Ala
            180                 185                 190

Ser Tyr Thr Lys Glu Asn Phe Glu Asp Glu Val Pro Phe Ala Gly Phe
        195                 200                 205

Asp Ser Glu Leu Ala Leu Ser Ser Ile Lys Arg Leu Lys Glu Val Val
    210                 215                 220

Ala Lys Glu Lys Pro Ile Ile Phe Phe Gly His Asp Ile Glu Gln Glu
225                 230                 235                 240

Lys Gly Cys Lys Val Phe Pro Glu Tyr Ile
                245                 250


<210> SEQ ID NO 28
<211> LENGTH: 250
<212> TYPE: PRT
<213> ORGANISM: Bacillus pseudomycoides

<400> SEQUENCE: 28

Met Thr Val Lys Lys Leu Tyr Phe Leu Pro Ala Gly Arg Cys Met Leu
1               5                   10                  15

Asp His Ser Ser Ile Asn Ser Thr Leu Thr Pro Gly Lys Leu Leu Asp
            20                  25                  30

Leu Pro Val Trp Cys Tyr Leu Leu Glu Thr Thr Glu Gly Pro Ile Leu
        35                  40                  45

Ile Asp Thr Gly Met Pro Glu Ser Ala Val Asp Asn Glu Asn Leu Phe
    50                  55                  60

Lys Gly Thr Phe Val Glu Gly Gln Ile Phe Pro Lys Met Lys Pro Asp
65                  70                  75                  80

Asp Ser Ile Val Asn Ile Leu Lys Arg Val Gly Tyr Ala Pro Glu Asp
                85                  90                  95

Leu Leu Cys Val Ile Ser Ser His Phe His Phe Asp His Ala Gly Gly
            100                 105                 110

Asn Gly Ser Phe Ser His Thr Pro Ile Ile Val Gln Arg Thr Glu Tyr
        115                 120                 125

Asp Ala Ala Leu His Arg Glu Glu Tyr Leu Lys Glu Cys Ile Leu Pro
    130                 135                 140

Asp Leu Asn Tyr Gln Ile Ile Glu Gly Asp Tyr Glu Val Met Pro Gly
145                 150                 155                 160

Val Gln Leu Leu Tyr Thr Pro Gly His Ser Pro Gly His Gln Ser Ile
                165                 170                 175

Phe Val Glu Thr Glu Lys Ser Gly Pro Val Leu Leu Thr Ile Asp Ala
            180                 185                 190

Ala Tyr Thr Gln Glu Asn Phe Glu Gln Gly Val Pro Phe Ala Gly Phe
        195                 200                 205

Asn Ser Glu Met Ala Ser Gln Ser Ile Asn Arg Leu Lys Glu Ile Val
    210                 215                 220

Leu Asp Glu Lys Pro Ile Ile Phe Phe Gly His Asp Met Glu Gln Glu
225                 230                 235                 240

Lys Arg Cys Lys Thr Phe Pro Glu Phe Leu
                245                 250
```

<210> SEQ ID NO 29
<211> LENGTH: 242
<212> TYPE: PRT
<213> ORGANISM: Bacillus subtilis

<400> SEQUENCE: 29

```
Ala Gly Leu Asn Lys Asp Gln Lys Arg Arg Ala Glu Gln Leu Thr Ser
1               5                   10                  15

Ile Phe Glu Asn Gly Thr Thr Glu Ile Gln Tyr Gly Tyr Val Glu Arg
            20                  25                  30

Leu Asp Asp Gly Arg Gly Tyr Thr Cys Gly Arg Ala Gly Phe Thr Thr
        35                  40                  45

Ala Thr Gly Asp Ala Leu Glu Val Val Glu Val Tyr Thr Lys Ala Val
    50                  55                  60

Pro Asn Asn Lys Leu Lys Lys Tyr Leu Pro Glu Leu Arg Arg Leu Ala
65                  70                  75                  80

Lys Glu Glu Ser Asp Asp Thr Ser Asn Leu Lys Gly Phe Ala Ser Ala
                85                  90                  95

Trp Lys Ser Leu Ala Asn Asp Lys Glu Phe Arg Ala Ala Gln Asp Lys
            100                 105                 110

Val Asn Asp His Leu Tyr Tyr Gln Pro Ala Met Lys Arg Ser Asp Asn
        115                 120                 125

Ala Gly Leu Lys Thr Ala Leu Ala Arg Ala Val Met Tyr Asp Thr Val
    130                 135                 140

Ile Gln His Gly Asp Gly Asp Asp Pro Asp Ser Phe Tyr Ala Leu Ile
145                 150                 155                 160

Lys Arg Thr Asn Lys Lys Ala Gly Gly Ser Pro Lys Asp Gly Ile Asp
                165                 170                 175

Glu Lys Lys Trp Leu Asn Lys Phe Leu Asp Val Arg Tyr Asp Asp Leu
            180                 185                 190

Met Asn Pro Ala Asn His Asp Thr Arg Asp Glu Trp Arg Glu Ser Val
        195                 200                 205

Ala Arg Val Asp Val Leu Arg Ser Ile Ala Lys Glu Asn Asn Tyr Asn
    210                 215                 220

Leu Asn Gly Pro Ile His Val Arg Ser Asn Glu Tyr Gly Asn Phe Val
225                 230                 235                 240

Ile Lys
```

<210> SEQ ID NO 30
<211> LENGTH: 469
<212> TYPE: PRT
<213> ORGANISM: Acidothermus cellulolyticus

<400> SEQUENCE: 30

```
Met Gly Thr Tyr Pro Ile Arg Ser Val Ser Gly Gly Val Ala Leu Ala
1               5                   10                  15

Ala Cys Ala Val Leu Thr Met Thr Thr Ala Ala Ala Ala Thr Pro Ile
            20                  25                  30

His Asp Ala Ser Ser Pro His Thr Ile Pro Pro His Ala Arg Leu Tyr
        35                  40                  45

Thr Pro Pro Pro Asp Lys Gly Ala Ile Lys Gln Ile Thr Asp Leu Leu
    50                  55                  60

Lys Ala Arg Asp Val Arg Asp Ala Arg Leu Ile Ala Glu Met Ile Ser
65                  70                  75                  80

Thr Pro Gln Ala Val Trp Phe Thr Gly Gly Thr Pro Asp Gln Val Arg
```

```
                85                  90                  95

Arg Asp Val His Arg Val Val Thr Lys Ala Ala Ala His His Ala Ile
            100                 105                 110

Pro Val Leu Val Ala Tyr Asn Ile Pro Phe Arg Asp Cys Ser Gln Tyr
        115                 120                 125

Ser Ala Gly Gly Ala Val Asp Thr Ala Ala Tyr Glu Ala Trp Ile Asp
    130                 135                 140

Gly Phe Ala Ala Gly Ile Gly Asp Lys Arg Ala Ile Val Leu Leu Glu
145                 150                 155                 160

Pro Asp Ser Leu Gly Ile Ile Pro Tyr Asn Thr Asp Ile Asn Gly Asn
                165                 170                 175

Ala Glu Trp Cys Lys Pro Asp Leu Ser Gly Thr Gly Leu Thr Pro Asp
            180                 185                 190

Glu Ala Asn Gln Ala Arg Tyr Asp Gln Leu Asn Tyr Ala Val Asp Ala
        195                 200                 205

Leu Glu Ala His Arg Asn Val Ser Val Tyr Leu Asp Gly Thr His Ser
    210                 215                 220

Gly Trp Leu Gly Val Gly Asp Ile Ala Gln Arg Leu Val Arg Ala Gly
225                 230                 235                 240

Val Gln Arg Ala Gln Gly Phe Phe Val Asn Val Ser Asn Tyr Gln Thr
                245                 250                 255

Thr Glu Arg Gln Ile Lys Tyr Gly Thr Trp Ile Ser Glu Cys Ile Ala
            260                 265                 270

Phe Ala Asn Asp Pro Glu Glu Gly Gly Trp Arg Leu Gly His Tyr Ser
        275                 280                 285

Trp Cys Ala Ser Gln Tyr Tyr Pro Ala Asn Pro Asn Asp Phe Ser Thr
    290                 295                 300

Trp Val Gln Thr Asp Gln Trp Tyr Ala Ser Asn Leu Gly Thr Ala Val
305                 310                 315                 320

Pro Thr Thr His Phe Val Ile Asp Thr Ser Arg Asn Gly Arg Gly Pro
                325                 330                 335

Asn Asp Met Thr Ala Tyr Ala Ala Ala Pro Tyr Asn Gln Pro Ala Ser
            340                 345                 350

Val Ile Ser Ala Leu Gln Gly Gly Ser Trp Cys Asn Pro Pro Gly Arg
        355                 360                 365

Gly Leu Gly Leu Arg Pro Thr Val Asn Thr Gly Val Pro Leu Leu Asp
    370                 375                 380

Ala Tyr Leu Trp Val Lys Ile Pro Gly Glu Ser Asp Gly Gln Cys Asp
385                 390                 395                 400

Ala Ala Gly Gly Ala Arg Ala Trp Asp Tyr Ser Ala Tyr Thr Glu Pro
                405                 410                 415

Gly Trp Pro Thr Asp Pro Ser Gln Gln Ala Leu Phe Asp Pro Leu Trp
            420                 425                 430

Gly Leu Tyr Asp Pro Pro Ala Gly Gln Trp Phe Pro Gln Gln Ala Leu
        435                 440                 445

Gln Leu Ala Gln Leu Ala Val Pro Pro Leu Gln Pro Gln Trp Pro Val
    450                 455                 460

Pro Pro Val His His
465
```

<210> SEQ ID NO 31
<211> LENGTH: 459
<212> TYPE: PRT
<213> ORGANISM: Trichoderma reesei

<400> SEQUENCE: 31

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
    370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr

```
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
    450                 455


<210> SEQ ID NO 32
<211> LENGTH: 418
<212> TYPE: PRT
<213> ORGANISM: Trichoderma reesei

<400> SEQUENCE: 32

Met Asn Lys Ser Val Ala Pro Leu Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320
```

-continued

```
Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Ser
385                 390                 395                 400

Ser Gly Asn Ser Trp Thr Asp Thr Ser Leu Val Ser Ser Cys Leu Ala
                405                 410                 415

Arg Lys


<210> SEQ ID NO 33
<211> LENGTH: 344
<212> TYPE: PRT
<213> ORGANISM: Trichoderma reesei

<400> SEQUENCE: 33

Met Ile Gln Lys Leu Ser Asn Leu Leu Val Thr Ala Leu Ala Val Ala
1               5                   10                  15

Thr Gly Val Val Gly His Gly His Ile Asn Asp Ile Val Ile Asn Gly
            20                  25                  30

Val Trp Tyr Gln Ala Tyr Asp Pro Thr Thr Phe Pro Tyr Glu Ser Asn
        35                  40                  45

Pro Pro Ile Val Val Gly Trp Thr Ala Ala Asp Leu Asp Asn Gly Phe
    50                  55                  60

Val Ser Pro Asp Ala Tyr Gln Asn Pro Asp Ile Ile Cys His Lys Asn
65                  70                  75                  80

Ala Thr Asn Ala Lys Gly His Ala Ser Val Lys Ala Gly Asp Thr Ile
                85                  90                  95

Leu Phe Gln Trp Val Pro Val Pro Trp Pro His Pro Gly Pro Ile Val
            100                 105                 110

Asp Tyr Leu Ala Asn Cys Asn Gly Asp Cys Glu Thr Val Asp Lys Thr
        115                 120                 125

Thr Leu Glu Phe Phe Lys Ile Asp Gly Val Gly Leu Leu Ser Gly Gly
    130                 135                 140

Asp Pro Gly Thr Trp Ala Ser Asp Val Leu Ile Ser Asn Asn Asn Thr
145                 150                 155                 160

Trp Val Val Lys Ile Pro Asp Asn Leu Ala Pro Gly Asn Tyr Val Leu
                165                 170                 175

Arg His Glu Ile Ile Ala Leu His Ser Ala Gly Gln Ala Asn Gly Ala
            180                 185                 190

Gln Asn Tyr Pro Gln Cys Phe Asn Ile Ala Val Ser Gly Ser Gly Ser
        195                 200                 205

Leu Gln Pro Ser Gly Val Leu Gly Thr Asp Leu Tyr His Ala Thr Asp
    210                 215                 220

Pro Gly Val Leu Ile Asn Ile Tyr Thr Ser Pro Leu Asn Tyr Ile Ile
225                 230                 235                 240

Pro Gly Pro Thr Val Val Ser Gly Leu Pro Thr Ser Val Ala Gln Gly
                245                 250                 255

Ser Ser Ala Ala Thr Ala Thr Ala Ser Ala Thr Val Pro Gly Gly Gly
            260                 265                 270
```

```
Ser Gly Pro Thr Ser Arg Thr Thr Thr Thr Ala Arg Thr Thr Gln Ala
        275                 280                 285

Ser Ser Arg Pro Ser Ser Thr Pro Pro Ala Thr Thr Ser Ala Pro Ala
    290                 295                 300

Gly Gly Pro Thr Gln Thr Leu Tyr Gly Gln Cys Gly Gly Ser Gly Tyr
305                 310                 315                 320

Ser Gly Pro Thr Arg Cys Ala Pro Pro Ala Thr Cys Ser Thr Leu Asn
                325                 330                 335

Pro Tyr Tyr Ala Gln Cys Leu Asn
            340


<210> SEQ ID NO 34
<211> LENGTH: 242
<212> TYPE: PRT
<213> ORGANISM: Trichoderma reesei

<400> SEQUENCE: 34

Met Lys Ala Thr Leu Val Leu Gly Ser Leu Ile Val Gly Ala Val Ser
1               5                   10                  15

Ala Tyr Lys Ala Thr Thr Thr Arg Tyr Tyr Asp Gly Gln Glu Gly Ala
            20                  25                  30

Cys Gly Cys Gly Ser Ser Ser Gly Ala Phe Pro Trp Gln Leu Gly Ile
        35                  40                  45

Gly Asn Gly Val Tyr Thr Ala Ala Gly Ser Gln Ala Leu Phe Asp Thr
    50                  55                  60

Ala Gly Ala Ser Trp Cys Gly Ala Gly Cys Gly Lys Cys Tyr Gln Leu
65                  70                  75                  80

Thr Ser Thr Gly Gln Ala Pro Cys Ser Ser Cys Gly Thr Gly Gly Ala
                85                  90                  95

Ala Gly Gln Ser Ile Ile Val Met Val Thr Asn Leu Cys Pro Asn Asn
            100                 105                 110

Gly Asn Ala Gln Trp Cys Pro Val Val Gly Gly Thr Asn Gln Tyr Gly
        115                 120                 125

Tyr Ser Tyr His Phe Asp Ile Met Ala Gln Asn Glu Ile Phe Gly Asp
    130                 135                 140

Asn Val Val Val Asp Phe Glu Pro Ile Ala Cys Pro Gly Gln Ala Ala
145                 150                 155                 160

Ser Asp Trp Gly Thr Cys Leu Cys Val Gly Gln Gln Glu Thr Asp Pro
                165                 170                 175

Thr Pro Val Leu Gly Asn Asp Thr Gly Ser Thr Pro Pro Gly Ser Ser
            180                 185                 190

Pro Pro Ala Thr Ser Ser Ser Pro Pro Ser Gly Gly Gly Gln Gln Thr
        195                 200                 205

Leu Tyr Gly Gln Cys Gly Gly Ala Gly Trp Thr Gly Pro Thr Thr Cys
    210                 215                 220

Gln Ala Pro Gly Thr Cys Lys Val Gln Asn Gln Trp Tyr Ser Gln Cys
225                 230                 235                 240

Leu Pro


<210> SEQ ID NO 35
<211> LENGTH: 249
<212> TYPE: PRT
<213> ORGANISM: Trichoderma reesei

<400> SEQUENCE: 35

Met Lys Ser Cys Ala Ile Leu Ala Ala Leu Gly Cys Leu Ala Gly Ser
```

1 5 10 15

Val Leu Gly His Gly Gln Val Gln Asn Phe Thr Ile Asn Gly Gln Tyr
20 25 30

Asn Gln Gly Phe Ile Leu Asp Tyr Tyr Tyr Gln Lys Gln Asn Thr Gly
35 40 45

His Phe Pro Asn Val Ala Gly Trp Tyr Ala Glu Asp Leu Asp Leu Gly
50 55 60

Phe Ile Ser Pro Asp Gln Tyr Thr Thr Pro Asp Ile Val Cys His Lys
65 70 75 80

Asn Ala Ala Pro Gly Ala Ile Ser Ala Thr Ala Ala Ala Gly Ser Asn
85 90 95

Ile Val Phe Gln Trp Gly Pro Gly Val Trp Pro His Pro Tyr Gly Pro
100 105 110

Ile Val Thr Tyr Val Val Glu Cys Ser Gly Ser Cys Thr Thr Val Asn
115 120 125

Lys Asn Asn Leu Arg Trp Val Lys Ile Gln Glu Ala Gly Ile Asn Tyr
130 135 140

Asn Thr Gln Val Trp Ala Gln Gln Asp Leu Ile Asn Gln Gly Asn Lys
145 150 155 160

Trp Thr Val Lys Ile Pro Ser Ser Leu Arg Pro Gly Asn Tyr Val Phe
165 170 175

Arg His Glu Leu Leu Ala Ala His Gly Ala Ser Ser Ala Asn Gly Met
180 185 190

Gln Asn Tyr Pro Gln Cys Val Asn Ile Ala Val Thr Gly Ser Gly Thr
195 200 205

Lys Ala Leu Pro Ala Gly Thr Pro Ala Thr Gln Leu Tyr Lys Pro Thr
210 215 220

Asp Pro Gly Ile Leu Phe Asn Pro Tyr Thr Thr Ile Thr Ser Tyr Thr
225 230 235 240

Ile Pro Gly Pro Ala Leu Trp Gln Gly
245

<210> SEQ ID NO 36
<211> LENGTH: 234
<212> TYPE: PRT
<213> ORGANISM: Trichoderma reesei

<400> SEQUENCE: 36

Met Lys Phe Leu Gln Val Leu Pro Ala Leu Ile Pro Ala Ala Leu Ala
1 5 10 15

Gln Thr Ser Cys Asp Gln Trp Ala Thr Phe Thr Gly Asn Gly Tyr Thr
20 25 30

Val Ser Asn Asn Leu Trp Gly Ala Ser Ala Gly Ser Gly Phe Gly Cys
35 40 45

Val Thr Ala Val Ser Leu Ser Gly Gly Ala Ser Trp His Ala Asp Trp
50 55 60

Gln Trp Ser Gly Gly Gln Asn Asn Val Lys Ser Tyr Gln Asn Ser Gln
65 70 75 80

Ile Ala Ile Pro Gln Lys Arg Thr Val Asn Ser Ile Ser Ser Met Pro
85 90 95

Thr Thr Ala Ser Trp Ser Tyr Ser Gly Ser Asn Ile Arg Ala Asn Val
100 105 110

Ala Tyr Asp Leu Phe Thr Ala Ala Asn Pro Asn His Val Thr Tyr Ser
115 120 125

```
Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Asn Tyr Ser Gly Asp Val Lys Asn Phe Phe
            180                 185                 190

Asn Tyr Leu Arg Asp Asn Lys Gly Tyr Asn Ala Ala Gly Gln Tyr Val
        195                 200                 205

Leu Ser Tyr Gln Phe Gly Thr Glu Pro Phe Thr Gly Ser Gly Thr Leu
    210                 215                 220

Asn Val Ala Ser Trp Thr Ala Ser Ile Asn
225                 230
```

<210> SEQ ID NO 37
<211> LENGTH: 513
<212> TYPE: PRT
<213> ORGANISM: Trichoderma reesei

<400> SEQUENCE: 37

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270
```

Cys Asp Pro Asp Gly Cys Asp Trp Asn Pro Tyr Arg Leu Gly Asn Thr
275 280 285

Ser Phe Tyr Gly Pro Gly Ser Ser Phe Thr Leu Asp Thr Thr Lys Lys
290 295 300

Leu Thr Val Val Thr Gln Phe Glu Thr Ser Gly Ala Ile Asn Arg Tyr
305 310 315 320

Tyr Val Gln Asn Gly Val Thr Phe Gln Gln Pro Asn Ala Glu Leu Gly
325 330 335

Ser Tyr Ser Gly Asn Glu Leu Asn Asp Asp Tyr Cys Thr Ala Glu Glu
340 345 350

Ala Glu Phe Gly Gly Ser Ser Phe Ser Asp Lys Gly Gly Leu Thr Gln
355 360 365

Phe Lys Lys Ala Thr Ser Gly Gly Met Val Leu Val Met Ser Leu Trp
370 375 380

Asp Asp Tyr Tyr Ala Asn Met Leu Trp Leu Asp Ser Thr Tyr Pro Thr
385 390 395 400

Asn Glu Thr Ser Ser Thr Pro Gly Ala Val Arg Gly Ser Cys Ser Thr
405 410 415

Ser Ser Gly Val Pro Ala Gln Val Glu Ser Gln Ser Pro Asn Ala Lys
420 425 430

Val Thr Phe Ser Asn Ile Lys Phe Gly Pro Ile Gly Ser Thr Gly Asn
435 440 445

Pro Ser Gly Gly Asn Pro Pro Gly Gly Asn Arg Gly Thr Thr Thr Thr
450 455 460

Arg Arg Pro Ala Thr Thr Thr Gly Ser Ser Pro Gly Pro Thr Gln Ser
465 470 475 480

His Tyr Gly Gln Cys Gly Gly Ile Gly Tyr Ser Gly Pro Thr Val Cys
485 490 495

Ala Ser Gly Thr Thr Cys Gln Val Leu Asn Pro Tyr Tyr Ser Gln Cys
500 505 510

Leu

<210> SEQ ID NO 38
<211> LENGTH: 471
<212> TYPE: PRT
<213> ORGANISM: Trichoderma reesei

<400> SEQUENCE: 38

Met Ile Val Gly Ile Leu Thr Thr Leu Ala Thr Leu Ala Thr Leu Ala
1 5 10 15

Ala Ser Val Pro Leu Glu Glu Arg Gln Ala Cys Ser Ser Val Trp Gly
20 25 30

Gln Cys Gly Gly Gln Asn Trp Ser Gly Pro Thr Cys Cys Ala Ser Gly
35 40 45

Ser Thr Cys Val Tyr Ser Asn Asp Tyr Tyr Ser Gln Cys Leu Pro Gly
50 55 60

Ala Ala Ser Ser Ser Ser Ser Thr Arg Ala Ala Ser Thr Thr Ser Arg
65 70 75 80

Val Ser Pro Thr Thr Ser Arg Ser Ser Ser Ala Thr Pro Pro Pro Gly
85 90 95

Ser Thr Thr Thr Arg Val Pro Pro Val Gly Ser Gly Thr Ala Thr Tyr
100 105 110

Ser Gly Asn Pro Phe Val Gly Val Thr Pro Trp Ala Asn Ala Tyr Tyr
115 120 125

```
Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470


<210> SEQ ID NO 39
<211> LENGTH: 744
<212> TYPE: PRT
<213> ORGANISM: Trichoderma reesei

<400> SEQUENCE: 39

Met Arg Tyr Arg Thr Ala Ala Ala Leu Ala Leu Ala Thr Gly Pro Phe
1               5                   10                  15

Ala Arg Ala Asp Ser His Ser Thr Ser Gly Ala Ser Ala Glu Ala Val
```

```
            20                  25                  30

Val Pro Pro Ala Gly Thr Pro Trp Gly Thr Ala Tyr Asp Lys Ala Lys
        35                  40                  45

Ala Ala Leu Ala Lys Leu Asn Leu Gln Asp Lys Val Gly Ile Val Ser
    50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
    130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
    210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
        275                 280                 285

Thr Asp Phe Asn Gly Asn Asn Arg Leu Trp Gly Pro Ala Leu Thr Asn
    290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
        355                 360                 365

Ala Asn Ile Leu Pro Leu Lys Lys Pro Ala Ser Ile Ala Val Val Gly
    370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
        435                 440                 445
```

```
Thr Ser Ser Gly Ala Ser Ala Ala Arg Gly Lys Asp Val Ala Ile Val
    450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val Val His
            500                 505                 510

Ser Val Gly Ala Ile Ile Leu Glu Gln Ile Leu Ala Leu Pro Gln Val
        515                 520                 525

Lys Ala Val Val Trp Ala Gly Leu Pro Ser Gln Glu Ser Gly Asn Ala
    530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
        595                 600                 605

Ser Tyr Thr Lys Phe Asn Tyr Ser Arg Leu Ser Val Leu Ser Thr Ala
    610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670

Ser Ala Pro Arg Thr Pro Pro Lys Gln Leu Arg Gly Phe Ala Lys Leu
        675                 680                 685

Asn Leu Thr Pro Gly Gln Ser Gly Thr Ala Thr Phe Asn Ile Arg Arg
    690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
                725                 730                 735

Leu Thr Ser Thr Leu Ser Val Ala
            740


<210> SEQ ID NO 40
<211> LENGTH: 466
<212> TYPE: PRT
<213> ORGANISM: Trichoderma reesei

<400> SEQUENCE: 40

Met Leu Pro Lys Asp Phe Gln Trp Gly Phe Ala Thr Ala Ala Tyr Gln
1               5                   10                  15

Ile Glu Gly Ala Val Asp Gln Asp Gly Arg Gly Pro Ser Ile Trp Asp
            20                  25                  30

Thr Phe Cys Ala Gln Pro Gly Lys Ile Ala Asp Gly Ser Ser Gly Val
        35                  40                  45

Thr Ala Cys Asp Ser Tyr Asn Arg Thr Ala Glu Asp Ile Ala Leu Leu
    50                  55                  60

Lys Ser Leu Gly Ala Lys Ser Tyr Arg Phe Ser Ile Ser Trp Ser Arg
```

-continued

```
65                  70                  75                  80

Ile Ile Pro Glu Gly Gly Arg Gly Asp Ala Val Asn Gln Ala Gly Ile
                85                  90                  95

Asp His Tyr Val Lys Phe Val Asp Asp Leu Leu Asp Ala Gly Ile Thr
            100                 105                 110

Pro Phe Ile Thr Leu Phe His Trp Asp Leu Pro Glu Gly Leu His Gln
        115                 120                 125

Arg Tyr Gly Gly Leu Leu Asn Arg Thr Glu Phe Pro Leu Asp Phe Glu
    130                 135                 140

Asn Tyr Ala Arg Val Met Phe Arg Ala Leu Pro Lys Val Arg Asn Trp
145                 150                 155                 160

Ile Thr Phe Asn Glu Pro Leu Cys Ser Ala Ile Pro Gly Tyr Gly Ser
                165                 170                 175

Gly Thr Phe Ala Pro Gly Arg Gln Ser Thr Ser Glu Pro Trp Thr Val
            180                 185                 190

Gly His Asn Ile Leu Val Ala His Gly Arg Ala Val Lys Ala Tyr Arg
        195                 200                 205

Asp Asp Phe Lys Pro Ala Ser Gly Asp Gly Gln Ile Gly Ile Val Leu
    210                 215                 220

Asn Gly Asp Phe Thr Tyr Pro Trp Asp Ala Ala Asp Pro Ala Asp Lys
225                 230                 235                 240

Glu Ala Ala Glu Arg Arg Leu Glu Phe Phe Thr Ala Trp Phe Ala Asp
                245                 250                 255

Pro Ile Tyr Leu Gly Asp Tyr Pro Ala Ser Met Arg Lys Gln Leu Gly
            260                 265                 270

Asp Arg Leu Pro Thr Phe Thr Pro Glu Glu Arg Ala Leu Val His Gly
        275                 280                 285

Ser Asn Asp Phe Tyr Gly Met Asn His Tyr Thr Ser Asn Tyr Ile Arg
    290                 295                 300

His Arg Ser Ser Pro Ala Ser Ala Asp Asp Thr Val Gly Asn Val Asp
305                 310                 315                 320

Val Leu Phe Thr Asn Lys Gln Gly Asn Cys Ile Gly Pro Glu Thr Gln
                325                 330                 335

Ser Pro Trp Leu Arg Pro Cys Ala Ala Gly Phe Arg Asp Phe Leu Val
            340                 345                 350

Trp Ile Ser Lys Arg Tyr Gly Tyr Pro Pro Ile Tyr Val Thr Glu Asn
        355                 360                 365

Gly Thr Ser Ile Lys Gly Glu Ser Asp Leu Pro Lys Glu Lys Ile Leu
    370                 375                 380

Glu Asp Asp Phe Arg Val Lys Tyr Tyr Asn Glu Tyr Ile Arg Ala Met
385                 390                 395                 400

Val Thr Ala Val Glu Leu Asp Gly Val Asn Val Lys Gly Tyr Phe Ala
                405                 410                 415

Trp Ser Leu Met Asp Asn Phe Glu Trp Ala Asp Gly Tyr Val Thr Arg
            420                 425                 430

Phe Gly Val Thr Tyr Val Asp Tyr Glu Asn Gly Gln Lys Arg Phe Pro
        435                 440                 445

Lys Lys Ser Ala Lys Ser Leu Lys Pro Leu Phe Asp Glu Leu Ile Ala
    450                 455                 460

Ala Ala
465

<210> SEQ ID NO 41
```

-continued

```
<211> LENGTH: 405
<212> TYPE: PRT
<213> ORGANISM: Aspergillus oryzae

<400> SEQUENCE: 41

Met Leu Pro Leu Leu Leu Cys Ile Val Pro Tyr Cys Trp Ser Ser Arg
1               5                   10                  15

Leu Asp Pro Arg Ala Ser Ser Phe Asp Tyr Asn Gly Glu Lys Val Arg
            20                  25                  30

Gly Val Asn Leu Gly Gly Trp Leu Val Leu Glu Pro Trp Ile Thr Pro
        35                  40                  45

Ser Ile Phe Asp Ala Ala Gly Ala Glu Ala Val Asp Glu Trp Ser Leu
    50                  55                  60

Thr Lys Ile Leu Gly Lys Glu Glu Ala Glu Ala Arg Leu Ser Ala His
65                  70                  75                  80

Trp Lys Ser Phe Val Ser Ala Gly Asp Phe Gln Arg Met Ala Asp Ala
                85                  90                  95

Gly Leu Asn His Val Arg Ile Pro Ile Gly Tyr Trp Ala Leu Gly Pro
            100                 105                 110

Leu Glu Gly Asp Pro Tyr Val Asp Gly Gln Leu Glu Tyr Leu Asp Lys
        115                 120                 125

Ala Val Glu Trp Ala Gly Ala Ala Gly Leu Lys Val Leu Ile Asp Leu
    130                 135                 140

His Gly Ala Pro Gly Ser Gln Asn Gly Phe Asp Asn Ser Gly Arg Arg
145                 150                 155                 160

Gly Ala Ile Gln Trp Gln Gln Gly Asp Thr Val Glu Gln Thr Leu Asp
                165                 170                 175

Ala Phe Asp Leu Leu Ala Glu Arg Tyr Leu Gly Ser Asp Thr Val Ala
            180                 185                 190

Ala Ile Glu Ala Ile Asn Glu Pro Asn Ile Pro Gly Gly Val Asp Gln
        195                 200                 205

Gly Lys Leu Gln Glu Tyr Tyr Gly Ser Val Tyr Gly Ile Val Asn Lys
    210                 215                 220

Tyr Asn Ala Gly Thr Ser Val Val Tyr Gly Asp Gly Phe Leu Pro Val
225                 230                 235                 240

Glu Ser Trp Asn Gly Phe Lys Thr Glu Gly Ser Lys Val Val Met Asp
                245                 250                 255

Thr His His Tyr His Met Phe Asp Asn Gly Leu Ile Ala Met Asp Ile
            260                 265                 270

Asp Ser His Ile Asp Ala Val Cys Gln Phe Ala His Gln His Leu Glu
        275                 280                 285

Ala Ser Asp Lys Pro Val Ile Val Gly Glu Trp Thr Gly Ala Val Thr
    290                 295                 300

Asp Cys Ala Lys Tyr Leu Asn Gly Lys Gly Asn Gly Ala Arg Tyr Asp
305                 310                 315                 320

Gly Ser Tyr Ala Ala Asp Lys Ala Ile Gly Asp Cys Ser Ser Leu Ala
                325                 330                 335

Thr Gly Phe Val Ser Lys Leu Ser Asp Glu Glu Arg Ser Asp Met Arg
            340                 345                 350

Arg Phe Ile Glu Ala Gln Leu Asp Ala Phe Glu Leu Lys Ser Gly Trp
        355                 360                 365

Val Phe Trp Thr Trp Lys Thr Glu Gly Ala Pro Gly Trp Asp Met Ser
    370                 375                 380

Asp Leu Leu Glu Ala Gly Val Phe Pro Thr Ser Pro Asp Asp Arg Glu
```

-continued

```
385                 390                 395                 400

Phe Pro Lys Gln Cys
                405


<210> SEQ ID NO 42
<211> LENGTH: 470
<212> TYPE: PRT
<213> ORGANISM: Bacillus subtilis

<400> SEQUENCE: 42

Ala Gly Thr Lys Thr Pro Val Ala Lys Asn Gly Gln Leu Ser Ile Lys
1               5                   10                  15

Gly Thr Gln Leu Val Asn Arg Asp Gly Lys Ala Val Gln Leu Lys Gly
            20                  25                  30

Ile Ser Ser His Gly Leu Gln Trp Tyr Gly Glu Tyr Val Asn Lys Asp
        35                  40                  45

Ser Leu Lys Trp Leu Arg Asp Asp Trp Gly Ile Thr Val Phe Arg Ala
    50                  55                  60

Ala Met Tyr Thr Ala Asp Gly Gly Tyr Ile Asp Asn Pro Ser Val Lys
65                  70                  75                  80

Asn Lys Val Lys Glu Ala Val Glu Ala Ala Lys Glu Leu Gly Ile Tyr
                85                  90                  95

Val Ile Ile Asp Trp His Ile Leu Asn Asp Gly Asn Pro Asn Gln Asn
            100                 105                 110

Lys Glu Lys Ala Lys Glu Phe Phe Lys Glu Met Ser Ser Leu Tyr Gly
        115                 120                 125

Asn Thr Pro Asn Val Ile Tyr Glu Ile Ala Asn Glu Pro Asn Gly Asp
    130                 135                 140

Val Asn Trp Lys Arg Asp Ile Lys Pro Tyr Ala Glu Glu Val Ile Ser
145                 150                 155                 160

Val Ile Arg Lys Asn Asp Pro Asp Asn Ile Ile Ile Val Gly Thr Gly
                165                 170                 175

Thr Trp Ser Gln Asp Val Asn Asp Ala Ala Asp Asp Gln Leu Lys Asp
            180                 185                 190

Ala Asn Val Met Tyr Ala Leu His Phe Tyr Ala Gly Thr His Gly Gln
        195                 200                 205

Phe Leu Arg Asp Lys Ala Asn Tyr Ala Leu Ser Lys Gly Ala Pro Ile
    210                 215                 220

Phe Val Thr Glu Trp Gly Thr Ser Asp Ala Ser Gly Asn Gly Gly Val
225                 230                 235                 240

Phe Leu Asp Gln Ser Arg Glu Trp Leu Lys Tyr Leu Asp Ser Lys Thr
                245                 250                 255

Ile Ser Trp Val Asn Trp Asn Leu Ser Asp Lys Gln Glu Ser Ser Ser
            260                 265                 270

Ala Leu Lys Pro Gly Ala Ser Lys Thr Gly Gly Trp Arg Leu Ser Asp
        275                 280                 285

Leu Ser Ala Ser Gly Thr Phe Val Arg Glu Asn Ile Leu Gly Thr Lys
    290                 295                 300

Asp Ser Thr Lys Asp Ile Pro Glu Thr Pro Ser Lys Asp Lys Pro Thr
305                 310                 315                 320

Gln Glu Asn Gly Ile Ser Val Gln Tyr Arg Ala Gly Asp Gly Ser Met
                325                 330                 335

Asn Ser Asn Gln Ile Arg Pro Gln Leu Gln Ile Lys Asn Asn Gly Asn
            340                 345                 350
```

```
Thr Thr Val Asp Leu Lys Asp Val Thr Ala Arg Tyr Trp Tyr Lys Ala
        355                 360                 365

Lys Asn Lys Gly Gln Asn Phe Asp Cys Asp Tyr Ala Gln Ile Gly Cys
    370                 375                 380

Gly Asn Val Thr His Lys Phe Val Thr Leu His Lys Pro Lys Gln Gly
385                 390                 395                 400

Ala Asp Thr Tyr Leu Glu Leu Gly Phe Lys Asn Gly Thr Leu Ala Pro
                405                 410                 415

Gly Ala Ser Thr Gly Asn Ile Gln Leu Arg Leu His Asn Asp Asp Trp
            420                 425                 430

Ser Asn Tyr Ala Gln Ser Gly Asp Tyr Ser Phe Phe Lys Ser Asn Thr
        435                 440                 445

Phe Lys Thr Thr Lys Lys Ile Thr Leu Tyr Asp Gln Gly Lys Leu Ile
    450                 455                 460

Trp Gly Thr Glu Pro Asn
465                 470


<210> SEQ ID NO 43
<211> LENGTH: 214
<212> TYPE: PRT
<213> ORGANISM: Bacillus subtilis

<400> SEQUENCE: 43

Gln Thr Gly Gly Ser Phe Phe Asp Pro Phe Asn Gly Tyr Asn Ser Gly
1               5                   10                  15

Phe Trp Gln Lys Ala Asp Gly Tyr Ser Asn Gly Asn Met Phe Asn Cys
            20                  25                  30

Thr Trp Arg Ala Asn Asn Val Ser Met Thr Ser Leu Gly Glu Met Arg
        35                  40                  45

Leu Ala Leu Thr Ser Pro Ala Tyr Asn Lys Phe Asp Cys Gly Glu Asn
    50                  55                  60

Arg Ser Val Gln Thr Tyr Gly Tyr Gly Leu Tyr Glu Val Arg Met Lys
65                  70                  75                  80

Pro Ala Lys Asn Thr Gly Ile Val Ser Ser Phe Phe Thr Tyr Thr Gly
                85                  90                  95

Pro Thr Asp Gly Thr Pro Trp Asp Glu Ile Asp Ile Glu Phe Leu Gly
            100                 105                 110

Lys Asp Thr Thr Lys Val Gln Phe Asn Tyr Tyr Thr Asn Gly Ala Gly
        115                 120                 125

Asn His Glu Lys Ile Val Asp Leu Gly Phe Asp Ala Ala Asn Ala Tyr
    130                 135                 140

His Thr Tyr Ala Phe Asp Trp Gln Pro Asn Ser Ile Lys Trp Tyr Val
145                 150                 155                 160

Asp Gly Gln Leu Lys His Thr Ala Thr Asn Gln Ile Pro Thr Thr Pro
                165                 170                 175

Gly Lys Ile Met Met Asn Leu Trp Asn Gly Thr Gly Val Asp Glu Trp
            180                 185                 190

Leu Gly Ser Tyr Asn Gly Val Asn Pro Leu Tyr Ala His Tyr Asp Trp
        195                 200                 205

Val Arg Tyr Thr Lys Lys
    210


<210> SEQ ID NO 44
<211> LENGTH: 839
<212> TYPE: PRT
<213> ORGANISM: Bacillus circulans
```

<400> SEQUENCE: 44

Ala Glu Thr Ala Gly Thr Thr Ile Thr Ser Met Ser Tyr Phe Ser Thr
1               5                   10                  15

Ala Asp Gly Pro Ile Ile Thr Lys Ser Gly Val Gly Gln Ala Ser Tyr
            20                  25                  30

Gly Phe Val Met Pro Ile Phe Asn Gly Gly Ser Ala Thr Trp Asn Asp
        35                  40                  45

Val Ala Gln Asp Leu Gly Val Lys Val Lys Val Asn Gly Ser Trp Val
    50                  55                  60

Asp Ile Asp Ser Val Ser Ser Phe Val Tyr Asn Gln Asn Trp Gly His
65                  70                  75                  80

Trp Asn Asp Gly Gly Phe Thr Gly Tyr Trp Phe Thr Leu Ser Ala Thr
                85                  90                  95

Thr Glu Ile Gln Leu Tyr Ser Lys Ala Asn Glu Val Thr Leu Glu Tyr
            100                 105                 110

Ser Leu Val Phe Gln Asn Ile Asn Lys Thr Thr Ile Thr Ala Met Thr
        115                 120                 125

Pro Thr Gln Gly Pro Gln Ile Thr Ala Gly Phe Thr Gly Gly Ala Gly
    130                 135                 140

Phe Thr Tyr Pro Ile Phe Asn His Asp Pro Ala Ile Thr Tyr Ala Ala
145                 150                 155                 160

Val Ala Asp Asp Leu Lys Val Tyr Val Lys Pro Val Asn Ser Ser Gln
                165                 170                 175

Trp Ile Asp Ile Asp Asn Asn Ala Ala Ser Gly Trp Ile Tyr Asp Gln
            180                 185                 190

Asn Phe Gly Gln Phe Thr Asp Gly Gly Gly Gly Tyr Trp Phe Asn Val
        195                 200                 205

Thr Glu Ser Ile Asn Val Lys Leu Glu Ser Lys Thr Ser Ser Thr Asn
    210                 215                 220

Ile Val Tyr Thr Ile Ser Phe Asn Glu Pro Val Arg Asn Ser Tyr Val
225                 230                 235                 240

Leu Thr Pro Tyr Glu Gly Thr Thr Phe Thr Ala Asp Ala Ser Gly Ala
                245                 250                 255

Ile Gly Ile Pro Leu Pro Lys Ile Asp Gly Gly Ala Pro Ile Gly Thr
            260                 265                 270

Glu Leu Gly Asn Phe Val Tyr Gln Ile Asn Ile Asn Gly Gln Trp Val
        275                 280                 285

Asp Leu Asp Asn Ser Ser Gln Ser Gly Phe Val Tyr Ser Ala Asn Gly
    290                 295                 300

Tyr Asn Asn Met Ser Ala Ala Asn Gln Trp Gly Tyr Trp Ala Asp His
305                 310                 315                 320

Ile Tyr Gly Leu Trp Phe Gln Pro Ile Gln Val Asp Met Gln Ile Arg
                325                 330                 335

Ile Gly Tyr Pro Leu Asn Gly Gln Ala Gly Gly Ser Val Gly Ser Asn
            340                 345                 350

Phe Val Asn Tyr Thr Leu Ile Gly Asn Pro Asp Ala Pro Arg Pro Asp
        355                 360                 365

Val Asn Asp Gln Glu Asp Ile Pro Ile Gly Thr Pro Asn Asp Ser Ala
    370                 375                 380

Ile Glu Gly Met Asn Leu Ile Trp Gln Asp Glu Phe Asn Gly Thr Ala
385                 390                 395                 400

Leu Asp Gln Ser Lys Trp Asn Tyr Glu Thr Gly Tyr Tyr Leu Asn Asp

-continued

```
                405                 410                 415

Asp Pro Asn Thr Trp Gly Trp Gly Asn Ser Glu Leu Gln His Tyr Thr
            420                 425                 430

Asp Arg Ala Gln Asn Val Phe Val Gln Asp Gly Lys Leu Asn Ile Lys
        435                 440                 445

Ala Leu Asn Glu Pro Lys Ser Phe Pro Gln Asp Pro Ser Arg Tyr Ala
    450                 455                 460

Gln Tyr Ser Ser Gly Lys Ile Asn Thr Lys Asp His Phe Ser Leu Lys
465                 470                 475                 480

Tyr Gly Arg Val Asp Phe Arg Ala Lys Leu Pro Thr Gly Asn Gly Ile
                485                 490                 495

Trp Pro Ala Leu Trp Met Leu Pro Gln Asp Asn Val Tyr Gly Thr Trp
            500                 505                 510

Ala Ser Ser Gly Glu Ile Asp Val Met Glu Ala Lys Gly Arg Leu Pro
        515                 520                 525

Gly Ser Thr Ser Gly Ala Val His Phe Gly Gly Gln Trp Pro Thr Asn
    530                 535                 540

Arg Tyr Leu Ser Gly Glu Tyr His Phe Pro Glu Gly Gln Thr Phe Ala
545                 550                 555                 560

Asn Asp Tyr His Val Tyr Ser Val Val Trp Glu Glu Asp Asn Ile Lys
                565                 570                 575

Trp Tyr Val Asp Gly Lys Phe Phe Phe Lys Val Thr Arg Asp Gln Trp
            580                 585                 590

Tyr Ser Ala Ala Ala Pro Asn Asn Pro Asn Ala Pro Phe Asp Gln Pro
        595                 600                 605

Phe Tyr Leu Ile Met Asn Leu Ala Ile Gly Gly Thr Phe Asp Gly Gly
    610                 615                 620

Arg Thr Pro Asp Pro Ser Asp Ile Pro Ala Thr Met Gln Val Asp Tyr
625                 630                 635                 640

Val Arg Val Tyr Lys Glu Gly Glu Gly Gly Gly Gln Asn Pro Gly Asn
                645                 650                 655

Val Pro Val Thr Gly Val Thr Val Asn Pro Thr Thr Ala Gln Val Glu
            660                 665                 670

Val Gly Gln Ser Val Gln Leu Asn Ala Ser Val Ala Pro Ser Asn Ala
        675                 680                 685

Thr Asn Lys Gln Val Thr Trp Ser Val Ser Gly Ser Ser Ile Ala Ser
    690                 695                 700

Val Ser Pro Asn Gly Leu Val Thr Gly Leu Ala Gln Gly Thr Thr Thr
705                 710                 715                 720

Val Thr Ala Thr Thr Ala Asp Gly Asn Lys Ala Ala Ser Ala Thr Ile
                725                 730                 735

Thr Val Ala Pro Ala Pro Ser Thr Val Ile Val Ile Gly Asp Glu Val
            740                 745                 750

Lys Gly Leu Lys Lys Ile Gly Asp Asp Leu Leu Phe Tyr Val Asn Gly
        755                 760                 765

Ala Thr Phe Ala Asp Leu His Tyr Lys Val Asn Asn Gly Gly Gln Leu
    770                 775                 780

Asn Val Ala Met Ala Pro Thr Gly Asn Gly Asn Tyr Thr Tyr Pro Val
785                 790                 795                 800

His Asn Leu Lys His Gly Asp Thr Val Glu Tyr Phe Phe Thr Tyr Asn
                805                 810                 815

Pro Gly Gln Gly Ala Leu Asp Thr Pro Trp Gln Thr Tyr Val His Gly
            820                 825                 830
```

Val Thr Gln Gly Thr Pro Glu
835

<210> SEQ ID NO 45
<211> LENGTH: 644
<212> TYPE: PRT
<213> ORGANISM: Bacillus circulans

<400> SEQUENCE: 45

Ala Gly Thr Thr Val Thr Ser Met Glu Tyr Phe Ser Pro Ala Asp Gly
1 5 10 15

Pro Val Ile Ser Lys Ser Gly Val Gly Lys Ala Ser Tyr Gly Phe Val
20 25 30

Met Pro Lys Phe Asn Gly Gly Ser Ala Thr Trp Asn Asp Val Tyr Ser
35 40 45

Asp Val Gly Val Asn Val Lys Val Gly Asn Asn Trp Val Asp Ile Asp
50 55 60

Gln Ala Gly Gly Tyr Ile Tyr Asn Gln Asn Trp Gly His Trp Ser Asp
65 70 75 80

Gly Gly Phe Asn Gly Tyr Trp Phe Thr Leu Ser Ala Thr Thr Glu Ile
85 90 95

Gln Leu Tyr Ser Lys Ala Asn Gly Val Lys Leu Glu Tyr Gln Leu Val
100 105 110

Phe Gln Asn Ile Asn Lys Thr Thr Ile Thr Ala Met Asn Pro Thr Gln
115 120 125

Gly Pro Gln Ile Thr Ala Ser Phe Thr Gly Gly Ala Gly Phe Thr Tyr
130 135 140

Pro Thr Phe Asn Asn Asp Ser Ala Val Thr Tyr Glu Ala Val Ala Asp
145 150 155 160

Asp Leu Lys Val Tyr Val Lys Pro Val Asn Ser Ser Ser Trp Ile Asp
165 170 175

Ile Asp Asn Asn Ala Ala Ser Gly Trp Ile Tyr Asp His Asn Phe Gly
180 185 190

Gln Phe Thr Asp Gly Gly Gly Gly Tyr Trp Phe Asn Val Thr Glu Ser
195 200 205

Ile Asn Val Lys Leu Glu Ser Lys Thr Ser Ser Ala Asn Leu Val Tyr
210 215 220

Thr Ile Thr Phe Asn Glu Pro Thr Arg Asn Ser Tyr Val Ile Thr Pro
225 230 235 240

Tyr Glu Gly Thr Thr Phe Thr Ala Asp Ala Asn Gly Ser Ile Gly Ile
245 250 255

Pro Leu Pro Lys Ile Asp Gly Gly Ala Pro Ile Ala Lys Glu Leu Gly
260 265 270

Asn Phe Val Tyr Gln Ile Asn Ile Asn Gly Gln Trp Val Asp Leu Ser
275 280 285

Asn Ser Ser Gln Ser Lys Phe Ala Tyr Ser Ala Asn Gly Tyr Asn Asn
290 295 300

Met Ser Asp Ala Asn Gln Trp Gly Tyr Trp Ala Asp Tyr Ile Tyr Gly
305 310 315 320

Leu Trp Phe Gln Pro Ile Gln Glu Asn Met Gln Ile Arg Ile Gly Tyr
325 330 335

Pro Leu Asn Gly Gln Ala Gly Gly Asn Ile Gly Asn Asn Phe Val Asn
340 345 350

Tyr Thr Phe Ile Gly Asn Pro Asn Ala Pro Arg Pro Asp Val Ser Asp

```
        355                 360                 365

Gln Glu Asp Ile Ser Ile Gly Thr Pro Thr Asp Pro Ala Ile Ala Gly
    370                 375                 380

Met Asn Leu Ile Trp Gln Asp Glu Phe Asn Gly Thr Thr Leu Asp Thr
385                 390                 395                 400

Ser Lys Trp Asn Tyr Glu Thr Gly Tyr Tyr Leu Asn Asn Asp Pro Ala
                405                 410                 415

Thr Trp Gly Trp Gly Asn Ala Glu Leu Gln His Tyr Thr Asn Ser Thr
            420                 425                 430

Gln Asn Val Tyr Val Gln Asp Gly Lys Leu Asn Ile Lys Ala Met Asn
        435                 440                 445

Asp Ser Lys Ser Phe Pro Gln Asp Pro Asn Arg Tyr Ala Gln Tyr Ser
    450                 455                 460

Ser Gly Lys Ile Asn Thr Lys Asp Lys Leu Ser Leu Lys Tyr Gly Arg
465                 470                 475                 480

Val Asp Phe Arg Ala Lys Leu Pro Thr Gly Asp Gly Val Trp Pro Ala
                485                 490                 495

Leu Trp Met Leu Pro Lys Asp Ser Val Tyr Gly Thr Trp Ala Ala Ser
            500                 505                 510

Gly Glu Ile Asp Val Met Glu Ala Arg Gly Arg Leu Pro Gly Ser Val
        515                 520                 525

Ser Gly Thr Ile His Phe Gly Gly Gln Trp Pro Val Asn Gln Ser Ser
    530                 535                 540

Gly Gly Asp Tyr His Phe Pro Glu Gly Gln Thr Phe Ala Asn Asp Tyr
545                 550                 555                 560

His Val Tyr Ser Val Val Trp Glu Glu Asp Asn Ile Lys Trp Tyr Val
                565                 570                 575

Asp Gly Lys Phe Phe Tyr Lys Val Thr Asn Gln Gln Trp Tyr Ser Thr
            580                 585                 590

Ala Ala Pro Asn Asn Pro Asn Ala Pro Phe Asp Glu Pro Phe Tyr Leu
        595                 600                 605

Ile Met Asn Leu Ala Val Gly Gly Asn Phe Asp Gly Gly Arg Thr Pro
    610                 615                 620

Asn Ala Ser Asp Ile Pro Ala Thr Met Gln Val Asp Tyr Val Arg Val
625                 630                 635                 640

Tyr Lys Glu Gln


<210> SEQ ID NO 46
<211> LENGTH: 442
<212> TYPE: PRT
<213> ORGANISM: Bacillus subtilis

<400> SEQUENCE: 46

Met Phe Gly Tyr Ser Met Val Gln Met Val Arg Ala Asn Ala His Lys
1               5                   10                  15

Leu Asp Trp Pro Leu Arg Glu Thr Val Leu Gln Leu Tyr Lys Pro Phe
            20                  25                  30

Lys Trp Thr Pro Cys Phe Leu His Lys Phe Phe Glu Thr Lys Leu Gln
        35                  40                  45

Asn Arg Lys Lys Met Ser Val Ile Ile Glu Phe Glu Glu Gly Cys His
    50                  55                  60

Glu Thr Gly Phe Gln Met Ala Gly Glu Val Leu Gln Lys Glu Lys Arg
65                  70                  75                  80

Ser Lys Leu Lys Ser Arg Phe Asn Lys Ile Asn Cys Cys Ser Ala Glu
```

```
                85                  90                  95

Val Thr Pro Ser Ala Leu His Ser Leu Leu Ser Glu Cys Ser Asn Ile
            100                 105                 110

Arg Lys Val Tyr Leu Asn Arg Glu Val Lys Ala Leu Leu Asp Thr Ala
        115                 120                 125

Thr Glu Ala Ser His Ala Lys Glu Val Val Arg Asn Gly Gln Thr Leu
    130                 135                 140

Thr Gly Lys Gly Val Thr Val Ala Val Val Asp Thr Gly Ile Tyr Pro
145                 150                 155                 160

His Pro Asp Leu Glu Gly Arg Ile Ile Gly Phe Ala Asp Met Val Asn
                165                 170                 175

Gln Lys Thr Glu Pro Tyr Asp Asp Asn Gly His Gly Thr His Cys Ala
            180                 185                 190

Gly Asp Val Ala Ser Ser Gly Ala Ser Ser Ser Gly Gln Tyr Arg Gly
        195                 200                 205

Pro Ala Pro Glu Ala Asn Leu Ile Gly Val Lys Val Leu Asn Lys Gln
    210                 215                 220

Gly Ser Gly Thr Leu Ala Asp Ile Ile Glu Gly Val Glu Trp Cys Ile
225                 230                 235                 240

Gln Tyr Asn Glu Asp Asn Pro Asp Glu Pro Ile Asp Ile Met Ser Met
                245                 250                 255

Ser Leu Gly Gly Asp Ala Leu Arg Tyr Asp His Glu Gln Glu Asp Pro
            260                 265                 270

Leu Val Arg Ala Val Glu Glu Ala Trp Ser Ala Gly Ile Val Val Cys
        275                 280                 285

Val Ala Ala Gly Asn Ser Gly Pro Asp Ser Gln Thr Ile Ala Ser Pro
    290                 295                 300

Gly Val Ser Glu Lys Val Ile Thr Val Gly Ala Leu Asp Asp Asn Asn
305                 310                 315                 320

Thr Ala Ser Ser Asp Asp Asp Thr Val Ala Ser Phe Ser Ser Arg Gly
                325                 330                 335

Pro Thr Val Tyr Gly Lys Glu Lys Pro Asp Ile Leu Ala Pro Gly Val
            340                 345                 350

Asn Ile Ile Ser Leu Arg Ser Pro Asn Ser Tyr Ile Asp Lys Leu Gln
        355                 360                 365

Lys Ser Ser Arg Val Gly Ser Gln Tyr Phe Thr Met Ser Gly Thr Ser
    370                 375                 380

Met Ala Thr Pro Ile Cys Ala Gly Ile Ala Ala Leu Ile Leu Gln Gln
385                 390                 395                 400

Asn Pro Asp Leu Thr Pro Asp Glu Val Lys Glu Leu Leu Lys Asn Gly
                405                 410                 415

Thr Asp Lys Trp Lys Asp Glu Asp Pro Asn Ile Tyr Gly Ala Gly Ala
            420                 425                 430

Val Asn Ala Glu Asn Ser Val Pro Gly Gln
        435                 440


<210> SEQ ID NO 47
<211> LENGTH: 778
<212> TYPE: PRT
<213> ORGANISM: Bacillus subtilis

<400> SEQUENCE: 47

Ala Pro Ala Ser Ser Lys Thr Ser Ala Asp Leu Glu Lys Ala Glu Val
1               5                   10                  15
```

-continued

```
Phe Gly Asp Ile Asp Met Thr Thr Ser Lys Lys Thr Thr Val Ile Val
            20                  25                  30

Glu Leu Lys Glu Lys Ser Leu Ala Glu Ala Lys Glu Ala Gly Glu Ser
        35                  40                  45

Gln Ser Lys Ser Lys Leu Lys Thr Ala Arg Thr Lys Ala Lys Asn Lys
    50                  55                  60

Ala Ile Lys Ala Val Lys Asn Gly Lys Val Asn Arg Glu Tyr Glu Gln
65                  70                  75                  80

Val Phe Ser Gly Phe Ser Met Lys Leu Pro Ala Asn Glu Ile Pro Lys
                85                  90                  95

Leu Leu Ala Val Lys Asp Val Lys Ala Val Tyr Pro Asn Val Thr Tyr
            100                 105                 110

Lys Thr Asp Asn Met Lys Asp Lys Asp Val Thr Ile Ser Glu Asp Ala
        115                 120                 125

Val Ser Pro Gln Met Asp Asp Ser Ala Pro Tyr Ile Gly Ala Asn Asp
    130                 135                 140

Ala Trp Asp Leu Gly Tyr Thr Gly Lys Gly Ile Lys Val Ala Ile Ile
145                 150                 155                 160

Asp Thr Gly Val Glu Tyr Asn His Pro Asp Leu Lys Lys Asn Phe Gly
                165                 170                 175

Gln Tyr Lys Gly Tyr Asp Phe Val Asp Asn Asp Tyr Asp Pro Lys Glu
            180                 185                 190

Thr Pro Thr Gly Asp Pro Arg Gly Glu Ala Thr Asp His Gly Thr His
        195                 200                 205

Val Ala Gly Thr Val Ala Ala Asn Gly Thr Ile Lys Gly Val Ala Pro
    210                 215                 220

Asp Ala Thr Leu Leu Ala Tyr Arg Val Leu Gly Pro Gly Gly Ser Gly
225                 230                 235                 240

Thr Thr Glu Asn Val Ile Ala Gly Val Glu Arg Ala Val Gln Asp Gly
                245                 250                 255

Ala Asp Val Met Asn Leu Ser Leu Gly Asn Ser Leu Asn Asn Pro Asp
            260                 265                 270

Trp Ala Thr Ser Thr Ala Leu Asp Trp Ala Met Ser Glu Gly Val Val
        275                 280                 285

Ala Val Thr Ser Asn Gly Asn Ser Gly Pro Asn Gly Trp Thr Val Gly
    290                 295                 300

Ser Pro Gly Thr Ser Arg Glu Ala Ile Ser Val Gly Ala Thr Gln Leu
305                 310                 315                 320

Pro Leu Asn Glu Tyr Ala Val Thr Phe Gly Ser Tyr Ser Ser Ala Lys
                325                 330                 335

Val Met Gly Tyr Asn Lys Glu Asp Asp Val Lys Ala Leu Asn Asn Lys
            340                 345                 350

Glu Val Glu Leu Val Glu Ala Gly Ile Gly Glu Ala Lys Asp Phe Glu
        355                 360                 365

Gly Lys Asp Leu Thr Gly Lys Val Ala Val Val Lys Arg Gly Ser Ile
    370                 375                 380

Ala Phe Val Asp Lys Ala Asp Asn Ala Lys Lys Ala Gly Ala Ile Gly
385                 390                 395                 400

Met Val Val Tyr Asn Asn Leu Ser Gly Glu Ile Glu Ala Asn Val Pro
                405                 410                 415

Gly Met Ser Val Pro Thr Ile Lys Leu Ser Leu Glu Asp Gly Glu Lys
            420                 425                 430

Leu Val Ser Ala Leu Lys Ala Gly Glu Thr Lys Thr Thr Phe Lys Leu
```

```
        435                 440                 445

Thr Val Ser Lys Ala Leu Gly Glu Gln Val Ala Asp Phe Ser Ser Arg
    450                 455                 460

Gly Pro Val Met Asp Thr Trp Met Ile Lys Pro Asp Ile Ser Ala Pro
465                 470                 475                 480

Gly Val Asn Ile Val Ser Thr Ile Pro Thr His Asp Pro Asp His Pro
                485                 490                 495

Tyr Gly Tyr Gly Ser Lys Gln Gly Thr Ser Met Ala Ser Pro His Ile
            500                 505                 510

Ala Gly Ala Val Ala Val Ile Lys Gln Ala Lys Pro Lys Trp Ser Val
        515                 520                 525

Glu Gln Ile Lys Ala Ala Ile Met Asn Thr Ala Val Thr Leu Lys Asp
    530                 535                 540

Ser Asp Gly Glu Val Tyr Pro His Asn Ala Gln Gly Ala Gly Ser Ala
545                 550                 555                 560

Arg Ile Met Asn Ala Ile Lys Ala Asp Ser Leu Val Ser Pro Gly Ser
                565                 570                 575

Tyr Ser Tyr Gly Thr Phe Leu Lys Glu Asn Gly Asn Glu Thr Lys Asn
            580                 585                 590

Glu Thr Phe Thr Ile Glu Asn Gln Ser Ser Ile Arg Lys Ser Tyr Thr
        595                 600                 605

Leu Glu Tyr Ser Phe Asn Gly Ser Gly Ile Ser Thr Ser Gly Thr Ser
    610                 615                 620

Arg Val Val Ile Pro Ala His Gln Thr Gly Lys Ala Thr Ala Lys Val
625                 630                 635                 640

Lys Val Asn Thr Lys Lys Thr Lys Ala Gly Thr Tyr Glu Gly Thr Val
                645                 650                 655

Ile Val Arg Glu Gly Gly Lys Thr Val Ala Lys Val Pro Thr Leu Leu
            660                 665                 670

Ile Val Lys Glu Pro Asp Tyr Pro Arg Val Thr Ser Val Ser Val Ser
        675                 680                 685

Glu Gly Ser Val Gln Gly Thr Tyr Gln Ile Glu Thr Tyr Leu Pro Ala
    690                 695                 700

Gly Ala Glu Glu Leu Ala Phe Leu Val Tyr Asp Ser Asn Leu Asp Phe
705                 710                 715                 720

Ala Gly Gln Ala Gly Ile Tyr Lys Asn Gln Asp Lys Gly Tyr Gln Tyr
                725                 730                 735

Phe Asp Trp Asp Gly Thr Ile Asn Gly Gly Thr Lys Leu Pro Ala Gly
            740                 745                 750

Glu Tyr Tyr Leu Leu Ala Tyr Ala Ala Asn Lys Gly Lys Ser Ser Gln
        755                 760                 765

Val Leu Thr Glu Glu Pro Phe Thr Val Glu
    770                 775


<210> SEQ ID NO 48
<211> LENGTH: 373
<212> TYPE: PRT
<213> ORGANISM: Engyodontium album

<400> SEQUENCE: 48

Met Met Ala Pro Ala Val Glu Gln Arg Ser Glu Ala Ala Pro Leu Ile
1               5                   10                  15

Glu Ala Arg Gly Glu Met Val Ala Asn Lys Tyr Ile Val Lys Phe Lys
            20                  25                  30
```

```
Glu Gly Ser Ala Leu Ser Ala Leu Asp Ala Ala Met Glu Lys Ile Ser
        35                  40                  45

Gly Lys Pro Asp His Val Tyr Lys Asn Val Phe Ser Gly Phe Ala Ala
    50                  55                  60

Thr Leu Asp Glu Asn Met Val Arg Val Leu Arg Ala His Pro Asp Val
65                  70                  75                  80

Glu Tyr Ile Glu Gln Asp Ala Val Val Thr Ile Asn Ala Ala Gln Thr
                85                  90                  95

Asn Ala Pro Trp Gly Leu Ala Arg Ile Ser Ser Thr Ser Pro Gly Thr
            100                 105                 110

Ser Thr Tyr Tyr Tyr Asp Glu Ser Ala Gly Gln Gly Ser Cys Val Tyr
        115                 120                 125

Val Ile Asp Thr Gly Ile Glu Ala Ser His Pro Glu Phe Glu Gly Arg
    130                 135                 140

Ala Gln Met Val Lys Thr Tyr Tyr Tyr Ser Ser Arg Asp Gly Asn Gly
145                 150                 155                 160

His Gly Thr His Cys Ala Gly Thr Val Gly Ser Arg Thr Tyr Gly Val
                165                 170                 175

Ala Lys Lys Thr Gln Leu Phe Gly Val Lys Val Leu Asp Asp Asn Gly
            180                 185                 190

Ser Gly Gln Tyr Ser Thr Ile Ile Ala Gly Met Asp Phe Val Ala Ser
        195                 200                 205

Asp Lys Asn Asn Arg Asn Cys Pro Lys Gly Val Val Ala Ser Leu Ser
    210                 215                 220

Leu Gly Gly Gly Tyr Ser Ser Ser Val Asn Ser Ala Ala Ala Arg Leu
225                 230                 235                 240

Gln Ser Ser Gly Val Met Val Ala Val Ala Ala Gly Asn Asn Asn Ala
                245                 250                 255

Asp Ala Arg Asn Tyr Ser Pro Ala Ser Glu Pro Ser Val Cys Thr Val
            260                 265                 270

Gly Ala Ser Asp Arg Tyr Asp Arg Arg Ser Ser Phe Ser Asn Tyr Gly
        275                 280                 285

Ser Val Leu Asp Ile Phe Gly Pro Gly Thr Ser Ile Leu Ser Thr Trp
    290                 295                 300

Ile Gly Gly Ser Thr Arg Ser Ile Ser Gly Thr Ser Met Ala Thr Pro
305                 310                 315                 320

His Val Ala Gly Leu Ala Ala Tyr Leu Met Thr Leu Gly Lys Thr Thr
                325                 330                 335

Ala Ala Ser Ala Cys Arg Tyr Ile Ala Asp Thr Ala Asn Lys Gly Asp
            340                 345                 350

Leu Ser Asn Ile Pro Phe Gly Thr Val Asn Leu Leu Ala Tyr Asn Asn
        355                 360                 365

Tyr Gln Ala Val Asp
    370
```

<210> SEQ ID NO 49
<211> LENGTH: 24
<212> TYPE: PRT
<213> ORGANISM: Bacillus thuringiensis

<400> SEQUENCE: 49

```
Met Lys Lys Lys Val Leu Ala Leu Ala Ala Ala Ile Thr Leu Val Ala
1               5                   10                  15

Pro Leu Gln Ser Val Ala Phe Ala
            20
```

<210> SEQ ID NO 50
<211> LENGTH: 28
<212> TYPE: PRT
<213> ORGANISM: Bacillus thuringiensis

<400> SEQUENCE: 50

Met Lys Gly Lys Leu Leu Lys Gly Val Leu Ser Leu Gly Val Gly Leu
1 5 10 15

Gly Ala Leu Tyr Ser Gly Thr Ser Ala Gln Ala Glu
20 25

<210> SEQ ID NO 51
<211> LENGTH: 24
<212> TYPE: PRT
<213> ORGANISM: Bacillus cereus

<400> SEQUENCE: 51

Met Lys Lys Lys Val Leu Ala Leu Ala Ala Ala Ile Thr Val Val Ala
1 5 10 15

Pro Leu Gln Ser Val Ala Phe Ala
20

<210> SEQ ID NO 52
<211> LENGTH: 29
<212> TYPE: PRT
<213> ORGANISM: Clostridium perfringens

<400> SEQUENCE: 52

Met Lys Arg Lys Ile Cys Lys Ala Leu Ile Cys Ala Thr Leu Ala Thr
1 5 10 15

Ser Leu Trp Ala Gly Ala Ser Thr Lys Val Tyr Ala Trp
20 25

<210> SEQ ID NO 53
<211> LENGTH: 29
<212> TYPE: PRT
<213> ORGANISM: Streptomyces chromofuscus

<400> SEQUENCE: 53

Met Leu Ala Gly Pro Leu Ala Ala Ala Leu Pro Ala Arg Ala Thr Thr
1 5 10 15

Gly Thr Pro Ala Phe Leu His Gly Val Ala Ser Gly Asp
20 25

<210> SEQ ID NO 54
<211> LENGTH: 31
<212> TYPE: PRT
<213> ORGANISM: Bacillus subtilis

<400> SEQUENCE: 54

Met Lys Phe Val Lys Arg Arg Ile Ile Ala Leu Val Thr Ile Leu Met
1 5 10 15

Leu Ser Val Thr Ser Leu Phe Ala Leu Gln Pro Ser Ala Lys Ala
20 25 30

<210> SEQ ID NO 55
<211> LENGTH: 28
<212> TYPE: PRT
<213> ORGANISM: Caldicellulosiruptor saccharolyticus

<400> SEQUENCE: 55

```
Met Cys Glu Asn Leu Glu Met Leu Asn Leu Ser Leu Ala Lys Thr Tyr
1               5                   10                  15

Lys Asp Tyr Phe Lys Ile Gly Ala Ala Val Thr Ala
            20                  25


<210> SEQ ID NO 56
<211> LENGTH: 28
<212> TYPE: PRT
<213> ORGANISM: Bacillus subtilis

<400> SEQUENCE: 56

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala
            20                  25


<210> SEQ ID NO 57
<211> LENGTH: 26
<212> TYPE: PRT
<213> ORGANISM: Bacillus subtilis

<400> SEQUENCE: 57

Met Arg Lys Lys Cys Ser Val Cys Leu Trp Ile Leu Val Leu Leu Leu
1               5                   10                  15

Ser Cys Leu Ser Gly Lys Ser Ala Tyr Ala
            20                  25


<210> SEQ ID NO 58
<211> LENGTH: 27
<212> TYPE: PRT
<213> ORGANISM: Bacillus stearothermophilus

<400> SEQUENCE: 58

Met Lys Leu Lys Lys Lys Met Leu Thr Leu Leu Leu Thr Ala Ser Met
1               5                   10                  15

Ser Phe Gly Leu Phe Gly Ala Thr Ser Ser Ala
            20                  25


<210> SEQ ID NO 59
<211> LENGTH: 35
<212> TYPE: PRT
<213> ORGANISM: Bacillus subtilis

<400> SEQUENCE: 59

Met Lys Ile Ser Met Gln Lys Ala Asp Phe Trp Lys Lys Ala Ala Ile
1               5                   10                  15

Ser Leu Leu Val Phe Thr Met Phe Phe Thr Leu Met Met Ser Glu Thr
            20                  25                  30

Val Phe Ala
        35


<210> SEQ ID NO 60
<211> LENGTH: 29
<212> TYPE: PRT
<213> ORGANISM: Bacillus subtilis

<400> SEQUENCE: 60

Met Lys Arg Ser Ile Ser Ile Phe Ile Thr Cys Leu Leu Ile Thr Leu
1               5                   10                  15

Leu Thr Met Gly Gly Met Ile Ala Ser Pro Ala Ser Ala
            20                  25
```

<210> SEQ ID NO 61
<211> LENGTH: 28
<212> TYPE: PRT
<213> ORGANISM: Bacillus subtilis

<400> SEQUENCE: 61

```
Met Pro Tyr Leu Lys Arg Val Leu Leu Leu Leu Val Thr Gly Leu Phe
1               5                   10                  15

Met Ser Leu Phe Ala Val Thr Ala Thr Ala Ser Ala
            20                  25
```

<210> SEQ ID NO 62
<211> LENGTH: 38
<212> TYPE: PRT
<213> ORGANISM: Bacillus circulans

<400> SEQUENCE: 62

```
Met Lys Arg Ser Gln Thr Ser Glu Lys Arg Tyr Arg Gln Arg Val Leu
1               5                   10                  15

Ser Leu Phe Leu Ala Val Val Met Leu Ala Ser Ile Gly Leu Leu Pro
            20                  25                  30

Thr Ser Lys Val Gln Ala
        35
```

<210> SEQ ID NO 63
<211> LENGTH: 38
<212> TYPE: PRT
<213> ORGANISM: Bacillus circulans

<400> SEQUENCE: 63

```
Met Lys Pro Ser His Phe Thr Glu Lys Arg Phe Met Lys Lys Val Leu
1               5                   10                  15

Gly Leu Phe Leu Val Val Val Met Leu Ala Ser Val Gly Val Leu Pro
            20                  25                  30

Thr Ser Lys Val Gln Ala
        35
```

<210> SEQ ID NO 64
<211> LENGTH: 28
<212> TYPE: PRT
<213> ORGANISM: Bacillus subtilis

<400> SEQUENCE: 64

```
Met Lys Lys Gly Ile Ile Arg Phe Leu Leu Val Ser Phe Val Leu Phe
1               5                   10                  15

Phe Ala Leu Ser Thr Gly Ile Thr Gly Val Gln Ala
            20                  25
```

<210> SEQ ID NO 65
<211> LENGTH: 32
<212> TYPE: PRT
<213> ORGANISM: Bacillus subtilis

<400> SEQUENCE: 65

```
Met Lys Lys Phe Pro Lys Lys Leu Leu Pro Ile Ala Val Leu Ser Ser
1               5                   10                  15

Ile Ala Phe Ser Ser Leu Ala Ser Gly Ser Val Pro Glu Ala Ser Ala
            20                  25                  30
```

<210> SEQ ID NO 66
<211> LENGTH: 41

-continued

<212> TYPE: PRT
<213> ORGANISM: Bacillus subtilis

<400> SEQUENCE: 66

Met Lys Lys Met Ser Leu Phe Gln Asn Met Lys Ser Lys Leu Leu Pro
1 5 10 15

Ile Ala Ala Val Ser Val Leu Thr Ala Gly Ile Phe Ala Gly Ala Glu
20 25 30

Leu Gln Gln Thr Glu Lys Ala Ser Ala
35 40

<210> SEQ ID NO 67
<211> LENGTH: 26
<212> TYPE: PRT
<213> ORGANISM: Bacillus subtilis

<400> SEQUENCE: 67

Met Lys Val Pro Lys Thr Met Leu Leu Ser Thr Ala Ala Gly Leu Leu
1 5 10 15

Leu Ser Leu Thr Ala Thr Ser Val Ser Ala
20 25

<210> SEQ ID NO 68
<211> LENGTH: 25
<212> TYPE: PRT
<213> ORGANISM: Bacillus subtilis

<400> SEQUENCE: 68

Met Lys Lys Ile Met Ser Ala Phe Val Gly Met Val Leu Leu Thr Ile
1 5 10 15

Phe Cys Phe Ser Pro Gln Ala Ser Ala
20 25

<210> SEQ ID NO 69
<211> LENGTH: 46
<212> TYPE: PRT
<213> ORGANISM: Bacillus thuringiensis

<400> SEQUENCE: 69

Met Pro Leu Asn Ile Ser Phe Ile Leu Lys Gly Glu Met Ala Met Arg
1 5 10 15

Ser Gln Lys Phe Thr Leu Leu Leu Leu Ser Leu Leu Leu Phe Leu Pro
20 25 30

Leu Phe Leu Thr Asn Phe Ile Thr Pro Asn Leu Ala Leu Ala
35 40 45

<210> SEQ ID NO 70
<211> LENGTH: 27
<212> TYPE: PRT
<213> ORGANISM: Bacillus thuringiensis

<400> SEQUENCE: 70

Met Leu Asn Lys Phe Lys Phe Phe Cys Cys Ile Leu Val Met Phe Leu
1 5 10 15

Leu Leu Pro Leu Ser Pro Phe Gln Thr Gln Ala
20 25

<210> SEQ ID NO 71
<211> LENGTH: 43
<212> TYPE: PRT
<213> ORGANISM: Bacillus thuringiensis

<400> SEQUENCE: 71

Met Asn Lys Ile Ile His Leu Asp Asn Phe Leu Tyr Arg Ser Val Asn
1 5 10 15

Met Leu Asn Lys Phe Lys Phe Phe Cys Cys Ile Leu Val Met Phe Leu
20 25 30

Leu Leu Pro Leu Ser Pro Phe Gln Thr Gln Ala
35 40

<210> SEQ ID NO 72
<211> LENGTH: 23
<212> TYPE: PRT
<213> ORGANISM: Bacillus pseudomycoides

<400> SEQUENCE: 72

Met Glu Tyr Lys Pro Leu Ile Met Gly Tyr Leu His Thr Trp Ser Lys
1 5 10 15

Gly Phe Ile Gly Gly Tyr Glu
20

<210> SEQ ID NO 73
<211> LENGTH: 25
<212> TYPE: PRT
<213> ORGANISM: Bacillus thuringiensis

<400> SEQUENCE: 73

Met Lys Lys Lys Val Leu Ala Leu Ala Ala Ala Ile Thr Leu Val Ala
1 5 10 15

Pro Leu Gln Ser Val Ala Phe Ala His
20 25

<210> SEQ ID NO 74
<211> LENGTH: 207
<212> TYPE: PRT
<213> ORGANISM: Bacillus subtilis

<400> SEQUENCE: 74

Ala Tyr Asp Asp Leu His Glu Gly Tyr Ala Thr Tyr Thr Gly Ser Gly
1 5 10 15

Tyr Ser Gly Gly Ala Phe Leu Leu Asp Pro Ile Pro Ser Asp Met Glu
20 25 30

Ile Thr Ala Ile Asn Pro Ala Asp Leu Asn Tyr Gly Gly Val Lys Ala
35 40 45

Ala Leu Ala Gly Ser Tyr Leu Glu Val Glu Gly Pro Lys Gly Lys Thr
50 55 60

Thr Val Tyr Val Thr Asp Leu Tyr Pro Glu Gly Ala Arg Gly Ala Leu
65 70 75 80

Asp Leu Ser Pro Asn Ala Phe Arg Lys Ile Gly Asn Met Lys Asp Gly
85 90 95

Lys Ile Asn Ile Lys Trp Arg Val Val Lys Ala Pro Ile Thr Gly Asn
100 105 110

Phe Thr Tyr Arg Ile Lys Glu Gly Ser Ser Arg Trp Trp Ala Ala Ile
115 120 125

Gln Val Arg Asn His Lys Tyr Pro Val Met Lys Met Glu Tyr Glu Lys
130 135 140

Asp Gly Lys Trp Ile Asn Met Glu Lys Met Asp Tyr Asn His Phe Val
145 150 155 160

Ser Thr Asn Leu Gly Thr Gly Ser Leu Lys Val Arg Met Thr Asp Ile
165 170 175

Arg Gly Lys Val Val Lys Asp Thr Ile Pro Lys Leu Pro Glu Ser Gly
180 185 190

Thr Ser Lys Ala Tyr Thr Val Pro Gly His Val Gln Phe Pro Glu
195 200 205

<210> SEQ ID NO 75
<211> LENGTH: 711
<212> TYPE: DNA
<213> ORGANISM: Bacillus mycoides
<220> FEATURE:
<221> NAME/KEY: misc_feature
<222> LOCATION: (20)..(21)
<223> OTHER INFORMATION: n is a, c, g, or t

<400> SEQUENCE: 75
ggagcacgcc gcgtgagtgn ngaaggcttt cgggtcgtaa aactctgttg ttagggaaga 60
acaagtgcta gttgaataag ctggcacctt gacggtacct aaccagaaag ccacggctaa 120
ctacgtgcca gcagccgcgg taatacgtag gtggcaagcg ttatccggaa ttattgggcg 180
taaagcgcgc gcaggtggtt tcttaagtct gatgtgaaag cccacggctc aaccgtggag 240
ggtcattgga aactgggaga cttgagtgca gaagaggaaa gtggaattcc atgtgtagcg 300
gtgaaatgcg tagagatatg gaggaacacc agtggcgaag gcgactttct ggtctgtaac 360
tgacactgag gcgcgaaagc gtggggagca aacaggatta gataccctgg tagtccacgc 420
cgtaaacgat gagtgctaag tgttagaggg tttccgccct ttagtgctga agttaacgca 480
ttaagcactc cgcctgggga gtacggccgc aaggctgaaa ctcaaaggaa ttgacggggg 540
cccgcacaag cggtggagca tgtggtttaa ttcgaagcaa cgcgaagaac cttaccaggt 600
cttgacatcc tctgaaaact ctagagatag agcttctcct tcgggagcag agtgacaggt 660
ggtgcatggt tgtcgtcagc tcgtgtcgtg agatgttggg ttaagtcccg c 711

<210> SEQ ID NO 76
<211> LENGTH: 719
<212> TYPE: DNA
<213> ORGANISM: Bacillus mycoides
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (640)..(642)
<223> OTHER INFORMATION: n is a, c, g, or t

<400> SEQUENCE: 76
aaagtctgac ggagcacgcc gcgtgagtga tgaaggcttt cgggtcgtaa aactctgttg 60
ttagggaaga acaagtgcta gttgaataag ctggcacctt gacggtacct aaccagaaag 120
ccacggctaa ctacgtgcca gcagccgcgg taatacgtag gtggcaagcg ttatccggaa 180
ttattgggcg taaagcgcgc gcaggtggtt tcttaagtct gatgtgaaag cccacggctc 240
aaccgtggag ggtcattgga aactgggaga cttgagtgca gaagaggaaa gtggaattcc 300
atgtgtagcg gtgaaatgcg tagagatatg gaggaacacc agtggcgaag gcgactttct 360
ggtctgtaac tgacactgag gcgcgaaagc gtggggagca aacaggatta gataccctgg 420
tagtccacgc cgtaaacgat gagtgctaag tgttagaggg tttccgccct ttagtgctga 480
agttaacgca ttaagcactc cgcctgggga gtacggccgc aaggctgaaa ctcaaaggaa 540
ttgacggggg cccgcacaag cggtggagca tgtggtttaa ttcgaagcaa cgcgaagaac 600

```
cttaccaggt cttgacatcc tctgaaaacn ctagagatan nncttctcct tcgggagcag    660

agtgacaggt ggtgcatggt tgtcgtcagc tcgtgtcgtg agatgttggg ttaagtccc     719
```

<210> SEQ ID NO 77
<211> LENGTH: 709
<212> TYPE: DNA
<213> ORGANISM: Bacillus mycoides

<400> SEQUENCE: 77

```
ggagcacgcc gcgtgagtga tgaaggcttt cgggtcgtaa aactctgttg ttagggaaga     60

acaagtgcta gttgaataag ctggcacctt gacggtacct aaccagaaag ccacggctaa    120

ctacgtgcca gcagccgcgg taatacgtag gtggcaagcg ttatccggaa ttattgggcg    180

taaagcgcgc gcaggtggtt tcttaagtct gatgtgaaag cccacggctc aaccgtggag    240

ggtcattgga aactgggaga cttgagtgca gaagaggaaa gtggaattcc atgtgtagcg    300

gtgaaatgcg tagagatatg gaggaacacc agtggcgaag gcgactttct ggtctgtaac    360

tgacactgag gcgcgaaagc gtggggagca aacaggatta gataccctgg tagtccacgc    420

cgtaaacgat gagtgctaag tgttagaggg tttccgccct ttagtgctga agttaacgca    480

ttaagcactc cgcctgggga gtacggccgc aaggctgaaa ctcaaaggaa ttgacggggg    540

cccgcacaag cggtggagca tgtggtttaa ttcgaagcaa cgcgaagaac cttaccaggt    600

cttgacatcc tctgacaacc ctagagatag ggcttcccct tcgggggcag agtgacaggt    660

ggtgcatggt tgtcgtcagc tcgtgtcgtg agatgttggg ttaagtccc                709
```

<210> SEQ ID NO 78
<211> LENGTH: 713
<212> TYPE: DNA
<213> ORGANISM: Bacillus cereus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t

<400> SEQUENCE: 78

```
gganaacgc  cgcgtgagtg angaaggctt tcgggtcgta aaactctgtt gttagggaag     60

aacaagtgct agttgaataa gctggcacct tgacggtacc taaccagaaa gccacggcta    120

actacgtgcc agcagccgcg gtaatacgta ggtggcaagc gttatccgga attattgggc    180

gtaaagcgcg cgcaggtggt ttcttaagtc tgatgtgaaa gcccacggct caaccgtgga    240

gggtcattgg aaactgggag acttgagtgc agaagaggaa agtggaattc catgtgtagc    300

ggtgaaatgc gtagagatat ggaggaacac cagtggcgaa ggcgactttc tggtctgtaa    360

ctgacactga ggcgcgaaag cgtggggagc aaacaggatt agataccctg gtagtccacg    420

ccgtaaacga tgagtgctaa gtgttagagg gtttccgccc tttagtgctg aagttaacgc    480

attaagcact ccgcctgggg agtacggccg caaggctgaa actcaaagga attgacgggg    540

gcccgcacaa gcggtggagc atgtggttta attcgaagca acgcgaagaa ccttaccagg    600

tcttgacatc ctctgaaaac tctagagata gagcttctcc ttcgggagca gagtgacagg    660

tggtgcatgg ttgtcgtcag ctcgtgtcgt gagatgntgg gttaagtccc gca           713
```

<210> SEQ ID NO 79
<211> LENGTH: 686
<212> TYPE: DNA
<213> ORGANISM: Bacillus cereus

<400> SEQUENCE: 79
aaggctttcg ggtcgtaaaa ctctgttgtt agggaagaac aagtgctagt tgaataagct 60
ggcaccttga cggtacctaa ccagaaagcc acggctaact acgtgccagc agccgcggta 120
atacgtaggt ggcaagcgtt atccggaatt attgggcgta aagcgcgcgc aggtggtttc 180
ttaagtctga tgtgaaagcc cacggctcaa ccgtggaggg tcattggaaa ctgggagact 240
tgagtgcaga agaggaaagt ggaattccat gtgtagcggt gaaatgcgta gagatatgga 300
ggaacaccag tggcgaaggc gactttctgg tctgtaactg acactgaggc gcgaaagcgt 360
ggggagcaaa caggattaga taccctggta gtccacgccg taaacgatga gtgctaagtg 420
ttagagggtt tccgcccttt agtgctgaag ttaacgcatt aagcactccg cctggggagt 480
acggccgcaa ggctgaaact caaaggaatt gacgggggcc cgcacaagcg gtggagcatg 540
tggtttaatt cgaagcaacg cgaagaacct taccaggtct tgacatcctc tgaaaaccct 600
agagataggg cttctccttc gggagcagag tgacaggtgg tgcatggttg tcgtcagctc 660
gtgtcgtgag atgttgggtt aagtcc 686

<210> SEQ ID NO 80
<211> LENGTH: 717
<212> TYPE: DNA
<213> ORGANISM: Bacillus mycoides
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 80
gtctgangga ncacgccgcg tgagtgatga aggctttcgg gtcgtaaaac tctgttgtta 60
gggaagaaca agtgctagtt gaataagctg gcaccttgac ggtacctaac cagaaagcca 120
cggctaacta cgtgccagca gccgcggtaa tacgtaggtg gcaagcgtta tccggaatta 180
ttgggcgtaa agcgcgcgca ggtggtttct taagtctgat gtgaaagccc acggctcaac 240
cgtggagggt cattggaaac tgggagactt gagtgcagaa gaggaaagtg gaattccatg 300
tgtagcggtg aaatgcgtag agatatggag gaacaccagt ggcgaaggcg actttctggt 360
ctgtaactga cactgaggcg cgaaagcgtg gggagcaaac aggattagat accctggtag 420
tccacgccgt aaacgatgag tgctaagtgt tagagggttt ccgcccttta gtgctgaagt 480
taacgcatta agcactccgc ctggggagta cggccgcaag gctgaaactc aaaggaattg 540
acgggggccc gcacaagcgg tggagcatgt ggtttaattc gaagcaacgc gaagaacctt 600
accaggtctt gacatcctct gacaacccta gagatagggc ttccccttcg gggcagagt 660 gacaggtggt gcatggttgt cgtcagctcg tgtcgtgaga tgttgggtta agtcccg 717

<210> SEQ ID NO 81
<211> LENGTH: 720
<212> TYPE: DNA
<213> ORGANISM: Bacillus cereus
<220> FEATURE:

<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 81
tntgacggan cacgccgcgt gagtgatgaa ggctttcggg tcgtaaaact ctgttgttag 60
ggaagaacaa gtgctagttg aataagctgg caccttgacg gtacctaacc agaaagccac 120
ggctaactac gtgccagcag ccgcggtaat acgtaggtgg caagcgttat ccggaattat 180
tgggcgtaaa gcgcgcgcag gtggtttctt aagtctgatg tgaaagccca cggctcaacc 240
gtggagggtc attggaaact gggagacttg agtgcagaag aggaaagtgg aattccatgt 300
gtagcggtga aatgcgtaga gatatggagg aacaccagtg gcgaaggcga ctttctggtc 360
tgtaactgac actgaggcgc gaaagcgtgg ggagcaaaca ggattagata ccctggtagt 420
ccacgccgta aacgatgagt gctaagtgtt agagggtttc cgccctttag tgctgaagtt 480
aacgcattaa gcactccgcc tggggagtac ggccgcaagg ctgaaactca aaggaattga 540
cgggggcccg cacaagcggt ggagcatgtg gtttaattcg aagcaacgcg aagaacctta 600
ccaggtcttg acatcctctg aaaaccctag agatagggct tctccttcgg gagcagagtg 660
acaggtggtg catggttgtc gtcagctcgt gtcgtgagat gttgggttaa gtcccgcaac 720

<210> SEQ ID NO 82
<211> LENGTH: 616
<212> TYPE: DNA
<213> ORGANISM: Bacillus thuringiensis
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (79)..(80)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (123)..(124)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (192)..(194)
<223> OTHER INFORMATION: n is a, c, g, or t
<220> FEATURE:
<221> NAME/KEY: misc_feature
<222> LOCATION: (205)..(206)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (385)..(387)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (458)..(459)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (499)..(499)

<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (518)..(518)
<223> OTHER INFORMATION: n is a, c, g, or t
<220> FEATURE:
<221> NAME/KEY: misc_feature
<222> LOCATION: (522)..(523)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (571)..(572)
<223> OTHER INFORMATION: n is a, c, g, or t
<220> FEATURE:
<221> NAME/KEY: misc_feature
<222> LOCATION: (593)..(595)
<223> OTHER INFORMATION: n is a, c, g, or t
<220> FEATURE:
<221> NAME/KEY: misc_feature
<222> LOCATION: (597)..(598)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t

<400> SEQUENCE: 82
ctttcnggnc gnaaaactct gttgttangg aanaacaant gctanttgaa taagctggcg 60
ccttgacggt acctaaccnn aaagccncgg ctaactacgt gccancagcc gcggtaatac 120
gtnngtggca agcgttatcc ggaattattg ggcgtaaagc gcgcgcaggt ggtttcttaa 180
ntctgatgtg annncccacg gctcnnccgt ggagggtcat tggaaactgg ganacttgag 240
tgcagaagag gaaagtggaa ttccatgtgt ancggtgaaa tgcgtanaga tatggangaa 300
cnccagtggc gaangcgact ttctggtctg taactgacac tgaggcgcga aagcgtgggg 360
agcaaacang attanatacc ctggnnntcc acgccgtana cnatgagtgc taagtgttan 420
agggtttccn ccctttagtg ctgaagttaa cgcattannc actccncctg gggagtacgg 480
ccgcaaggct gaaactcana ggaattgacn ggngcccnca cnngcggtgg agcatgtggt 540
ttaattcnaa gcaacncnaa naaccttacc nngtcttgac atcctctgaa aannntnnag 600
atagggcttc tccntc 616

<210> SEQ ID NO 83
<211> LENGTH: 703
<212> TYPE: DNA
<213> ORGANISM: Bacillus cereus
<220> FEATURE:
<221> NAME/KEY: misc_feature
<222> LOCATION: (701)..(701)
<223> OTHER INFORMATION: n is a, c, g, or t

<400> SEQUENCE: 83
cacgccgcgt gagtgatgaa ggctttcggg tcgtaaaact ctgttgttag ggaagaacaa 60
gtgctagttg aataagctgg caccttgacg gtacctaacc agaaagccac ggctaactac 120
gtgccagcag ccgcggtaat acgtaggtgg caagcgttat ccggaattat tgggcgtaaa 180
gcgcgcgcag gtggtttctt aagtctgatg tgaaagccca cggctcaacc gtggagggtc 240
attggaaact gggagacttg agtgcagaag aggaaagtgg aattccatgt gtagcggtga 300
aatgcgtaga gatatggagg aacaccagtg gcgaaggcga ctttctggtc tgtaactgac 360
actgaggcgc gaaagcgtgg ggagcaaaca ggattagata ccctggtagt ccacgccgta 420
aacgatgagt gctaagtgtt agagggtttc cgccctttag tgctgaagtt aacgcattaa 480
gcactccgcc tggggagtac ggccgcaagg ctgaaactca aaggaattga cgggggcccg 540
cacaagcggt ggagcatgtg gtttaattcg aagcaacgcg aagaacctta ccaggtcttg 600
acatcctctg aaaaccctag agatagggct tctccttcgg gagcagagtg acaggtggtg 660
catggttgtc gtcagctcgt gtcgtgagat gttgggttaa ntc 703

<210> SEQ ID NO 84
<211> LENGTH: 717
<212> TYPE: DNA
<213> ORGANISM: Bacillus thuringiensis
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 84
ctganggnnc aacgccgcgt gagtgatgaa ggctttcggg tcgtaaaact ctgttgttag 60
ggaagaacaa gtgctagttg aataagctgg caccttgacg gtacctaacc agaaagccac 120
ggctaactac gtgccagcag ccgcggtaat acgtaggtgg caagcgttat ccggaattat 180
tgggcgtaaa gcgcgcgcag gtggtttctt aagtctgatg tgaaagccca cggctcaacc 240
gtggagggtc attggaaact gggagacttg agtgcagaag aggaaagtgg aattccatgt 300
gtagcggtga aatgcgtaga gatatggagg aacaccagtg gcgaaggcga ctttctggtc 360
tgtaactgac actgaggcgc gaaagcgtgg ggagcaaaca ggattagata ccctggtagt 420
ccacgccgta aacgatgagt gctaagtgtt agagggtttc cgccctttag tgctgaagtt 480
aacgcattaa gcactccgcc tggggagtac ggccgcaagg ctgaaactca aaggaattga 540
cgggggcccg cacaagcggt ggagcatgtg gtttaattcg aagcaacgcg aagaacctta 600
ccaggtcttg acatcctctg aaaaccctag agatagggct tctccttcgg gagcagagtg 660
acaggtggtg catggttgtc gtcagctcgt gtcgtgagat gttgggttaa gtcccgc 717

<210> SEQ ID NO 85
<211> LENGTH: 712
<212> TYPE: DNA
<213> ORGANISM: Bacillus megaterium
<220> FEATURE:
<221> NAME/KEY: misc_feature
<222> LOCATION: (4)..(4)

<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t

<400> SEQUENCE: 85
ggancacgcc gcgtgagtga tgaaggcttt cgggtcgtaa aactctgttg ttagggaaga 60
acaagtacna gagtaactgc tngtaccttg acggtaccta accagaaagc cacggctaac 120
tacgtgccag cagccgcggt aatacgtagg tggcaagcgt tatccggaat tattgggcgt 180
aaagcgcgcg caggcggttt cttaagtctg atgtgaaagc ccacggctca accgtggagg 240
gtcattggaa actggggaac ttgagtgcag aagagaaaag cggaattcca cgtgtagcgg 300
tgaaatgcgt agagatgtgg aggaacacca gtggcgaagg cggctttttg gtctgtaact 360
gacgctgagg cgcgaaagcg tggggagcaa acaggattag ataccctggt agtccacgcc 420
gtaaacgatg agtgctaagt gttagagggt ttccgccctt tagtgctgca gctaacgcat 480
taagcactcc gcctggggag tacggtcgca agactgaaac tcaaaggaat tgacgggggc 540
ccgcacaagc ggtggagcat gtggtttaat tcgaagcaac gcgaagaacc ttaccaggtc 600
ttgacatcct ctgacaactc tagagataga gcgttcccct tcgggggaca gagtgacagg 660
tggtgcatgg ttgtcgtcag ctcgtgtcgt gagatgttgg gttaagtccc gc 712

<210> SEQ ID NO 86
<211> LENGTH: 714
<212> TYPE: DNA
<213> ORGANISM: Bacillus sp.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (16)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t

<400> SEQUENCE: 86
ggancacgcc gcgtgnnnng nngaaggttt tcggatcgta aagctctgtt gttagggaag 60
aacaagtgca agagtaactg cttgcacctt gacggtacct aaccagaaag ccacggctaa 120
ctacgtgcca gcagccgcgg taatacgtag gtggcaagcg ttgtccggaa ttattgggcg 180
taaagggctc gcaggcggtt tcttaagtct gatgtgaaag cccccggctc aaccggggag 240
ggtcattgga aactgggaaa cttgagtgca gaagaggaga gtggaattcc acgtgtagcg 300
gtgaaatgcg tagagatgtg gaggaacacc agtggcgaag gcgactctct ggtctgtaac 360
tgacgctgag gagcgaaagc gtggggagcg aacaggatta gataccctgg tagtccacgc 420
cgtaaacgat gagtgctaag tgttaggggg tttccgcccc ttagtgctgc agctaacgca 480
ttaagcactc cgcctgggga gtacggtcgc aagactgaaa ctcaaaggaa ttgacggggg 540
cccgcacaag cggtggagca tgtggtttaa ttcgaagcaa cgcgaagaac cttaccaggt 600
cttgacatcc tctgacaacc ctagagatag ggctttccct tcggggacag agtgacaggt 660
ggtgcatggt tgtcgtcagc tcgtgtcgtg agatgttggg ttaagtcccg caac 714

<210> SEQ ID NO 87
<211> LENGTH: 718
<212> TYPE: DNA
<213> ORGANISM: Bacillus circulans
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 87
aagtctgang gancacgccg cgtgagtgat gaaggttttc ggatcgtaaa actctgttgt 60
tagggaagaa caagtacaag agtaactgct tgtaccttga cggtacctaa ccagaaagcc 120
acggctaact acgtgccagc agccgcggta atacgtaggt ggcaagcgtt gtccggaatt 180
attgggcgta aagcgcgcgc aggcggtcct ttaagtctga tgtgaaagcc cacggctcaa 240
ccgtggaggg tcattggaaa ctgggggact tgagtgcaga agagaagagt ggaattccac 300
gtgtagcggt gaaatgcgta gagatgtgga ggaacaccag tggcgaaggc gactctttgg 360
tctgtaactg acgctgaggc gcgaaagcgt ggggagcaaa caggattaga taccctggta 420
gtccacgccg taaacgatga gtgctaagtg ttagagggtt tccgcccttt agtgctgcag 480
caaacgcatt aagcactccg cctggggagt acggccgcaa ggctgaaact caaaggaatt 540
gacgggggcc cgcacaagcg gtggagcatg tggtttaatt cgaagcaacg cgaagaacct 600
taccaggtct tgacatcctc tgacactcct agagatagga cgttcccctt cgggggacag 660
agtgacaggt ggtgcatggt tgtcgtcagc tcgtgtcgtg agatgttggg ttaagtcc 718

<210> SEQ ID NO 88
<211> LENGTH: 718
<212> TYPE: DNA
<213> ORGANISM: Bacillus subtilis
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 88
gtctgnngga ncacgccgcg tgagtgatga aggttttcgg atcgtaaagc tctgttgtta 60
gggaagaaca agtaccgttc gaatagggcg gtaccttgac ggtacctaac cagaaagcca 120
cggctaacta cgtgccagca gccgcggtaa tacgtaggtg gcaagcgttg tccggaatta 180
ttgggcgtaa agggctcgca ggcggtttct taagtctgat gtgaaagccc ccggctcaac 240
cggggagggt cattggaaac tggggaactt gagtgcagaa gaggagagtg gaattccacg 300
tgtagcggtg aaatgcgtag agatgtggag gaacaccagt ggcgaaggcg actctctggt 360
ctgtaactga cgctgaggag cgaaagcgtg gggagcgaac aggattagat accctggtag 420
tccacgccgt aaacgatgag tgctaagtgt tagggggttt ccgcccctta gtgctgcagc 480
taacgcatta agcactccgc ctggggagta cggtcgcaag actgaaactc aaaggaattg 540
acgggggccc gcacaagcgg tggagcatgt ggtttaattc gaagcaacgc gaagaacctt 600
accaggtctt gacatcctct gacaatccta gagataggac gtccccttcg gggcagagt 660 gacaggtggt gcatggttgt cgtcagctcg tgtcgtgaga tgttgggtta agtcccgc 718

<210> SEQ ID NO 89
<211> LENGTH: 713
<212> TYPE: DNA
<213> ORGANISM: Lysinibacillus fusiformis
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t

<400> SEQUENCE: 89
ctgatggagc acgccgcgtg agtgaagaag gatttcggtt cgtaaaactc tgttgtaagg 60
gaagaacaag tacagtagta actggctgta ccttgacggt accttattag aaagccacgg 120
ctaactacgt gccagcagcc gcggtaatac gtaggtggca agcgttgtcc ggaattattg 180
ggcgtaaagc gcgcgcaggt ggtttcttaa gtctgatgtg aaagcccacg gctcaaccgt 240
ggagggtcat tggaaactgg gagacttgag tgcagaagag gatagtggaa ttccaagtgt 300
agcggtgaaa tgcgtagaga tttggaggaa caccagtggc gaaggcgact atctggtctg 360
taactgacac tgaggcgcga aagcgtgggg agcaaacagg attagatacc ctggtagtcc 420
acgccgtaaa cgatgagtgc taagtgttag gggtttccg cccttagtg ctgcagctaa 480 cgcattaagc actccgcctg gggagtacgg tcgcaagact gaaactcaaa ggaattgacg 540
ggggcccgca caagcggtgg agcatgtggt ttaattcgaa gcaacgcgaa gaaccttacc 600
aggtcttgac atcccgttga ccactgtaga gatatggttt ccccttcggg ggcaacggtg 660
acaggtggtg catggttgtc gtcagctcgt gtcgtgagat gntgggttaa ntc 713

<210> SEQ ID NO 90
<211> LENGTH: 715
<212> TYPE: DNA
<213> ORGANISM: Lysinibacillus sphaericus
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t

<400> SEQUENCE: 90
ctgatggagc ancgccgcgt gagtgaagaa ggttttcgga tcgtaaaact ctgttgtaag 60
ggaagaacaa gtacagtagt aactggctgt accttgacgg taccttatta gaaagccacg 120
gctaactacg tgccagcagc cgcggtaata cgtaggtggc aagcgttgtc cggaattatt 180
gggcgtaaag cgcgcgcagg cggtccttta agtctgatgt gaaagcccac ggctcaaccg 240
tggagggtca ttggaaactg gggacttga gtgcagaaga ggaaagtgga attccaagtg 300
tagcggtgaa atgcgtagag atttggagga acaccagtgg cgaaggcgac tttctggtct 360
gtaactgacg ctgaggcgcg aaagcgtggg gagcaaacag gattagatac cctggtagtc 420
cacgccgtaa acgatgagtg ctaagtgtta gggggtttcc gcccttagt gctgcagcta 480 acgcattaag cactccgcct ggggagtacg gtcgcaagac tgaaactcaa aggaattgac 540
gggggcccgc acaagcggtg gagcatgtgg tttaattcga agcaacgcga agaaccttac 600
caggtcttga catcccgttg accactgtag agatatagtt tccccttcgg gggcaacggt 660
gacaggtggt gcatggttgt cgtcagctcg tgtcgtgaga tgtngggtta antcc 715

<210> SEQ ID NO 91
<211> LENGTH: 717
<212> TYPE: DNA
<213> ORGANISM: Bacillus aryabhattai
<220> FEATURE:
<221> NAME/KEY: misc_feature
<222> LOCATION: (3)..(4)
<223> OTHER INFORMATION: n is a, c, g, or t

<400> SEQUENCE: 91
ggnncaacgc cgcgtgagtg atgaaggctt tcgggtcgta aaactctgtt gttagggaag 60
aacaagtacg agagtaactg ctcgtacctt gacggtacct aaccagaaag ccacggctaa 120
ctacgtgcca gcagccgcgg taatacgtag gtggcaagcg ttatccggaa ttattgggcg 180
taaagcgcgc gcaggcggtt tcttaagtct gatgtgaaag cccacggctc aaccgtggag 240
ggtcattgga aactggggaa cttgagtgca gaagagaaaa gcggaattcc acgtgtagcg 300
gtgaaatgcg tagagatgtg gaggaacacc agtggcgaag gcggcttttt ggtctgtaac 360
tgacgctgag gcgcgaaagc gtggggagca aacaggatta gataccctgg tagtccacgc 420
cgtaaacgat gagtgctaag tgttagaggg tttccgccct ttagtgctgc agctaacgca 480
ttaagcactc cgcctgggga gtacggtcgc aagactgaaa ctcaaaggaa ttgacggggg 540
cccgcacaag cggtggagca tgtggtttaa ttcgaagcaa cgcgaagaac cttaccaggt 600
cttgacatcc tctgacaact ctagagatag agcgttcccc ttcgggggac agagtgacag 660
gtggtgcatg gttgtcgtca gctcgtgtcg tgagatgttg ggttaagtcc cgcaacg 717

<210> SEQ ID NO 92
<211> LENGTH: 718
<212> TYPE: DNA
<213> ORGANISM: Bacillus aryabhattai
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 92
tctganggnn cacgccgcgt gagtgatgaa ggctttcggg tcgtaaaact ctgttgttag 60
ggaagaacaa gtacgagagt aactgctcgt accttgacgg tacctaacca gaaagccacg 120
gctaactacg tgccagcagc cgcggtaata cgtaggtggc aagcgttatc cggaattatt 180
gggcgtaaag cgcgcgcagg cggtttctta agtctgatgt gaaagcccac ggctcaaccg 240
tggagggtca ttggaaactg gggaacttga gtgcagaaga gaaaagcgga attccacgtg 300
tagcggtgaa atgcgtagag atgtggagga acaccagtgg cgaaggcggc tttttggtct 360
gtaactgacg ctgaggcgcg aaagcgtggg gagcaaacag gattagatac cctggtagtc 420
cacgccgtaa acgatgagtg ctaagtgtta gagggtttcc gccctttagt gctgcagcta 480
acgcattaag cactccgcct ggggagtacg gtcgcaagac tgaaactcaa aggaattgac 540
gggggcccgc acaagcggtg gagcatgtgg tttaattcga agcaacgcga agaaccttac 600

```
caggtcttga catcctctga caactctaga gatagagcgt tccccttcgg gggacagagt    660

gacaggtggt gcatggttgt cgtcagctcg tgtcgtgaga tgttgggtta agtcccgc      718


<210> SEQ ID NO 93
<211> LENGTH: 716
<212> TYPE: DNA
<213> ORGANISM: Bacillus flexus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 93

ggancaacgc cgcgtgagtg angaaggctt tcgggtcgta aaactctgtt gttagggaag     60

aacaagtaca agagtaactg cttgtacctt gacggtacct aaccagaaag ccacggctaa    120

ctacgtgcca gcagccgcgg taatacgtag gtggcaagcg ttatccggaa ttattgggcg    180

taaagcgcgc gcaggcggtt tcttaagtct gatgtgaaag cccacggctc aaccgtggag    240

ggtcattgga aactggggaa cttgagtgca gaagagaaaa gcggaattcc acgtgtagcg    300

gtgaaatgcg tagagatgtg gaggaacacc agtggcgaag gcggcttttt ggtctgtaac    360

tgacgctgag gcgcgaaagc gtggggagca aacaggatta gataccctgg tagtccacgc    420

cgtaaacgat gagtgctaag tgttagaggg tttccgccct ttagtgctgc agctaacgca    480

ttaagcactc cgcctgggga gtacggtcgc aagactgaaa ctcaaaggaa ttgacggggg    540

cccgcacaag cggtggagca tgtggtttaa ttcgaagcaa cgcgaagaac cttaccaggt    600

cttgacatcc tctgacaact ctagagatag agcgttcccc ttcgggggac agagtgacag    660

gtggtgcatg gttgtcgtca gctcgtgtcg tgagatgttg ggttaagtcc cgcaac        716


<210> SEQ ID NO 94
<211> LENGTH: 676
<212> TYPE: DNA
<213> ORGANISM: Paracoccus kondratievae
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 94

gccgcgtgag tgnnnaagnc cctagggttg taaagctctt tcanctggga agataatgac     60

tgtaccagca gaagaagccc cggctaactc cgtgccagca gccgcggtaa tacggagggg    120

gctagcgttg ttcggaatta ctgggcgtaa agcgcacgta ggcggaccgg aaagttgggg    180

gtgaaatccc ggggctcaac cccggaactg ccttcaaaac tatcggtctg gagttcgaga    240

gaggtgagtg gaattccgag tgtagaggtg aaattcgtag atattcggag gaacaccagt    300

ggcgaaggcg gctcactggc tcgatactga cgctgaggtg cgaaagcgtg gggagcaaac    360

aggattagat accctggtag tccacgccgt aaacgatgaa tgccagtcgt cgggcagcat    420

gctgttcggt gacacaccta acggattaag cattccgcct ggggagtacg gtcgcaagat    480
```

taaaactcaa aggaattgac gggggcccgc acaagcggtg gagcatgtgg tttaattcga 540
agcaacgcgc agaaccttac caacccttga catcccagga cagcccgaga gatcgggtct 600
ccacttcggt ggcctggaga caggtgctgc atggctgtcg tcagctcgtg tcgtgagatg 660
ttcggttaag tccggc 676

<210> SEQ ID NO 95
<211> LENGTH: 728
<212> TYPE: DNA
<213> ORGANISM: Enterobacter cloacae
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (719)..(719)
<223> OTHER INFORMATION: n is a, c, g, or t
<220> FEATURE:
<221> NAME/KEY: misc_feature
<222> LOCATION: (721)..(722)
<223> OTHER INFORMATION: n is a, c, g, or t

<400> SEQUENCE: 95
ctgnngcagc cntgccgcgt gtatgaagaa ggncttcggg ttgtaaagta ctttcagcgg 60
ggaggaaggt gttgtggtta ataaccacag caattgacgt tacccgcaga agaagcaccg 120
gctaactccg tgccagcagc cgcggtaata cggagggtgc aagcgttaat cggaattact 180
gggcgtaaag cgcacgcagg cggtctgtca agtcggatgt gaaatccccg ggctcaacct 240
gggaactgca ttcgaaactg gcaggctaga gtcttgtaga ggggggtaga attccaggtg 300
tagcggtgaa atgcgtagag atctggagga ataccggtgg cgaaggcggc cccctggaca 360
aagactgacg ctcaggtgcg aaagcgtggg gagcaaacag gattagatac cctggtagtc 420
cacgccgtaa acgatgtcga tttggaggtt gtgcccttga ggcgtggctt ccggagctaa 480
cgcgttaaat cgaccgcctg gggagtacgg ccgcaaggtt aaaactcaaa tgaattgacg 540
ggggcccgca caagcggtgg agcatgtggt ttaattcgat gcaacgcgaa gaaccttacc 600
tggtcttgac atccacagaa ctttccagag atggattggt gccttcggga actgtgagac 660
aggtgctgca tggctgtcgt cagctcgtgt tgtgaaatgt tgggttaagt cccgcaacna 720 nncgcaac 728

<210> SEQ ID NO 96
<211> LENGTH: 717
<212> TYPE: DNA
<213> ORGANISM: Bacillus nealsonii
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 96

```
tgnngganca acgccgcgtg agtgatgaag gttttcggat cgtaaaactc tgttgttagg     60

gaagaacaag tacgagagta actgctcgta ccttgacggt acctaaccag aaagccacgg    120

ctaactacgt gccagcagcc gcggtaatac gtaggtggca agcgttgtcc ggaattattg    180

ggcgtaaagc gcgcgcaggc ggtcctttaa gtctgatgtg aaagcccacg gctcaaccgt    240

ggagggtcat tggaaactgg gggacttgag tgcagaagag aagagtggaa ttccacgtgt    300

agcggtgaaa tgcgtagaga tgtggaggaa caccagtggc gaaggcgact ctttggtctg    360

taactgacgc tgaggcgcga aagcgtgggg agcaaacagg attagatacc ctggtagtcc    420

acgccgtaaa cgatgagtgc taagtgttag agggtttccg ccctttagtg ctgcagcaaa    480

cgcattaagc actccgcctg gggagtacgg ccgcaaggct gaaactcaaa ggaattgacg    540

ggggcccgca caagcggtgg agcatgtggt ttaattcgaa gcaacgcgaa gaaccttacc    600

aggtcttgac atctcctgac aatcctagag ataggacgtt ccccttcggg ggacaggatg    660

acaggtggtg catggttgtc gtcagctcgt gtcgtgagat gttgggttaa gtcccgc       717
```

<210> SEQ ID NO 97
<211> LENGTH: 702
<212> TYPE: DNA
<213> ORGANISM: Bacillus subtilis

<400> SEQUENCE: 97

```
cgccgcgtga gtgatgaagg ttttcggatc gtaaagctct gttgttaggg aagaacaagt     60

gccgttcaaa tagggcggca ccttgacggt acctaaccag aaagccacgg ctaactacgt    120

gccagcagcc gcggtaatac gtaggtggca agcgttgtcc ggaattattg ggcgtaaagg    180

gctcgcaggc ggtttcttaa gtctgatgtg aaagcccccg gctcaaccgg ggagggtcat    240

tggaaactgg ggaacttgag tgcagaagag gagagtggaa ttccacgtgt agcggtgaaa    300

tgcgtagaga tgtggaggaa caccagtggc gaaggcgact ctctggtctg taactgacgc    360

tgaggagcga aagcgtgggg agcgaacagg attagatacc ctggtagtcc acgccgtaaa    420

cgatgagtgc taagtgttag ggggtttccg ccccttagtg ctgcagctaa cgcattaagc    480

actccgcctg gggagtacgg tcgcaagact gaaactcaaa ggaattgacg ggggcccgca    540

caagcggtgg agcatgtggt ttaattcgaa gcaacgcgaa gaaccttacc aggtcttgac    600

atcctctgac aatcctagag ataggacgtc cccttcgggg gcagagtgac aggtggtgca    660

tggttgtcgt cagctcgtgt cgtgagatgt tgggttaagt cc                       702
```

<210> SEQ ID NO 98
<211> LENGTH: 680
<212> TYPE: DNA
<213> ORGANISM: Alcaligenes faecalis
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (262)..(264)
<223> OTHER INFORMATION: n is a, c, g, or t
<220> FEATURE:
<221> NAME/KEY: misc_feature
<222> LOCATION: (272)..(273)
<223> OTHER INFORMATION: n is a, c, g, or t

<400> SEQUENCE: 98

```
cttcgggttg taaagtactt ttggcagaga agaaaaggta tctcctaata cgagatactg     60

ctgacggtat ctgcagaata agcaccggct aactacgtgc cancagccgc ggtaatacgt    120
```

```
agggtgcaag cgttaatcgg aattactggg cgtaaagcgt gtgtaggcgg ttcggaaaga    180

aagatgtgaa atcccagggc tcaaccttgg aactgcattt ttaactgccg agctagagta    240

tgtcagaggg gggtagaatt cnnntgtagc anngaaatgc gtagatatgt ggaggaatac    300

cgatggcgaa ggcagccccc tgggataata ctgacgctca gacacgaaag cgtggggagc    360

aaacaggatt agataccctg gtagtccacg ccctaaacga tgtcaactag ctgttggggc    420

cgttaggcct tagtagcgca gctaacgcgt gaagttgacc gcctggggag tacggtcgca    480

agattaaaac tcaaaggaat tgacggggac ccgcacaagc ggtggatgat gtggattaat    540

tcgatgcaac gcgaaaaacc ttacctaccc ttgacatgtc tggaaagccg aagagatttg    600

gccgtgctcg caagagaacc ggaacacagg tgctgcatgg ctgtcgtcag ctcgtgtcgt    660

gagatgttgg gttaagtccc                                                680
```

<210> SEQ ID NO 99
<211> LENGTH: 640
<212> TYPE: DNA
<213> ORGANISM: Paenibacillus massiliensis
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (13)..(17)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:

-continued

<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (189)..(190)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (210)..(211)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (344)..(344)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (364)..(365)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (417)..(418)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (443)..(444)
<223> OTHER INFORMATION: n is a, c, g, or t
<220> FEATURE:
<221> NAME/KEY: misc_feature
<222> LOCATION: (446)..(446)

<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (471)..(472)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (490)..(490)
<223> OTHER INFORMATION: n is a, c, g, or t
<220> FEATURE:
<221> NAME/KEY: misc_feature
<222> LOCATION: (492)..(496)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t
<220> FEATURE:
<221> NAME/KEY: misc_feature
<222> LOCATION: (509)..(509)
<223> OTHER INFORMATION: n is a, c, g, or t
<220> FEATURE:
<221> NAME/KEY: misc_feature
<222> LOCATION: (516)..(517)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (562)..(562)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (571)..(572)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(598)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (607)..(608)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (637)..(640)
<223> OTHER INFORMATION: n is a, c, g, or t

<400> SEQUENCE: 99
cttanngnnt gannnnnctt gnnaanaaag ccccggctaa ctacntgcca ncanccgcgg 60
taatacntan ggngcaagcg ttgtccggaa ttattgggcg taaagcgcgc gcaggcggtc 120
ntttaagtct ggtgtttaag cccggggctc aaccccggat cncncgggaa actggatgac 180
ttgantgcnn aanaagagag tggaattccn ngtgtancgg tgaaatgcnt ananatgtgn 240
angaacacca ntggcnaang cnactctctg ggctgtaact gacnctgang cncgaaagcg 300
tggggagcaa acangattan ataccctggt antccacgcc ntanacnatn antgctaggt 360
gttnngggtt tcnataccct tgntgccnaa nttaacacat taancactcc gcctggnnan 420
tacngtcnca anantgaaac tcnnangaan tgacngggac ccgcacaagc nntgnantat 480
gtggtttaan tnnnnncaac ncnaanaanc ttaccnngnc ttgacatctn aatgaccngn 540
gcananatgt ncctttcctt cngnacattc nngacaggtg gtgcatggnt gtcntcnnct 600
cntgtcnngn gatgttgggt taantccccg cancnannnn 640

<210> SEQ ID NO 100
<211> LENGTH: 678
<212> TYPE: DNA

<213> ORGANISM: Bacillus subtilis
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t

<400> SEQUENCE: 100
aagctctgtt gttagggaag aacaagtacc gttcgaatag ggcggtacct tgacggtacc 60
taaccagaaa gccacggcta actacgtgcc agcagccgcg gtaatacgta ggtggcaagc 120
gttgtccgga attattgggc gtaaagggct cgcaggcggt ttcttaagtc tgatgtgaaa 180
gcccccggct caaccgggga gggtcattgg aaactgggga acttgagtgc agaagaggag 240
agtggaattc cacgtgtagc ggtgaaatgc gtagagatgt ggaggaacac cagtggcgaa 300
ggcgactctc tggtctgtaa ctgacgctga ggagcgaaag cgtggggagc gaacaggatt 360
agataccctg gtagtccacg ccgtaaacga tgagtgctaa gtgttagggg gtttccgccc 420
cttantgctg cagctaacgc attaagcact ccgcctgggg agtacggtcg caagactgaa 480
actcaaagga attgacgggg gcccgcacaa gcggtggagc atgtggttta attcgaagca 540
acgcgaanaa ccttaccagg tcttgacatc ctctgacaat cctagagata ggacgtcccc 600
ttcgggggca gagtgacagg tggtgcatgg ttgtcgtcan ctcgtgtcgt gagatgttgg 660
nttaagtccc gcaacgag 678

<210> SEQ ID NO 101
<211> LENGTH: 743
<212> TYPE: DNA
<213> ORGANISM: Bacillus megaterium
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (689)..(691)
<223> OTHER INFORMATION: n is a, c, g, or t
<220> FEATURE:
<221> NAME/KEY: misc_feature
<222> LOCATION: (693)..(708)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (716)..(717)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (729)..(730)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (740)..(741)
<223> OTHER INFORMATION: n is a, c, g, or t

<400> SEQUENCE: 101

```
aagnctttcg gnncgtaaaa ctctgttgtt agggaagaac aagtacgaga gtaactgctc     60

gtaccttgac ggtacctaac cagaaagcca cggctaacta cgtgccagca gccgcggtaa    120

tacgtaggtg gcaagcgtta tccggaatta ttgggcgtaa agcgcgcgca ggcggtttct    180

taagtctgat gtgaaagccc acggctcaac cgtggagggt cattggaaac tggggaactt    240

gagtgcagaa gagaaaagcg gaattccacg tgtagcggtg aaatgcgtag agatgtggag    300

gaacaccagt ggcgaaggcg gctttttggt ctgtaactga cgctgaggcg cgaaagcgtg    360

gggagcaaac aggattagat accctggtag tccacgccgt aaacgatgag tgctaagtgt    420

tagagggttt ccgcccttta gtgctgcagc taacgcatta agcactccgc ctggggagta    480

cggtcgcaag actgaaactc aaaggaattg acgggggccc gcacaagcgg tggagcatgt    540

ggtttaattc gaagcaacgc gaagaacctt accaggtctt gacatcctct gacaactcta    600

gagatagagc gttccccttc gggggacaga gtgacaggtg gtgcatggtt gtcgtcagct    660

cgtgtcgtga gatgttgggt taagtcccnn ncnnnnnnnn nnnnnnnntc tnaganncgn    720

gctgacnann ccangcaccn ngg                                            743
```

<210> SEQ ID NO 102
<211> LENGTH: 980
<212> TYPE: DNA
<213> ORGANISM: Bacillus thuringiensis
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (729)..(730)
<223> OTHER INFORMATION: n is a, c, g, or t
<220> FEATURE:
<221> NAME/KEY: misc_feature
<222> LOCATION: (746)..(747)
<223> OTHER INFORMATION: n is a, c, g, or t
<220> FEATURE:
<221> NAME/KEY: misc_feature
<222> LOCATION: (749)..(750)
<223> OTHER INFORMATION: n is a, c, g, or t
<220> FEATURE:
<221> NAME/KEY: misc_feature
<222> LOCATION: (775)..(776)
<223> OTHER INFORMATION: n is a, c, g, or t
<220> FEATURE:
<221> NAME/KEY: misc_feature
<222> LOCATION: (785)..(786)
<223> OTHER INFORMATION: n is a, c, g, or t
<220> FEATURE:
<221> NAME/KEY: misc_feature
<222> LOCATION: (812)..(816)
<223> OTHER INFORMATION: n is a, c, g, or t
<220> FEATURE:
<221> NAME/KEY: misc_feature
<222> LOCATION: (835)..(837)

-continued

<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (846)..(847)
<223> OTHER INFORMATION: n is a, c, g, or t
<220> FEATURE:
<221> NAME/KEY: misc_feature
<222> LOCATION: (851)..(853)
<223> OTHER INFORMATION: n is a, c, g, or t
<220> FEATURE:
<221> NAME/KEY: misc_feature
<222> LOCATION: (884)..(890)
<223> OTHER INFORMATION: n is a, c, g, or t
<220> FEATURE:
<221> NAME/KEY: misc_feature
<222> LOCATION: (893)..(893)
<223> OTHER INFORMATION: n is a, c, g, or t
<220> FEATURE:
<221> NAME/KEY: misc_feature
<222> LOCATION: (896)..(897)
<223> OTHER INFORMATION: n is a, c, g, or t
<220> FEATURE:
<221> NAME/KEY: misc_feature
<222> LOCATION: (902)..(902)
<223> OTHER INFORMATION: n is a, c, g, or t
<220> FEATURE:
<221> NAME/KEY: misc_feature
<222> LOCATION: (907)..(907)
<223> OTHER INFORMATION: n is a, c, g, or t
<220> FEATURE:
<221> NAME/KEY: misc_feature
<222> LOCATION: (911)..(912)
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
<220> FEATURE:
<221> NAME/KEY: misc_feature
<222> LOCATION: (923)..(925)
<223> OTHER INFORMATION: n is a, c, g, or t
<220> FEATURE:
<221> NAME/KEY: misc_feature
<222> LOCATION: (931)..(931)
<223> OTHER INFORMATION: n is a, c, g, or t
<220> FEATURE:
<221> NAME/KEY: misc_feature
<222> LOCATION: (937)..(939)
<223> OTHER INFORMATION: n is a, c, g, or t
<220> FEATURE:
<221> NAME/KEY: misc_feature
<222> LOCATION: (942)..(944)
<223> OTHER INFORMATION: n is a, c, g, or t
<220> FEATURE:
<221> NAME/KEY: misc_feature
<222> LOCATION: (946)..(950)
<223> OTHER INFORMATION: n is a, c, g, or t
<220> FEATURE:
<221> NAME/KEY: misc_feature
<222> LOCATION: (952)..(954)
<223> OTHER INFORMATION: n is a, c, g, or t
<220> FEATURE:
<221> NAME/KEY: misc_feature
<222> LOCATION: (956)..(956)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t

<400> SEQUENCE: 102

```
tggacgaagt ctgacgganc acgccgcgtg agtgatgaag gctttcgggt cgtaaaactc     60

tgttgttagg gaagaacaag tgctagttga ataagctggc accttgacgg tacctaacca    120

gaaagccacg gctaactacg tgccagcagc cgcggtaata cgtaggtggc aagcgttatc    180

cggaattatt gggcgtaaag cgcgcgcagg tggtttctta agtctgatgt gaaagcccac    240

ggctcaaccg tggagggtca ttggaaactg ggagacttga gtgcagaaga ggaaagtgga    300

attccatgtg tagcggtgaa atgcgtagag atatggagga acaccagtgg cgaaggcgac    360

tttctggtct gtaactgaca ctgaggcgcg aaagcgtggg gagcaaacag gattagatac    420

cctggtagtc cacgccgtaa acgatgagtg ctaagtgtta gagggtttcc gccctttagt    480

gctgaagtta acgcattaag cactccgcct ggggagtacg gccgcaaggc tgaaactcaa    540

aggaattgac gggggcccgc acaagcggtg gagcatgtgg tttaattcga agcaacgcga    600

agaaccttac caggtcttga catcctctga aaaccctaga gatagggctt ctccttcggg    660

agcagagtga caggtggtgc atggttgtcg tcagctcgtg tcgtgagatg ttgggttaag    720

tcccgcaann ggccgcaacc caacanncnn cgacacgagc tgacgacaac catgnnccac    780

cagtnnctct gctctcgaag gagaagcccc annnnnaggg tttttcgagg atgtnnngan    840

ctggtnnggg nnntcgcgtt gcttcgaatt aaaccacatg ctcnnnnnnn tgnggnnccc    900

cnagtcnatt nnttngagtc tannnctgga nccggannna annngnnnnn gnnnanttgc    960

gttaattggg gnaancccgg                                                980
```

```
<210> SEQ ID NO 103
<211> LENGTH: 731
<212> TYPE: DNA
<213> ORGANISM: Bacillus mycoides
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (725)..(727)
<223> OTHER INFORMATION: n is a, c, g, or t

<400> SEQUENCE: 103

agtctgnngg ancacgccgc gtgagtgnng aaggctttcg ggtcgtaaaa ctctgttgtt     60

agggaagaac aagtgctagt tgaataagct ggcaccttga cggtacctaa ccagaaagcc    120

acggctaact acgtgccagc agccgcggta atacgtaggt ggcaagcgtt atccggaatt    180

attgggcgta aagcgcgcgc aggtggtttc ttaagtctga tgtgaaagcc cacggctcaa    240

ccgtggaggg tcattggaaa ctgggagact tgagtgcaga agaggaaagt ggaattccat    300

gtgtagcggt gaaatgcgta gagatatgga ggaacaccag tggcgaaggc gactttctgg    360

tctgtaactg acactgaggc gcgaaagcgt ggggagcaaa caggattaga taccctggta    420

gtccacgccg taaacgatga gtgctaagtg ttagagggtt tccgcccttt agtgctgaag    480
```

ttaacgcatt aagcactccg cctggggagt acggccgcaa ggctgaaact caaaggaatt 540
gacgggggcc cgcacaagcg gtggagcatg tggtttaatt cgaagcaacg cgaagaacct 600
taccaggtct tgacatcctc tgacaaccct agagataggg cttccccttc gggggcagag 660
tgacaggtgg tgcatggttg tcgtcagctc gtgtcgtgag atgttgggtt aagtcccgca 720
acnannngca a 731

<210> SEQ ID NO 104
<211> LENGTH: 714
<212> TYPE: DNA
<213> ORGANISM: Bacillus pseudomycoides
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t

<400> SEQUENCE: 104 ctganggane acgccgcgtg agtgatgaag gctttcgggt cgtaaaactc tgttgttagg 60
gaagaacaag tgctagttga ataagctggc accttgacgg tacctaacca gaaagccacg 120
gctaactacg tgccagcagc cgcggtaata cgtaggtggc aagcgttatc cggaattatt 180
gggcgtaaag cgcgcgcagg tggtttctta agtctgatgt gaaagcccac ggctcaaccg 240
tggagggtca ttggaaactg ggagacttga gtgcagaaga ggaaagtgga attccatgtg 300
tagcggtgaa atgcgtagag atatggagga acaccagtgg cgaaggcgac tttctggtct 360
gtaactgaca ctgaggcgcg aaagcgtggg gagcaaacag gattagatac cctggtagtc 420
cacgccgtaa acgatgagtg ctaagtgtta gagggtttcc gccctttagt gctgaagtta 480
acgcattaag cactccgcct ggggagtacg gccgcaaggc tgaaactcaa aggaattgac 540
gggggcccgc acaagcggtg gagcatgtgg tttaattcga agcaacgcga agaaccttac 600
caggtcttga catcctctga aaactctaga gatagagctt ctccttcggg agcagagtga 660
caggtggtgc atggttgtcg tcagctcgtg tcgtgagatg ntgggntaag tccc 714

<210> SEQ ID NO 105
<211> LENGTH: 740
<212> TYPE: DNA
<213> ORGANISM: Bacillus cereus
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (733)..(734)
<223> OTHER INFORMATION: n is a, c, g, or t
<220> FEATURE:
<221> NAME/KEY: misc_feature
<222> LOCATION: (736)..(740)
<223> OTHER INFORMATION: n is a, c, g, or t

<400> SEQUENCE: 105

```
tctgnnggan caacnccgcg tgagtgatga angctttcgg gtcgtaaaac tctgttgtta     60

gggaagaaca agtgctagtt gaataagctg gcaccttgac ggtacctaac cagaaagcca    120

cggctaacta cgtgccagca gccgcggtaa tacgtaggtg gcaagcgtta tccggaatta    180

ttgggcgtaa agcgcgcgca ggtggtttct taagtctgat gtgaaagccc acggctcaac    240

cgtggagggt cattggaaac tgggagactt gagtgcagaa gaggaaagtg gaattccatg    300

tgtagcggtg aaatgcgtag agatatggag gaacaccagt ggcgaaggcg actttctggt    360

ctgtaactga cactgaggcg cgaaagcgtg gggagcaaac aggattagat accctggtag    420

tccacgccgt aaacgatgag tgctaagtgt tagagggttt ccgcccttta gtgctgaagt    480

taacgcatta agcactccgc ctggggagta cggccgcaag gctgaaactc aaaggaattg    540

acgggggccc gcacaagcgg tggagcatgt ggtttaattc gaagcaacgc gaagaacctt    600

accaggtctt gacatcctct gaaaacccta gagatagggc ttctccttcg ggagcagagt    660

gacaggtggt gcatggttgt cgtcagctcg tgtcgtgaga tgntgggtta agtcccgcaa    720

cganccgcaa ccnnannnnn                                                740
```

<210> SEQ ID NO 106
<211> LENGTH: 850
<212> TYPE: DNA
<213> ORGANISM: Bacillus pumilus
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (718)..(733)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (739)..(741)
<223> OTHER INFORMATION: n is a, c, g, or t
<220> FEATURE:
<221> NAME/KEY: misc_feature
<222> LOCATION: (743)..(744)
<223> OTHER INFORMATION: n is a, c, g, or t
<220> FEATURE:

```
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (753)..(754)
<223> OTHER INFORMATION: n is a, c, g, or t
<220> FEATURE:
<221> NAME/KEY: misc_feature
<222> LOCATION: (756)..(757)
<223> OTHER INFORMATION: n is a, c, g, or t
<220> FEATURE:
<221> NAME/KEY: misc_feature
<222> LOCATION: (767)..(768)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t
<220> FEATURE:
<221> NAME/KEY: misc_feature
<222> LOCATION: (779)..(784)
<223> OTHER INFORMATION: n is a, c, g, or t
<220> FEATURE:
<221> NAME/KEY: misc_feature
<222> LOCATION: (787)..(788)
<223> OTHER INFORMATION: n is a, c, g, or t
<220> FEATURE:
<221> NAME/KEY: misc_feature
<222> LOCATION: (791)..(792)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (799)..(800)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (809)..(810)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (818)..(818)
<223> OTHER INFORMATION: n is a, c, g, or t
<220> FEATURE:
<221> NAME/KEY: misc_feature
<222> LOCATION: (826)..(826)
<223> OTHER INFORMATION: n is a, c, g, or t
<220> FEATURE:
<221> NAME/KEY: misc_feature
<222> LOCATION: (829)..(831)
<223> OTHER INFORMATION: n is a, c, g, or t
<220> FEATURE:
<221> NAME/KEY: misc_feature
<222> LOCATION: (835)..(835)
<223> OTHER INFORMATION: n is a, c, g, or t
<220> FEATURE:
<221> NAME/KEY: misc_feature
<222> LOCATION: (838)..(841)
<223> OTHER INFORMATION: n is a, c, g, or t
```

<220> FEATURE:
<221> NAME/KEY: misc_feature
<222> LOCATION: (846)..(848)
<223> OTHER INFORMATION: n is a, c, g, or t

<400> SEQUENCE: 106 ctganggane acgccgcgtg agtgatgaag gttttcggat cgtaaagctc tgttgttagg 60
gaagaacaag tgcgagagta actgctcgca ccttgacggt acctaaccag aaagccacgg 120
ctaactacgt gccagcagcc gcggtaatac gtaggtggca agcgttgtcc ggaattattg 180
ggcgtaaagg gctcgcaggc ggtttcttaa gtctgatgtg aaagcccccg gctcaaccgg 240
ggagggtcat tggaaactgg gaaacttgag tgcagaagag gagagtggaa ttccacgtgt 300
agcggtgaaa tgcgtagaga tgtggaggaa caccagtggc gaaggcgact ctctggtctg 360
taactgacgc tgaggagcga aagcgtgggg agcgaacagg attagatacc ctggtagtcc 420
acgccgtaaa cgatgagtgc taagtgttag ggggtttccg ccccttagtg ctgcagctaa 480
cgcattaagc actccgcctg gggagtacgg tcgcaagact gaaactcaaa ggaattgacg 540
ggggcccgca caagcggtgg agcatgtggt ttaattcgaa gcaacgcgaa gaaccttacc 600
aggtcttgac atcctctgac aaccctagag atagggcttt cccttcgggg acagagtgac 660
aggtggtgca tggttgtcgt cagctcgtgt cgtgagatgt tgggttaagt cccgnacnnn 720
nnnnnnnnnn nnncntctnn nanncgngct gannanncca tgcaccnncn gtcantctnn 780
nnnnggnnaa nncntattnn tngggtngnn cagangangt cagacnggnn nggtnctnnn 840 nttgcnnnat 850

<210> SEQ ID NO 107
<211> LENGTH: 711
<212> TYPE: DNA
<213> ORGANISM: Bacillus mycoides
<220> FEATURE:
<221> NAME/KEY: misc_feature
<222> LOCATION: (20)..(21)
<223> OTHER INFORMATION: n is a, c, g, or t

<400> SEQUENCE: 107
ggagcacgcc gcgtgagtgn ngaaggcttt cgggtcgtaa aactctgttg ttagggaaga 60
acaagtgcta gttgaataag ctggcacctt gacggtacct aaccagaaag ccacggctaa 120
ctacgtgcca gcagccgcgg taatacgtag gtggcaagcg ttatccggaa ttattgggcg 180
taaagcgcgc gcaggtggtt tcttaagtct gatgtgaaag cccacggctc aaccgtggag 240
ggtcattgga aactgggaga cttgagtgca gaagaggaaa gtggaattcc atgtgtagcg 300
gtgaaatgcg tagagatatg gaggaacacc agtggcgaag gcgactttct ggtctgtaac 360
tgacactgag gcgcgaaagc gtggggagca aacaggatta gataccctgg tagtccacgc 420
cgtaaacgat gagtgctaag tgttagaggg tttccgccct ttagtgctga agttaacgca 480
ttaagcactc cgcctgggga gtacggccgc aaggctgaaa ctcaaaggaa ttgacggggg 540
cccgcacaag cggtggagca tgtggtttaa ttcgaagcaa cgcgaagaac cttaccaggt 600
cttgacatcc tctgaaaact ctagagatag agcttctcct tcgggagcag agtgacaggt 660
ggtgcatggt tgtcgtcagc tcgtgtcgtg agatgttggg ttaagtcccg c 711

<210> SEQ ID NO 108
<211> LENGTH: 21
<212> TYPE: PRT
<213> ORGANISM: Artificial Sequence
<220> FEATURE:

```
<223> OTHER INFORMATION: Primer

<400> SEQUENCE: 108

Ala Cys Thr Cys Cys Thr Ala Cys Gly Gly Gly Ala Gly Gly Cys Ala
1               5                   10                  15

Gly Cys Ala Gly Thr
            20


<210> SEQ ID NO 109
<211> LENGTH: 16
<212> TYPE: PRT
<213> ORGANISM: Artificial Sequence
<220> FEATURE:
<223> OTHER INFORMATION: Primer

<400> SEQUENCE: 109

Gly Gly Gly Thr Thr Gly Cys Gly Cys Thr Cys Gly Thr Thr Gly Cys
1               5                   10                  15


<210> SEQ ID NO 110
<211> LENGTH: 16
<212> TYPE: PRT
<213> ORGANISM: Artificial Sequence
<220> FEATURE:
<223> OTHER INFORMATION: Primer

<400> SEQUENCE: 110

Gly Gly Gly Thr Thr Gly Cys Gly Cys Thr Cys Gly Thr Thr Ala Cys
1               5                   10                  15


<210> SEQ ID NO 111
<211> LENGTH: 996
<212> TYPE: DNA
<213> ORGANISM: Bacillus thuringiensis

<400> SEQUENCE: 111

atgaatttag ctaaattccc gagaaaaaaa tatacagaat catatacacc aattgaaaag      60

ttaaacaatt tttctgaagc acttggtggc ccgactattt attttaaacg agatgattta     120

cttggtttaa cagccggtgg taataagacg agaaagttag aatttttagt tgcggatgca     180

caggaaaagg gtgcagatac gttaattaca gctggtggta ttcagtcaaa tcattgccgc     240

ctgacacttg ctgctgcggt aaaagaaaaa atgaaatgta ttcttgtatt agaggaaggg     300

cttgagccag aagagaagag agactttaac ggaaactatt tcttatatca cttattaggt     360

gctgaaaacg tcattgttgt accgaacgga gcagacctga tggaagagat gaataaagta     420

gcgaaagaag taagtgaaaa aggtagtaca ccatatgtaa ttccagttgg tggatcaaac     480

cctacgggcg caatgggata cgttgcttgt gcgcaagaaa ttatggcgca atcatttgag     540

caaggaattg atttcagttc agttgtttgt gtaagtggta gcggcggtat gcatgctggt     600

ttaattactg gtttttctgg aacacaaagc catattcctg taatcgggat taatgtaagt     660

agaggaaaag ctgagcaaga agagaaagta gcaaaacttg tagatgaaac ttcagcacac     720

gttggtattc caaactttat ctcgcgcgac gctgttacgt gctttgatga atatgtagga     780

ccaggctatg cgttaccaac gccggaaatg gtagaggcag ttcagttact tgcgaaaaca     840

gaaggtattt tacttgatcc agtgtataca ggtaaggcag tagcgggatt aatcgactta     900

attagaaaag gtaaatttaa taaggaagac aatattttat tcgtacattc aggtggttca     960

ccagctttat atgcgaatac ttctttattt gcgtaa                                996
```

<210> SEQ ID NO 112
<211> LENGTH: 996
<212> TYPE: DNA
<213> ORGANISM: Bacillus thuringiensis

<400> SEQUENCE: 112
atgaatttag ctaaattccc gagaaaaaaa tatacagaat catatacacc aattgaaaag 60
ttaaacaatt tttctgaagc acttggtggc ccgactattt attttaaacg agatgattta 120
cttggtttaa cagccggtgg taataagacg agaaagttag aatttttagt tgcggatgca 180
caggaaaagg gtgcagatac gttaattaca gctggtggta ttcagtcaaa tcattgccgc 240
ctgacacttg ctgctgcggt aaaagaaaaa atgaaatgta ttcttgtatt agaggaaggg 300
cttgagccag aagagaagag agactttaac ggaaactatt tcttatatca cttattaggt 360
gctgaaaacg tcattgttgt accgaacgga gcagacctga tggaagagat gaataaagta 420
gcgaaagaag taagtgaaaa aggtagtaca ccatatgtaa ttccagttgg tggatcaaac 480
cctacgggcg caatgggata cgttgcttgt gcgcaagaaa ttatggcgca atcatttgag 540
caaggaattg atttcagttc agttgtttgt gtaagtggta gcggcggtat gcatgctggt 600
ttaattactg gtttttctgg aacacaaagc catattcctg taatcgggat taatgtaagt 660
agaggaaaag ctgagcaaga agagaaagta gcaaaacttg tagatgaaac ttcagcacac 720
gttggtattc caaactttat ctcgcgcgac gctgttacgt gctttgatga atatgtagga 780
ccaggctatg cgttaccaac gccggaaatg gtagaggcag ttcagttact tgcgaaaaca 840
gaaggtattt tacttgatcc agtgtatgaa ggtaaggcag tagcgggatt aatcgactta 900
attagaaaag gtaaatttaa taaggaagac aatattttat tcgtacattt aggtggttca 960
ccagctttat atgcgaatac ttctttattt gcgtaa 996

<210> SEQ ID NO 113
<211> LENGTH: 331
<212> TYPE: PRT
<213> ORGANISM: Bacillus thuringiensis

<400> SEQUENCE: 113

Met Asn Leu Ala Lys Phe Pro Arg Lys Lys Tyr Thr Glu Ser Tyr Thr
1 5 10 15

Pro Ile Glu Lys Leu Asn Asn Phe Ser Glu Ala Leu Gly Gly Pro Thr
20 25 30

Ile Tyr Phe Lys Arg Asp Asp Leu Leu Gly Leu Thr Ala Gly Gly Asn
35 40 45

Lys Thr Arg Lys Leu Glu Phe Leu Val Ala Asp Ala Gln Glu Lys Gly
50 55 60

Ala Asp Thr Leu Ile Thr Ala Gly Gly Ile Gln Ser Asn His Cys Arg
65 70 75 80

Leu Thr Leu Ala Ala Ala Val Lys Glu Lys Met Lys Cys Ile Leu Val
85 90 95

Leu Glu Glu Gly Leu Glu Pro Glu Glu Lys Arg Asp Phe Asn Gly Asn
100 105 110

Tyr Phe Leu Tyr His Leu Leu Gly Ala Glu Asn Val Ile Val Val Pro
115 120 125

Asn Gly Ala Asp Leu Met Glu Glu Met Asn Lys Val Ala Lys Glu Val
130 135 140

Ser Glu Lys Gly Ser Thr Pro Tyr Val Ile Pro Val Gly Gly Ser Asn
145 150 155 160

```
Pro Thr Gly Ala Met Gly Tyr Val Ala Cys Ala Gln Glu Ile Met Ala
                165                 170                 175

Gln Ser Phe Glu Gln Gly Ile Asp Phe Ser Ser Val Val Cys Val Ser
            180                 185                 190

Gly Ser Gly Gly Met His Ala Gly Leu Ile Thr Gly Phe Ser Gly Thr
        195                 200                 205

Gln Ser His Ile Pro Val Ile Gly Ile Asn Val Ser Arg Gly Lys Ala
    210                 215                 220

Glu Gln Glu Glu Lys Val Ala Lys Leu Val Asp Glu Thr Ser Ala His
225                 230                 235                 240

Val Gly Ile Pro Asn Phe Ile Ser Arg Asp Ala Val Thr Cys Phe Asp
                245                 250                 255

Glu Tyr Val Gly Pro Gly Tyr Ala Leu Pro Thr Pro Glu Met Val Glu
            260                 265                 270

Ala Val Gln Leu Leu Ala Lys Thr Glu Gly Ile Leu Leu Asp Pro Val
        275                 280                 285

Tyr Thr Gly Lys Ala Val Ala Gly Leu Ile Asp Leu Ile Arg Lys Gly
    290                 295                 300

Lys Phe Asn Lys Glu Asp Asn Ile Leu Phe Val His Ser Gly Gly Ser
305                 310                 315                 320

Pro Ala Leu Tyr Ala Asn Thr Ser Leu Phe Ala
                325                 330


<210> SEQ ID NO 114
<211> LENGTH: 331
<212> TYPE: PRT
<213> ORGANISM: Bacillus thuringiensis

<400> SEQUENCE: 114

Met Asn Leu Ala Lys Phe Pro Arg Lys Lys Tyr Thr Glu Ser Tyr Thr
1               5                   10                  15

Pro Ile Glu Lys Leu Asn Asn Phe Ser Glu Ala Leu Gly Gly Pro Thr
            20                  25                  30

Ile Tyr Phe Lys Arg Asp Asp Leu Leu Gly Leu Thr Ala Gly Gly Asn
        35                  40                  45

Lys Thr Arg Lys Leu Glu Phe Leu Val Ala Asp Ala Gln Glu Lys Gly
    50                  55                  60

Ala Asp Thr Leu Ile Thr Ala Gly Gly Ile Gln Ser Asn His Cys Arg
65                  70                  75                  80

Leu Thr Leu Ala Ala Ala Val Lys Glu Lys Met Lys Cys Ile Leu Val
                85                  90                  95

Leu Glu Glu Gly Leu Glu Pro Glu Glu Lys Arg Asp Phe Asn Gly Asn
            100                 105                 110

Tyr Phe Leu Tyr His Leu Leu Gly Ala Glu Asn Val Ile Val Val Pro
        115                 120                 125

Asn Gly Ala Asp Leu Met Glu Glu Met Asn Lys Val Ala Lys Glu Val
    130                 135                 140

Ser Glu Lys Gly Ser Thr Pro Tyr Val Ile Pro Val Gly Gly Ser Asn
145                 150                 155                 160

Pro Thr Gly Ala Met Gly Tyr Val Ala Cys Ala Gln Glu Ile Met Ala
                165                 170                 175

Gln Ser Phe Glu Gln Gly Ile Asp Phe Ser Ser Val Val Cys Val Ser
            180                 185                 190

Gly Ser Gly Gly Met His Ala Gly Leu Ile Thr Gly Phe Ser Gly Thr
        195                 200                 205
```

```
Gln Ser His Ile Pro Val Ile Gly Ile Asn Val Ser Arg Gly Lys Ala
    210                 215                 220

Glu Gln Glu Glu Lys Val Ala Lys Leu Val Asp Glu Thr Ser Ala His
225                 230                 235                 240

Val Gly Ile Pro Asn Phe Ile Ser Arg Asp Ala Val Thr Cys Phe Asp
                245                 250                 255

Glu Tyr Val Gly Pro Gly Tyr Ala Leu Pro Thr Pro Glu Met Val Glu
            260                 265                 270

Ala Val Gln Leu Leu Ala Lys Thr Glu Gly Ile Leu Leu Asp Pro Val
        275                 280                 285

Tyr Glu Gly Lys Ala Val Ala Gly Leu Ile Asp Leu Ile Arg Lys Gly
    290                 295                 300

Lys Phe Asn Lys Glu Asp Asn Ile Leu Phe Val His Leu Gly Gly Ser
305                 310                 315                 320

Pro Ala Leu Tyr Ala Asn Thr Ser Leu Phe Ala
                325                 330


<210> SEQ ID NO 115
<211> LENGTH: 259
<212> TYPE: PRT
<213> ORGANISM: Bacillus cereus

<400> SEQUENCE: 115

His Glu Asn Asp Gly Gly Ser Lys Ile Lys Ile Val His Arg Trp Ser
1               5                   10                  15

Ala Glu Asp Lys His Lys Glu Gly Val Asn Ser His Leu Trp Ile Val
            20                  25                  30

Asn Arg Ala Ile Asp Ile Met Ser Arg Asn Lys Thr Leu Val Lys Gln
        35                  40                  45

Asp Arg Val Ala Leu Leu Asn Glu Trp Arg Thr Glu Leu Glu Asn Gly
    50                  55                  60

Ile Tyr Ala Ala Asp Tyr Glu Asn Pro Tyr Tyr Asp Asn Ser Thr Phe
65                  70                  75                  80

Ala Ser His Phe Tyr Asp Pro Asp Asn Gly Lys Thr Tyr Ile Pro Tyr
                85                  90                  95

Ala Lys Gln Ala Lys Glu Thr Gly Ala Lys Tyr Phe Lys Leu Ala Gly
            100                 105                 110

Glu Ser Tyr Lys Asn Lys Asp Met Lys Gln Ala Phe Phe Tyr Leu Gly
        115                 120                 125

Leu Ser Leu His Tyr Leu Gly Asp Val Asn Gln Pro Met His Ala Ala
    130                 135                 140

Asn Phe Thr Asn Leu Ser Tyr Pro Gln Gly Phe His Ser Lys Tyr Glu
145                 150                 155                 160

Asn Phe Val Asp Thr Ile Lys Asp Asn Tyr Lys Val Thr Asp Gly Asn
                165                 170                 175

Gly Tyr Trp Asn Trp Lys Gly Thr Asn Pro Glu Asp Trp Ile His Gly
            180                 185                 190

Ala Ala Val Val Ala Lys Gln Asp Tyr Ala Gly Ile Val Asn Asp Asn
        195                 200                 205

Thr Lys Asp Trp Phe Val Arg Ala Ala Val Ser Gln Glu Tyr Ala Asp
    210                 215                 220

Lys Trp Arg Ala Glu Val Thr Pro Met Thr Gly Lys Arg Leu Met Asp
225                 230                 235                 240

Ala Gln Arg Val Thr Ala Gly Tyr Ile Gln Leu Trp Phe Asp Thr Tyr
```

-continued

```
                245                 250                 255

Gly Asp Arg


<210> SEQ ID NO 116
<211> LENGTH: 326
<212> TYPE: PRT
<213> ORGANISM: Bacillus cereus

<400> SEQUENCE: 116

Met Arg Asn Lys Lys Leu Ile Leu Lys Leu Phe Ile Cys Ser Thr Ile
1               5                   10                  15

Phe Ile Thr Phe Val Phe Ala Leu His Asp Lys Arg Val Val Ala Ala
            20                  25                  30

Ser Ser Val Asn Glu Leu Glu Asn Trp Ser Lys Trp Met Gln Pro Ile
        35                  40                  45

Pro Asp Asn Ile Pro Leu Ala Arg Ile Ser Ile Pro Gly Thr His Asp
    50                  55                  60

Ser Gly Thr Phe Lys Leu Gln Asn Pro Ile Lys Gln Val Trp Gly Met
65                  70                  75                  80

Thr Gln Glu Tyr Asp Phe Arg Tyr Gln Met Asp His Gly Ala Arg Ile
                85                  90                  95

Phe Asp Ile Arg Gly Arg Leu Thr Asp Asp Asn Thr Ile Val Leu His
            100                 105                 110

His Gly Pro Leu Tyr Leu Tyr Val Thr Leu His Glu Phe Ile Asn Glu
        115                 120                 125

Ala Lys Gln Phe Leu Lys Asp Asn Pro Ser Glu Thr Ile Ile Met Ser
    130                 135                 140

Leu Lys Lys Glu Tyr Glu Asp Met Lys Gly Ala Glu Asn Ser Phe Ser
145                 150                 155                 160

Ser Thr Phe Glu Lys Asn Tyr Phe Val Asp Pro Ile Phe Leu Lys Thr
                165                 170                 175

Glu Gly Asn Ile Lys Leu Gly Asp Ala Arg Gly Lys Ile Val Leu Leu
            180                 185                 190

Lys Arg Tyr Ser Gly Ser Asn Glu Ser Gly Gly Tyr Asn Asn Phe Tyr
        195                 200                 205

Trp Pro Asp Asn Glu Thr Phe Thr Thr Thr Val Asn Lys Asn Val Asn
    210                 215                 220

Val Thr Val Gln Asp Lys Tyr Lys Val Ser Tyr Asp Glu Lys Val Lys
225                 230                 235                 240

Ser Ile Lys Asp Thr Ile Asn Glu Thr Met Asn Asn Ser Glu Asp Leu
                245                 250                 255

Asn His Leu Tyr Ile Asn Phe Thr Ser Leu Ser Ser Gly Gly Thr Ala
            260                 265                 270

Trp Asn Ser Pro Tyr Tyr Tyr Ala Ser Tyr Ile Asn Pro Glu Ile Ala
        275                 280                 285

Ala Tyr Ile Lys Gln Glu Asn Pro Lys Arg Val Gly Trp Val Ile Gln
    290                 295                 300

Asp Tyr Ile Ser Asp Lys Trp Ser Pro Ile Leu Tyr Gln Glu Val Ile
305                 310                 315                 320

Arg Thr Asn Lys Ser Leu
                325


<210> SEQ ID NO 117
<211> LENGTH: 407
<212> TYPE: PRT
```

<213> ORGANISM: Acidovorax avenae

<400> SEQUENCE: 117

Met Ser Gly Gly His Arg Val Ala Leu Leu Gln Gly Ser Ala Glu Leu
1 5 10 15

Phe Ser Ala Leu Val Ala Asp Met Asp Ala Ala Leu Ser Asp Ile Gln
20 25 30

Phe Glu Thr Tyr Ile Phe Asp Cys Thr Gly Ser Gly Ala Asp Ile Ala
35 40 45

Glu Ala Leu Ile Arg Ala Ala Arg Arg Gly Val Arg Val His Leu Val
50 55 60

Val Asp Gly Val Gly Thr Gly Arg Leu Cys Ser Pro Trp Pro Glu Arg
65 70 75 80

Phe Glu Glu Ala Gly Val Arg Met Gln Val Tyr Ser Pro Leu Gly Pro
85 90 95

Leu Gly Leu Leu Leu Pro Arg Arg Trp Arg Arg Leu His Arg Lys Leu
100 105 110

Cys Val Val Asp Gly Cys Val Leu Tyr Cys Gly Gly Ile Asn Val Leu
115 120 125

Asp Asp Leu His Asp Pro Asn His Gly Ala Leu Glu Ser Pro Arg Phe
130 135 140

Asp Phe Ala Val Arg Val Glu Gly Arg Leu Val Glu Glu Ala Gly Glu
145 150 155 160

Ala Met Glu Gln Val Trp Trp Arg Leu Gln Ala Thr Arg Asp Ala Arg
165 170 175

Gln Arg Arg Leu Ala Asp Leu Met Cys Asp Leu Arg Ala Ala Ala Gln
180 185 190

Ala Arg Gln Ala Glu Arg Leu Ala Arg Glu Ala Ala Pro Gly Gly Ala
195 200 205

Ala Ala Ala His Gly Leu Arg Ala Gly Leu Leu Leu Arg Asp Asn Leu
210 215 220

Arg Asn Arg Ser Arg Ile Glu Arg Ala Tyr Arg Arg Ala Ile Gly Asn
225 230 235 240

Ala Arg His Glu Val Ile Ile Ala Asn Ala Tyr Phe Leu Pro Gly Arg
245 250 255

Lys Leu Arg His Ala Leu Val Leu Ala Ala Arg Arg Gly Val Arg Val
260 265 270

Arg Leu Leu Leu Gln Gly Arg Tyr Glu Tyr Phe Met Gln Tyr His Ala
275 280 285

Ala Arg Pro Val Tyr Gly Ala Leu Leu Ala Ala Gly Val Glu Ile His
290 295 300

Glu Tyr Ala Pro Ser Phe Leu His Ala Lys Val Ala Val Ile Asp Ala
305 310 315 320

Gln Gly Glu His Pro Trp Ala Thr Val Gly Ser Ser Asn Leu Asp Pro
325 330 335

Leu Ser Met Leu Leu Ala Arg Glu Ala Asn Val Val Val Glu Asp Ala
340 345 350

Gly Phe Ala Arg Ala Leu Arg Ala Arg Leu Val Asp Ala Met Glu His
355 360 365

Ala Gly Arg Gln Leu Asp Pro Gln Ala Tyr Gly Ala Arg Pro Trp Gly
370 375 380

Gln Arg Leu Arg Asp Arg Val Ala Phe Ala Leu Met Arg Leu Ala Leu
385 390 395 400

```
Trp Val Thr Gly Ser Arg Tyr
                405


<210> SEQ ID NO 118
<211> LENGTH: 320
<212> TYPE: PRT
<213> ORGANISM: Burkholderia cepacia

<400> SEQUENCE: 118

Ala Ala Gly Tyr Ala Ala Thr Arg Tyr Pro Ile Ile Leu Val His Gly
1               5                   10                  15

Leu Ser Gly Thr Asp Lys Tyr Ala Gly Val Leu Glu Tyr Trp Tyr Gly
            20                  25                  30

Ile Gln Glu Asp Leu Gln Gln Asn Gly Ala Thr Val Tyr Val Ala Asn
        35                  40                  45

Leu Ser Gly Phe Gln Ser Asp Asp Gly Pro Asn Gly Arg Gly Glu Gln
    50                  55                  60

Leu Leu Ala Tyr Val Lys Thr Val Leu Ala Ala Thr Gly Ala Thr Lys
65                  70                  75                  80

Val Asn Leu Val Gly His Ser Gln Gly Gly Leu Ser Ser Arg Tyr Val
                85                  90                  95

Ala Ala Val Ala Pro Asp Leu Val Ala Ser Val Thr Thr Ile Gly Thr
            100                 105                 110

Pro His Arg Gly Ser Glu Phe Ala Asp Phe Val Gln Asp Val Leu Ala
        115                 120                 125

Tyr Asp Pro Thr Gly Leu Ser Ser Ser Val Ile Ala Ala Phe Val Asn
    130                 135                 140

Val Phe Gly Ile Leu Thr Ser Ser Ser His Asn Thr Asn Gln Asp Ala
145                 150                 155                 160

Leu Ala Ala Leu Gln Thr Leu Thr Thr Ala Arg Ala Ala Thr Tyr Asn
                165                 170                 175

Gln Asn Tyr Pro Ser Ala Gly Leu Gly Ala Pro Gly Ser Cys Gln Thr
            180                 185                 190

Gly Ala Pro Thr Glu Thr Val Gly Gly Asn Thr His Leu Leu Tyr Ser
        195                 200                 205

Trp Ala Gly Thr Ala Ile Gln Pro Thr Leu Ser Val Phe Gly Val Thr
    210                 215                 220

Gly Ala Thr Asp Thr Ser Thr Leu Pro Leu Val Asp Pro Ala Asn Val
225                 230                 235                 240

Leu Asp Leu Ser Thr Leu Ala Leu Phe Gly Thr Gly Thr Val Met Ile
                245                 250                 255

Asn Arg Gly Ser Gly Gln Asn Asp Gly Leu Val Ser Lys Cys Ser Ala
            260                 265                 270

Leu Tyr Gly Lys Val Leu Ser Thr Ser Tyr Lys Trp Asn His Leu Asp
        275                 280                 285

Glu Ile Asn Gln Leu Leu Gly Val Arg Gly Ala Tyr Ala Glu Asp Pro
    290                 295                 300

Val Ala Val Ile Arg Thr His Ala Asn Arg Leu Lys Leu Ala Gly Val
305                 310                 315                 320


<210> SEQ ID NO 119
<211> LENGTH: 453
<212> TYPE: PRT
<213> ORGANISM: Pseudomonas fluorescens

<400> SEQUENCE: 119
```

-continued

```
Ile Thr Leu Tyr Ser Tyr His Asn Leu Asp Asn Gly Phe Ala Val Gly
1               5                   10                  15

Tyr Gln His Asn Gly Leu Gly Leu Gly Leu Pro Ala Thr Leu Val Gly
            20                  25                  30

Ala Leu Leu Gly Ser Thr Asp Ser Gln Gly Val Ile Pro Gly Ile Pro
        35                  40                  45

Trp Asn Pro Asp Ser Glu Lys Ala Ala Leu Glu Ala Val Gln Lys Ala
    50                  55                  60

Gly Trp Thr Pro Ile Ser Ala Ser Ala Leu Gly Tyr Ala Gly Lys Val
65                  70                  75                  80

Asp Ala Arg Gly Thr Phe Phe Gly Glu Lys Ala Gly Tyr Thr Thr Ala
                85                  90                  95

Gln Val Glu Val Leu Gly Lys Tyr Asp Asp Ala Gly Lys Leu Leu Glu
            100                 105                 110

Ile Gly Ile Gly Phe Arg Gly Thr Ser Gly Pro Arg Glu Thr Leu Ile
        115                 120                 125

Ser Asp Ser Ile Gly Asp Leu Ile Ser Asp Leu Leu Ala Ala Leu Gly
    130                 135                 140

Pro Lys Asp Tyr Ala Lys Asn Tyr Ala Gly Glu Ala Phe Gly Gly Leu
145                 150                 155                 160

Leu Lys Asn Val Ala Asp Tyr Ala Gly Ala His Gly Leu Thr Gly Lys
                165                 170                 175

Asp Val Val Val Ser Gly His Ser Leu Gly Gly Leu Ala Val Asn Ser
            180                 185                 190

Met Ala Asp Leu Ser Asn Tyr Lys Trp Ala Gly Phe Tyr Lys Asp Ala
        195                 200                 205

Asn Tyr Val Ala Tyr Ala Ser Pro Thr Gln Ser Ala Gly Asp Lys Val
    210                 215                 220

Leu Asn Ile Gly Tyr Glu Asn Asp Pro Val Phe Arg Ala Leu Asp Gly
225                 230                 235                 240

Ser Ser Phe Asn Leu Ser Ser Leu Gly Val His Asp Lys Pro His Glu
                245                 250                 255

Ser Thr Thr Asp Asn Ile Val Ser Phe Asn Asp His Tyr Ala Ser Thr
            260                 265                 270

Leu Trp Asn Val Leu Pro Phe Ser Ile Val Asn Leu Pro Thr Trp Val
        275                 280                 285

Ser His Leu Pro Thr Ala Tyr Gly Asp Gly Met Thr Arg Ile Leu Glu
    290                 295                 300

Ser Gly Phe Tyr Asp Gln Met Thr Arg Asp Ser Thr Val Ile Val Ala
305                 310                 315                 320

Asn Leu Ser Asp Pro Ala Arg Ala Asn Thr Trp Val Gln Asp Leu Asn
                325                 330                 335

Arg Asn Ala Glu Pro His Lys Gly Asn Thr Phe Ile Ile Gly Ser Asp
            340                 345                 350

Gly Asn Asp Leu Ile Gln Gly Gly Asn Gly Ala Asp Phe Ile Glu Gly
        355                 360                 365

Gly Lys Gly Asn Asp Thr Ile Arg Asp Asn Ser Gly His Asn Thr Phe
    370                 375                 380

Leu Phe Ser Gly His Phe Gly Asn Asp Arg Val Ile Gly Tyr Gln Pro
385                 390                 395                 400

Thr Asp Lys Leu Val Phe Lys Asp Val Gln Gly Ser Thr Asp Leu Arg
                405                 410                 415

Asp His Ala Lys Val Val Gly Ala Asp Thr Val Leu Thr Phe Gly Ala
```

```
            420                 425                 430

Asp Ser Val Thr Leu Val Gly Val Gly His Gly Gly Leu Trp Thr Glu
        435                 440                 445

Gly Val Val Ile Gly
    450


<210> SEQ ID NO 120
<211> LENGTH: 355
<212> TYPE: PRT
<213> ORGANISM: Burkholderia stearothermophilus

<400> SEQUENCE: 120

Met Asp Lys Leu Ile Val Asp Asp Leu His Leu Ser Tyr Gly Ala Asn
1               5                   10                  15

Pro Ile Leu Lys Gly Val Ser Phe Glu Leu Lys Ala Gly Glu Val Val
            20                  25                  30

Cys Leu Leu Gly Ala Ser Gly Ser Gly Lys Thr Thr Leu Leu Arg Ala
        35                  40                  45

Val Ala Gly Leu Glu Gln Pro Ser Asp Gly Arg Ile Gln Leu Asp Asp
    50                  55                  60

Arg Val Phe Phe Asp Gly Ala Lys Arg Val Asp Leu Pro Val Glu Gln
65                  70                  75                  80

Arg Ser Leu Gly Leu Val Phe Gln Ser Tyr Ala Leu Trp Pro His Arg
                85                  90                  95

Thr Val Ala Asp Asn Val Gly Tyr Gly Leu Lys Leu Arg Arg Val Ala
            100                 105                 110

Pro Ala Glu Gln Lys Arg Arg Val Gln Ser Ala Leu Asp Gln Leu Gly
        115                 120                 125

Leu Gly His Leu Ala Glu Arg Phe Pro His Gln Leu Ser Gly Gly Gln
    130                 135                 140

Gln Gln Arg Val Ala Ile Ala Arg Ala Leu Val Tyr Asn Pro Pro Val
145                 150                 155                 160

Ile Leu Leu Asp Glu Pro Leu Ser Asn Leu Asp Ala Lys Leu Arg Glu
                165                 170                 175

Glu Ala Arg Ala Trp Leu Arg Glu Leu Ile Val Ser Leu Gly Leu Ser
            180                 185                 190

Ala Leu Cys Val Thr His Asp Gln Thr Glu Ala Met Ala Met Ser Asp
        195                 200                 205

Arg Ile Leu Leu Leu Arg Asn Gly Arg Ile Glu Gln Glu Gly Thr Pro
    210                 215                 220

Ala Glu Leu Tyr Gly Ala Pro Arg Ser Leu Tyr Thr Ala Glu Phe Met
225                 230                 235                 240

Gly Ser Asn Asn Arg Ile Asp Ala Arg Val Ala Ala Ile Asp Gly Glu
                245                 250                 255

Cys Val Thr Leu Ala Gly Asp Gly Trp Glu Ile Arg Ala Met Ala Arg
            260                 265                 270

Asp Thr Leu Ala Pro Gly Gln Asp Ala Gln Ala Val Ile Arg Leu Glu
        275                 280                 285

Arg Val Gln Val Thr Asp Gly Pro Gly Ala Asn Arg Leu Gln Ala Asp
    290                 295                 300

Leu Val Thr Ser Met Tyr Leu Gly Asp Arg Trp Glu Tyr Leu Phe His
305                 310                 315                 320

Cys Gly Asp Met Arg Leu Arg Ala Phe Gly His Val Pro Arg Ala Ala
                325                 330                 335
```

Gly Lys His Trp Ile Glu Phe Pro Thr Asn Asp Cys Trp Ala Phe Ala
340 345 350

Lys Ala Gly
355

<210> SEQ ID NO 121
<211> LENGTH: 258
<212> TYPE: PRT
<213> ORGANISM: Thermomyces lanuginosus

<400> SEQUENCE: 121

Met Val Gly Phe Thr Pro Val Ala Leu Ala Ala Leu Ala Ala Thr Gly
1 5 10 15

Ala Leu Ala Phe Pro Ala Gly Asn Ala Thr Glu Leu Glu Lys Arg Gln
20 25 30

Thr Thr Pro Asn Ser Glu Gly Trp His Asp Gly Tyr Tyr Tyr Ser Trp
35 40 45

Trp Ser Asp Gly Gly Ala Gln Ala Thr Tyr Thr Asn Leu Glu Gly Gly
50 55 60

Thr Tyr Glu Ile Ser Trp Gly Asp Gly Gly Asn Leu Val Gly Gly Lys
65 70 75 80

Gly Trp Asn Pro Gly Leu Asn Ala Arg Ala Val Arg Val Pro Gln Asp
85 90 95

Arg Asn Arg Ile Val Ile Arg Pro Arg Ser Phe Glu Ser Leu Lys Ala
100 105 110

Phe Leu Thr Pro Thr Ser Leu Thr Cys Thr Gln Ile His Phe Glu Gly
115 120 125

Val Tyr Gln Pro Asn Gly Asn Ser Tyr Leu Ala Val Tyr Gly Trp Thr
130 135 140

Arg Asn Pro Leu Val Glu Tyr Tyr Ile Val Glu Asn Phe Gly Thr Tyr
145 150 155 160

Asp Pro Ser Ser Gly Ala Thr Asp Leu Gly Thr Val Glu Cys Asp Gly
165 170 175

Ser Ile Tyr Arg Leu Gly Lys Thr Thr Arg Val Asn Ala Pro Ser Ile
180 185 190

Asp Gly Thr Gln Thr Phe Asp Gln Tyr Trp Ser Val Arg Gln Asp Lys
195 200 205

Arg Thr Ser Gly Thr Val Gln Thr Gly Cys His Phe Asp Ala Trp Ala
210 215 220

Arg Ala Gly Leu Asn Val Asn Gly Asp His Tyr Tyr Gln Ile Val Ala
225 230 235 240

Thr Glu Gly Tyr Phe Ser Ser Gly Tyr Ala Arg Ile Thr Val Ala Asp
245 250 255

Val Gly

<210> SEQ ID NO 122
<211> LENGTH: 860
<212> TYPE: PRT
<213> ORGANISM: Neocallimastix patriciarum

<400> SEQUENCE: 122

Met Lys Phe Ser Ser Ala Asn Lys Ile Leu Phe Ser Gly Leu Val Ala
1 5 10 15

Ser Ala Asn Ala Tyr Asp Leu Leu Lys Asp Tyr Ala Gly Asp Leu Lys
20 25 30

Ile Gly Val Ala Ala Asn Ala Met Arg Phe Ser Asn Ser Asn Tyr Val

```
        35                  40                  45

Asn Ala Met Lys Ala Phe Asn Met Met Val Ala Glu Asn Asp Cys Lys
    50                  55                  60

Leu Ser Gly Ile Gln Gln Gln Lys Gly Val Tyr Asn Phe Asn Gly Cys
65                  70                  75                  80

Asp Asn His Tyr Asn Lys Ala Lys Glu Leu Gly Met Glu Phe Arg Gly
                85                  90                  95

His Cys Leu Ile Trp His Ser Tyr Gln Pro Ser Trp Phe Gln Asn Ala
            100                 105                 110

Asp Ala Asn Thr Leu Lys Asn Ala Ile Val Asp His Ile Thr Lys Thr
        115                 120                 125

Leu Gln His Tyr Glu Gly Lys Ile Lys Val Trp Asp Val Val Asn Glu
    130                 135                 140

Ala Ile Asp Asp Asn Ser Asn Gly Asn Gly Trp Asn Met Arg Arg Ser
145                 150                 155                 160

Phe Leu Tyr Asn Lys Val Pro Asn Phe Val Asp Leu Ala Phe Gln Thr
                165                 170                 175

Ala Arg Lys Val Ser Pro Asn Thr Lys Leu Phe Tyr Asn Asp Tyr Asn
            180                 185                 190

Ala Glu Gly Val Tyr Ala Lys Ala Glu Ser Ile Tyr Asn Phe Val Ser
        195                 200                 205

Asp Leu Lys Lys Arg Asn Ile Pro Ile Asp Gly Val Gly Leu Gln Tyr
    210                 215                 220

His Val Gly Ala Lys Glu Gln Pro Ser Tyr Asn Lys Ile Asn Asp Leu
225                 230                 235                 240

Ile Gly Arg Tyr Cys Lys Leu Gly Leu Glu Val His Ile Thr Glu Leu
                245                 250                 255

Asp Val Lys Leu Gln Gly Asp Gln Asn Gly Gln Ser Gln Ala Phe Ser
            260                 265                 270

Asn Ala Leu Lys Ala Cys Leu Ala Asn Ser Cys Cys Lys Ala Phe Leu
        275                 280                 285

Val Trp Gly Val Gly Asp Asn Asp Ser Trp Leu Gly Ala Asn Glu Gln
    290                 295                 300

Ala Leu Leu Phe Asn Gly Ser Tyr Gln Pro Lys Pro Val Tyr Asn Thr
305                 310                 315                 320

Leu Leu Asn Ile Leu Lys Thr Ser Ala Arg Pro Ala Ser Ser Ser Ala
                325                 330                 335

Lys Thr Leu Pro Gly Asn Ser Lys Ser Lys Thr Leu Pro Gly Val Asn
            340                 345                 350

Ser Lys Thr Leu Pro Gly Asn Lys Ser Lys Thr Leu Pro Gly Ala Ser
        355                 360                 365

Lys Thr Leu Pro Gly Asn Lys Ser Lys Thr Leu Pro Gly Gly Asn Ser
    370                 375                 380

Asn Thr Leu Pro Gly Asn Lys Ser Lys Thr Leu Pro Gly Gly Asn Ser
385                 390                 395                 400

Lys Thr Leu Pro Gly Asn Lys Ser Arg Thr Leu Pro Gly Gly Asn Ser
                405                 410                 415

Lys Thr Leu Pro Gly Gly Lys Ser Arg Thr Leu Pro Gly Gly Asn Ser
            420                 425                 430

Lys Thr Leu Pro Gly Gly Lys Ser Lys Thr Leu Pro Gly Gly Asn Ser
        435                 440                 445

Lys Thr Leu Pro Gly Gly Lys Ser Lys Thr Leu Pro Gly Gly Asn Ser
    450                 455                 460
```

Lys Thr Leu Pro Gly Gly Ser Ser Lys Thr Leu Pro Gly Gly Lys Ser
465 470 475 480

Lys Thr Leu Pro Gly Gly Asn Ser Lys Thr Leu Pro Gly Gly Ser Ser
485 490 495

Lys Thr Leu Pro Gly Gly Lys Ser Lys Thr Leu Pro Gly Gly Ser Ser
500 505 510

Lys Thr Leu Pro Gly Gly Lys Ser Lys Thr Leu Pro Gly Gly Asn Ser
515 520 525

Lys Thr Leu Pro Gly Gly Asn Ser Lys Thr Leu Pro Gly Gly Ser Ser
530 535 540

Lys Thr Leu Pro Gly Gly Lys Ser Lys Thr Leu Pro Gly Gly Asn Ser
545 550 555 560

Lys Thr Leu Pro Gly Gly Ser Ser Lys Thr Leu Pro Gly Gly Lys Ser
565 570 575

Lys Thr Leu Pro Gly Gly Asn Ser Lys Thr Leu Pro Gly Gly Asn Ser
580 585 590

Lys Thr Leu Pro Gly Gly Lys Ser Lys Thr Leu Pro Gly Gly Asn Ser
595 600 605

Lys Thr Leu Pro Gly Gly Ser Ser Lys Thr Leu Pro Gly Gly Lys Ser
610 615 620

Lys Thr Leu Pro Gly Gly Ser Ser Lys Thr Leu Pro Gly Gly Lys Ser
625 630 635 640

Lys Thr Leu Pro Gly Gly Asn Ser Lys Thr Leu Pro Gly Gly Asn Ser
645 650 655

Lys Thr Leu Pro Gly Gly Ser Ser Lys Thr Leu Pro Gly Gly Lys Ser
660 665 670

Lys Thr Leu Pro Gly Gly Ser Ser Lys Thr Leu Pro Gly Gly Lys Ser
675 680 685

Lys Thr Leu Pro Gly Gly Asn Ser Lys Thr Leu Pro Gly Gly Lys Ser
690 695 700

Lys Thr Leu Pro Gly Gly Asn Ser Lys Thr Leu Pro Gly Gly Lys Ser
705 710 715 720

Lys Thr Leu Pro Gly Gly Asn Ser Lys Thr Leu Pro Gly Gly Lys Ser
725 730 735

Lys Thr Leu Pro Gly Gly Asn Ser Lys Thr Leu Pro Gly Gly Ser Ser
740 745 750

Lys Thr Leu Pro Gly Gly Lys Ser Lys Thr Leu Pro Gly Gly Asn Ser
755 760 765

Lys Thr Leu Pro Gly Gly Lys Ser Lys Thr Leu Pro Gly Gly Asn Thr
770 775 780

Lys Thr Leu Pro Gly Gly Ala Cys Lys Pro Thr Thr Val Thr Val Thr
785 790 795 800

Gln Lys Val Thr Val Thr Val Thr Val Glu Ser Gln Pro Thr Gln Gly
805 810 815

Gly Met Asn Gln Gly Gly Gly Asn Cys Ala Ala Lys Trp Gly Gln Cys
820 825 830

Gly Gly Asn Gly Phe Asn Gly Pro Thr Cys Cys Gln Asn Gly Ser Arg
835 840 845

Cys Gln Phe Val Asn Glu Trp Tyr Ser Gln Cys Leu
850 855 860

<210> SEQ ID NO 123
<211> LENGTH: 535

<212> TYPE: PRT
<213> ORGANISM: Bacillus pumilus

<400> SEQUENCE: 123

```
Met Lys Ile Thr Asn Pro Val Leu Lys Gly Phe Asn Pro Asp Pro Ser
1               5                   10                  15

Ile Cys Arg Ala Gly Glu Asp Tyr Tyr Met Ala Val Ser Thr Phe Glu
            20                  25                  30

Trp Phe Pro Gly Val Gln Ile Tyr His Ser Lys Asp Leu Ile His Trp
        35                  40                  45

Arg Leu Ala Ala Arg Pro Leu Gln Lys Thr Ser Gln Leu Asp Met Lys
    50                  55                  60

Gly Asn Pro Asp Ser Gly Gly Val Trp Ala Pro Cys Leu Ser Tyr Ala
65                  70                  75                  80

Asp Gly Gln Phe Trp Leu Ile Tyr Ser Asp Ile Lys Val Val Asp Gly
                85                  90                  95

Pro Phe Lys Asp Gly His Asn Tyr Leu Val Thr Ala Asp Ala Val Asp
            100                 105                 110

Gly Glu Trp Ser Asp Pro Val Arg Leu Asn Ser Ser Gly Phe Asp Pro
        115                 120                 125

Ser Leu Phe His Asp Pro Ser Gly Lys Lys Tyr Val Leu Asn Met Leu
    130                 135                 140

Trp Asp His Arg Glu Lys His His Ser Phe Ala Gly Ile Ala Leu Gln
145                 150                 155                 160

Glu Tyr Ser Val Ser Glu Lys Lys Leu Val Gly Glu Arg Lys Val Ile
                165                 170                 175

Phe Lys Gly Thr Pro Ile Lys Leu Thr Glu Ala Pro His Leu Tyr Tyr
            180                 185                 190

Ile Asn Asp Val Tyr Tyr Leu Leu Thr Ala Glu Gly Gly Thr Arg Tyr
        195                 200                 205

Glu His Ala Ala Thr Ile Ala Arg Ser Ser Arg Ile Asp Gly Pro Tyr
    210                 215                 220

Glu Val His Pro Asp Asn Pro Ile Leu Thr Ala Phe His Ala Pro Ser
225                 230                 235                 240

His Pro Leu Gln Lys Cys Gly His Ala Ser Ile Val Gln Thr His Thr
                245                 250                 255

Asn Glu Trp Tyr Leu Ala His Leu Thr Gly Arg Pro Ile His Ser Ser
            260                 265                 270

Lys Glu Ser Ile Phe Gln Gln Arg Gly Trp Cys Pro Leu Gly Arg Glu
        275                 280                 285

Thr Ala Ile Gln Lys Leu Glu Trp Lys Asp Gly Trp Pro Tyr Val Val
    290                 295                 300

Gly Gly Lys Glu Gly Leu Leu Glu Val Glu Ala Pro Ala Met Ser Val
305                 310                 315                 320

Lys Glu Phe Ser Pro Thr Tyr His Ile Val Asp Glu Phe Lys Asp Ser
                325                 330                 335

Ser Leu Asn Arg His Phe Gln Thr Leu Arg Ile Pro Phe Thr Asp Gln
            340                 345                 350

Ile Gly Ser Val Thr Glu Asn Pro His His Leu Arg Leu Tyr Gly Gln
        355                 360                 365

Glu Ser Leu Thr Ser Lys Phe Thr Gln Ala Phe Val Ala Arg Arg Trp
    370                 375                 380

Gln Ser Phe Tyr Phe Glu Ala Glu Thr Ala Val Ser Phe Phe Pro Lys
385                 390                 395                 400
```

```
Asn Phe Gln Gln Ala Ala Gly Leu Val Asn Tyr Tyr Asn Thr Glu Asn
                405                 410                 415

Trp Thr Ala Leu Gln Val Thr Tyr Asp Asp Ala Leu Gly Arg Ile Leu
            420                 425                 430

Glu Leu Ser Val Cys Glu Asn Leu Ala Phe Ser Gln Pro Leu Ile Lys
        435                 440                 445

Lys Ile Ile Ile Pro Asp Glu Ile Pro Tyr Val Tyr Leu Lys Val Thr
    450                 455                 460

Val Gln Arg Glu Thr Tyr Thr Tyr Ser Tyr Ser Phe Asp Gln Gln Glu
465                 470                 475                 480

Trp Glu Lys Ile Asp Val Pro Leu Glu Ser Thr His Leu Ser Asp Asp
                485                 490                 495

Phe Ile Arg Gly Gly Gly Phe Phe Thr Gly Ala Phe Val Gly Met Gln
            500                 505                 510

Cys Gln Asp Thr Ser Gly Glu Arg Leu Pro Ala Asp Phe Lys Tyr Phe
        515                 520                 525

Arg Tyr Glu Glu Thr Thr Glu
    530                 535


<210> SEQ ID NO 124
<211> LENGTH: 238
<212> TYPE: PRT
<213> ORGANISM: Streptomyces species N174

<400> SEQUENCE: 124

Ala Gly Ala Gly Leu Asp Asp Pro His Lys Lys Glu Ile Ala Met Glu
1               5                   10                  15

Leu Val Ser Ser Ala Glu Asn Ser Ser Leu Asp Trp Lys Ala Gln Tyr
            20                  25                  30

Lys Tyr Ile Glu Asp Ile Gly Asp Gly Arg Gly Tyr Thr Gly Gly Ile
        35                  40                  45

Ile Gly Phe Cys Ser Gly Thr Gly Asp Met Leu Glu Leu Val Gln His
    50                  55                  60

Tyr Thr Asp Leu Glu Pro Gly Asn Ile Leu Ala Lys Tyr Leu Pro Ala
65                  70                  75                  80

Leu Lys Lys Val Asn Gly Ser Ala Ser His Ser Gly Leu Gly Thr Pro
                85                  90                  95

Phe Thr Lys Asp Trp Ala Thr Ala Ala Lys Asp Thr Val Phe Gln Gln
            100                 105                 110

Ala Gln Asn Asp Glu Arg Asp Arg Val Tyr Phe Asp Pro Ala Val Ser
        115                 120                 125

Gln Ala Lys Ala Asp Gly Leu Arg Ala Leu Gly Gln Phe Ala Tyr Tyr
    130                 135                 140

Asp Ala Ile Val Met His Gly Pro Gly Asn Asp Pro Thr Ser Phe Gly
145                 150                 155                 160

Gly Ile Arg Lys Thr Ala Met Lys Lys Ala Arg Thr Pro Ala Gln Gly
                165                 170                 175

Gly Asp Glu Thr Thr Tyr Leu Asn Ala Phe Leu Asp Ala Arg Lys Ala
            180                 185                 190

Ala Met Leu Thr Glu Ala Ala His Asp Asp Thr Ser Arg Val Asp Thr
        195                 200                 205

Glu Gln Arg Val Phe Leu Lys Ala Gly Asn Leu Asp Leu Asn Pro Pro
    210                 215                 220

Leu Lys Trp Lys Thr Tyr Gly Asp Pro Tyr Val Ile Asn Ser
```

225 230 235

<210> SEQ ID NO 125
<211> LENGTH: 363
<212> TYPE: PRT
<213> ORGANISM: Paenibacillus species

<400> SEQUENCE: 125

Ala Asp Ala Ser Gln Ile Val Ser Glu Met Gly Ala Gly Trp Asn Leu
1 5 10 15

Gly Asn Gln Leu Glu Ala Ala Val Asn Gly Thr Pro Asn Glu Thr Ala
20 25 30

Trp Gly Asn Pro Thr Val Thr Pro Glu Leu Ile Lys Lys Val Lys Ala
35 40 45

Ala Gly Phe Lys Ser Ile Arg Ile Pro Val Ser Tyr Leu Asn Asn Ile
50 55 60

Gly Ser Ala Pro Asn Tyr Thr Ile Asn Ala Ala Trp Leu Asn Arg Ile
65 70 75 80

Gln Gln Val Val Asp Tyr Ala Tyr Asn Glu Gly Leu Tyr Val Ile Ile
85 90 95

Asn Ile His Gly Asp Gly Tyr Asn Ser Val Gln Gly Gly Trp Leu Leu
100 105 110

Val Asn Gly Gly Asn Gln Thr Ala Ile Lys Glu Lys Tyr Lys Lys Val
115 120 125

Trp Gln Gln Ile Ala Thr Lys Phe Ser Asn Tyr Asn Asp Arg Leu Ile
130 135 140

Phe Glu Ser Met Asn Glu Val Phe Asp Gly Asn Tyr Gly Asn Pro Asn
145 150 155 160

Ser Ala Tyr Tyr Thr Asn Leu Asn Ala Tyr Asn Gln Ile Phe Val Asp
165 170 175

Thr Val Arg Gln Thr Gly Gly Asn Asn Asn Ala Arg Trp Leu Leu Val
180 185 190

Pro Gly Trp Asn Thr Asn Ile Asp Tyr Thr Val Gly Asn Tyr Gly Phe
195 200 205

Thr Leu Pro Thr Asp Asn Tyr Arg Ser Ser Ala Ile Pro Ser Ser Gln
210 215 220

Lys Arg Ile Met Ile Ser Ala His Tyr Tyr Ser Pro Trp Asp Phe Ala
225 230 235 240

Gly Glu Glu Asn Gly Asn Ile Thr Gln Trp Gly Ala Thr Ser Thr Asn
245 250 255

Pro Ala Lys Lys Ser Thr Trp Gly Gln Glu Asp Tyr Leu Glu Ser Gln
260 265 270

Phe Lys Ser Met Tyr Asp Lys Phe Val Thr Gln Gly Tyr Pro Val Val
275 280 285

Ile Gly Glu Phe Gly Ser Ile Asp Lys Thr Ser Tyr Asp Ser Ser Asn
290 295 300

Asn Val Tyr Arg Ala Ala Tyr Ala Lys Ala Val Thr Ala Lys Ala Lys
305 310 315 320

Lys Tyr Lys Met Val Pro Val Tyr Trp Asp Asn Gly His Asn Gly Gln
325 330 335

His Gly Phe Ala Leu Phe Asn Arg Ser Asn Asn Thr Val Thr Gln Gln
340 345 350

Asn Ile Ile Asn Ala Ile Met Gln Gly Met Gln
355 360

<210> SEQ ID NO 126
<211> LENGTH: 442
<212> TYPE: PRT
<213> ORGANISM: Helix pomatia

<400> SEQUENCE: 126

```
Met Leu Ser Leu Val Ile Ala Leu Cys Val Val Gly Ser Leu Ser Ala
1               5                   10                  15

His Leu Pro Glu Val Phe Val His Tyr Gln Asp Gly Ala Leu His Phe
            20                  25                  30

Lys Met Gln His Val Pro Gly Leu Lys Glu Val Asn Phe Asn Tyr Gln
        35                  40                  45

Leu Gly Ser Gln Ala Lys Asn Val Ile Pro Lys Met Gly Thr Ala Asn
    50                  55                  60

Lys Gly Gly Asp Gly Tyr Trp His Leu Thr Asp Lys Lys Ile Asp Leu
65                  70                  75                  80

Gln Pro Gly Asp Ser Ile Gln Tyr Asn Ala Val Ala Trp Gly Thr Ala
                85                  90                  95

Gly Lys Leu His Ala Pro Val Ala Ser Trp Val Tyr Ala Pro Glu Pro
            100                 105                 110

Thr Arg Gly Pro Arg Arg Leu Arg Gly Ala Val Met Phe Arg Asp Asp
        115                 120                 125

Phe Asn Gly Gly Gly Leu Asp Thr Asn Asn Trp Asn Tyr Glu Val Ser
    130                 135                 140

Met Tyr Gly Gly Met Asn Trp Glu Phe Gln Val Tyr Thr Asn Asp Lys
145                 150                 155                 160

Ser Asn Val Tyr Thr Asn Asn Gly Lys Leu Phe Leu Lys Pro Thr Lys
                165                 170                 175

Thr Val Asp Asp Pro Arg Trp Asp Glu Asn Phe Leu His Ser Gly Val
            180                 185                 190

Met Asp Val Ala Gln Ile Trp Gly Tyr Cys Thr Gln Ser Ala Gln Tyr
        195                 200                 205

Gly Cys His Arg Glu Gly Lys Asn Gly Ile Leu Pro Pro Val Met Ser
    210                 215                 220

Gly Lys Val Lys Ser Lys Pro Val Leu Lys Tyr Gly Thr Val Glu Val
225                 230                 235                 240

Arg Ala Arg Ile Pro Lys Gly Asp Trp Leu Trp Pro Ala Ile Trp Met
                245                 250                 255

Leu Pro Arg Asp Ser His Tyr Gly Gly Trp Pro Arg Ser Gly Glu Ile
            260                 265                 270

Asp Ile Met Glu Ser Arg Gly Asn Val Arg Ala Ser Gly His Gly Val
        275                 280                 285

Asn Glu Val Ser Ser Thr Leu His Trp Gly Thr Ser Ala Gly Asp Asn
    290                 295                 300

His Tyr Gly Gln Thr Thr His Ala Lys Gln Ala Ala Asp Trp Ser Asn
305                 310                 315                 320

Ser Phe His Thr Trp Arg Leu Glu Trp Thr His Asp His Ile Ala Thr
                325                 330                 335

Phe Val Asp Asn Gln Gln Ile Leu Arg Val Thr Pro Pro Ser Gly Gly
            340                 345                 350

Phe Ser Glu Leu Gly His Thr Ser Asn Ile Trp Ala Gly Asn Asp Lys
        355                 360                 365

Met Ala Pro Phe Asp Lys Glu Phe Tyr Ala Ile Phe Asn Val Ala Val
    370                 375                 380
```

Gly Gly Thr Asn Gly Phe Phe Pro Glu Asn Trp Asp Tyr Gly Tyr Pro
385 390 395 400

Lys Pro Trp Ser Asn Thr Ser Pro His Ala Ala Gln Asp Trp Trp Asn
405 410 415

Gly Arg Ser Lys Trp Glu Ser Ser Trp Gln Gly Asp Lys Val Ala Met
420 425 430

Glu Ile Asp Tyr Ile Glu Met Arg Tyr Leu
435 440

<210> SEQ ID NO 127
<211> LENGTH: 374
<212> TYPE: PRT
<213> ORGANISM: Aspergillus saitoi

<400> SEQUENCE: 127

Ala Pro Ala Pro Thr Arg Lys Gly Phe Thr Ile Asn Gln Ile Ala Arg
1 5 10 15

Pro Ala Asn Lys Thr Arg Thr Val Asn Leu Pro Gly Leu Tyr Ala Arg
20 25 30

Ser Leu Ala Lys Phe Gly Gly Thr Val Pro Gln Ser Val Lys Glu Ala
35 40 45

Ala Ser Lys Gly Ser Ala Val Thr Thr Pro Gln Asn Asn Asp Glu Glu
50 55 60

Tyr Leu Thr Pro Val Thr Val Gly Lys Ser Thr Leu His Leu Asp Phe
65 70 75 80

Asp Thr Gly Ser Ala Asp Leu Trp Val Phe Ser Asp Glu Leu Pro Ser
85 90 95

Ser Glu Gln Thr Gly His Asp Leu Tyr Thr Pro Ser Ser Ser Ala Thr
100 105 110

Lys Leu Ser Gly Tyr Ser Trp Asp Ile Ser Tyr Gly Asp Gly Ser Ser
115 120 125

Ala Ser Gly Asp Val Tyr Arg Asp Thr Val Thr Val Gly Gly Val Thr
130 135 140

Thr Asn Lys Gln Ala Val Glu Ala Ala Ser Lys Ile Ser Ser Glu Phe
145 150 155 160

Val Gln Asp Thr Ala Asn Asp Gly Leu Leu Gly Leu Ala Phe Ser Ser
165 170 175

Ile Asn Thr Val Gln Pro Lys Ala Gln Thr Thr Phe Phe Asp Thr Val
180 185 190

Lys Ser Gln Leu Asp Ser Pro Leu Phe Ala Val Gln Leu Lys His Asp
195 200 205

Ala Pro Gly Val Tyr Asp Phe Gly Tyr Ile Asp Asp Ser Lys Tyr Thr
210 215 220

Gly Ser Ile Thr Tyr Thr Asp Ala Asp Ser Ser Gln Gly Tyr Trp Gly
225 230 235 240

Phe Ser Thr Asp Gly Tyr Ser Ile Gly Asp Gly Ser Ser Ser Ser Ser
245 250 255

Gly Phe Ser Ala Ile Ala Asp Thr Gly Thr Thr Leu Ile Leu Leu Asp
260 265 270

Asp Glu Ile Val Ser Ala Tyr Tyr Glu Gln Val Ser Gly Ala Gln Glu
275 280 285

Ser Tyr Glu Ala Gly Gly Tyr Val Phe Ser Cys Ser Thr Asp Leu Pro
290 295 300

Asp Phe Thr Val Val Ile Gly Asp Tyr Lys Ala Val Val Pro Gly Lys

```
305                 310                 315                 320

Tyr Ile Asn Tyr Ala Pro Val Ser Thr Gly Ser Ser Thr Cys Tyr Gly
                325                 330                 335

Gly Ile Gln Ser Asn Ser Gly Leu Gly Leu Ser Ile Leu Gly Asp Val
            340                 345                 350

Phe Leu Lys Ser Gln Tyr Val Val Phe Asn Ser Glu Gly Pro Lys Leu
        355                 360                 365

Gly Phe Ala Ala Gln Ala
    370


<210> SEQ ID NO 128
<211> LENGTH: 298
<212> TYPE: PRT
<213> ORGANISM: Bacillus sp.

<400> SEQUENCE: 128

Ala Ala Ala Thr Gly Phe Tyr Val Asn Gly Gly Lys Leu Tyr Asp Ser
1               5                   10                  15

Thr Gly Lys Pro Phe Tyr Met Arg Gly Ile Asn His Gly His Ser Trp
            20                  25                  30

Phe Lys Asn Asp Leu Asn Thr Ala Ile Pro Ala Ile Ala Lys Thr Gly
        35                  40                  45

Ala Asn Thr Val Arg Ile Val Leu Ser Asn Gly Thr Gln Tyr Thr Lys
    50                  55                  60

Asp Asp Leu Asn Ser Val Lys Asn Ile Ile Asn Val Val Asn Ala Asn
65                  70                  75                  80

Lys Met Ile Ala Val Leu Glu Val His Asp Ala Thr Gly Lys Asp Asp
                85                  90                  95

Phe Asn Ser Leu Asp Ala Ala Val Asn Tyr Trp Ile Ser Ile Lys Glu
            100                 105                 110

Ala Leu Ile Gly Lys Glu Asp Arg Val Ile Val Asn Ile Ala Asn Glu
        115                 120                 125

Trp Tyr Gly Thr Trp Asn Gly Ser Ala Trp Ala Asp Gly Tyr Lys Lys
    130                 135                 140

Ala Ile Pro Lys Leu Arg Asp Ala Gly Ile Lys Asn Thr Leu Ile Val
145                 150                 155                 160

Asp Ala Ala Gly Trp Gly Gln Tyr Pro Gln Ser Ile Val Asp Tyr Gly
                165                 170                 175

Gln Ser Val Phe Ala Ala Asp Ser Gln Lys Asn Thr Ala Phe Ser Ile
            180                 185                 190

His Met Tyr Glu Tyr Ala Gly Lys Asp Ala Ala Thr Val Lys Ser Asn
        195                 200                 205

Met Glu Asn Val Leu Asn Lys Gly Leu Ala Leu Ile Ile Gly Glu Phe
    210                 215                 220

Gly Gly Tyr His Thr Asn Gly Asp Val Asp Glu Tyr Ala Ile Met Lys
225                 230                 235                 240

Tyr Gly Leu Glu Lys Gly Val Gly Trp Leu Ala Trp Ser Trp Tyr Gly
                245                 250                 255

Asn Ser Ser Gly Leu Asn Tyr Leu Asp Leu Ala Thr Gly Pro Asn Gly
            260                 265                 270

Ser Leu Thr Ser Tyr Gly Asn Thr Val Val Asn Asp Thr Tyr Gly Ile
        275                 280                 285

Lys Asn Thr Ser Gln Lys Ala Gly Ile Phe
    290                 295
```

<210> SEQ ID NO 129
<211> LENGTH: 349
<212> TYPE: PRT
<213> ORGANISM: Aspergillus japonicus

<400> SEQUENCE: 129

Ala Pro Ser Arg Val Ser Asp Phe Thr Lys Arg Ser Thr Cys Thr Phe
1               5                   10                  15

Thr Asp Ala Ala Thr Ala Ser Glu Ser Lys Thr Ser Cys Ser Asp Ile
            20                  25                  30

Val Leu Lys Asp Ile Thr Val Pro Ala Gly Glu Thr Leu Asn Leu Lys
        35                  40                  45

Asp Pro Asn Asp Gly Thr Thr Val Thr Phe Glu Gly Thr Thr Thr Trp
    50                  55                  60

Glu Tyr Glu Glu Trp Asp Gly Pro Leu Leu Arg Ile Ser Gly Lys Asp
65                  70                  75                  80

Ile Thr Val Thr Gln Ser Ser Asp Ala Val Leu Asp Gly Asn Gly Ala
                85                  90                  95

Lys Trp Trp Asp Gly Glu Gly Thr Asn Gly Gly Lys Thr Lys Pro Lys
            100                 105                 110

Phe Phe Tyr Ala His Asp Leu Asp Asp Ser Lys Ile Ser Gly Leu Tyr
        115                 120                 125

Ile Lys Asn Thr Pro Val Gln Ala Ile Ser Val Glu Ser Asp Asn Leu
    130                 135                 140

Val Ile Glu Asp Val Thr Ile Asp Asn Ser Asp Gly Asp Ser Glu Gly
145                 150                 155                 160

Gly His Asn Thr Asp Gly Phe Asp Ile Ser Glu Ser Thr Tyr Ile Thr
                165                 170                 175

Ile Thr Gly Ala Thr Val Lys Asn Gln Asp Asp Cys Val Ala Ile Asn
            180                 185                 190

Ser Gly Glu Asn Ile Tyr Phe Ser Gly Gly Thr Cys Ser Gly Gly His
        195                 200                 205

Gly Leu Ser Ile Gly Ser Val Gly Gly Arg Asp Asp Asn Thr Val Lys
    210                 215                 220

Asn Val Thr Phe Ile Asp Ser Thr Val Ser Asp Ser Glu Asn Gly Val
225                 230                 235                 240

Arg Ile Lys Thr Val Tyr Asp Ala Thr Gly Thr Val Glu Asp Ile Thr
                245                 250                 255

Tyr Ser Asn Ile Gln Leu Ser Gly Ile Ser Asp Tyr Gly Ile Val Ile
            260                 265                 270

Glu Gln Asp Tyr Glu Asn Gly Asp Pro Thr Gly Thr Pro Ser Asn Gly
        275                 280                 285

Val Thr Ile Ser Asp Val Thr Leu Glu Asp Ile Thr Gly Ser Val Asp
    290                 295                 300

Ser Asp Ala Val Glu Ile Tyr Ile Leu Cys Gly Asp Gly Ser Cys Ser
305                 310                 315                 320

Asp Trp Thr Met Ser Gly Ile Asp Ile Thr Gly Gly Glu Thr Ser Ser
                325                 330                 335

Asp Cys Glu Asn Val Pro Ser Gly Ala Ser Cys Asp Gln
            340                 345

<210> SEQ ID NO 130
<211> LENGTH: 310
<212> TYPE: PRT
<213> ORGANISM: Triticum aestivum

<400> SEQUENCE: 130

Glu Leu Pro Leu Val Glu His Pro Ala Lys Asn Asp Gly Ser Leu Ser
1               5                   10                  15

Leu Leu Val Val Gly Asp Trp Gly Arg Asn Gly Thr Tyr Asn Gln Ser
            20                  25                  30

Arg Val Ala Glu Gln Met Gly Lys Val Gly Glu Arg Leu Asp Ile Asp
        35                  40                  45

Phe Val Val Ser Thr Gly Asp Asn Phe Tyr Glu Asn Gly Leu Thr Gly
    50                  55                  60

Val His Asp Gln Gln Phe Glu Glu Ser Phe Thr Asn Ile Tyr Thr Ala
65                  70                  75                  80

Gln Ser Leu Gln Lys Pro Trp Tyr Leu Val Leu Gly Asn His Asp Tyr
                85                  90                  95

Arg Gly Asp Ala Leu Ala Gln Leu Asp Pro Val Met Arg Lys Leu Asp
            100                 105                 110

Glu Arg Phe Val Cys Met Arg Ser Phe Leu Val Asn Ala Glu Ile Val
        115                 120                 125

Glu Phe Phe Phe Ile Asp Thr Thr Pro Phe Gln Leu Lys Tyr Trp Thr
    130                 135                 140

His Pro Lys Asp Ser His Tyr Asp Trp Arg Gly Val Ala Pro Arg Lys
145                 150                 155                 160

Asp Tyr Ile Ala Asn Leu Leu Lys Asp Leu Asp Glu Ala Met Lys Lys
                165                 170                 175

Ser Thr Ala Lys Trp Lys Ile Ala Ile Gly His His Thr Met Arg Ser
            180                 185                 190

Val Ser Asp His Gly Asp Thr Glu Glu Leu Leu Gln Leu Leu Leu Pro
        195                 200                 205

Val Leu Lys Val Asn Gly Ile Asp Phe Tyr Ile Asn Gly His Asp His
    210                 215                 220

Cys Leu Glu His Ile Ser Ser Arg Asp Ser Pro Ile Gln Tyr Phe Thr
225                 230                 235                 240

Ser Gly Gly Gly Ser Lys Ala Trp Arg Gly Val Tyr Gln Pro Asn Asp
                245                 250                 255

Asp Lys Ile Gln Phe Phe Tyr Asp Gly Gln Gly Phe Met Ser Leu Gln
            260                 265                 270

Leu Asn Gln Asp Gln Ala Asp Phe Ile Phe Tyr Asp Val Ser Gly Lys
        275                 280                 285

Val Leu Tyr Glu Phe Thr Ser His Lys Thr Asn His Phe Gln Pro Ser
    290                 295                 300

Ile Tyr Val Thr Ala Glu
305                 310

<210> SEQ ID NO 131
<211> LENGTH: 447
<212> TYPE: PRT
<213> ORGANISM: Triticum aestivum

<400> SEQUENCE: 131

Arg Ser Glu Phe Pro Ser Thr Asp Met Pro Leu Asp Ser Glu Trp Phe
1               5                   10                  15

Ala Thr Pro Lys Gly Tyr Asn Ala Pro Gln Gln Val His Ile Thr Gln
            20                  25                  30

Gly Asp Tyr Asp Gly Lys Ala Val Ile Val Ser Trp Val Thr Pro Ser
        35                  40                  45

-continued

```
Glu Pro Ala Pro Ser Gln Val Phe Tyr Ser Lys Glu Glu Asn Arg Tyr
    50                  55                  60

Asp Gln Lys Ala Glu Gly Thr Met Thr Asn Tyr Thr Phe Tyr Asp Tyr
65                  70                  75                  80

Lys Ser Gly Tyr Ile His His Cys Leu Val Asp Gly Leu Glu Tyr Asn
                85                  90                  95

Thr Lys Tyr Tyr Tyr Lys Ile Gly Thr Gly Asp Ser Ala Arg Glu Phe
            100                 105                 110

Trp Phe Gln Thr Pro Pro Ala Ile Asp Thr Asp Ala Ser Tyr Thr Phe
        115                 120                 125

Gly Ile Ile Gly Asp Leu Gly Gln Thr Phe Asn Ser Leu Ser Thr Leu
    130                 135                 140

Gln His Tyr Leu Lys Ser Gly Gly Glu Ser Val Leu Phe Val Gly Asp
145                 150                 155                 160

Leu Ser Tyr Ala Asp Arg Tyr Gln His Asn Asp Gly Ile Arg Trp Asp
                165                 170                 175

Ser Trp Gly Arg Phe Val Glu Arg Ser Thr Ala Tyr Gln Pro Trp Ile
            180                 185                 190

Trp Asn Ser Gly Asn His Glu Ile Glu Tyr Arg Pro Asp Leu Gly Glu
        195                 200                 205

Thr Ser Thr Phe Lys Pro Tyr Leu His Arg Tyr Ser Thr Pro Tyr Leu
    210                 215                 220

Ala Ser Lys Ser Ser Ser Pro Met Trp Tyr Ala Val Arg Arg Ala Ser
225                 230                 235                 240

Ala His Ile Ile Val Leu Ser Ser Tyr Ser Pro Phe Val Lys Tyr Thr
                245                 250                 255

Pro Gln Trp Met Trp Leu Lys Gly Glu Leu Lys Arg Val Asp Arg Glu
            260                 265                 270

Lys Thr Pro Trp Leu Ile Val Leu Met His Ala Pro Met Tyr Asn Ser
        275                 280                 285

Asn Asn Ala His Tyr Met Glu Gly Glu Ser Met Arg Ala Ala Phe Glu
    290                 295                 300

Lys Trp Phe Val Lys Tyr Lys Val Asp Leu Val Phe Ala Gly His Val
305                 310                 315                 320

His Ala Tyr Glu Arg Ser Tyr Arg Ile Ser Asn Ile Asn Tyr Asn Val
                325                 330                 335

Thr Ser Gly Asn Arg Tyr Pro Val Pro Asp Lys Ser Ala Pro Val Tyr
            340                 345                 350

Ile Thr Val Gly Asp Gly Gly Asn Gln Glu Gly Leu Ala Trp Arg Phe
        355                 360                 365

Asn Asp Pro Gln Pro Asp Tyr Ser Ala Phe Arg Glu Ala Ser Phe Gly
    370                 375                 380

His Ser Thr Leu Gln Leu Val Asn Arg Thr His Ala Val Tyr Gln Trp
385                 390                 395                 400

Asn Arg Asn Asp Asp Gly Lys His Val Pro Thr Asp Asn Val Val Phe
                405                 410                 415

His Asn Gln Tyr Trp Ala Gly Asn Thr Arg Arg Arg Arg Leu Lys Lys
            420                 425                 430

Lys His Leu Arg Tyr Glu Ser Leu Gln Ser Leu Met Ser Met Leu
        435                 440                 445
```

<210> SEQ ID NO 132
<211> LENGTH: 530

<212> TYPE: PRT
<213> ORGANISM: Triticum aestivum

<400> SEQUENCE: 132

Ala Ala Glu Pro Ala Ser Thr Leu Thr Gly Pro Ser Arg Pro Val Thr
1 5 10 15

Val Ala Leu Arg Lys Asp Arg Gly His Ala Val Asp Leu Pro Asp Thr
20 25 30

Asp Pro Arg Val Gln Arg Arg Ala Thr Gly Trp Ala Pro Glu Gln Ile
35 40 45

Thr Val Ala Leu Ser Ala Ala Pro Thr Ser Ala Trp Val Ser Trp Ile
50 55 60

Thr Gly Glu Phe Gln Met Gly Gly Thr Val Lys Pro Leu Asn Pro Gly
65 70 75 80

Thr Val Ala Ser Val Val Arg Tyr Gly Leu Ala Ala Asp Ser Leu Val
85 90 95

His Glu Ala Thr Gly Asp Ala Leu Val Tyr Ser Gln Leu Tyr Pro Phe
100 105 110

Glu Gly Leu Gln Asn Tyr Thr Ser Gly Ile Ile His His Val Arg Leu
115 120 125

Gln Gly Leu Glu Pro Ala Thr Lys Tyr Tyr Tyr Gln Cys Gly Asp Pro
130 135 140

Gly Ile Pro Gly Ala Met Ser Ala Val His Ala Phe Arg Thr Met Pro
145 150 155 160

Ala Val Gly Pro Arg Ser Tyr Pro Gly Arg Ile Ala Val Val Gly Asp
165 170 175

Leu Gly Leu Thr Tyr Asn Thr Thr Ser Thr Val Asp His Met Val Ser
180 185 190

Asn Arg Pro Asp Leu Val Leu Leu Val Gly Asp Val Cys Tyr Ala Asn
195 200 205

Met Tyr Leu Thr Asn Gly Thr Gly Ala Asp Cys Tyr Ser Cys Ala Phe
210 215 220

Gly Lys Ser Thr Pro Ile His Glu Thr Tyr Gln Pro Arg Trp Asp Tyr
225 230 235 240

Trp Gly Arg Tyr Met Glu Ala Val Thr Ser Gly Thr Pro Met Met Val
245 250 255

Val Glu Gly Asn His Glu Ile Glu Glu Gln Ile Gly Asn Lys Thr Phe
260 265 270

Ala Ala Tyr Arg Ser Arg Phe Ala Phe Pro Ser Thr Glu Ser Gly Ser
275 280 285

Phe Ser Pro Phe Tyr Tyr Ser Phe Asp Ala Gly Gly Ile His Phe Ile
290 295 300

Met Leu Ala Ala Tyr Ala Asp Tyr Ser Arg Ser Gly Glu Gln Tyr Arg
305 310 315 320

Trp Leu Val Lys Asp Leu Ala Lys Val Asp Arg Ala Val Thr Pro Trp
325 330 335

Leu Val Ala Gly Trp His Ala Pro Trp Tyr Thr Thr Tyr Lys Ala His
340 345 350

Tyr Arg Glu Val Glu Cys Met Arg Val Ala Met Glu Glu Leu Leu Tyr
355 360 365

Ser His Gly Leu Asp Ile Ala Phe Thr Gly His Val His Ala Tyr Glu
370 375 380

Arg Ser Asn Arg Val Phe Asn Tyr Thr Leu Asp Pro Cys Gly Ala Val
385 390 395 400

His Ile Ser Val Gly Asp Gly Gly Asn Arg Glu Lys Met Ala Thr Thr
405 410 415

His Ala Asp Glu Pro Gly His Cys Pro Asp Pro Arg Pro Lys Pro Asn
420 425 430

Ala Phe Ile Gly Cys Phe Cys Ala Phe Asn Phe Thr Ser Gly Pro Ala
435 440 445

Ala Gly Arg Phe Cys Trp Asp Arg Gln Pro Asp Tyr Ser Ala Tyr Arg
450 455 460

Glu Ser Ser Phe Gly His Gly Ile Leu Glu Val Lys Asn Glu Thr His
465 470 475 480

Ala Leu Trp Arg Trp His Arg Asn Gln Asp His Tyr Gly Ser Ala Gly
485 490 495

Asp Glu Ile Tyr Ile Val Arg Glu Pro His Arg Cys Leu His Lys His
500 505 510

Asn Ser Thr Arg Pro Ala His Gly Arg Gln Asn Thr Thr Arg Glu Ser
515 520 525

Gly Gly
530

<210> SEQ ID NO 133
<211> LENGTH: 521
<212> TYPE: PRT
<213> ORGANISM: Triticum aestivum

<400> SEQUENCE: 133

Ala Ala Glu Pro Ala Ser Thr Leu Thr Gly Pro Ser Arg Pro Val Thr
1 5 10 15

Val Thr Leu Arg Glu Asp Arg Gly His Ala Val Asp Leu Pro Asp Thr
20 25 30

Asp Pro Arg Val Gln Arg Arg Ala Thr Gly Trp Ala Pro Glu Gln Ile
35 40 45

Ala Val Ala Leu Ser Ala Ala Pro Thr Ser Ala Trp Val Ser Trp Ile
50 55 60

Thr Gly Glu Phe Gln Met Gly Gly Thr Val Lys Pro Leu Asp Pro Gly
65 70 75 80

Thr Val Ala Ser Val Val Arg Tyr Gly Leu Ala Ala Asp Ser Leu Val
85 90 95

Arg Gln Ala Thr Gly Asp Ala Leu Val Tyr Ser Gln Leu Tyr Pro Phe
100 105 110

Glu Gly Leu Gln Asn Tyr Thr Ser Gly Ile Ile His His Val Arg Leu
115 120 125

Gln Gly Leu Glu Pro Ala Thr Lys Tyr Tyr Tyr Gln Cys Gly Asp Pro
130 135 140

Ala Leu Pro Gly Ala Met Ser Ala Val His Ala Phe Arg Thr Met Pro
145 150 155 160

Ala Val Gly Pro Arg Ser Tyr Pro Gly Arg Ile Ala Val Val Gly Asp
165 170 175

Leu Gly Leu Thr Tyr Asn Thr Thr Ser Thr Val Asp His Met Ala Ser
180 185 190

Asn Arg Pro Asp Leu Val Leu Leu Leu Gly Asp Val Ser Tyr Ala Asn
195 200 205

Leu Tyr Leu Thr Asn Gly Thr Gly Ala Asp Cys Tyr Ser Cys Ala Phe
210 215 220

Gly Lys Ser Thr Pro Ile His Glu Thr Tyr Gln Pro Arg Trp Asp Tyr

-continued

```
225                 230                 235                 240

Trp Gly Arg Tyr Met Glu Ala Val Thr Ser Gly Thr Pro Met Val Val
                245                 250                 255

Val Glu Gly Asn His Glu Ile Glu Glu Gln Ile Gly Asn Lys Thr Phe
            260                 265                 270

Ala Ala Tyr Arg Ser Arg Phe Ala Phe Pro Ser Thr Glu Ser Gly Ser
        275                 280                 285

Phe Ser Pro Phe Tyr Tyr Ser Phe Asp Ala Gly Gly Ile His Phe Val
    290                 295                 300

Met Leu Gly Ala Tyr Ala Asp Tyr Gly Arg Ser Gly Glu Gln Tyr Arg
305                 310                 315                 320

Trp Leu Glu Lys Asp Leu Ala Lys Val Asp Arg Ser Val Thr Pro Trp
                325                 330                 335

Leu Val Ala Gly Trp His Ala Pro Trp Tyr Thr Thr Tyr Lys Ala His
            340                 345                 350

Tyr Arg Glu Val Glu Cys Met Arg Val Ala Met Glu Glu Leu Leu Tyr
        355                 360                 365

Ser His Gly Leu Asp Ile Ala Phe Thr Gly His Val His Ala Tyr Glu
    370                 375                 380

Arg Ser Asn Arg Val Phe Asn Tyr Thr Leu Asp Pro Cys Gly Ala Val
385                 390                 395                 400

His Ile Ser Val Gly Asp Gly Gly Asn Arg Glu Lys Met Ala Thr Thr
                405                 410                 415

His Ala Asp Glu Pro Gly His Cys Pro Glu Pro Arg Ala Lys Pro Asn
            420                 425                 430

Ala Phe Ile Gly Gly Phe Cys Ala Phe Asn Phe Thr Ser Gly Pro Ala
        435                 440                 445

Ala Gly Arg Phe Cys Trp Asp Arg Gln Pro Asp Tyr Ser Ala Tyr Arg
    450                 455                 460

Glu Ser Ser Phe Gly His Gly Ile Leu Glu Val Lys Asn Glu Thr His
465                 470                 475                 480

Ala Leu Trp Arg Trp His Arg Asn Gln Asp Met Tyr Gly Ser Ala Gly
                485                 490                 495

Asp Glu Ile Tyr Ile Val Arg Glu Pro His Arg Cys Leu His Lys His
            500                 505                 510

Asn Ser Thr Arg Pro Thr His Gly Arg
        515                 520


<210> SEQ ID NO 134
<211> LENGTH: 521
<212> TYPE: PRT
<213> ORGANISM: Triticum aestivum

<400> SEQUENCE: 134

Ala Ala Ala Ala Glu Pro Ala Ser Thr Leu Glu Gly Pro Ser Trp Pro
1               5                   10                  15

Val Thr Val Pro Leu Arg Glu Asp Arg Gly His Ala Val Asp Leu Pro
            20                  25                  30

Asp Thr Asp Pro Arg Val Gln Arg Arg Val Thr Gly Trp Ala Pro Glu
        35                  40                  45

Gln Ile Ala Val Ala Leu Ser Ala Ala Pro Thr Ser Ala Trp Val Ser
    50                  55                  60

Trp Ile Thr Gly Asp Phe Gln Met Gly Gly Ala Val Lys Pro Leu Asp
65                  70                  75                  80
```

-continued

```
Pro Gly Thr Val Gly Ser Val Val Arg Tyr Gly Leu Ala Ala Asp Ser
                85                  90                  95

Leu Val Arg Glu Ala Thr Gly Asp Ala Leu Val Tyr Ser Gln Leu Tyr
            100                 105                 110

Pro Phe Glu Gly Leu Gln Asn Tyr Thr Ser Gly Ile Ile His His Val
        115                 120                 125

Arg Leu Gln Gly Leu Glu Pro Gly Thr Lys Tyr Tyr Tyr Gln Cys Gly
    130                 135                 140

Asp Pro Ala Ile Pro Gly Ala Thr Ser Ala Val His Ala Phe Arg Thr
145                 150                 155                 160

Met Pro Ala Val Gly Pro Arg Ser Tyr Pro Gly Arg Ile Ala Val Val
                165                 170                 175

Gly Asp Leu Gly Leu Thr Tyr Asn Thr Thr Ser Thr Val Glu His Met
            180                 185                 190

Ala Ser Asn Gln Pro Asp Leu Val Leu Leu Leu Gly Asp Val Ser Tyr
        195                 200                 205

Ala Asn Leu Tyr Leu Thr Asn Gly Thr Gly Thr Asp Cys Tyr Ser Cys
    210                 215                 220

Ser Phe Ala Lys Ser Thr Pro Ile His Glu Thr Tyr Gln Pro Arg Trp
225                 230                 235                 240

Asp Tyr Trp Gly Arg Tyr Met Glu Ser Val Thr Ser Thr Thr Pro Met
                245                 250                 255

Met Val Val Glu Gly Asn His Glu Ile Glu Gln Gln Ile Gly Asn Lys
            260                 265                 270

Thr Phe Ala Ala Tyr Ser Ala Arg Phe Ala Phe Pro Ser Lys Glu Ser
        275                 280                 285

Asp Ser Phe Ser Pro Phe Tyr Tyr Ser Phe Asp Ala Gly Gly Ile His
    290                 295                 300

Phe Ile Met Leu Ala Ala Tyr Ala Ala Tyr Ser Lys Ser Gly Glu Gln
305                 310                 315                 320

Tyr Arg Trp Leu Glu Lys Asp Leu Ala Lys Val Asp Arg Ser Val Thr
                325                 330                 335

Pro Trp Leu Val Ala Gly Trp His Ala Pro Trp Tyr Ser Thr Tyr Lys
            340                 345                 350

Ala His Tyr Arg Glu Ala Glu Cys Met Arg Val Ala Met Glu Glu Leu
        355                 360                 365

Leu Tyr Ser Tyr Gly Leu Asp Ile Val Phe Thr Gly His Val His Ala
    370                 375                 380

Tyr Glu Arg Ser Asn Arg Val Phe Asn Tyr Thr Leu Asp Pro Cys Gly
385                 390                 395                 400

Ala Val His Ile Ser Val Gly Asp Gly Gly Asn Arg Glu Lys Met Ala
                405                 410                 415

Thr Thr His Ala Asp Asp Pro Gly Arg Cys Pro Glu Pro Leu Ser Thr
            420                 425                 430

Pro Asp Asp Phe Met Gly Gly Phe Cys Ala Phe Asn Phe Thr Ser Asp
        435                 440                 445

Pro Ala Ala Gly Ser Phe Cys Trp Asp Arg Gln Pro Asp Tyr Ser Ala
    450                 455                 460

Tyr Arg Glu Ser Ser Phe Gly His Gly Ile Leu Glu Val Lys Asn Glu
465                 470                 475                 480

Thr His Ala Leu Trp Lys Trp His Arg Asn Gln Asp Leu Tyr Gln Gly
                485                 490                 495

Gly Val Gly Asp Glu Ile Tyr Ile Val Arg Glu Pro Glu Arg Cys Leu
```

-continued 500 505 510

Leu Lys Ser Ser Ile Ala Ala Tyr Phe
515 520

<210> SEQ ID NO 135
<211> LENGTH: 24
<212> TYPE: PRT
<213> ORGANISM: Bacillus cereus

<400> SEQUENCE: 135

Met Lys Lys Lys Val Leu Ala Leu Ala Ala Ala Ile Thr Leu Val Ala
1 5 10 15

Pro Leu Gln Asn Val Ala Phe Ala
20

<210> SEQ ID NO 136
<211> LENGTH: 876
<212> TYPE: DNA
<213> ORGANISM: Bacillus thuringiensis

<400> SEQUENCE: 136
tctgacggag caacgccgcg tgagtgatga aggctttcgg gtcgtaaaac tctgttgtta 60
gggaagaaca agtgctagtt gaataagctg gcaccttgac ggtacctaac cagaaagcca 120
cggctaacta cgtgccagca gccgcggtaa tacgtaggtg gcaagcgtta tccggaatta 180
ttgggcgtaa agcgcgcgca ggtggtttct taagtctgat gtgaaagccc acggctcaac 240
cgtggagggt cattggaaac tgggagactt gagtgcagaa gaggaaagtg gaattccatg 300
tgtagcggtg aaatgcgtag agatatggag gaacaccagt ggcgaaggcg actttctggt 360
ctgtaactga cactgaggcg cgaaagcgtg gggagcaaac aggattagat accctggtag 420
tccacgccgt aaacgatgag tgctaagtgt tagagggttt ccgcccttta gtgctgaagt 480
taacgcatta agcactccgc ctggggagta cggccgcaag gctgaaactc aaaggaattg 540
acgggggccc gcacaagcgg tggagcatgt ggtttaattc gaagcaacgc gaagaacctt 600
accaggtctt gacatcctct gaaaacccta gagatagggc ttctccttcg ggagcagagt 660
gacaggtggt gcatggttgt cgtcagctcg tgtcgtgaga tgttgggtta agtcccgcaa 720
cgagcgcaac ccttgatctt agttgccatc attaagttgg gcactctaag gtgactgccg 780
gtgacaaacc ggaggaaggt ggggatgacg tcaaatcatc atgcccctta tgacctgggc 840
tacacacgtg ctacaatgga cggtacaaag agctgc 876

<210> SEQ ID NO 137
<211> LENGTH: 44
<212> TYPE: PRT
<213> ORGANISM: Burkholderia cepacia

<400> SEQUENCE: 137

Met Ala Arg Thr Met Arg Ser Arg Val Val Ala Gly Ala Val Ala Cys
1 5 10 15

Ala Met Ser Ile Ala Pro Phe Ala Gly Thr Thr Ala Val Met Thr Leu
20 25 30

Ala Thr Thr His Ala Ala Met Ala Ala Thr Ala Pro
35 40

<210> SEQ ID NO 138
<211> LENGTH: 23
<212> TYPE: PRT
<213> ORGANISM: Pseudomonas fluorescens

<400> SEQUENCE: 138

Met Gly Ile Phe Asp Tyr Lys Asn Leu Gly Thr Glu Gly Ser Lys Thr
1 5 10 15

Leu Phe Ala Asp Ala Met Ala
20

<210> SEQ ID NO 139
<211> LENGTH: 40
<212> TYPE: PRT
<213> ORGANISM: Streptomyces species N174

<400> SEQUENCE: 139

Met His Ser Gln His Arg Thr Ala Arg Ile Ala Leu Ala Val Val Leu
1 5 10 15

Thr Ala Ile Pro Ala Ser Leu Ala Thr Ala Gly Val Gly Tyr Ala Ser
20 25 30

Thr Gln Ala Ser Thr Ala Val Lys
35 40

<210> SEQ ID NO 140
<211> LENGTH: 32
<212> TYPE: PRT
<213> ORGANISM: Paenibacillus species

<400> SEQUENCE: 140

Met Phe Lys Lys Trp Lys Lys Phe Gly Ile Ser Ser Leu Ala Leu Val
1 5 10 15

Leu Val Ala Ala Val Ala Phe Thr Gly Trp Ser Ala Lys Ala Ser Ala
20 25 30

<210> SEQ ID NO 141
<211> LENGTH: 20
<212> TYPE: PRT
<213> ORGANISM: Aspergillus saitoi

<400> SEQUENCE: 141

Met Val Val Phe Ser Lys Thr Ala Ala Leu Val Leu Gly Leu Ser Thr
1 5 10 15

Ala Val Ser Ala
20

<210> SEQ ID NO 142
<211> LENGTH: 28
<212> TYPE: PRT
<213> ORGANISM: Bacillus sp.

<400> SEQUENCE: 142

Met Ala Lys Leu Gln Lys Gly Thr Ile Leu Thr Val Ile Ala Ala Leu
1 5 10 15

Met Phe Val Ile Leu Gly Ser Ala Ala Pro Lys Ala
20 25

<210> SEQ ID NO 143
<211> LENGTH: 21
<212> TYPE: PRT
<213> ORGANISM: Aspergillus japonicus

<400> SEQUENCE: 143

Met Pro Ser Ala Lys Pro Leu Phe Cys Leu Ala Thr Leu Ala Gly Ala
1 5 10 15

-continued

```
Ala Leu Ala Ala Pro
            20


<210> SEQ ID NO 144
<211> LENGTH: 25
<212> TYPE: PRT
<213> ORGANISM: Triticum aestivum

<400> SEQUENCE: 144

Met Ala Arg Gly Ser Met Ala Ala Val Leu Ala Val Leu Ala Val Ala
1               5                   10                  15

Ala Leu Arg Cys Ala Pro Ala Ala Ala
            20                  25


<210> SEQ ID NO 145
<211> LENGTH: 30
<212> TYPE: PRT
<213> ORGANISM: Triticum aestivum

<400> SEQUENCE: 145

Met Arg Gly Leu Gly Phe Ala Ala Leu Ser Leu His Val Leu Leu Cys
1               5                   10                  15

Leu Ala Asn Gly Val Ser Ser Arg Arg Thr Ser Ser Tyr Val
            20                  25                  30


<210> SEQ ID NO 146
<211> LENGTH: 18
<212> TYPE: PRT
<213> ORGANISM: Triticum aestivum

<400> SEQUENCE: 146

Met Trp Trp Gly Ser Leu Arg Leu Leu Leu Leu Leu Ala Ala Ala Val
1               5                   10                  15

Ala Ala


<210> SEQ ID NO 147
<211> LENGTH: 15
<212> TYPE: PRT
<213> ORGANISM: Triticum aestivum

<400> SEQUENCE: 147

Met Gly Ile Trp Arg Gly Ser Leu Pro Leu Leu Leu Leu Ala Ala
1               5                   10                  15
```

METHODS FOR PROMOTING PLANT HEALTH USING FREE ENZYMES AND MICROORGANISMS THAT OVEREXPRESS ENZYMES

CROSS-REFERENCE TO RELATED APPLICATIONS

This application claims the benefit of U.S. Provisional Application Ser. No. 62/309,426, filed on Mar. 16, 2016, the entirety of which is herein incorporated by reference.

FIELD OF THE INVENTION

Methods for stimulating plant growth and/or promoting plant health using free enzymes or recombinant microorganisms that overexpress enzymes are provided. Plant seeds treated with free enzymes or recombinant microorganisms that overexpress enzymes are also provided. Compositions comprising a fertilizer and an enzyme or a recombinant microorganism that overexpresses an enzyme are provided. Modified enzymes having ACC deaminase activity, recombinant microorganisms expressing the modified enzymes, plant seeds treated with the modified enzymes or recombinant microorganisms, and methods for stimulating plant growth and/or promoting plant health using the modified enzymes or recombinant microorganisms are also provided.

BACKGROUND OF THE INVENTION

Within the zone surrounding a plant's roots is a region called the rhizosphere. In the rhizosphere, bacteria, fungi, and other organisms compete for nutrients and for binding to the root structures of the plant. Both detrimental and beneficial bacteria and fungi can occupy the rhizosphere. The bacteria, fungi, and the root system of the plant can all be influenced by the actions of enzymes in the rhizosphere. Augmentation of soil or treatment of plants with certain of these enzymes would have beneficial effects on the overall populations of beneficial soil bacteria and fungi, create a healthier overall soil environment for plant growth, improve plant growth, and provide for the protection of plants against certain bacterial and fungal pathogens. The environment around the roots of a plant (the rhizosphere) is a unique mixture of bacteria, fungi, nutrients, and roots that has different qualities than that of native soil. The symbiotic relationship between these organisms is unique, and could be altered for the better with inclusion of exogenous proteins.

Thus, there exists a need in the art for a method for effectively delivering enzymes and other proteins to plants. Furthermore, there exists a need in the art for a enhancing the response of plants to enzymes and providing benefit to the grower.

SUMMARY OF THE INVENTION

An enzyme is provided. The enzyme comprises an amino acid sequence encoding an enzyme having 1-aminocyclopropane-1-carboxylate deaminase (ACC deaminase) activity and a signal peptide. The signal peptide results in secretion of the enzyme when the enzyme is expressed in a microorganism. Recombinant microorganisms that express the enzyme are also provided. Formulations comprising the enzyme or the recombinant microorganism and an agriculturally acceptable carrier are also provided. Plant seeds treated with the enzyme, the recombinant microorganism, or the formulation are also provided.

An enzyme having ACC deaminase activity is provided. The amino acid sequence of the enzyme comprises at least one amino acid substitution relative to the sequence of a wild-type D-cysteine desulfhydrase or ACC deaminase enzyme from a *Bacillus* genus bacterium. The amino acid substitution results in increased ACC deaminase activity as compared to the ACC deaminase as compared to ACC deaminase activity of the wild-type D-cysteine desulfhydrase or ACC deaminase enzyme under the same conditions. Recombinant microorganisms that express the enzyme are also provided. Formulations comprising the enzyme or the recombinant microorganism and an agriculturally acceptable carrier are also provided. Plant seeds treated with the enzyme, the recombinant microorganism, or the formulation are also provided.

A method for stimulating plant growth and/or promoting plant health is provided. The method comprises applying any of the enzymes having ACC deaminase activity or a formulation comprising such an enzyme and an agriculturally acceptable carrier to a plant growth medium, a plant, a plant seed, or an area surrounding a plant or a plant seed.

Another method for stimulating plant growth and/or promoting plant health is provided. The method comprises applying any of the recombinant microorganisms that express an enzyme having ACC deaminase activity or a formulation comprising such a recombinant microorganism and an agriculturally acceptable carrier to a plant growth medium, a plant, a plant seed, or an area surrounding a plant or a plant seed.

Yet another method for stimulating plant growth and/or promoting plant health is provided. The method comprises applying a free enzyme to a plant growth medium, a plant, a plant seed, or an area surrounding a plant or a plant seed. The enzyme is selected from a phospholipase, a lipase, a xylanase, a xylosidase, a lactonase, a mannanase, a pectinase, a chitosanase, a protease, an acid phosphatase, a non-cellulolytic glucanase, an ACC deaminase, and combinations of any thereof.

Another method for stimulating plant growth and/or promoting plant health is provided. The method comprises applying two or more free enzymes to a plant growth medium, a plant, a plant seed, or an area surrounding a plant or a plant seed. The enzymes are independently selected from a phospholipase, a lipase, a xylanase, a xylosidase, a lactonase, a chitosanase, a protease, a phytase, an acid phosphatase, a mannanase, a pectinase, a glucanase, and an ACC deaminase.

A further method for stimulating plant growth and/or promoting plant health is provided. The method comprises applying a free enzyme to a plant or a plant seed. The enzyme comprises a glucanase. Applying the enzyme to the plant seed comprises: (a) applying the enzyme to the plant seed at the time of planting; or (b) coating the plant seed with the enzyme.

Yet another method for stimulating plant growth and/or promoting plant health is provided. The method comprises applying a free enzyme to a plant growth medium, a plant, a plant seed, or an area surrounding a plant or a plant seed. The enzyme comprises a glucanase. The method further comprises applying an expansin protein to the plant growth medium, the plant, the plant seed, or the area surrounding a plant or a plant seed.

Another method for stimulating plant growth and/or promoting plant health is provided. The method comprises applying a free enzyme to a plant or a plant seed. The enzyme comprises a phytase.

A further method for stimulating plant growth and/or promoting plant health is provided. The method comprises applying a fertilizer and a free enzyme to a plant growth medium, an area surrounding a plant or a plant seed, or to a plant or a plant seed. The free enzyme comprises a phytase.

A further method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a mannanase, a pectinase, a protease, a phytase, an acid phosphatase, and combinations of any thereof. The enzyme or expansin protein is expressed during vegetative growth of the recombinant microorganism.

Another method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein further comprises a signal peptide that results in secretion of the enzyme or expansin protein.

Another method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a phytase, a mannanase, a pectinase, an acid phosphatase, and combinations of any thereof. The enzyme or expansin protein is not bound to the exosporium of a recombinant *Bacillus cereus* family member.

A further method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a phytase, a mannanase, a pectinase, an acid phosphatase, and combinations of any thereof. The enzyme or expansin protein is not part of a fusion protein.

A treated plant seed is provided. The plant seed is treated with a free enzyme. The enzyme is selected from a phospholipase, a lipase, a xylanase, a xylosidase, a mannanase, a pectinase, a lactonase, a chitosanase, a protease, a phytase, an acid phosphatase, a non-cellulolytic glucanase, an ACC deaminase, and combinations of any thereof.

Another treated plant seed is provided. The plant seed is treated with two or more free enzymes, wherein the enzymes are independently selected from a phospholipase, a lipase, a xylanase, a xylosidase, a lactonase, a chitosanase, a mannanase, a pectinase, a protease, a phytase, an acid phosphatase, a glucanase, and an ACC deaminase.

A coated plant seed is provided. The plant seed is coated with a free enzyme. The enzyme comprises a glucanase.

A treated plant seed is provided. The plant seed is treated with a free enzyme and an expansin protein. The enzyme comprises a glucanase.

A plant seed is provided. The plant seed is coated with a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a phytase, a mannanase, a pectinase, an acid phosphatase, an ACC deaminase, and combinations of any thereof. The enzyme or expansin protein is expressed during vegetative growth of the recombinant microorganism.

Another plant seed is provided. The plant seed is coated with a recombinant microorganism. The recombinant microorganism expresses an enzyme or expansin protein, wherein expression of the enzyme is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein further comprises a signal peptide that results in secretion of the enzyme or expansin protein.

Yet another plant seed is provided. The plant seed is coated with a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein is not bound to the exosporium of a recombinant *Bacillus cereus* family member.

Another plant seed is provided. The plant seed is coated with a recombinant microorganism. The recombinant microorganism expresses an enzyme or an expansin protein, wherein expression of the enzyme or expansin protein is increased as compared to the expression level the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein is not part of a fusion protein.

A composition is provided. The composition comprises a fertilizer and an enzyme or an expansin protein. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof.

Another composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein is expressed during vegetative growth of the recombinant microorganism.

Yet another composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein further comprises a signal peptide that results in secretion of the enzyme or expansin protein.

A further composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein is not bound to the exosporium of a recombinant *Bacillus cereus* family member.

Another composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein is not part of a fusion protein.

The features of the invention are further defined in the appended claims and the list of embodiments provided below in the Section entitled "EMBODIMENTS." Other objects and features will be in part apparent and in part pointed out hereinafter.

Definitions

When the articles "a," "an," "one," "the," and "said" are used herein, they mean "at least one" or "one or more" unless otherwise indicated.

The term "*Bacillus cereus* family member" as used herein refers to any *Bacillus* species that is capable of producing an exosporium. Thus, the *Bacillus cereus* family of bacteria includes the species *Bacillus anthracis, Bacillus cereus, Bacillus thuringiensis, Bacillus mycoides, Bacillus pseudomycoides, Bacillus samanii, Bacillus gaemokensis, Bacillus weihenstephensis*, and *Bacillus toyoiensis. Bacillus cereus* family members are also referred to in the art as "*Bacillus cereus* senso lato."

The terms "composition" and "formulation" are used interchangeably herein to refer to a mixture of two or more chemical or biological substances (for example, a mixture of an enzyme and an agriculturally acceptable carrier or a mixture of a recombinant microorganism and an agriculturally acceptable carrier).

The terms "comprising," "including," and "having" are intended to be inclusive and mean that there may be additional elements other than the listed elements.

The term "foliar" used herein with respect to the application of enzymes or recombinant microorganisms to plants means that the enzyme or recombinant microorganism is applied to one or more aerial portions of the plant, including stems, leaves, fruits, flowers, or other exposed aerial portions of the plant.

The term "free enzyme" as used herein refers to an enzyme preparation that is substantially free of intact cells. The term "free enzyme" includes, but is not limited to, crude cell extracts containing an enzyme, partially purified, substantially purified, or purified enzyme. Free enzymes can optionally be immobilized on a chemical matrix or support to allow for controlled release of the enzyme. Free enzyme preparations preferably do not include enzymes bound to exosporium of a *Bacillus cereus* family member. Free enzymes also preferably do not include enzymes bound to exosporium of an intact *Bacillus cereus* family member spore.

The term "fusion protein" as used herein refers to a protein having a polypeptide sequence that comprises sequences derived from two or more separate proteins. A fusion protein can be generated by joining together a nucleic acid molecule that encodes all or part of a first polypeptide with a nucleic acid molecule that encodes all or part of a second polypeptide to create a nucleic acid sequence which, when expressed, yields a single polypeptide having functional properties derived from each of the original proteins.

The term "germination rate" as used herein refers to the number of seeds that germinate during a particular time period. For example, a germination rate of 85% indicates that 85 out of 100 seeds germinate during a given time period.

The term "glucanase" as used herein refers to any enzyme that is capable of hydrolyzing a glycoside bond. The term "non-cellulolytic glucanase" as used herein refers to any glucanase whose primary enzyme activity is not directed to cellulose or cellulose subunits as a substrate. A non-cellulolytic glucanase is preferably incapable of using cellulose as a substrate.

The term "immobilizing" as used herein in reference to immobilizing an enzyme on a matrix or support refers to the binding of the enzyme to the matrix or support such that the enzyme is maintained on the matrix or support or released from the support over a controlled period of time, instead of dissipating into the environment in an uncontrolled manner.

The terms "native sequence," "native amino acid sequence," "wild-type sequence," and "wild-type amino acid sequence" are used interchangeably herein to refer to an amino acid sequence as it exists in a naturally occurring protein.

The terms "overexpress" and "overexpression" as used herein in reference to recombinant microorganisms mean that the recombinant microorganism has been modified such that the recombinant microorganism expresses a protein (e.g., an enzyme) at a level that is increased as compared to the expression level of the same protein a wild-type microorganism of the same kind under the same conditions.

A "plant growth medium" includes any material that is capable of supporting the growth of a plant.

The terms "promoting plant growth" and "stimulating plant growth" are used interchangeably herein, and refer to the ability to enhance or increase at least one of the plant's height, weight, leaf size, root size, fruit size, or stem size, and/or the ability to increase protein yield from the plant and/or to increase crop yield.

The term "promoting plant health" refers to any beneficial effect on the health of a plant, including but not limited to increased germination rate, increased synchronous germination, decreased susceptibility to a pathogen, decreased susceptibility to an environmental stress (e.g., drought, flood, heat, freezing, salt, heavy metals, low pH, high pH, or a combination of any thereof), increased crop yield, increased root nodulation, and increased nutrient uptake and/or nutrient content (e.g., increased sugar uptake or sugar content or increased protein uptake or protein content).

The term "rhizosphere" is used interchangeably with "root zone" to denote that segment of the soil that surrounds the roots of a plant and is influenced by them.

The term "partially purified" as used herein in reference to the enzymes means that a crude preparation of the enzyme (e.g., a cell lysate) has been subjected to procedures that remove at least some non-enzyme components (e.g., waste proteins, dead cell material, excess water, and/or unwanted cell debris). In a partially purified enzyme preparation, the enzyme preferably comprises at least 1% of the total protein content in the preparation, more preferably at least 3% of the total protein content in the preparation, and even more preferably greater than 5% of the total protein content in the preparation.

The term "substantially purified" as used herein in reference to the enzymes means that the enzyme preparation has been subjected to procedures that remove a substantial amount of non-enzyme components (e.g., waste proteins, dead cell material, excess water, and/or unwanted cell debris). In a substantially purified enzyme preparation, the enzyme preferably comprises greater than 30% of the total protein content in the preparation, more preferably greater than about 40% of the total protein content in the preparation, and even more preferably greater than 50% of the total protein content in the preparation.

The term "synergistically effective amount" as used herein refers an amount of a first substance (e.g., a first enzyme) that when used in combination with a second substance (e.g., a second enzyme) that produces a biological effect that is greater than the sum of the biological effects of each of the respective first and second substances when used alone.

DESCRIPTION OF THE PREFERRED EMBODIMENTS

The present invention is generally directed methods stimulating plant growth and/or promoting plant health. The methods comprise applying free enzymes, expansin proteins, or recombinant bacteria that overexpress enzymes to a plant growth medium, a plant, a plant seed, or an area surrounding a plant seed. The present invention is also directed to seeds treated or coated with free enzymes or recombinant bacteria that overexpress enzymes. The present invention is also directed to compositions comprising a fertilizer and an enzyme or recombinant bacteria that overexpress an enzyme. The use of free enzymes or recombinant bacteria that overexpress enzymes for delivering enzymes to plants allows for short bursts of enzyme activity, which in turn provides a safe, short-lived impact on the plant with limited residual materials remaining on harvestable plant material. Alternatively, in situations where a more prolonged effect is desired, the free enzymes can be immobilized on a matrix or support in order to provide controlled release of the enzymes.

I. Enzyme and Expansin Protein Sequences

For ease of reference, illustrative sequences for wild-type and modified ACC deaminase enzymes, as well as sequences for the other enzymes and the expansin proteins that can be used in connection with the methods, seeds, and compositions described herein, are provided below.

A. D-Cysteine Desulfhydrases and ACC Deaminases

For ease of reference, descriptions of illustrative D-cysteine desulfhydrase and 1-aminocyclopropane-1-carboxylate deaminase (ACC deaminase) nucleotide sequences are provided in Table 1 below, together with their SEQ ID NOs. Table 2 below provides the corresponding amino acid sequences for the nucleotide sequences listed in Table 1. As explained in greater detail hereinbelow, mutation of certain amino acids in a wild-type D-cysteine desulfhydrase or ACC deaminase enzyme can result in an enzyme having increased ACC deaminase activity as compared to the ACC deaminase activity of the wild-type enzyme under the same conditions.

In Table 1, SEQ ID NOs. 1-3 and 111 are nucleotide sequences for wild-type enzymes that exhibit both ACC deaminase and D-cysteine desulfhydrase activity, and SEQ ID NOs. 4-6 and 112 are nucleotide sequences that code for corresponding versions of these enzymes having two amino acid substitutions relative to the wild-type sequence that result in increased ACC deaminase activity. Thus, for example, SEQ ID NO: 1 provides the nucleotide sequence for a wild-type enzyme, and SEQ ID NO: 4 provides the nucleotide sequence for the same enzyme wherein the nucleotide sequence has been altered to encode an enzyme having two amino acid substitutions relative to the enzyme encoded by SEQ ID NO: 1. Similarly, SEQ ID NO: 2 provides the nucleotide sequence for a wild-type enzyme, and SEQ ID NO: 5 provides the nucleotide sequence for the same enzyme wherein the nucleotide sequence has been altered to encode an enzyme having two amino acid substitutions relative to the enzyme encoded by SEQ ID NO: 2. Likewise, SEQ ID NO: 3 is a wild-type sequence and SEQ ID NO: 6 provides the corresponding altered sequence, and SEQ ID NO 111 is a wild-type sequence and SEQ ID NO: 112 provides the corresponding altered sequence.

In Table 2, SEQ ID NOs. 7-9 and 113 are amino acid sequences for wild-type enzymes that exhibit both ACC deaminase and D-cysteine desulfhydrase activity, and SEQ ID NOs. 10-12 and 114 are amino acid sequences for the corresponding versions of these enzymes having two amino acid substitutions relative to the wild-type sequence that result in increased enzyme activity. Thus, SEQ ID NO: 7 is a wild-type sequence and SEQ ID NO: 10 provides the amino acid sequence for the same enzyme having the two amino acid substitutions relative to the wild-type sequence. SEQ ID NOs. 8 and 11, 9 and 12, and 113 and 114 are related to one another in the same manner. The substituted amino acids are shown in SEQ ID NOs. 10-12 and 114 in Table 2 in bold and underlined text.

TABLE 1

Nucleotide sequences for D-cysteine desulfhydrases and ACC deaminases

| Enzyme | SEQ ID NO. for nucleotide sequence |
|---|---|
| D-Cysteine Desulfhydrase (ACC deaminase native 1b) Wild-type, *Bacillus thuringiensis* | 1 |
| D-Cysteine Desulfhydrase (ACC deaminase native 2b) Wild-type, *Bacillus pseudomycoides* | 2 |
| D-Cysteine Desulfhydrase (ACC deaminase native 3b) Wild-type, *Bacillus thuringiensis* | 3 |
| D-Cysteine Desulfhydrase (ACC deaminase) Wild-type, *Bacillus thuringiensis* strain IS5056 | 111 |
| D-Cysteine Desulfhydrase (ACC deaminase native 1b) With mutations, *Bacillus thuringiensis* | 4 |
| D-Cysteine Desulfhydrase (ACC deaminase native 2b) With mutations, *Bacillus pseudomycoides* | 5 |
| D-Cysteine Desulfhydrase (ACC deaminase native 3b) With mutations, *Bacillus thuringiensis* | 6 |
| ACC deaminase (D-Cysteine Desulfhydrase) With mutations, *Bacillus thuringiensis* strain IS5056 | 112 |

TABLE 2

Amino acid sequences for D-cysteine desulfhydrases and ACC deaminases

| Enzyme (SEQ ID NO) | Amino acid sequence |
|---|---|
| D-Cysteine Desulfhydrase<br>(ACC deaminase native 1b)<br>Wild-type<br>*Bacillus thuringiensis*<br>(SEQ ID NO 7) | MNLAKFPRKKYTESYTPIEKLNNFSEALGGPTIYFKRDDLLGLT<br>AGGNKTRKLEFLVADAEAKGADTLITAGGIQSNHCRLTLAAA<br>VKEKMKCILVLEEGLEPEEKPDFNGNYFLYHLLGAENVIVVPN<br>GADLMEEMHKVAKEVSEKGNTPYVIPVGGSNPTGAMGYVAC<br>AQEIMAQSFDQGIDFSTVVCVSGSAGMHAGLITGFAGTQSHIP<br>VIGINVSRGKAEQEEKVAKLVDETSAHVGIPNFIPRDAVTCFDE<br>YVGPGYALPTPEMVEAVQLLAKTEGILLDPVYTGKAVAGLIDL<br>IKKGTFNKEDNILFVHSGGSPALYANTSLFA |
| D-Cysteine Desulfhydrase<br>(ACC deaminase native 2b)<br>Wild-type<br>*Bacillus pseudomycoides*<br>(SEQ ID NO 8) | MNLAKFPRKKYTESYTPIEKLNHFSEVLGGPSIYFKRDDLLGLT<br>AGGNKTRKLEFLVADAQAKGVDTLITAGGIQSNHCRLTLAAA<br>VKEKMKCILVLEEGLEPEEKPDFNGNYFLYHLLGAENVIVVPN<br>GTDLMDEMQKVAKEVTEKGHTPYVIPVGGSNPTGAMGYIAC<br>AEEIMAQSFEQGIDFNAVVCVSGSGGMHAGLITGFYGRQTGIPI<br>IGMNVSRGKAEQEEKVCKLVQETSAHVGIPNSIPREAVTCFDE<br>YVGPGYALPTPEMVEAVQLLAKTEGILLDPVYTGKAVAGLIDII<br>RKGTFKKEDNILFVHSGGSPALYANTSLFS |
| D-Cysteine Desulfhydrase<br>(ACC deaminase native 3b)<br>Wild-type<br>*Bacillus thuringiensis*<br>(SEQ ID NO 9) | MNLAKFPRKKYTESYTPIEKLNNFSEVLGGPTIYFKRDDLLGLT<br>AGGNKTRKLEFLVADAQAKGADTLITAGGIQSNHCRLTLAAA<br>VKEKMKCILVLEEGLEPEEKPDFNGNYFLYHLLGAENVIVVPN<br>GADLMEEMHKVAKEVSEKGNTPYVIPVGGSNPTGAMGYVAC<br>AQEIMAQSFEQGIDFSSVVCVSGSGGMHAGLITGFAGTQSHIPV<br>IGINVSRGKAEQEEKVAKLVDETSAHVGIPNFISRDAVTCFDQY<br>VGPGYALPTQEMVEAVQLLAKTEGILLDPVYTGKAVAGLIDLI<br>KKGTFNKEDNILFVHSGGSPALYANTSLFA |
| D-Cysteine Desulfhydrase<br>(ACC deaminase)<br>*Bacillus thuringiensis*<br>strain IS5056<br>Wild-type<br>(SE Q ID NO : 113) | MNLAKFPRKKYTESYTPIEKLNNFSEALGGPTIYFKRDDLLGLT<br>AGGNKTRKLEFLVADAQEKGADTLITAGGIQSNHCRLTLAAA<br>VKEKMKCILVLEEGLEPEEKRDFNGNYFLYHLLGAENVIVVPN<br>GADLMEEMNKVAKEVSEKGSTPYVIPVGGSNPTGAMGYVAC<br>AQEIMAQSFEQGIDFSSVVCVSGSGGMHAGLITGFSGTQSHIPV<br>IGINVSRGKAEQEEKVAKLVDETSAHVGIPNFISRDAVTCFDEY<br>VGPGYALPTPEMVEAVQLLAKTEGILLDPVYTGKAVAGLIDLI<br>RKGKFNKEDNILFVHSGGSPALYANTSLFA |
| D-Cysteine Desulfhydrase<br>(ACC deaminase native 1b)<br>With mutations<br>*Bacillus thuringiensis*<br>(SEQ ID NO 10) | MNLAKFPRKKYTESYTPIEKLNNFSEALGGPTIYFKRDDLLGLT<br>AGGNKTRKLEFLVADAEAKGADTLITAGGIQSNHCRLTLAAA<br>VKEKMKCILVLEEGLEPEEKPDFNGNYFLYHLLGAENVIVVPN<br>GADLMEEMHKVAKEVSEKGNTPYVIPVGGSNPTGAMGYVAC<br>AQEIMAQSFDQGIDFSTVVCVSGSAGMHAGLITGFAGTQSHIP<br>VIGINVSRGKAEQEEKVAKLVDETSAHVGIPNFIPRDAVTCFDE<br>YVGPGYALPTPEMVEAVQLLAKTEGILLDPVY**E**GKAVAGLIDL<br>IKKGTFNKEDNILFVH**L**GGSPALYANTSLFA |

TABLE 2 -continued

Amino acid sequences for D-cysteine desulfhydrases and ACC deaminases

| Enzyme (SEQ ID NO) | Amino acid sequence |
|---|---|
| D-Cysteine Desulfhydrase<br>(ACC deaminase native 2b)<br>With mutations<br>*Bacillus pseudomycoides*<br>(SEQ ID NO 11) | MNLAKFPRKKYTESYTPIEKLNHFSEVLGGPSIYFKRDDLLGLT<br>AGGNKTRKLEFLVADAQAKGVDTLITAGGIQSNHCRLTLAAA<br>VKEKMKCILVLEEGLEPEEKPDFNGNYFLYHLLGAENVIVVPN<br>GTDLMDEMQKVAKEVTEKGHTPYVIPVGGSNPTGAMGYIAC<br>AEEIMAQSFEQGIDFNAVVCVSGSGGMHAGLITGFYGRQTGIPI<br>IGMNVSRGKAEQEEKVCKLVQETSAHVGIPNSIPREAVTCFDE<br>YVGPGYALPTPEMVEAVQLLAKTEGILLDPVY**E**GKAVAGLIDI<br>IRKGTFKKEDNILFVH**L**GGSPALYANTSLFS |
| D-Cysteine Desulfhydrase<br>(ACC deaminase native 3b)<br>With mutations<br>*Bacillus thuringiensis*<br>(SEQ ID NO 12) | MNLAKFPRKKYTESYTPIEKLNNFSEVLGGPTIYFKRDDLLGLT<br>AGGNKTRKLEFLVADAQAKGADTLITAGGIQSNHCRLTLAAA<br>VKEKMKCILVLEEGLEPEEKPDFNGNYFLYHLLGAENVIVVPN<br>GADLMEEMHKVAKEVSEKGNTPYVIPVGGSNPTGAMGYVAC<br>AQEIMAQSFEQGIDFSSVVCVSGSGGMHAGLITGFAGTQSHIPV<br>IGINVSRGKAEQEEKVAKLVDETSAHVGIPNFISRDAVTCFDQY<br>VGPGYALPTQEMVEAVQLLAKTEGILLDPVY**E**GKAVAGLIDLI<br>KKGTFNKEDNILFVH**L**GGSPALYANTSLFA |
| ACC deaminase<br>(D-Cysteine Desulfhydrase)<br>*Bacillus thuringiensis*<br>strain IS5056, with<br>mutations)<br>(SEQ ID NO: 114) | MNLAKFPRKKYTESYTPIEKLNNFSEALGGPTIYFKRDDLLGLT<br>AGGNKTRKLEFLVADAQEKGADTLITAGGIQSNHCRLTLAAA<br>VKEKMKCILVLEEGLEPEEKRDFNGNYFLYHLLGAENVIVVPN<br>GADLMEEMNKVAKEVSEKGSTPYVIPVGGSNPTGAMGYVAC<br>AQEIMAQSFEQGIDFSSVVCVSGSGGMHAGLITGFSGTQSHIPV<br>IGINVSRGKAEQEEKVAKLVDETSAHVGIPNFISRDAVTCFDEY<br>VGPGYALPTPEMVEAVQLLAKTEGILLDPVY**E**GKAVAGLIDLI<br>RKGKFNKEDNILFVH**L**GGSPALYANTSLFA |

B. Phospholipases

For ease of reference, descriptions of illustrative phospholipase amino acid sequences are provided in Table 3 below, together with their SEQ ID NOs.

TABLE 3

Amino acid sequences for phospholipases

| Enzyme | SEQ ID NO. for amino acid sequence |
|---|---|
| Phospholipase 2, *Bacillus thuringiensis* | 13 |
| Phospholipase C, *Bacillus thuringiensis* | 14 |
| Phospholipase C<br>(Zinc dependent phospholipase C (alpha toxin))<br>*Bacillus thuringiensis* serovar israelensis 4Q7 | 15 |
| Phospholipase C ((nSMase) hydrolysis of sphingomyelin to ceramide and phosphorylcholine)<br>*Bacillus thuringiensis* serovar israelensis 4Q7 | 16 |
| Phospholipase C (Zinc dependent phospholipase C (alpha toxin)), *Bacillus cereus* ATCC 10987 | 17 |
| Phospholipase C<br>*Clostridium perfringens* str 13 (*C. welchii*) Type I | 18 |
| Phospholipase D, *Streptomyces chromofuscus* | 19 |
| Phosphatidylcholine-specific phospholipase C<br>*Bacillus cereus* | 115 |
| Phosphatidylinositol phospholipase C<br>*Bacillus cereus* | 116 |
| Phospholipase D (PLD) *Acidovorax avenae* | 117 |

The native amino acid sequences of the phospholipases of SEQ ID NOs. 13, 14, and 15 include the signal peptide sequence MKKKVLALAAAITLVAPLQSVAFA (SEQ ID NO: 49) at the amino-terminus of the sequence, immediately preceding the first amino acid of SEQ ID NOs. 13, 14, and 15. This signal peptide is not included in SEQ ID NOs. 13, 14, or 15. However, the signal peptide of SEQ ID NO: 49, or another signal peptide, can optionally be included at the amino-terminus of the phospholipases of any of SEQ ID NOs. 13, 14, and 15, or at the amino-terminus of any of the other enzymes or expansin proteins described herein.

The native amino acid sequence of the phospholipase of SEQ ID NO: 16 includes the signal peptide MKGKLLKGVLSLGVGLGALYSGTSAQAE (SEQ ID NO: 50) at the amino-terminus of the sequence, immediately preceding the first amino acid of SEQ ID NO: 16. This signal peptide is not included in SEQ ID NO: 16. However, the signal peptide of SEQ ID NO: 50, or another signal peptide, can optionally be included at the amino terminus of the phospholipase of SEQ ID NO: 16, or at the amino-terminus of any of the other enzymes or expansin proteins described herein.

The native amino acid sequence of the phospholipase of SEQ ID NO: 17 includes the signal peptide MKKKVLALAAAITVVAPLQSVAFA (SEQ ID NO: 51) at the amino terminus of the sequence, immediately preceding the first amino acid of SEQ ID NO: 17. This signal peptide is not included in SEQ ID NO: 17. However, the signal peptide of SEQ ID NO: 51, or another signal peptide, can optionally be included at the amino terminus of the phospholipase of SEQ ID NO: 17, or at the amino terminus of any of the other enzymes or expansin proteins described herein.

The native amino acid sequence of the phospholipase of SEQ ID NO: 18 includes the signal peptide MKRKICKALICATLATSLWAGASTKVYAW (SEQ ID NO: 52) at the amino-terminus of the sequence, immediately preceding the first amino acid of SEQ ID NO: 18. This signal peptide is not included in SEQ ID NO: 18. However, the signal peptide of SEQ ID NO: 52, or another signal peptide, can optionally be included at the amino terminus of the phospholipase of SEQ ID NO: 18, or at the amino-terminus of any of the other enzymes or expansin proteins described herein.

The native amino acid sequence of the phospholipase of SEQ ID NO: 19 includes the signal peptide MLAGPLAAALPARATTGTPAFLHGVASGD (SEQ ID NO: 53) at the amino-terminus of the sequence, immediately preceding the first amino acid of SEQ ID NO: 19. This signal peptide is not included in SEQ ID NO: 19. However, the signal peptide of SEQ ID NO: 53, or another signal peptide, can optionally be included at the amino terminus of the phospholipase of SEQ ID NO: 19, or at the amino-terminus of any of the other enzymes or expansin proteins described herein.

The native amino acid sequence of the phospholipase of SEQ ID NO: 115 includes the signal peptide MKKKVLALAAAITLVAPLQNVAFA (SEQ ID NO: 135) at the amino-terminus of the sequence, immediately preceding the first amino acid of SEQ ID NO: 115. This signal peptide is not included in SEQ ID NO: 115. However, the signal peptide of SEQ ID NO: 135, or another signal peptide, can optionally be included at the amino-terminus of the phospholipase of SEQ ID NO: 115, or at the amino-terminus of any of the other enzymes or expansin proteins described herein.

C. Lipases

For ease of reference, descriptions of illustrative lipase amino acid sequences are provided in Table 4 below, together with their SEQ ID NOs.

TABLE 4

Amino acid sequences for lipases

| Enzyme | SEQ ID NO. for amino acid sequence |
|---|---|
| Lipase 1 (4Q7 BG78_03400)<br>*Bacillus thuringiensis* serovar israelensis 4Q7 | 20 |
| Lipase 2 (Bsub168 estA)<br>*Bacillus subtilis* subsp. *subtilis* str. 168 | 21 |
| Lipase, *Burkholderia cepacia* | 118 |
| Lipase, *Pseudomonas fluorescens* | 119 |
| Lipase, *Burkholderia stearothermophilus* | 120 |

The native amino acid sequence of the lipase of SEQ ID NO: 21 includes the signal peptide MKFVKRRIIALVTILMLSVTSLFALQPSAKA (SEQ ID NO: 54) at the amino-terminus of the sequence, immediately preceding the first amino acid of SEQ ID NO: 21. This signal peptide is not included in SEQ ID NO: 21. However, the signal peptide of SEQ ID NO: 54, or another signal peptide, can optionally be included at the amino terminus of the lipase of SEQ ID NO: 21, or at the amino-terminus of any of the other enzymes or expansin proteins described herein.

The native amino acid sequence of the lipase of SEQ ID NO: 118 includes the signal peptide MARTMRSRVVAGAVACAMSIAPFAGTTAVMTLATTHAAMAATAP (SEQ ID NO: 137) at the amino-terminus of the sequence, immediately preceding the first amino acid of SEQ ID NO: 118. This signal peptide is not included in SEQ ID NO: 118. However, the signal peptide of SEQ ID NO: 137, or another signal peptide, can optionally be included at the amino-terminus of the lipase of SEQ ID NO: 118, or at the amino-terminus of any of the other enzymes of expansin proteins described herein.

The native amino acid sequence of the lipase of SEQ ID NO: 119 includes the signal peptide MGIFDYKNLGTEGSKTLFADAMA (SEQ ID NO: 138) at the amino-terminus of the sequence, immediately preceding the first amino acid of SEQ ID NO: 119. This signal peptide is not included in SEQ ID NO: 119. However, the signal peptide of SEQ ID NO: 138, or another signal peptide, can optionally be included at the amino-terminus of SEQ ID NO: 119, or at the amino terminus of any of the other enzymes or expansin proteins described herein.

D. Xylanases

For ease of reference, descriptions of illustrative xylanase amino acid sequences are provided in Table 5 below, together with their SEQ ID NOs.

TABLE 5

Amino acid sequences for xylanases

| Enzyme | SEQ ID NO. for amino acid sequence |
|---|---|
| β-xylanase 3 (CsacDSM8903 2408)<br>*Caldicellulosiruptor saccharolyticus* DSM 8903 | 22 |
| β-xylanase 2 (Bsub168 xynA)<br>*Bacillus subtilis* subsp. *subtilis* str. 168 | 23 |
| β-xylanase 1 (Bsub168 xynD)<br>*Bacillus subtilis* subsp. *subtilis* str. 168 | 24 |
| β-xylanase 4 (Bstearo xynA)<br>*Geobacillus stearothermophilus* (*Bacillus stearothermophilus*) | 25 |
| Xylanase, *Thermomyces lanuginosus* | 121 |
| P-Xylanase, *Neocallimastix patriciarum* | 122 |

The native amino acid sequence of the xylanase of SEQ ID NO: 22 includes the signal peptide MCENLEMLNLSLAKTYKDYFKIGAAVTA (SEQ ID NO: 55) at the amino-terminus of the sequence, immediately preceding the first amino acid of SEQ ID NO: 22. This signal peptide is not included in SEQ ID NO: 22. However, the signal peptide of SEQ ID NO: 55, or another signal peptide, can optionally be included at the amino terminus of the xylanase of SEQ ID NO: 22, or at the amino-terminus of any of the other enzymes or expansin proteins described herein.

The native amino acid sequence of the xylanase of SEQ ID NO: 23 includes the signal peptide MFKFKKNFLVGLSAALMSISLFSATASA (SEQ ID NO: 56) at the amino-terminus of the sequence, immediately preceding the first amino acid of SEQ ID NO: 23. This signal peptide is not included in SEQ ID NO: 23. However, the signal peptide of SEQ ID NO: 56, or another signal peptide, can optionally be included at the amino terminus of the xylanase of SEQ ID NO: 23, or at the amino-terminus of any of the other enzymes or expansin proteins described herein.

The native amino acid sequence of the xylanase of SEQ ID NO: 24 includes the signal peptide MRKKCSVCLWILVLLLSCLSGKSAYA (SEQ ID NO: 57) at the amino-terminus of the sequence, immediately preceding the first amino acid of SEQ ID NO: 24. This signal peptide is not included in SEQ ID NO: 24. However, the signal peptide of SEQ ID NO: 57, or another signal peptide, can optionally be included at the amino terminus of the xylanase of SEQ ID NO: 24, or at the amino-terminus of any of the other enzymes or expansin proteins described herein.

The native amino acid sequence of the xylanase of SEQ ID NO: 25 includes the signal peptide MKLKKKMLTLLLTASMSFGLFGATSSA (SEQ ID NO: 58) at the amino-terminus of the sequence, immediately preceding the first amino acid of SEQ ID NO: 25. This signal peptide is not included in SEQ ID NO: 25. However, the signal peptide of SEQ ID NO: 58, or another signal peptide, can optionally be included at the amino terminus of the xylanase of SEQ ID NO: 25, or at the amino-terminus of any of the other enzymes or expansin proteins described herein.

E. Xylosidases

For ease of reference, descriptions of illustrative xylosidase amino acid sequences are provided in Table 6 below, together with their SEQ ID NOs.

TABLE 6

| Amino acid sequences for xylosidases | |
|---|---|
| Enzyme | SEQ ID NO. for amino acid sequence |
| Xylosidase (CsacDSM8903 2404) *Caldicellulosiruptor saccharolyticus* DSM 8903 | 26 |
| Xylosidase, *Bacillus pumilus* | 123 |

F. Lactonases

For ease of reference, descriptions of illustrative lactonase amino acid sequences are provided in Table 7 below, together with their SEQ ID NOs.

TABLE 7

| Amino acid sequences for lactonases | |
|---|---|
| Enzyme | SEQ ID NO. for amino acid sequence |
| Lactonase (AiiA), *Bacillus thuringiensis* strain B184 | 27 |
| Lactonase (AiiA), *Bacillus pseudomycoides* strain B30 | 28 |

G. Chitosanases

For ease of reference, descriptions of illustrative chitosanase amino acid sequences are provided in Table 8 below, together with their SEQ ID NOs.

TABLE 8

| Amino acid sequences for chitosanases | |
|---|---|
| Enzyme | SEQ ID NO. for amino acid sequence |
| Chitosanase (Bsub168 csn) *Bacillus subtilis* subsp. *subtilis* str. 168 | 29 |
| Chitosanase, *Streptomyces* species N174 | 124 |

The native amino acid sequence of the chitosanase of SEQ ID NO: 29 includes the signal peptide MKISMQKADFWKKAAISLLVFTMFFTLMMSETVFA (SEQ ID NO: 59) at the amino-terminus of the sequence, immediately preceding the first amino acid of SEQ ID NO: 29. This signal peptide is not included in SEQ ID NO: 29. However, the signal peptide of SEQ ID NO: 59, or another signal peptide, can optionally be included at the amino terminus of the chitosanase of SEQ ID NO: 29, or at the amino-terminus of any of the other enzymes or expansin proteins described herein.

The native amino acid sequence of the chitosanase of SEQ ID NO: 124 includes the signal peptide MHSQHRTARIALAVVLTAIPASLATAGVGYASTQASTAVK (SEQ ID NO: 139) at the amino-terminus of the sequence, immediately preceding the first amino acid of SEQ ID NO: 124. This signal peptide is not included in SEQ ID NO: 124. However, the signal peptide of SEQ ID NO: 139), or another signal peptide, can optionally be included at the amino-terminus of the chitosanase of SEQ ID NO: 124, or at the amino terminus of any of the other enzymes or expansin proteins described herein.

H. Glucanases

For ease of reference, descriptions of illustrative glucanase amino acid sequences are provided in Table 9 below, together with their SEQ ID NOs.

TABLE 9

| Amino acid sequences for glucanases | |
|---|---|
| Enzyme | SEQ ID NO. for amino acid sequence |
| Endo-1,4-β-D-glucanase, *Acidothermus cellulolyticus* | 30 |
| Endoglucanase I, *Trichoderma reesei* | 31 |
| Endoglucanase II, *Trichoderma reesei* | 32 |
| Endoglucanase IV, *Trichoderma reesei* | 33 |
| Endoglucanase V, *Trichoderma reesei* | 34 |
| Endoglucanase VII, *Trichoderma reesei* | 35 |
| beta-1,4-endoglucanase, *Trichoderma reesei* | 36 |
| Cellobiohydrolase I, *Trichoderma reesei* | 37 |
| Cellobiohydrolase II, *Trichoderma reesei* | 38 |
| beta-Glucosidase I, *Trichoderma reesei* | 39 |
| beta-Glucosidase II, *Trichoderma reesei* | 40 |
| exo-1,3-β-D-Glucanase, *Aspergillus oryzae* | 41 |
| Endoglucanase B1,4 *Bacillus subtilis* subsp. *subtilis* str. 168 | 42 |
| Lichenase (Bsub 168 bglS) *Bacillus subtilis* subsp. *subtilis* str. 168 | 43 |
| Beta-(1,3) endoglucanase (BglH) *Bacillus circulans* strain IAM1165 | 44 |
| Beta-(1,3) glucosidase (GclA) *Bacillus circulans* strain WL-12 | 45 |
| Xyloglucanase, *Paenibacillus* species | 125 |
| β-1,3-D-glucanase, *Helix pomatia* | 126 |

The native amino acid sequence of the glucanase of SEQ ID NO: 42 includes the signal peptide MKRSISIFITCLLITLLTMGGMIASPASA (SEQ ID NO: 60) at the amino-terminus of the sequence, immediately preceding the first amino acid of SEQ ID NO: 42. This signal peptide is not included in SEQ ID NO: 42. However, the signal peptide of SEQ ID NO: 60, or another signal peptide, can optionally be included at the amino terminus of the glucanase of SEQ ID NO: 42, or at the amino-terminus of any of the other enzymes or expansin proteins described herein.

The native amino acid sequence of the glucanase of SEQ ID NO: 43 includes the signal peptide MPYLKRVLLLLVTGLFMSLFAVTATASA (SEQ ID NO: 61) at the amino-terminus of the sequence, immediately preceding the first amino acid of SEQ ID NO: 43. This signal peptide is not included in SEQ ID NO: 43. However, the signal peptide of SEQ ID NO: 61, or another signal peptide, can optionally be included at the amino terminus of the glucanase of SEQ ID NO: 43, or at the amino-terminus of any of the other enzymes or expansin proteins described herein.

The native amino acid sequence of the glucanase of SEQ ID NO: 44 includes the signal peptide MKRSQTSEKRYRQRVLSLFLAVVMLASIGLLPTSKVQA (SEQ ID NO: 62) at the amino-terminus of the sequence, immediately preceding the first amino acid of SEQ ID NO: 44. This signal peptide is not included in SEQ ID NO: 44. However, the signal peptide of SEQ ID NO: 62, or another signal peptide, can optionally be included at the amino terminus of the glucanase of SEQ ID NO: 44, or at the amino-terminus of any of the other enzymes or expansin proteins described herein.

The native amino acid sequence of the glucanase of SEQ ID NO: 45 includes the signal peptide MKPSHFTEKRFMKKVLGLFLVVVMLASVGVLPTSKVQA (SEQ ID NO: 63) at the amino-terminus of the sequence, immediately preceding the first amino acid of SEQ ID NO: 45. This signal peptide is not included in SEQ ID NO: 45. However, the signal peptide of SEQ ID NO: 63, or another signal peptide, can optionally be included at the amino terminus of the glucanase of SEQ ID NO: 45, or at the amino-terminus of any of the other enzymes or expansin proteins described herein.

The native amino acid sequence of the glucanase of SEQ ID NO: 125 includes the signal peptide MFKKWKKFGISSLALVLVAAVAFTGWSAKASA (SEQ ID NO: 140) at the amino-terminus of the sequence, immediately preceding the first amino acid of SEQ ID NO: 125. This signal peptide is not included in SEQ ID NO: 125. However, the signal peptide of SEQ ID NO: 140, or another signal peptide, can optionally be included at the amino-terminus of the glucanase of SEQ ID NO: 125, or at the amino-terminus of any of the other enzymes or expansin proteins described herein.

I. Proteases

For ease of reference, descriptions of illustrative protease amino acid sequences are provided in Table 10 below, together with their SEQ ID NOs.

TABLE 10

Amino acid sequences for proteases

| Enzyme | SEQ ID NO. for amino acid sequence |
|---|---|
| Protease 1 (Bsub168 aprX) *Bacillus subtilis* subsp. *subtilis* str. 168 | 46 |
| Protease 2 (Bsub168 vpr) *Bacillus subtilis* subsp. *subtilis* str. 168 | 47 |
| Protease 3 Engyodontium album (*Tritirachium album*) | 48 |
| Protease (aminopeptidase), *Aspergillus saitoi* | 127 |

The native amino acid sequence of the protease of SEQ ID NO: 47 includes the signal peptide MKKGIIRFLLVSFVLFFALSTGITGVQA (SEQ ID NO: 64) at the amino-terminus of the sequence, immediately preceding the first amino acid of SEQ ID NO: 47. This signal peptide is not included in SEQ ID NO: 47. However, the signal peptide of SEQ ID NO: 64, or another signal peptide, can optionally be included at the amino terminus of the protease of SEQ ID NO: 47, or at the amino-terminus of any of the other enzymes or expansin proteins described herein.

The native amino acid sequence of the protease of SEQ ID NO: 127 includes the signal peptide MVVFSKTAALVLGLSTAVSA (SEQ ID NO: 141) at the amino-terminus of the sequence, immediately preceding the first amino acid of SEQ ID NO: 127. This signal peptide is not included in SEQ ID NO: 127. However, the signal peptide of SEQ ID NO: 141, or another signal peptide, can optionally be included at the amino-terminus of the protease of SEQ ID NO: 127, or at the amino-terminus of any of the other enzymes or expansin proteins described herein.

J. Mannanases

For ease of reference, a description of an illustrative mannanase amino acid sequence is provided in Table 11 below, together with its SEQ ID NO.

TABLE 11

Amino acid sequence for a mannanase

| Enzyme | SEQ ID NO. for amino acid sequence |
|---|---|
| Mannanase, *Bacillus* sp. | 128 |

The native amino acid sequence of the mannanase of SEQ ID NO: 128 includes the signal peptide MAKLQKGTILTVIAALMFVILGSAAPKA (SEQ ID NO: 142) at the amino-terminus of the sequence, immediately preceding the first amino acid of SEQ ID NO: 128. This signal peptide is not included in SEQ ID NO: 128. However, the signal peptide of SEQ ID NO: 142, or another signal peptide, can optionally be included at the amino-terminus of the mannanase of SEQ ID NO: 128, or at the amino-terminus of any of the other enzymes or expansin proteins described herein.

K. Pectinases

For ease of reference, a description of an illustrative pectinase amino acid sequence is provided in Table 12 below, together with its SEQ ID NO.

TABLE 12

Amino acid sequence for a pectinase

| Enzyme (SEQ ID NO) | SEQ ID NO. for amino acid sequence |
|---|---|
| Pectolyase, *Aspergillus japonicus* | 129 |

The native amino acid sequence of the pectolyase of SEQ ID NO: 129 includes the signal peptide MPSAKPLFCLATLAGAALAAP (SEQ ID NO: 143) at the amino-terminus of the sequence, immediately preceding the first amino acid of SEQ ID NO: 129. This signal peptide is not included in SEQ ID NO: 129. However, the signal peptide of SEQ ID NO: 143, or another signal peptide, can optionally be included at the amino-terminus of the pectolyase of SEQ ID NO: 129, or at the amino-terminus of any of the other enzymes or expansin proteins described herein.

L. Acid Phosphatases

For ease of reference, descriptions of illustrative acid phosphatase amino acid sequences are provided in Table 13 below, together with their SEQ ID NOs.

TABLE 13

Amino acid sequences for acid phosphatases

| Enzyme | SEQ ID NO. for amino acid sequence |
|---|---|
| Acid phosphatase, *Triticum aestivum* | 130 |
| Acid phosphatase, *Triticum aestivum* | 131 |

The native amino acid sequence of the acid phosphatase of SEQ ID NO: 130 includes the signal peptide MARGSMAAVLAVLAVAALRCAPAAA (SEQ ID NO: 144) at the amino-terminus of the sequence, immediately preceding the first amino acid of SEQ ID NO: 130. This signal peptide is not included in SEQ ID NO: 130. However, the signal peptide of SEQ ID NO: 144, or another signal peptide, can optionally be included at the amino-terminus of the acid phosphatase of SEQ ID NO: 130, or at the amino-terminus of any of the other enzymes or expansin proteins described herein.

The native amino acid sequence of the acid phosphatase of SEQ ID NO: 131 includes the signal peptide MRGLGFAALSLHVLLCLANGVSSRRTSSYV (SEQ ID NO: 145) at the amino-terminus of the sequence, immediately preceding the first amino acid of SEQ ID NO: 131. This signal peptide is not included in SEQ ID NO: 131. However, the signal peptide of SEQ ID NO: 145, or another signal peptide, can optionally be included at the amino-terminus of the acid phosphatase of SEQ ID NO: 131, or at the amino-terminus of any of the other enzymes or expansin proteins described herein.

M. Phytases

For ease of reference, descriptions of illustrative phytase amino acid sequences are provided in Table 14 below, together with their SEQ ID NOs.

TABLE 14

| Amino acid sequences for phytases | |
|---|---|
| Enzyme | SEQ ID NO. for amino acid sequence |
| Phytase, *Triticum aestivum* | 132 |
| Phytase, *Triticum aestivum* | 133 |
| Phytase, *Triticum aestivum* | 134 |

The native amino acid sequence of the phytase of SEQ ID NO: 132 includes the signal peptide MWWGSLRLLLL-LAAAVAA (SEQ ID NO: 146) at the amino-terminus of the sequence, immediately preceding the first amino acid of SEQ ID NO: 132. This signal peptide is not included in SEQ ID NO: 132. However, the signal peptide of SEQ ID NO: 146, or another signal peptide, can optionally be included at the amino-terminus of the phytase of SEQ ID NO: 132, or at the amino-terminus of any of the other enzymes or expansin proteins described herein.

The native amino acid sequence of the phytase of SEQ ID NO: 133 includes the signal peptide MWWGSLRLLLL-LAAAVAA (SEQ ID NO: 146) at the amino-terminus of the sequence, immediately preceding the first amino acid of SEQ ID NO: 133. This signal peptide is not included in SEQ ID NO: 133. However, the signal peptide of SEQ ID NO: 146, or another signal peptide, can optionally be included at the amino-terminus of the phytase of SEQ ID NO: 133, or at the amino-terminus of any of the other enzymes or expansin proteins described herein.

The native amino acid sequence of the phytase of SEQ ID NO: 134 includes the signal peptide MGIWRGSLPLLL-LAA (SEQ ID NO: 147) at the amino-terminus of the sequence, immediately preceding the first amino acid of SEQ ID NO: 134. This signal peptide is not included in SEQ ID NO: 134. However, the signal peptide of SEQ ID NO: 147, or another signal peptide, can optionally be included at the amino-terminus of the phytase of SEQ ID NO: 134, or at the amino-terminus of any of the other enzymes or expansin proteins described herein.

N. Expansin Proteins

For ease of reference, an illustrative expansin amino acid sequences is provided in Table 15 below, together with its SEQ ID NOs.

TABLE 15

| Amino acid sequence for an expansin | |
|---|---|
| Expansin Protein | SEQ ID NO. for amino acid sequence |
| Expansin (Bsub168 exlX) *Bacillus subtilis* subsp. subtilis str. 168 | 74 |

The native amino acid sequence of the expansin protein of SEQ ID NO: 74 includes the signal peptide MKKIM-SAFVGMVLLTIFCFSPQASA (SEQ ID NO: 68) at the amino terminus of the sequence, immediately preceding the first amino acid of SEQ ID NO: 74. This signal peptide is not included in SEQ ID NO: 74. However, the signal peptide of SEQ ID NO: 74, or another signal peptide, can optionally be included at the amino terminus of the protease of SEQ ID NO: 74, at the amino terminus of any of the enzymes described herein, or at the amino terminus of another expansin protein.

O. Mutations that Increase Enzyme Activity

In any of the enzymes described herein, including both free enzymes and enzymes that are expressed by a recombinant microorganism, the enzyme can comprise at least one amino acid substitution relative to the sequence of a wild-type sequence of the same enzyme, and wherein the amino acid substitution results in increased activity of the enzyme as compared to the enzyme activity of the wild-type enzyme under the same conditions.

II. Modified Enzymes Having ACC Deaminase Activity

Modified 1-aminocyclopropane-1-carboxylate (ACC) deaminase enzymes are provided. ACC deaminases and D-cysteine desulfhydrases (DCD) often have similar amino acid sequences and can have overlapping enzyme activities, being able to act on both 1-aminocyclopropane-1-carboxylate (ACC) and D-cysteine as substrates. Some enzymes only have one of these activities, while others are able to act both as ACC deaminases and as D-cysteine desulfhydrases. ACC deaminases cleave ACC into ammonia and alpha-ketobutyrate, while D-cysteine desulfhydrases converts D-cysteine into pyruvate, $H_2S$, and ammonia. ACC is the immediate precursor of ethylene, which can cause undesirable effects in plants if present at high levels.

Thus, an enzyme having increased ACC deaminase activity would be beneficial for use in agriculture in order to reduce ACC levels and thereby reduce ethylene levels. Application of ACC deaminase to a plant growth medium, a plant, a plant seed, or an area surrounding a plant or a plant seed can stimulate plant growth, promote plant health (e.g., by increasing nutrient uptake), and slow fruit ripening. These effects in turn lead to increased yields, early season vigor, and resistance of plants to early season stresses. ACC deaminases can also protect plants from pathogens as well as abiotic stresses.

As explained in greater detail below, mutations can be made in enzymes that exhibit D-cysteine desulfhydrase and/or ACC deaminase activity in order to increase the ACC deaminase activity of the enzyme. In addition, enzymes having ACC deaminase activity can be modified to include a signal peptide that results in secretion of the enzyme when it is expressed in a microorganism, allowing for easier production and purification of the enzyme. Such modifications (mutations and the addition of a signal peptide) can be used individually or in combination with one another. All plants make ACC and respond to ethylene, and thus such modified ACC deaminase enzymes have broad applicability.

Amino acid sequences for three wild-type enzymes are provided above in Table 2 as SEQ ID NOs. 7-9 and 113. Sequences for the corresponding versions of these wild-type enzymes that have two amino acid substitutions that result in increased ACC deaminase activity are provided above in Table 2 as SEQ ID NOs. 10-12 and 114.

Naturally occurring ACC deaminase is not a secreted protein. ACC deaminases are found in many types of microorganisms, including bacteria of the Phyla Bacteriodetes, Firmicutes, and Actinobacteria, and bacteria of the genera *Pseudomonas, Bacillus, Rhizobium, Bradyrhizobium*, as well as many others. However, the ACC deaminases found in these bacteria are intracellular, and have limited exposure to the substrate ACC from the host plants that they colonize.

A modified ACC deaminase is provided herein that comprises a signal peptide that results in secretion of the ACC deaminase from a microorganism in which it is expressed. This ACC deaminase can be expressed in a microorganism, which can then be applied to a plant growth medium, a plant, a plant seed, or an area surrounding a plant or a plant seed. The ACC deaminase is secreted by the microorganism where it comes into contact with its substrate. The secreted ACC deaminase is thus able to stimulate growth of the plant and/or promote health of the plant.

An enzyme is provided. The enzyme comprises an amino acid sequence encoding an enzyme having 1-aminocyclopropane-1-carboxylate deaminase (ACC deaminase) activity and a signal peptide that results in secretion of the enzyme when the enzyme is expressed in a microorganism.

The enzyme having ACC deaminase activity can comprise an enzyme from a *Bacillus* genus bacterium.

In addition or in the alternative, one or more amino acid substitutions can be introduced into the amino acid sequence of an ACC deaminase enzyme to increase enzyme activity.

An enzyme having ACC deaminase activity is provided. The amino acid sequence of the enzyme comprises at least one amino acid substitution relative to the sequence of a wild-type D-cysteine desulfhydrase or ACC deaminase enzyme from a *Bacillus* genus bacterium. The amino acid substitution results in increased ACC deaminase activity as compared to the ACC deaminase activity of the wild-type D-cysteine desulfhydrase or ACC deaminase enzyme under the same conditions.

The enzyme comprising the at least one amino acid substitution can further comprise a signal peptide that results in secretion of enzyme when the enzyme is expressed in a microorganism.

For any of the enzymes having ACC deaminase activity, the microorganism in which the enzyme is expressed can comprise a bacterium of the genus *Bacillus*, a bacterium of the genus *Pseudomonas*, a bacterium of the genus *Rhizobium*, a bacterium of the genus *Paenibacillus*, a bacterium of the genus *Lysinibacillus*, a bacterium of the genus *Paracoccus*, a bacterium of the genus *Mesorhizobium*, a bacterium of the genus *Bradyrhizobium*, a bacterium of the genus *Actinobacter*, a bacterium of the genus *Arthrobacter*, a bacterium of the genus *Azotobacter*, a bacterium of the genus *Azosprillium*, a pink-pigmented facultative methyltrophic bacterium, a mycorrhizal fungus, a fungus of the genus *Glomus*, a fungus of the genus *Trichoderma*, a fungus of the genus *Kluyera*, a fungus of the genus *Gliocladium*, or a combination of any thereof.

For example, the microorganism can comprise a bacterium of the genus *Bacillus*, a bacterium of the genus *Lysinibacillus*, a bacterium of the genus *Pseudomonas*, a bacterium of the genus *Paenibacillus*, or a combination of any thereof.

For any of the enzymes having ACC deaminase activity, the enzyme can comprise a *Bacillus thuringiensis* enzyme or a *Bacillus pseudomycoides* enzyme.

The enzyme can comprise an amino acid sequence having at least 70% identity to any one of SEQ ID NOs. 7-9 and 113, wherein the enzyme has ACC deaminase activity.

The enzyme can comprise an amino acid sequence having at least 75% identity to any one of SEQ ID NOs. 7-9 and 113, wherein the enzyme has ACC deaminase activity.

The enzyme can comprise an amino acid sequence having at least 80% identity to any one of SEQ ID NOs. 7-9 and 113, wherein the enzyme has ACC deaminase activity.

The enzyme can comprise an amino acid sequence having at least 85% identity to any one of SEQ ID NOs. 7-9 and 113, wherein the enzyme has ACC deaminase activity.

The enzyme can comprise an amino acid sequence having at least 90% identity to any one of SEQ ID NOs. 7-9 and 113, wherein the enzyme has ACC deaminase activity.

The enzyme can comprise an amino acid sequence having at least 95% identity to any one of SEQ ID NOs. 7-9 and 113, wherein the enzyme has ACC deaminase activity.

The enzyme can comprise an amino acid sequence having at least 98% identity to any one of SEQ ID NOs. 7-9 and 113, wherein the enzyme has ACC deaminase activity.

The enzyme can comprise an amino acid sequence having at least 99% identity to any one of SEQ ID NOs. 7-9 and 113, wherein the enzyme has ACC deaminase activity.

The enzyme can comprise two amino acid substitutions relative to the sequence of the wild-type D-cysteine desulfhydrase or ACC deaminase enzyme, wherein the amino acid substitutions result in increased ACC deaminase activity as compared to the ACC deaminase activity of the wild-type enzyme, under the same conditions.

For example, the amino acid sequence of the enzyme can comprise a substitution of the threonine residue at position 290 of SEQ ID NO: 7 with a glutamic acid residue and a substitution of the serine residue at position 317 of SEQ ID NO: 7 with a leucine residue.

The amino acid sequence of the enzyme can comprise a substitution of the threonine residue at position 290 of SEQ ID NO: 8 with a glutamic acid residue and a substitution of the serine residue at position 317 of SEQ ID NO: 8 with a leucine residue.

The amino acid sequence of the enzyme can comprise a substitution of the threonine residue at position 290 of SEQ ID NO: 9 with a glutamic acid residue and a substitution of the serine residue at position 317 of SEQ ID NO: 9 with a leucine residue.

The amino acid sequence of the enzyme can comprise a substitution of the threonine residue at position 290 of SEQ ID NO: 113 with a glutamic acid residue and a substitution of the serine residue at position 317 of SEQ ID NO: 113 with a leucine residue.

The enzyme can comprise any one of SEQ ID NOs. 10, 11, 12, or 14.

Where the enzyme having ACC deaminase activity comprises the signal peptide but does not comprise any amino acid substitutions relative to the sequence of a wild-type D-cysteine desulfhydrase or ACC deaminase enzyme, the ACC deaminase an comprise an amino acid sequence having 100% identity to any one of SEQ ID NOs. 7-9 and 113.

Signal peptides that can be used to modify the enzymes having ACC deaminase activity are described further in Section XII below.

III. Recombinant Bacteria that Express the Modified Enzymes Having ACC Deaminase Activity, and Formulations Containing the Modified Enzymes or the Recombinant Bacterial that Express the Modified Enzymes Recombinant microorganisms that express any of the enzymes described above in Section II are also provided.

In any of the recombinant microorganisms that express an enzyme described above in Section II, the expression of the enzyme is preferably increased as compared to the level of expression of the enzyme in a wild-type microorganism of the same kind under the same conditions.

Suitable microorganisms that can be used for expression of the enzymes are described below in Section XIII.

Formulations comprising an agriculturally acceptable carrier and any of the modified enzymes described above in Section II above or a recombinant microorganism that expresses any of the modified e enzymes are also provided. Suitable carriers that can be used in such formulations and further formulation components are described below in Section XVI.

IV. Methods for Stimulating Plant Growth and/or Promoting Plant Health

Methods for stimulating plant growth and/or promoting plant health are provided. As described in greater detail below, the methods comprise applying an enzyme, expansin protein, or a recombinant microorganism that expresses an enzyme or an expansin protein to a plant growth medium, a plant, a plant seed, or an area surrounding a plant or a plant seed.

Application of the enzymes or expansin proteins or the recombinant bacteria preferably results in delivery of higher levels of enzyme or expansin protein to the plant growth medium, the plant, the plant seed, or the area surrounding the plant or plant seed than the levels of the enzyme or expansin protein that would be found in nature in the plant growth medium the plant seed, or the area surrounding the plant or the plant seed.

A. Modified Enzymes Having ACC Deaminase Activity

A method for stimulating plant growth and/or promoting plant health is provided. The method comprises applying any of the enzymes having ACC deaminase activity described above in Section II to a plant growth medium, a plant, a plant seed, or an area surrounding a plant or a plant seed. Alternatively, the method can comprise applying a formulation comprising an agriculturally acceptable carrier and any of the enzymes having ACC deaminase activity described above in Section II to a plant growth medium, a plant, a plant seed, or an area surrounding a plant or a plant seed.

A further method for stimulating plant growth and/or promoting plant health is provided. The method comprises applying any of the recombinant microorganisms that express an enzyme having ACC deaminase activity described above in Section III to a plant growth medium, a plant, a plant seed, or an area surrounding a plant or a plant seed. Alternatively, the method can comprise applying a formulation comprising an agriculturally acceptable carrier and any of the recombinant microorganisms that express an enzyme having ACC deaminase activity described above in Section III to a plant growth medium, a plant, a plant seed, or an area surrounding a plant or a plant seed.

For example, the method can comprise applying any of the enzymes described in Section II above to the plant growth medium, plant, plant seed, or area surrounding the plant or the plant seed.

The method can comprise applying free enzyme to the plant growth medium, plant, plant seed, or area surrounding the plant or the plant seed.

The method can comprise applying any of the recombinant organisms described above in Section III to the plant growth medium, plant, plant seed, or area surrounding the plant or the plant seed.

The effects of any of the enzymes having ACC deaminase activity described in this section or elsewhere herein on plants can be tested, for example, by measurements of increases in root mass, increases in plant height, increases in yield, increases in nodulation, changes to leaf senescence, changes in seed germination, and delay in fruit ripening.

B. Phospholipases, Lipases, Xylanases, Xylosidases, Lactonases, Chitosanases, Glucanases Proteases, Mannanases, Pectinases, Acid Phosphatases, Phytases, ACC Deaminases, and Expansin Proteins 1. Free Enzymes As described in greater detail below, methods for stimulating plant growth and/or promoting plant health involving the use of phospholipases, lipases, xylosidases, lactonases, chitosanases, glucanases, proteases, mannanases, pectinases, acid phosphatases, phytases, ACC deaminases, and/or expansin proteins and/or recombinant bacteria expressing such enzymes or expansin proteins are provided.

A method for stimulating plant growth and/or promoting plant health is provided. The method comprises applying a free enzyme to a plant growth medium, a plant, a plant seed, or an area surrounding a plant or a plant seed. The enzyme is selected from a phospholipase, a lipase, a xylanase, a xylosidase, a lactonase, a mannanase, a pectinase, a chitosanase, a protease, an acid phosphatase, a non-cellulolytic glucanase, an ACC deaminase, and combinations of any thereof.

The enzyme is preferably selected from a phospholipase, a lipase, a xylanase, a xylosidase, a mannanase, a pectinase, a lactonase, a chitosanase, a protease, a phytase, an acid phosphatase, an ACC deaminase, and combinations of any thereof.

Another method for stimulating plant growth and/or promoting plant health is provided. The method comprises applying two or more free enzymes to a plant growth medium, a plant, a plant seed, or an area surrounding a plant or a plant seed. The enzymes are independently selected from a phospholipase, a lipase, a xylanase, a xylosidase, a lactonase, a chitosanase, a protease, a phytase, an acid phosphatase, a mannanase, a pectinase, a glucanase, and an ACC deaminase.

A further method for stimulating plant growth and/or promoting plant health is provided. The method comprises applying a free enzyme to a plant or a plant seed. The enzyme comprises a glucanase. Applying the enzyme to the plant seed comprises: (a) applying the enzyme to the plant seed at the time of planting; or (b) coating the plant seed with the enzyme.

In the method comprising applying a free enzyme to a plant or a plant seed, wherein the enzyme comprises a glucanase, the method can comprise coating the plant seed with a seed coating formulation comprising the enzyme and an agriculturally acceptable carrier.

In the method comprising applying a free enzyme to a plant or a plant seed, wherein the enzyme comprises a glucanase, the method can further comprise applying the enzyme or an expansin protein to the plant growth medium or an area surrounding a plant or a plant seed. For example, the method can comprise applying the enzyme or the expansin protein to the plant growth medium. The method can comprise applying the enzyme and the expansin protein to the plant growth medium.

Yet another method for stimulating plant growth and/or promoting plant health is provided. The method comprises applying a free enzyme to a plant growth medium, a plant, a plant seed, or an area surrounding a plant or a plant seed. The enzyme comprises a glucanase. The method further comprises applying an expansin protein to the plant growth medium, the plant, the plant seed, or the area surrounding a plant or a plant seed.

In the method comprising applying a free enzyme and an expansin protein, applying the enzyme or the expansin protein to the plant seed comprises: (a) applying the enzyme or expansin protein to the plant seed at the time of planting; or (b) coating the plant seed with the enzyme or expansin protein. For example, the method can comprise coating the plant seed with a seed coating formulation comprising an agriculturally acceptable carrier and the enzyme, the expansin protein, or both the enzyme and the expansin protein.

Another method for stimulating plant growth and/or promoting plant health is provided. The method comprises applying a free enzyme to a plant or a plant seed. The enzyme comprises a phytase.

A further method for stimulating plant growth and/or promoting plant health is provided. The method comprises applying a fertilizer and a free enzyme to a plant growth medium, an area surrounding a plant or a plant seed, or to a plant or a plant seed. The free enzyme comprises a phytase.

2. Recombinant Microorganisms

A method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a mannanase, a pectinase, a protease, a phytase, an acid phosphatase, and combinations of any thereof. The enzyme or expansin protein is expressed during vegetative growth of the recombinant microorganism.

Another method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein further comprises a signal peptide that results in secretion of the enzyme or expansin protein.

A further method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a phytase, a mannanase, a pectinase, an acid phosphatase, and combinations of any thereof. The enzyme or expansin protein is not bound to the exosporium of a recombinant *Bacillus cereus* family member.

Yet another method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a phytase, a mannanase, a pectinase, an acid phosphatase, and combinations of any thereof. The enzyme or expansin protein is not part of a fusion protein.

In any of the methods, the enzyme or expansin protein can be expressed during vegetative growth of the recombinant microorganism.

Where the enzyme or expansin protein is expressed during vegetative growth of the recombinant microorganism, the recombinant microorganism can be a spore-forming microorganism.

In any of the methods other than the methods where the enzyme is not part of a fusion protein, the enzyme or expansin protein can further comprise a signal peptide that results in secretion of the enzyme or expansin protein. Suitable signal peptides are described in Section XII below.

In any of the methods, the enzyme or expansin protein is suitably not bound to the exosporium of a recombinant *Bacillus cereus* family member.

In any of the methods, the enzyme or expansin protein is suitably not bound to the exosporium of an intact *Bacillus cereus* family member spore.

In any of the methods other than the methods that involve the use of a signal peptide, the enzyme or expansin protein is suitably not part of a fusion protein.

C. Routes for Delivery of Enzymes, Expansins, and/or Recombinant Microorganisms to Plants In any of the methods described herein, the method can comprise applying the enzyme or the recombinant microorganism to the plant growth medium. For example, the enzyme or recombinant microorganism can be applied in-furrow or can be included in a soil amendment. Alternatively, or in addition, the enzyme or recombinant microorganism can be impregnated onto a dry particle, a vermiculite or other matrix, a plastic polymer, a peat moss or potting mix, prior to application to the plant growth medium. The enzyme or recombinant microorganism can also be applied to the plant growth medium via a water source, a drip irrigation line, a broadcast liquid application to the soil, or a broadcast dry application to the soil.

The plant growth medium can comprise or consist essentially of a fertilizer. The mixture of the fertilizer and the enzyme or recombinant microorganism can then be applied to soil or another plant growth medium using standard fertilizer application, methods, including in-furrow fertilizer application, 2×2 fertilizer application, broadcast fertilizer application, fertilizer impregnation, drip irrigation lines, topdressing applications, and the like.

In any of the methods described herein, the method can comprise applying the enzyme, the expansin protein, or the recombinant microorganism to the plant.

In any of the methods described herein, the method can comprise applying the enzyme, the expansin protein, or the recombinant microorganism to roots of the plant.

In any of the methods described herein, the method can comprise applying the enzyme, the expansin protein, or the recombinant microorganism foliarly.

In any of the methods described herein, the method can comprise applying the enzyme, the expansin protein, or the recombinant microorganism to the plant seed.

Where the method comprises applying the enzyme, the expansin protein, or the recombinant microorganism to a plant seed, applying the enzyme, the expansin protein, or the recombinant organism to the plant seed can comprise: (a) applying the enzyme, the expansin protein, or the recombinant organism to the plant seed at the time of planting; or (b) coating the plant seed with the enzyme, the expansin protein, or the recombinant organism.

For example, the method can comprise coating the plant seed with a seed coating formulation comprising: an agriculturally acceptable carrier and the enzyme, the expansin protein, the recombinant microorganism, or a combination thereof.

V. Plant Seeds

Plant seeds treated with an enzyme, expansin protein, or a recombinant microorganism that expresses an enzyme or expansin protein are also provided.

A. Plant Seeds Treated with Modified Enzymes Having ACC Deaminase Activity

A treated plant seed is provided. The plant seed is treated with any of the enzymes having ACC deaminase activity described above in Section II. Alternatively, the plant seed is treated with a formulation comprising any of the enzymes having ACC deaminase activity described above in Section II and an agriculturally acceptable carrier.

A further plant seed is provided. The plant seed is treated with any of the recombinant microorganisms that express an enzyme having ACC deaminase activity described above in Section III. Alternatively, the plant seed is treated with a formulation comprising any of the recombinant microorganisms that express an enzyme having ACC deaminase activity described above in Section III.

B. Plant Seeds Treated with Enzymes or Recombinant Microorganisms

Plant seeds treated with enzymes, expansin proteins, or recombinant bacteria are provided.

1. Free Enzymes

A treated plant seed is provided. The plant seed is treated with a free enzyme. The enzyme is selected from a phospholipase, a lipase, a xylanase, a xylosidase, a mannanase, a pectinase, a lactonase, a chitosanase, a protease, a phytase, an acid phosphatase, a non-cellulolytic glucanase, an ACC deaminase, and combinations of any thereof.

The enzyme is preferably selected from a phospholipase, a lipase, a xylanase, a xylosidase, a mannanase, a pectinase, a lactonase, a chitosanase, a protease, a phytase, an acid phosphatase, an ACC deaminase, and combinations of any thereof.

Another treated plant seed is provided. The plant seed is treated with two or more free enzymes, wherein the enzymes are independently selected from a phospholipase, a lipase, a xylanase, a xylosidase, a lactonase, a chitosanase, a mannanase, a pectinase, a protease, a phytase, an acid phosphatase, a glucanase, and an ACC deaminase.

A treated plant seed is provided. The plant seed is treated with a free enzyme and an expansin protein. The enzyme comprises a glucanase.

A coated plant seed is provided. The plant seed is coated with a free enzyme. The enzyme comprises a glucanase.

2. Recombinant Microorganisms

A plant seed is provided. The plant seed is coated with a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a phytase, a mannanase, a pectinase, an acid phosphatase, an ACC deaminase, and combinations of any thereof. The enzyme or expansin protein is expressed during vegetative growth of the recombinant microorganism.

Another plant seed is provided. The plant seed is coated with a recombinant microorganism. The recombinant microorganism expresses an enzyme or expansin protein, wherein expression of the enzyme is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein further comprises a signal peptide that results in secretion of the enzyme or expansin protein.

A further plant seed is provided. The plant seed is coated with a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein is not bound to the exosporium of a recombinant *Bacillus cereus* family member.

Yet another plant seed is provided. The plant seed is coated with a recombinant microorganism. The recombinant microorganism expresses an enzyme or an expansin protein, wherein expression of the enzyme or expansin protein is increased as compared to the expression level the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein is not part of a fusion protein.

In any of the seeds, the enzyme or expansin protein can be expressed during vegetative growth of the recombinant microorganism.

Where the enzyme or expansin protein is expressed during vegetative growth of the recombinant microorganism, the recombinant microorganism can be a spore-forming microorganism.

In any of the seeds other than the seeds where the enzyme is not part of a fusion protein, the enzyme or expansin protein can further comprise a signal peptide that results in secretion of the enzyme or expansin protein. Suitable signal peptides are described in Section XII below.

In any of the seeds, the enzyme or expansin protein is suitably not bound to the exosporium of a recombinant *Bacillus cereus* family member.

In any of the seeds, the enzyme or expansin protein is suitably not bound to the exosporium of an intact *Bacillus cereus* family member spore.

In any of the seeds other than the seeds that involve the use of a signal peptide, the enzyme or expansin protein is suitably not part of a fusion protein.

C. Coated Plant Seeds

For any of the plant seeds, the plant seed can be coated with the enzyme, the recombinant microorganism, the expansin protein, or a combination of any thereof.

For example, the plant seed can be coated with the enzyme and the expansin protein.

Any of the plant seeds can be coated with a seed coating formulation comprising the enzyme, the recombinant microorganism, the expansin protein, or a combination of any thereof, and an agriculturally acceptable carrier.

VI. Compositions

Compositions comprising a fertilizer and an enzyme or expansin protein, or a recombinant microorganism that overexpresses an enzyme or an expansin protein, are provided.

A. Enzymes

A composition is provided. The composition comprises a fertilizer and an enzyme or an expansin protein. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof.

The enzyme preferably comprises a free enzyme.

B. Recombinant Microorganisms

A composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein is expressed during vegetative growth of the recombinant microorganism.

Another composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein further comprises a signal peptide that results in secretion of the enzyme or expansin protein.

Yet another composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein is not bound to the exosporium of a recombinant *Bacillus cereus* family member.

A further composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein is not part of a fusion protein.

In any of the compositions, the enzyme or expansin protein can be expressed during vegetative growth of the recombinant microorganism.

Where the enzyme or expansin protein is expressed during vegetative growth of the recombinant microorganism, the recombinant microorganism can be a spore-forming microorganism.

In any of the compositions other than the compositions where the enzyme is not part of a fusion protein, the enzyme or expansin protein can further comprise a signal peptide that results in secretion of the enzyme or expansin protein. Suitable signal peptides are described in Section XII below.

In any of the compositions, the enzyme or expansin protein is suitably not bound to the exosporium of a recombinant *Bacillus cereus* family member.

In any of the compositions, the enzyme or expansin protein is suitably not bound to the exosporium of an intact *Bacillus cereus* family member spore.

In any of the compositions other than the compositions that involve the use of a signal peptide, the enzyme or expansin protein is suitably not part of a fusion protein.

C. Carriers and Additional Agrochemicals

In any of the compositions, the composition can further comprise an agriculturally acceptable carrier, a further agrochemical in addition to the fertilizer, or a combination thereof. Suitable carriers and agrochemicals are described in Section XVI below.

VII. Enzymes and Expansin Proteins for Use with the Methods, Plant Seeds, or Compositions Phospholipases, lipases, xylanases, xylosidases, lactonases, chitosanases, proteases, glucanases, expansin proteins, phytases, acid phosphatases, pectinases, mannanases, and ACC deaminases that are suitable for use in connection with the methods, seeds, and compositions are described below.

A. Phospholipases

The enzyme can comprise a phospholipase.

Phospholipases can be used for any of the plant growth stimulating or plant health promoting purposes described herein, but are especially suitable for stimulating plant growth, increasing nutrient uptake, and/or increasing root development and nodulation. Increasing root nodulation enhances the ability of the plant to form symbiotic relationships with nitrogen fixing microorganisms in the soil, resulting in increased nitrogen uptake and enhanced growth rates. These effects also lead to decreased susceptibility to environmental stresses such as drought.

Phospholipases are enzymes that have specific activity on phospholipids, releasing free fatty acids from complex phospholipids. Phospholipases can be broken down into five major classes: phospholipase A, phospholipase B, phospholipase C, phospholipase D, and phospholipase E. Each of these classes acts on specific types of phospholipids.

Where the enzyme comprises a phospholipase, the phospholipase can comprise a phospholipase A, a phospholipase B, a phospholipase C, a phospholipase D, a phospholipase E, or a combination of any thereof.

For example, the phospholipase can comprise a phospholipase A, a phospholipase C, a phospholipase D, or a combination of any thereof.

When the phospholipase comprises the phospholipase A, the phospholipase A can comprise a phospholipase A1, a phospholipase A2, or a combination thereof.

The phospholipase A2 can comprise a Group IIA phospholipase A2, a Group IIC phospholipase A2, a Group IID phospholipase A2, a Group TIE phospholipase A2, a Group IIF phospholipase A2, a Group III phospholipase A2, a Group IVA phospholipase A2, a Group IVB phospholipase A2, a Group IVC phospholipase A2, a Group IVD phospholipase A2, a Group WE phospholipase A2, a Group VIF phospholipase A2, a Group V phospholipase A2, a Group VI phospholipase A2, a Group VII phospholipase A2, a Group X phospholipase A2, a Group XIIA phospholipase A2, a Group XIIB phospholipase A2, a Group XV phospholipase A2, a Group XVI phospholipase A2. or a combination of any thereof.

When the phospholipase comprises the phospholipase B, the phospholipase B can comprise a phospholipase B1.

When the phospholipase comprises the phospholipase C, the phospholipase C can comprise a phospholipase C beta 1, a phospholipase C beta 2, a phospholipase C beta 3, a phospholipase C beta 4, a phospholipase C delta 1, a phospholipase C delta 3, a phospholipase C delta 4, a phospholipase C epsilon 1, a phospholipase C gamma 1, a phospholipase C gamma 2, a phospholipase C eta 1, a phospholipase C eta 2, a phospholipase C zeta 1, or a combination of any thereof.

When the phospholipase comprises the phospholipase D, the phospholipase D can comprise a phospholipase D1, a phospholipase D2, a phospholipase D member 3, a phospholipase D member 4, a phospholipase D member 5, a phospholipase D member 6, or a combination of any thereof.

The phospholipase can comprise a 1-alkyl-2-acetylglycerophosphocholine esterase, a phosphatidylinositol deacylase, a phosphoinositide phospholipase C, a sphingomyelin phosphodiesterase, a sphingomyelin phosphodiesterase D, an alkylglycerophosphoethanolamine phosphodiesterase, a variant-surface-glycoprotein phospholipase C, a glycosylphosphatidylinositol phospholipase D, an N-acetylphosphatidylethanolamine-hydrolysing phospholipase D, a phosphatidylinositol diacylglycerol-lyase, a glycosylphosphatidylinositol diacylglycerol-lyase, a patatin-like phospholipase domain containing protein 2 (PNPLA2), a patatin-like phospholipase domain containing protein 3 (PNPLA3), or a combination of any thereof.

The phospholipase can comprise a *Streptomyces* phospholipase (e.g., a *Streptomyces chromofuscus* phospholipase such as *Streptomyces chromofuscus* phospholipase D), a *Bacillus* phospholipase (e.g., a *Bacillus cereus* phospholipase such as *Bacillus cereus* phosphatidylcholine-specific phospholipase C or *Bacillus cereus* phosphatidylinositol-specific phospholipase C, or a *Bacillus thuringiensis* phospholipase), a *Clostridium* phospholipase (e.g., a *Clostridium perfringens* phospholipase such as *Clostridium perfringens* phospholipase C), or a combination of any thereof.

The phospholipase can comprise an amino acid sequence having at least 70% identity to any one of SEQ ID NOs. 13-19 and 115-117.

The phospholipase can comprise an amino acid sequence having at least 75% identity to any one of SEQ ID NOs. 13-19 and 115-117.

The phospholipase can comprise an amino acid sequence having at least 80% identity to any one of SEQ ID NOs. 13-19 and 115-117.

The phospholipase can comprise an amino acid sequence having at least 85% identity to any one of SEQ ID NOs. 13-19 and 115-117.

The phospholipase can comprise an amino acid sequence having at least 90% identity to any one of SEQ ID NOs. 13-19 and 115-117.

The phospholipase can comprise an amino acid sequence having at least 95% identity to any one of SEQ ID NOs. 13-19 and 115-117.

The phospholipase can comprise an amino acid sequence having at least 98% identity to any one of SEQ ID NOs. 13-19 and 115-117.

The phospholipase can comprise an amino acid sequence having at least 99% identity to any one of SEQ ID NOs. 13-19 and 115-117.

The phospholipase can comprise an amino acid sequence having 100% identity to any one of SEQ ID NOs. 13-19 and 115-117.

Where the phospholipase comprises a *Bacillus cereus* phosphatidylcholine-specific phospholipase C (e.g., SEQ ID NO: 115), the method can further comprise applying a mannanase (e.g., SEQ ID NO: 128) or a xyloglucanase (e.g., SEQ ID NO: 125) to the plant growth medium, plant, plant seed, or area surrounding the plant or the plant seed.

Where the phospholipase comprises a *Bacillus cereus* phosphatidylcholine-specific phospholipase C (e.g., SEQ ID NO: 115), the seed can be further treated with a mannanase (e.g., SEQ ID NO: 128) or a xyloglucanase (e.g., SEQ ID NO: 125).

Where the phospholipase comprises a *Bacillus cereus* phosphatidylcholine-specific phospholipase C (e.g., SEQ ID NO: 115), the composition can further comprise a mannanase (e.g., SEQ ID NO: 128) or a xyloglucanase (e.g., SEQ ID NO: 125).

The *Bacillus cereus* phosphatidylcholine-specific phospholipase C and the mannanase can be present in the method, on the seed, or in the composition in synergistically effective amounts.

The *Bacillus cereus* phosphatidylcholine-specific phospholipase C and the xyloglucanase can be present in the method, on the seed, or in the composition in synergistically effective amounts.

B. Lipases

The enzyme can comprise a lipase.

Lipases are enzymes that have specific activity to lipids, cleaving fatty acid chains off of larger lipid molecules such as triglycerides. Lipases can be used for any of the plant growth stimulating or plant health-promoting purposes described herein, but are particularly well-suited for stimulating plant growth and enhancing nutrient uptake. These effects in turn lead to increased crop yields, improved early season vigor, and decreased susceptibility of plants to early season stresses.

The lipase can comprise a carboxyl ester lipase, a diacylglycerol lipase alpha, a diacylglycerol lipase beta, a lipase A, a hepatic lipase, a hormone-sensitive lipase, a gastric lipase, an endothelial lipase, a member H lipase, a lipase family member I, a lipase family member J, a lipase family member K, a lipase family member M, a lipase family member N, a lipoprotein lipase, a monoglyceride lipase, a pancreatic lipase-related protein 2, a pancreatic lipase-related protein 3, an acylglycerol lipase, a galactolipase, a lipoprotein lipase, or a combination of any thereof.

The lipase can comprise a *Bacillus subtilis* lipase, a *Bacillus thuringiensis* lipase, a *Bacillus cereus* lipase, a *Bacillus clausii* lipase, a *Burkholderia cepacia* lipase, a *Burkholderia stearothermophilus* lipase, a *Pseudomonas* lipase, or a combination of any thereof.

The lipase can comprise an amino acid sequence having at least 70% identity with SEQ ID NO: 20, 21, and 118-120.

The lipase can comprise an amino acid sequence having at least 75% identity with SEQ ID NO: 20, 21, and 118-120.

The lipase can comprise an amino acid sequence having at least 80% identity with SEQ ID NO: 20, 21, and 118-120.

The lipase can comprise an amino acid sequence having at least 85% identity with SEQ ID NO: 20, 21, and 118-120.

The lipase can comprise an amino acid sequence having at least 90% identity with SEQ ID NO: 20, 21, and 118-120.

The lipase can comprise an amino acid sequence having at least 95% identity with SEQ ID NO: 20, 21, and 118-120.

The lipase can comprise an amino acid sequence having at least 98% identity with SEQ ID NO: 20, 21, and 118-120.

The lipase can comprise an amino acid sequence having at least 99% identity with SEQ ID NO: 20, 21, and 118-120.

The lipase can comprise an amino acid sequence having 100% identity with SEQ ID NO: 20, 21, and 118-120.

C. Xylanases

The enzyme can comprise a xylanase.

Xylanases act on the polysaccharide xylan, a common sugar found in plants and in the soil. Xylanases can be used as a seed treatment, delivered to the plant growth medium (e.g., via in furrow application or as a soil amendment), or applied as a foliar treatment onto plants to generate smaller sugar chains that can be taken up by the plant or used to feed the surrounding microbiome.

Where the enzyme comprises a xylanase, the xylanase can comprise a beta-xylanase.

For example the beta-xylanase can comprise a glucurono-arabinoxylan endo-1,4-beta-xylanase, an exo-1,4-beta-xylanase, an endo-1,4-beta-xylanase, or a combination of any thereof.

The xylanase can comprise a *Caldicellulosiruptor* xylanase (e.g., a *Caldicellulosiruptor saccharolyticus* xylanase), a *Bacillus* xylanase (e.g., a *Bacillus subtilis* or *Bacillus stearothermophilus* xylanase), a *Neocallimastix* xylanase (e.g., a *Neocallimastix patriciarum* xylanase), a *Thermomyces* xylanase (e.g., a *Thermomyces lanuginosus* xylanase), or a combination of any thereof.

The xylanase can comprise an amino acid sequence having at least 70% identity to any one of SEQ ID NOs. 22-25, 121, and 122.

The xylanase can comprise an amino acid sequence having at least 75% identity to any one of SEQ ID NOs. 22-25, 121, and 122.

The xylanase can comprise an amino acid sequence having at least 80% identity to any one of SEQ ID NOs. 22-25, 121, and 122.

The xylanase can comprise an amino acid sequence having at least 85% identity to any one of SEQ ID NOs. 22-25, 121, and 122.

The xylanase can comprise an amino acid sequence having at least 90% identity to any one of SEQ ID NOs. 22-25, 121, and 122.

The xylanase can comprise an amino acid sequence having at least 95% identity to any one of SEQ ID NOs. 22-25, 121, and 122.

The xylanase can comprise an amino acid sequence having at least 98% identity to any one of SEQ ID NOs. 22-25, 121, and 122.

The xylanase can comprise an amino acid sequence having at least 99% identity to any one of SEQ ID NOs. 22-25, 121, and 122.

The xylanase can comprise an amino acid sequence having 100% identity to any one of SEQ ID NOs. 22-25, 121, and 122.

D. Xylosidases

The enzyme can comprise a xylosidase.

Xylosidases cleave single xylose molecules off of shorter fragments of xylan, a common polysaccharide found in plants and in the soil. Xylosidases can be used as a seed treatment, delivered to the plant growth medium (e.g., via in furrow application or as a soil amendment), or applied as a foliar treatment onto plants to generate smaller sugar chains that can be taken up by the plant or used to feed the surrounding microbiome.

For example, the xylosidase can comprise a *Caldicellulosiruptor saccharolyticus* xylosidase, a *Bacillus pumilus* xylosidase, or a combination thereof.

The xylosidase can comprise an amino acid sequence having at least 70% identity to SEQ ID NO: 26 or 123.

The xylosidase can comprise an amino acid sequence having at least 75% identity to SEQ ID NO: 26 or 123.

The xylosidase can comprise an amino acid sequence having at least 80% identity to SEQ ID NO: 26 or 123.

The xylosidase can comprise an amino acid sequence having at least 85% identity to SEQ ID NO: 26 or 123.

The xylosidase can comprise an amino acid sequence having at least 90% identity to SEQ ID NO: 26 or 123.

The xylosidase can comprise an amino acid sequence having at least 95% identity to SEQ ID NO: 26 or 123.

The xylosidase can comprise an amino acid sequence having at least 98% identity to SEQ ID NO: 26 or 123.

The xylosidase can comprise an amino acid sequence having at least 99% identity to SEQ ID NO: 26 or 123.

The xylosidase can comprise an amino acid sequence having 100% identity to SEQ ID NO: 26 or 123.

E. Lactonases

The enzyme can comprise a lactonase.

Lactonases can be used for any of the plant growth stimulating or plant health promoting purposes described herein, but are especially suitable for decreasing the susceptibility of plants to pathogens. Lactonases are also described as acyl-homoserine lactonases and are metalloenzymes produced by certain species of bacteria. For example, lactonases can be found in bacteria of the Phyla Bacteriodetes, Firmicutes, Actinobacteria, and in bacteria of the genera of *Pseudomonas* and *Bacillus*, as well as others. Lactonases target and inactivate acylated homoserine lactones. Lactonases hydrolyze the ester bonds of small hormone-like molecules commonly known as homoserine lactones. In the hydrolysis of these lactone bonds, lactonase acts to prevent these homoserine lactones from binding to their transcriptionally-regulated targets and thereby interfere with quorum sensing. However, lactonase secretion from naturally occurring bacteria that colonize soil or plants is limited and inducible, and thus it would be desirable to providing higher levels of lactonase to the environment of a plant.

Free lactonases or recombinant bacteria expressing lactonases can be applied to plants (e.g., foliarly or as a seed treatment) or a plant growth medium in order to reduce the levels of lactones in the environment. Without being bound to any particular theory, it is believed that this reduction in the level of lactones can in turn lead to reduction in plant disease, as well as a secondary increase in plant growth and development.

When expressed in a recombinant microorganism, the addition of a secretion signal to the lactonase would allow the microbe to secrete the lactonase into the environment. Suitable secretion signals are described further below in Section XII.

Where the enzyme comprises a lactonase, the lactonase can comprise a 1,4-lactonase, a 2-pyrone-4,6-dicarboxylate lactonase, a 3-oxoadipate enol-lactonase, an actinomycin lactonase, a deoxylimonate A-ring-lactonase, a gluconolactonase, an L-rhamnono-1,4-lactonase, a limonin-D-ring-lactonase, a steroid-lactonase, a triacetate-lactonase, a xylono-1,4-lactonase, or a combination of any thereof.

The lactonase can comprise a *Bacillus* lactonase (e.g., a *Bacillus thuringiensis* lactonase, a *Bacillus pseudomycoides* lactonase, or a combination thereof), an *Agrobacterium* lactonase, a *Rhodococcus* lactonase, a *Streptomyces* lactonase, an *Arthrobacter* lactonase, a *Sphingomonas* lactonase, a *Pseudomonas* lactonase, a *Klebsiella* lactonase, or a combination of any thereof.

The lactonase can comprise an AiiA.

The lactonase is preferably specific for a bacterial lactone homoserine signaling molecule.

The lactonase can comprise an amino acid sequence having at least 70% identity to SEQ ID NO: 27 or 28.

The lactonase can comprise an amino acid sequence having at least 75% identity to SEQ ID NO: 27 or 28.

The lactonase can comprise an amino acid sequence having at least 80% identity to SEQ ID NO: 27 or 28.

The lactonase can comprise an amino acid sequence having at least 85% identity to SEQ ID NO: 27 or 28.

The lactonase can comprise an amino acid sequence having at least 90% identity to SEQ ID NO: 27 or 28.

The lactonase can comprise an amino acid sequence having at least 95% identity to SEQ ID NO: 27 or 28.

The lactonase can comprise an amino acid sequence having at least 98% identity to SEQ ID NO: 27 or 28.

The lactonase can comprise an amino acid sequence having at least 99% identity to SEQ ID NO: 27 or 28.

The lactonase can comprise an amino acid sequence having 100% identity to SEQ ID NO: 27 or 28.

F. Chitosanases

The enzyme can comprise a chitosanase.

Chitosanases can be used for any of the plant growth stimulating or plant health promoting purposes described herein, but are especially suitable for increasing nutrient uptake and increasing plant growth. This in turn leads to increased crop yield, improved early season vigor, and decreased susceptibility to early season stresses. Chitosanases are also useful for protecting plants from pathogens.

The chitosanase can comprise an exo-1,4-beta-D-glucosaminidase, an endo-1,4-beta-d-glucosaminidase, or a combination thereof.

The chitosanase can comprise a *Bacillus subtilis* chitosanase, a *Streptomyces* chitosanase, or a combination of any thereof.

The chitosanase can comprise an amino acid sequence having at least 70% identity to SEQ ID NO: 29 or 124.

The chitosanase can comprise an amino acid sequence having at least 75% identity to SEQ ID NO: 29 or 124.

The chitosanase can comprise an amino acid sequence having at least 80% identity to SEQ ID NO: 29 or 124.

The chitosanase can comprise an amino acid sequence having at least 85% identity to SEQ ID NO: 29 or 124.

The chitosanase can comprise an amino acid sequence having at least 90% identity to SEQ ID NO: 29 or 124.

The chitosanase can comprise an amino acid sequence having at least 95% identity to SEQ ID NO: 29 or 124.

The chitosanase can comprise an amino acid sequence having at least 98% identity to SEQ ID NO: 29 or 124.

The chitosanase can comprise an amino acid sequence having at least 99% identity to SEQ ID NO: 29 or 124.

The chitosanase can comprise an amino acid sequence having 100% identity to SEQ ID NO: 29 or 124.

G. Proteases

The enzyme can comprise a protease.

Proteases can be used for any of the plant growth stimulating or plant health promoting purposes described herein, but are particularly useful for increasing nutrient uptake and stimulating plant growth. This in turn leads to increased crop yield, improved early season vigor, and decreased susceptibility to early season stresses. Proteases are also useful for protecting plants from pathogens.

The protease can comprise a subtilisin, an acid protease, an alkaline protease, a proteinase, a peptidase, an endopeptidase, an exopeptidase, a thermolysin, a papain, a pepsin, a trypsin, a pronase, a carboxylase, a serine protease, a glutamate protease, an aspartate protease, a cysteine protease, a threonine protease, an asparagine protease, a histidine protease, a metalloprotease, or a combination of any thereof.

For example, the protease can comprise a cysteine protease, a serine protease, a threonine protease, an aspartate protease, an asparagine protease, a metalloprotease, a glutamate protease, or a combination of any thereof.

For example, the protease can comprise a metalloprotease, a serine protease, an aspartate protease, a histidine protease, or a combination of any thereof.

The protease preferably does not consist of a methionine aminopeptidase.

The protease preferably does not comprise a methionine aminopeptidase.

The protease can comprise comprises a *Bacillus* protease (e.g., a *Bacillus subtilis* protease), an *Aspergillus* protease, or a combination thereof.

The protease can comprise an amino acid sequence having at least 70% identity to any one of SEQ ID NOs. 46-48 and 127.

The protease can comprise an amino acid sequence having at least 75% identity to any one of SEQ ID NOs. 46-48 and 127.

The protease can comprise an amino acid sequence having at least 80% identity to any one of SEQ ID NOs. 46-48 and 127.

The protease can comprise an amino acid sequence having at least 85% identity to any one of SEQ ID NOs. 46-48 and 127.

The protease can comprise an amino acid sequence having at least 90% identity to any one of SEQ ID NOs. 46-48 and 127.

The protease can comprise an amino acid sequence having at least 95% identity to any one of SEQ ID NOs. 46-48 and 127.

The protease can comprise an amino acid sequence having at least 98% identity to any one of SEQ ID NOs. 46-48 and 127.

The protease can comprise an amino acid sequence having at least 99% identity to any one of SEQ ID NOs. 46-48 and 127.

The protease can comprise an amino acid sequence having at least 100% identity to any one of SEQ ID NOs. 46-48 and 127.

H. Glucanases

The enzyme can comprise a glucanase.

Glucanases can be used for any of the plant growth stimulating or plant health promoting purposes described herein, but are particularly useful for increasing nutrient uptake and stimulating plant growth. This in turn leads to increased crop yield, improved early season vigor, and decreased susceptibility to early season stresses. Glucanases can also be used for protecting plants from pathogens and for reducing susceptibility to an environmental stress in a plant.

Glucanases use water to break chemical bonds between individual glucose molecules glucans, which are long chain polysaccharides. Glucans can be broken down into two types, alpha glucan, consisting of primarily alpha chains of glucose molecules, and beta glucans, consisting of primarily beta chains of glucose molecules. Common alpha glucans include dextrans, glycogens, pullalans, and starch. Alpha glucans generally include combinations of alpha 1,4; alpha 1,6, and/or alpha 1,3 glucans and branches. Glucanases that are specific for cleaving alpha linkages are called alpha-glucanases. Beta glucanases are specific to beta linkages between glucans. Common beta glucans include cellulose, laminarin, lichenin, zymosan. Beta glucans are commonly found with b1,3; b1,4, and/or b1,6 linkages between glucose molecules. Glucanases can be either "exo" or "endo" depending on the location of the cleavage of the polysaccharide. Alpha-, beta-, exo- and endo-glucanases are all effective for stimulating plant growth.

The glucanase can comprise an endoglucanase, an exoglucanase, or a combination thereof.

The glucanase comprises an alpha-glucanase, a beta-glucanase, or a combination thereof.

Where the glucanase comprises an alpha-glucanase, the alpha-glucanase can comprise an amylase, an alpha-1,4-glucanase, an alpha-1,6-glucanase, or a combination of any thereof.

Where the glucanase comprises a beta-glucanase, the beta-glucanase can comprise an endo-beta-glucanase, an exo-beta-glucanase, or a combination thereof.

The beta-glucanase can comprise a beta-1,3-glucanase, a beta 1,3/1,4 glucanase, a beta-1,4-glucanase, a beta-1,6-glucanase, or a combination of any thereof.

For example, the beta-glucanase can comprise the beta-1,3-glucanase, the beta-1,4-glucanase, or a combination thereof.

The beta-1,3-glucanase can comprise a beta-1,3-endoglucanase.

The beta-1,4-glucanase can comprise a beta-1,4-endoglucanase.

The glucanase can comprise a cellulase, a glycoside hydrolase, a xyloglucan:xyloglucosyl transferase, a cycloheptaglucanase, an oligoxyloglucan beta-glycosidase, a cyclohexaglucanase, a xyloglucanase, a cellulose 1,4-beta-cellobiosidase, a glucan endo-1,3-beta-D-glucosidase, a cyclomaltodextrinase, a glucan 1,3-beta-glucosidase, a glucan endo-1,3-alpha-glucosidase, an endo-1,3(4)-beta-glucanase, an exo-beta-1,4-glucanase, a lichenase, a laminarinase, a glucan 1,4-beta-glucosidase, a glucan endo-1,6-beta-glucosidase, a glucan 1,3-alpha-glucosidase, an amylopectinase, a laminarinase, or a combination of any thereof.

The glucanase can comprise a non-cellulolytic glucanase.

In any of the methods, seeds, or compositions wherein the glucanase comprises a non-cellulolytic glucanase, the non-cellulolytic glucanase can comprise a xyloglucanase, a lichenase, an amylase, an amyloglucanase, amyloglucosidase, a laminarinase, a beta-1,3-glucanase, a beta-1,6-glucanase, a beta-1,3/1,4-glucanase, an alpha-1,4-glucanase, an alpha 1,6-glucanase, or a combination of any thereof.

Where the glucanase comprises a xyloglucanase, the xyloglucanase can comprise a xyloglucan-specific endo-beta-1,4-glucanase, a xyloglucan-specific exo-beta-1,4-glucanase, or a combination thereof.

The xyloglucanase can comprise a *Paenibacillus* glucanase.

Where the glucanase comprises a xyloglucanase (e.g., SEQ ID NO: 125), the method can further comprise applying a mannanase (e.g., SEQ ID NO: 128) to the plant growth medium, plant, plant seed, or area surrounding the plant or the plant seed.

Where the glucanase comprises a xyloglucanase (e.g., SEQ ID NO: 125), the seed can be further treated with a mannanase (e.g., SEQ ID NO: 128).

Where the glucanase comprises a xyloglucanase (e.g., SEQ ID NO: 125), the composition can further comprise a mannanase (e.g., SEQ ID NO: 128).

The xyloglucanase and the mannanase can be present in the method, on the seed, or in the composition in synergistically effective amounts.

The glucanase can comprise a cellulase.

The glucanase can comprise an endocellulase, an exocellulase, or a combination thereof.

The glucanase can comprise an *Acidothermus* glucanase, a *Trichoderma* glucanase, an *Aspergillus* glucanase, a *Paenibacillus* glucanase, a *Helix* glucanase, a *Bacillus* glucanase, or a combination of any thereof.

For example, the glucanase can comprise a *Bacillus circulans* glucanase, a *Bacillus subtilis* glucanase (e.g., a *Bacillus subtilis* endoglucanase or a *Bacillus subtilis* beta-glucosidase), a *Bacillus thuringiensis* glucanase (e.g., a *Bacillus thuringiensis* endoglucanase or a *Bacillus thuringiensis* beta-glucosidase), a *Bacillus cereus* glucanase (e.g., a *Bacillus cereus* endoglucanase or a *Bacillus cereus* beta-glucosidase), a *Trichoderma reesei* glucanase (e.g., a *Trichoderma reesei* exocellulase or a *Trichoderma reesi* beta-1,4-endoglucanase), a *Bacillus clausii* glucanase (e.g., a *Bacillus clausii* endoglucanase or a *Bacillus clausii* beta-glucosidase), a *Helix pomatia* glucanase (e.g., a *Helix pomatia* beta-1,3 endoglucanase), an *Acidothermus cellulolyticus* glucanase (e.g., a *Acidothermus cellulolyticus* beta-1,4 endoglucanase), or a combination of any thereof.

The glucanase can comprise an amino acid sequence having at least 70% identity to any one of SEQ ID NOs. 30-45, 125, and 126.

The glucanase can comprise an amino acid sequence having at least 75% identity to any one of SEQ ID NOs. 30-45, 125, and 126.

The glucanase can comprise an amino acid sequence having at least 80% identity to any one of SEQ ID NOs. 30-45, 125, and 126.

The glucanase can comprise an amino acid sequence having at least 85% identity to any one of SEQ ID NOs. 30-45, 125, and 126.

The glucanase can comprise an amino acid sequence having at least 90% identity to any one of SEQ ID NOs. 30-45, 125, and 126.

The glucanase can comprise an amino acid sequence having at least 95% identity to any one of SEQ ID NOs. 30-45, 125, and 126.

The glucanase can comprise an amino acid sequence having at least 98% identity to any one of SEQ ID NOs. 30-45, 125, and 126.

The glucanase can comprise an amino acid sequence having at least 99% identity to any one of SEQ ID NOs. 30-45, 125, and 126.

The glucanase can comprise an amino acid sequence having 100% identity to any one of SEQ ID NOs. 30-45, 125, and 126.

Where a glucanase is applied in a formulation, or where a seed is coated with a seed coating formulation comprising a glucanase, the formulation can suitably comprise additional agrochemicals and/or a microbial inoculant. For example, the formulation can suitably comprise a fungicide, insecticide, a nematicide, a fertilizer, a plant hormone, a bacterial inoculant, a fungal inoculant, or a combination of any thereof. Particular fungicides, insecticides, nematicides, fertilizers, plant hormones, bacterial inoculants, and fungal inoculants are described in Section XVI below.

I. Phytases

The enzyme can comprise a phytase.

Phytases act on phytic acids in soil, a source of free phosphate for plant growth. Phytases remove select phosphates off of the phytic acids, and the freed phosphates can be taken up by nearby plants.

Where the enzyme comprises a phytase, the phytase can comprise a *Triticum aestivum* phytase.

The phytase can comprise an amino acid sequence having at least 70% identity to any one of SEQ ID NOs. 132-134.

The phytase can comprise an amino acid sequence having at least 75% identity to any one of SEQ ID NOs. 132-134.

The phytase can comprise an amino acid sequence having at least 80% identity to any one of SEQ ID NOs. 132-134.

The phytase can comprise an amino acid sequence having at least 85% identity to any one of SEQ ID NOs. 132-134.

The phytase can comprise an amino acid sequence having at least 90% identity to any one of SEQ ID NOs. 132-134.

The phytase can comprise an amino acid sequence having at least 95% identity to any one of SEQ ID NOs. 132-134.

The phytase can comprise an amino acid sequence having at least 98% identity to any one of SEQ ID NOs. 132-134.

The phytase can comprise an amino acid sequence having at least 99% identity to any one of SEQ ID NOs. 132-134.

The phytase can comprise an amino acid sequence having 100% identity to any one of SEQ ID NOs. 132-134.

The phytase can comprise a mixture of phytases comprising SEQ ID NOs. 132, 133, and 134.

J. Acid Phosphatases

The enzyme can comprise an acid phosphatase.

Acid phosphatases act on insoluble and less soluble forms of phosphates in the soil, and release them from for uptake by plants.

Where the enzyme comprises an acid phosphatase, the acid phosphatase can comprise a *Triticum aestivum* acid phosphatase.

The acid phosphatase can comprise an amino acid sequence having at least 70% identity to SEQ ID NO: 130 or 131.

The acid phosphatase can comprise an amino acid sequence having at least 75% identity to SEQ ID NO: 130 or 131.

The acid phosphatase can comprise an amino acid sequence having at least 80% identity to SEQ ID NO: 130 or 131.

The acid phosphatase can comprise an amino acid sequence having at least 85% identity to SEQ ID NO: 130 or 131.

The acid phosphatase can comprise an amino acid sequence having at least 90% identity to SEQ ID NO: 130 or 131.

The acid phosphatase can comprise an amino acid sequence having at least 95% identity to SEQ ID NO: 130 or 131.

The acid phosphatase can comprise an amino acid sequence having at least 98% identity to SEQ ID NO: 130 or 131.

The acid phosphatase can comprise an amino acid sequence having at least 99% identity to SEQ ID NO: 130 or 131.

The acid phosphatase can comprise an amino acid sequence having 100% identity to SEQ ID NO: 130 or 131.

The acid phosphatase can comprise a mixture of acid phosphatases comprising SEQ ID NOs. 130 and 131.

In any of the methods described herein that involve the use of an acid phosphatase, the method can further comprise applying a second enzyme to the plant growth medium, the plant, the plant seed, or the area surrounding the plant or the plant seed.

In any of the plant seeds described herein that are treated or coated with an acid phosphatase, the seed can be further treated or coated with a second enzyme.

Any of the compositions described herein that comprise an acid phosphatase can further comprise a second enzyme.

The second enzyme can comprise a lipase, a phospholipase, a glucanase, a xylanase, a pectinase, a mannanase, a lichenase, or a combination of any thereof. The lipase, phospholipase, glucanase, xylanase, pectinase, mannanase, or lichenase, can comprise any of the lipases, phospholipases, glucanases, xylanases, pectinases, mannanases, or lichenases described herein.

K. Pectinases

The enzyme can comprise a pectinase.

Pectinases act on pectin and related polysaccharides to release small sugars. The small sugars are in turn taken up by the plant as carbon sources and can also feed the inherent microbes that surround the plant.

Where the enzyme comprises a pectinase, the pectinase can comprise a pectolyase.

For example, the pectolyase can comprise an *Aspergillus japonicus* pectolyase.

The pectolyase can comprise an amino acid sequence having at least 70% identity to SEQ ID NO: 129.

The pectolyase can comprise an amino acid sequence having at least 75% identity to SEQ ID NO: 129.

The pectolyase can comprise an amino acid sequence having at least 80% identity to SEQ ID NO: 129.

The pectolyase can comprise an amino acid sequence having at least 85% identity to SEQ ID NO: 129.

The pectolyase can comprise an amino acid sequence having at least 90% identity to SEQ ID NO: 129.

The pectolyase can comprise an amino acid sequence having at least 95% identity to SEQ ID NO: 129.

The pectolyase can comprise an amino acid sequence having at least 98% identity to SEQ ID NO: 129.

The pectolyase can comprise an amino acid sequence having at least 99% identity to SEQ ID NO: 129.

The pectolyase can comprise an amino acid sequence having 100% identity to SEQ ID NO: 129.

L. Mannanases

The enzyme can comprise a mannanase.

Mannanases act on glucomannans and related polysaccharides to release small sugars. The small sugars are in turn taken up by the plant as carbon sources and can also feed the inherent microbes that surround the plant.

Where the enzyme comprises a mannanase, the mannanase can comprise a *Bacillus* mannanase.

The mannanase can comprise an amino sequence having at least 70% identity to SEQ ID NO: 128.

The mannanase can comprise an amino sequence having at least 75% identity to SEQ ID NO: 128.

The mannanase can comprise an amino sequence having at least 80% identity to SEQ ID NO: 128.

The mannanase can comprise an amino sequence having at least 85% identity to SEQ ID NO: 128.

The mannanase can comprise an amino sequence having at least 90% identity to SEQ ID NO: 128.

The mannanase can comprise an amino sequence having at least 95% identity to SEQ ID NO: 128.

The mannanase can comprise an amino sequence having at least 98% identity to SEQ ID NO: 128.

The mannanase can comprise an amino sequence having at least 99% identity to SEQ ID NO: 128.

The mannanase can comprise an amino sequence having 100% identity to SEQ ID NO: 128.

M. ACC Deaminases

The enzyme can comprise an ACC deaminase.

The ACC deaminase can comprise any of the enzymes described above in Section II.

The ACC deaminase can comprise an amino acid sequence having at least 70% identity to any one of SEQ ID NOs. 7-12, 113, and 114.

The ACC deaminase can comprise an amino acid sequence having at least 75% identity to any one of SEQ ID NOs. 7-12, 113, and 114.

The ACC deaminase can comprise an amino acid sequence having at least 80% identity to any one of SEQ ID NOs. 7-12, 113, and 114.

The ACC deaminase can comprise an amino acid sequence having at least 85% identity to any one of SEQ ID NOs. 7-12, 113, and 114.

The ACC deaminase can comprise an amino acid sequence having at least 90% identity to any one of SEQ ID NOs. 7-12, 113, and 114.

The ACC deaminase can comprise an amino acid sequence having at least 95% identity to any one of SEQ ID NOs. 7-12, 113, and 114.

The ACC deaminase can comprise an amino acid sequence having at least 98% identity to any one of SEQ ID NOs. 7-12, 113, and 114.

The ACC deaminase can comprise an amino acid sequence having at least 99% identity to any one of SEQ ID NOs. 7-12, 113, and 114.

The ACC deaminase can comprise an amino acid sequence having 100% identity to any one of SEQ ID NOs. 7-12, 113, and 114.

N. Expansin Proteins

Expansin proteins aid plant walls in expanding during growth of the plant. Expansins are thus particularly useful in any of the methods for stimulating plant growth described herein.

The expansin protein can comprise an amino acid sequence having at least 70% identity to SEQ ID NO: 74.

The expansin protein can comprise an amino acid sequence having at least 75% identity to SEQ ID NO: 74.

The expansin protein can comprise an amino acid sequence having at least 80% identity to SEQ ID NO: 74.

The expansin protein can comprise an amino acid sequence having at least 85% identity to SEQ ID NO: 74.

The expansin protein can comprise an amino acid sequence having at least 90% identity to SEQ ID NO: 74.

The expansin protein can comprise an amino acid sequence having at least 95% identity to SEQ ID NO: 74.

The expansin protein can comprise an amino acid sequence having at least 98% identity to SEQ ID NO: 74.

The expansin protein can comprise an amino acid sequence having at least 99% identity to SEQ ID NO: 74.

The expansin protein can comprise an amino acid sequence having at least 100% identity to SEQ ID NO: 74.

VIII. Use of Fertilizers and/or Biostimulants with the Methods, Seeds, and Compositions In any of the methods described herein, the method can further comprise applying a fertilizer, a biostimulant, or a combination thereof to the plant growth medium, the plant, the plant seed, or the area surrounding the plant or the plant seed.

For any of the plant seeds described herein, the plant seed can be further treated or coated with a fertilizer, a biostimulant, or a combination thereof.

For any of the methods, seeds, or compositions described herein, the fertilizer can comprise nitrogen, phosphate (e.g., monoammonium phosphate, diammonium phosphate, orthophosphate, orthopolyphosphate, or a combination of any thereof), potassium (e.g., potassium acetate), zinc, iron, selenium, boron, copper, or a combination of any thereof.

For example, the fertilizer can comprise 12% ammoniacal nitrogen and 58% available phosphate.

Additional fertilizers that can be used are described in Section XVI below.

The biostimulant can comprise a gibberellic acid, an indole-3-butyric acid, a kinetin, an auxin, an auxin homolog or derivative, or a combination of any thereof.

In any of the methods or seeds involving the use of a fertilizer and/or a biostimulant, the enzyme suitably comprises an acid phosphatase, a phospholipase, a mannanase, a glucanase, or a combination of any thereof. The acid phosphatase, phospholipase, mannanase, or glucanase can comprise any of the acid phosphatases, phospholipases, mannanases, or glucanase described herein.

IX. Enzyme Preparations

In any of the methods, seeds, or compositions described herein involving the use of a free enzyme and/or an expansin protein, the enzyme or expansin protein can comprise a crude cell extract containing the enzyme or expansin protein, a partially purified enzyme or expansin protein, or a substantially purified enzyme or expansin protein.

In any of the methods, seeds, or compositions described herein involving the use of a free enzyme and/or an expansin protein, the enzyme or expansin protein preferably does not comprise enzyme or expansin protein bound to exosporium of a *Bacillus cereus* family member.

In any of the methods, seeds, or compositions described herein involving the use of a free enzyme and/or expansin protein, the enzyme or expansin protein is preferably not bound to the exosporium of an intact *Bacillus cereus* family member spore.

X. Immobilization of the Enzyme and/or Expansin Protein

In any of the methods, seeds, or compositions described herein comprising the use of a free enzyme and/or an expansin protein, the enzyme or expansin protein can comprise enzyme or expansin protein that is immobilized on a matrix or support.

The matrix or support can comprise charcoal, biochar, nanocarbon, agarose, an alginate, cellulose, a cellulose derivative, silica, plastic, stainless steel, glass, polystyrene, a ceramic, dolomite, a clay, diatomaceous earth, talc, a polymer, a gum, a water-dispersable material, or a combination of any thereof.

Immobilization of the enzyme or expansin protein on the matrix or support preferably results in a slower release of the enzyme or expansin protein into the environment or onto the plant or the plant seed as compared to the release rate for the same non-immobilized enzyme or expansin proteins under the same conditions.

XI. Methods for Making Free Enzyme

Free enzyme can be prepared by a number of standard biochemical and molecular biology methods which are generally known in the art. For example, a gene encoding an enzyme can be amplified from chromosomal DNA using the polymerase chain reaction (PCR), and cloned into a suitable vector (e.g., a plasmid vector). The vector suitably comprises a multiple cloning site into which the DNA molecule encoding the fusion protein can be easily inserted. The vector also suitably contains a selectable marker, such as an antibiotic resistance gene, such that bacteria transformed, transfected, or mated with the vector can be readily identified and isolated. Where the vector is a plasmid, the plasmid suitably also comprises an origin of replication. Alternatively, DNA coding for the enzyme protein can be integrated into the chromosomal DNA of the microorganism host.

The host can then be cultured and enzyme harvested from the cultures. A crude cell extract can be used or the enzyme can be partially or substantially purified using standard biochemical techniques.

Suitable hosts for large-scale production of enzymes include but are not limited to *Bacillus* species (e.g., *Bacillus subtilis, Bacillus licheniformis, Bacillus coagulans, Bacillus megaterium, Bacillus thuringiensis, Bacillus fusiformis, Bacillus cereus*, or *Bacillus mycoides*), *Escherichia coli, Aspergillus niger, Aspergillus oryzae, Streptomyces* species, *Klebsiella* species, *Mucor* species, *Rhizopus* species, *Mortierella* species, *Kluyveromyces* species, *Candida* species, *Penicillium chrysogenum, Trichoderma* species *Saccharomyces cerevisiae, Pichia pastoris, Hansenula polymorpha, Kluyveromyces lactis, Yarrowia lipolytica, Schizosaccharomyces pombe*, and *Candida utilitis*.

Enzymes can be used as collected from whole fermentation broth, or partially or substantially purified from the fermentation batch culture.

Alternatively, enzymes can be produced by screening microorganisms and selecting microorganisms that express high levels of the enzyme. This can be done by initial selection, enrichment, and/or screening in nutritional media that contains an enzyme substrate as a nutrient source for the microorganisms. Often additional selection is performed using differential nutrition media that has an indicator to demonstrate the enzyme levels and activity of the enzymes produced by the identified microorganisms. These microorganisms can be mutated and screened for isolates that product enhanced levels of these enzymes. These microorganism can be utilized in large batch and continuous fermentation methods to create and secrete ample quantities of enzymes. Optimization of the fermentation process and conditions can generally increase the output of the microorganisms.

Enzymes can also be produced at high levels using eukaryotic cell lines, many of which can be engineered to secrete high levels of enzymes, with the advantages of different levels of critical posttranslational modifications and reduction in host enzyme production issues. These can also be scalable to larger cell culture production scale vessels and enzymes purified and treated as above. Examples of suitable eukaryotic cell lines for producing enzymes include, but are not limited to: insect cells derived from insects such as *Bombyx mori, Mamestra brassicae, Spodoptera frupperda, Trichoplusiani*, or *Drosophila melanogaster*; and vertebrate cell lines derived from a vertebrate such as a mouse, rat, hamster, human, or dog.

Other potential sources of enzymes include cell-free protein expression vectors, including those derived from animal, bacterial, fungal, and plant origins.

Transgenic organisms such as plants, rabbit, mice, chicken, or frogs can also be used for the production of recombinant enzymes. For examples, plants can be engineered to overexpress enzymes, and the enzymes can then be collected from the plant and purified or used as crude extract. Such production systems allow for low cost expression of the enzymes and provide a source of material to deliver to plants. These methods have the added advantage of being easily scaled up and with minimal effort.

In each of these production systems, the yield and quality of the desired enzymes can be improved through processes of genetic engineering and formulation. For example, genetic engineering could involve creation of high level expression cassettes and production systems, removal of protease and degradative genes from the production microorganism, optimization of the enzyme for heat stability and long term storage stability, and enhancement of the ability of the enzyme or the production microorganism to secrete mature enzyme into the media for ease of collection and use. Additionally, expression strains can be used to induce point mutations that can lead to increased ability to produce adequate or increased levels of enzymes. In some cases, the production microorganism can also be used and delivered to the plant seed, vicinity around the plant, to the plant roots, or near the plant to get the desired effect in situ on the plant.

Other sources of enzymes include extraction from animal, plant, insect, seaweed, or other biological extracts. Common sources of industrial scale enzymes created and/or purified in this manner include porcine and bovine internal tissues, such as abomasum, liver, mucosas, pancreas, as well as plant sources such as *Carica papaya*. Another example would be the purification of glucanases from barley.

Many commercial sources of enzymes come from tissues that have high levels of target enzymes that can be used as is or in purified forms for agricultural uses.

XII. Signal Peptides

Any signal peptide can be used to modify any of the enzymes described herein such that the enzyme will be secreted from a host microorganism in which it is expressed. The type of signal peptide used will depend primarily on the identity of the host microorganism, since the secretion machinery of different microorganisms will vary in their ability to recognize specific signal peptides. Illustrative signal peptide sequences are provided below in Table 16, together with the bacterial species in which the signal peptides are found in nature. The signal peptides will result in secretion of a protein to which they are linked in the genus of bacteria in which they are found as well as closely related genera. For example, a signal sequence from *Bacillus thuringiensis* will cause secretion of a protein in bacteria of the genus *Bacillus*, as well as bacteria of the genera *Paenibacillus* and *Lysinibacillus*.

For ease of reference, descriptions of amino acid sequences for illustrative signal peptides that can be added to any of the enzymes or expansin proteins described herein to cause secretion of the enzyme or expansin proteins from a microorganism in which it is expressed are provided below in Table 16. Any of the signal peptides listed in Table 16 below can be added at the amino terminus of any of the enzymes or expansin proteins described herein to cause secretion of the enzyme or expansin protein.

TABLE 16

Amino acid sequences for signal peptides

| Source Species for Signal Peptide | SEQ ID NO. for amino acid sequence |
|---|---|
| *Bacillus thuringiensis* | 49 |
| *Bacillus thuringiensis* serovar israelensis 4Q7 | 50 |
| *Bacillus cereus* ATCC 10987 | 51 |
| *Clostridium perfingens* | 52 |
| *Streptomyces chromofuscus* | 53 |
| *Bacillus subtilis* subsp. *subtilis* str. 168 | 54 |
| *Caldicellulosiruptor saccharolyticus* | 55 |
| *Bacillus subtilis* subsp. *subtilis* str. 168 | 56 |
| *Bacillus subtilis* subsp. *subtilis* str. 168 | 57 |

TABLE 16-continued

| Amino acid sequences for signal peptides | |
|---|---|
| Source Species for Signal Peptide | SEQ ID NO. for amino acid sequence |
| *Geobacillus stearothermophilus* (*Bacillus stearothermophilus*) | 58 |
| *Bacillus subtilis* subsp. *subtilis* str. 168 | 59 |
| *Bacillus subtilis* subsp. *subtilis* str. 168 | 60 |
| *Bacillus subtilis* subsp. *subtilis* str. 168 | 61 |
| *Bacillus circulans* | 62 |
| *Bacillus circulans* | 63 |
| *Bacillus subtilis* subsp. *subtilis* str. 168 | 64 |
| *Bacillus subtilis* subsp. *subtilis* str. 168 | 65 |
| *Bacillus subtilis* subsp. *subtilis* str. 168 | 66 |
| *Bacillus subtilis* subsp. *subtilis* str. 168 | 67 |
| *Bacillus subtilis* subsp. *subtilis* str. 168 | 68 |
| *Bacillus thuringiensis* | 69 |
| *Bacillus thuringiensis* | 70 |
| *Bacillus thuringiensis* | 71 |
| *Bacillus pseudomycoides* | 72 |
| *Bacillus thuringiensis* serovar israelensis 4Q7 | 73 |
| *Bacillus cereus* | 135 |
| *Burkholderia cepacia* | 137 |
| *Pseudomonas fluorescens* | 138 |
| *Streptomyces* species N174 | 139 |
| *Paenibacillus* species | 140 |
| *Aspergillus saitoi* | 141 |
| *Bacillus* sp. | 142 |
| *Aspergillus japonicus* | 143 |
| *Triticum aestivum* | 144 |
| *Triticum aestivum* | 145 |
| *Triticum aestivum* | 146 |
| *Triticum aestivum* | 147 |

For example, the signal peptide can comprise an amino acid sequence having at least 70% identity to with any one of SEQ ID NOs. 49-73,135 and 137-147.

For example, the signal peptide can comprise an amino acid sequence having at least 75% identity to with any one of SEQ ID NOs. 49-73,135 and 137-147.

For example, the signal peptide can comprise an amino acid sequence having at least 80% identity to with any one of SEQ ID NOs. 49-73,135 and 137-147.

For example, the signal peptide can comprise an amino acid sequence having at least 85% identity to with any one of SEQ ID NOs. 49-73,135 and 137-147.

For example, the signal peptide can comprise an amino acid sequence having at least 90% identity to with any one of SEQ ID NOs. 49-73, 135 and 137-147.

For example, the signal peptide can comprise an amino acid sequence having at least 95% identity to with any one of SEQ ID NOs. 49-73, 135 and 137-147.

For example, the signal peptide can comprise an amino acid sequence having at least 98% identity to with any one of SEQ ID NOs. 49-73, 135 and 137-147.

For example, the signal peptide can comprise an amino acid sequence having at least 99% identity to with any one of SEQ ID NOs. 49-73, 135 and 137-147.

For example, the signal peptide can comprise an amino acid sequence having 100% identity to with any one of SEQ ID NOs. 49-73, 135 and 137-147.

Signal peptides suitable for use in bacteria of the genus *Bacillus*, bacteria of the genus *Paenibacillus*, or bacteria of the genus *Lysinibacillus* are provided in SEQ ID NOs. 49-51, 54, 56-73, 135, 139, 140, and 142.

Thus, for example, the signal peptide can comprise an amino acid sequence having at least 70% identity with any one of SEQ ID NOs. 49-51, 54, 56-73, 135, 139, 140, and 142.

The signal peptide can comprise an amino acid sequence having at least 75% identity with any one of SEQ ID NOs. 49-51, 54, 56-73, 135, 139, 140, and 142.

The signal peptide can comprise an amino acid sequence having at least 80% identity with any one of SEQ ID NOs. 49-51, 54, 56-73, 135, 139, 140, and 142.

The signal peptide can comprise an amino acid sequence having at least 85% identity with any one of SEQ ID NOs. 49-51, 54, 56-73, 135, 139, 140, and 142.

The signal peptide can comprise an amino acid sequence having at least 90% identity with any one of SEQ ID NOs. 49-51, 54, 56-73, 135, 139, 140, and 142.

The signal peptide can comprise an amino acid sequence having at least 95% identity with any one of SEQ ID NOs. 49-51, 54, 56-73, 135, 139, 140, and 142.

The signal peptide can comprise an amino acid sequence having at least 98% identity with any one of SEQ ID NOs. 49-51, 54, 56-73, 135, 139, 140, and 142.

The signal peptide can comprise an amino acid sequence having at least 99% identity with any one of SEQ ID NOs. 49-51, 54, 56-73, 135, 139, 140, and 142.

The signal peptide can comprise an amino acid sequence having 100% identity with any one of SEQ ID NOs. 49-51, 54, 56-73, 135, 139, 140, and 142.

Thus, for example, when the signal peptide comprises an amino acid sequence having at least 70%, at least 75%, at least 80%, at least 85%, at least 90%, at least 95%, at least 98%, at least 99%, or 100% sequence identity with any one of SEQ ID NOs. 49-51, 54, 56-73, 135, 139, 140, and 142, the microorganism in which the enzyme or expansin protein is expressed suitably comprises a bacterium of the genus *Bacillus*, a bacterium of the genus *Paenibacillus*, a bacterium of the genus *Lysinibacillus*, a bacterium of the genus *Pseudomonas*, or a combination of any thereof.

For example, the microorganism can comprise *Bacillus mycoides, Bacillus pseudomycoides, Bacillus cereus, Bacillus firmus, Bacillus thuringiensis, Bacillus megaterium, Bacillus subtilis, Bacillus aryabbattai, Bacillus amyloliquefaciens, Bacillus circulans, Bacillus flexus, Bacillus nealsonii, Bacillus pumulis, Bacillus licheniformis, Lysinibacillus macroides, Lysinibacillus sphericus, Lysinibacillus fusiformis*, or a combination of any thereof.

The microorganism preferably comprises *Bacillus thuringiensis, Bacillus cereus, Bacillus pseudomycoides, Bacillus mycoides, Lysinibacillus macroides, Lysinibacillus fusiformis, Lysinibacillus sphericus*, or a combination of any thereof.

The signal peptide is preferably present at the amino terminus of the enzyme or expansin protein.

XIII. Recombinant Microorganisms

Recombinant microorganisms, formulations and compositions containing the recombinant microorganisms, methods for using the recombinant microorganisms, and seeds treated with the recombinant microorganisms are described herein above.

In any of the recombinant microorganisms, formulations, compositions, methods, or seeds described herein, the enzyme or expansin protein can be expressed under the control of a constitutive promoter.

In any of the recombinant microorganisms, formulations, compositions, methods, or seeds described herein, the enzyme or expansin protein can be expressed under the control of an inducible promoter.

For any of the recombinant microorganisms, formulations, compositions, methods, or seeds described herein, the recombinant microorganism can comprise a bacterium of the genus *Bacillus*, a bacterium of the genus *Paenibacillus*, a bacterium of the genus *Lysinibacillus*, a fungus of the genus *Penicillium*, a bacterium of the genus *Glomus*, a bacterium of the genus *Pseudomonas*, a bacterium of the genus *Arthrobacter*, a bacterium of the genus *Paracoccus*, a bacterium of the genus *Rhizobium*, a bacterium of the genus *Bradyrhizobium*, a bacterium of the genus *Azosprillium*, a bacterium of the genus *Enterobacter*, a bacterium of the genus *Escherichia*, or a combination of any thereof.

Where the recombinant microorganism comprises a recombinant spore-forming microorganism, the recombinant spore-forming microorganism can comprise a bacterium of the genus *Bacillus*, a bacterium of the genus *Paenibacillus*, a bacterium of the genus *Lysinibacillus*, a fungus of the genus *Penicillium*, a fungus of the genus *Glomus*, or a combination of any thereof.

For any of the recombinant microorganisms, formulations, compositions, methods, or seeds described herein, the recombinant microorganism suitably comprises a bacterium of the genus *Bacillus*, a bacterium of the genus *Paenibacillus*, a bacterium of the genus *Lysinibacillus*, or a combination of any thereof.

For example, the recombinant microorganism can comprise *Bacillus mycoides, Bacillus pseudomycoides, Bacillus cereus, Bacillus thuringiensis, Bacillus megaterium, Bacillus subtilis, Bacillus aryabbattai, Bacillus amyloliquefaciens, Bacillus circulans, Bacillus flexus, Bacillus nealsonii, Bacillus pumulis, Lysinibacillus macroides, Lysinibacillus sphericus, Lysinibacillus fusiformis*, or a combination of any thereof.

The recombinant microorganism suitably comprises *Bacillus thuringiensis, Bacillus cereus, Bacillus pseudomycoides, Lysinibacillus macroides, Lysinibacillus sphericus, Lysinibacillus fusiformis*, or a combination thereof.

For any of the recombinant microorganisms, formulations, methods, or seeds described herein, the recombinant microorganism can comprise a plant-growth promoting strain of bacteria, an endophytic strain of bacteria, or a strain of bacteria that is both plant-growth promoting and endophytic.

The strain can produce an insecticidal toxin (e.g., a Cry toxin), produce a fungicidal compound (e.g., a β-1,3-glucanase, a chitosanase, a lyticase, or a combination thereof), produce a nematicidal compound (e.g., a Cry toxin), produce a bacteriocidal compound, be resistant to one or more antibiotics, comprise one or more freely replicating plasmids, bind to plant roots, colonize plant roots, form biofilms, solubilize nutrients, secrete organic acids, or combinations thereof.

For example, the strain can comprise:

(a) *Bacillus aryabhattai* CAP53 (NRRL No. B-50819),
(b) *Bacillus aryabhattai* CAP56 (NRRL No. B-50817),
(c) *Bacillus flexus* BT054 (NRRL No. B-50816),
(d) *Paracoccus kondratievae* NC35 (NRRL No. B-50820),
(e) *Bacillus mycoides* BT155 (NRRL No. B-50921),
(f) *Enterobacter cloacae* CAP12 (NRRL No. B-50822),
(g) *Bacillus nealsonii* BOBA57 (NRRL No. NRRL B-50821),
(h) *Bacillus mycoides* EE118 (NRRL No. B-50918),
(i) *Bacillus subtilis* EE148 (NRRL No. B-50927),
(j) *Alcaligenes faecalis* EE107 (NRRL No. B-50920),
(k) *Bacillus mycoides* EE141 (NRRL NO. B-50916),
(l) *Bacillus mycoides* BT46-3 (NRRL No. B-50922),
(m)*Bacillus cereus* family member EE128 (NRRL No. B-50917),
(n) *Paenibacillus massiliensis* BT23 (NRRL No. B-50923),
(o) *Bacillus cereus* family member EE349 (NRRL No. B-50928),
(p) *Bacillus subtilis* EE218 (NRRL No. B-50926),
(q) *Bacillus megaterium* EE281 (NRRL No. B-50925),
(r) *Bacillus cereus* family member EE-B00377 (NRRL B-67119);
(s) *Bacillus pseudomycoides* EE-B00366 (NRRL B-67120),
(t) *Bacillus mycoides* EE-B00363 (NRRL B-67121),
(u) *Bacillus pumilus* EE-B00143 (NRRL B-67123),
(v) *Bacillus thuringiensis* EE-B00184 (NRRL B-67122),
(w)*Bacillus mycoides* EE116 (NRRL No. B-50919),
(x) *Bacillus cereus* family member EE417 (NRRL No. B-50974),
(y) *Bacillus subtilis* EE442 (NRRL No. B-50975),
(z) *Bacillus subtilis* EE443 (NRRL No. B-50976),
(aa) *Bacillus cereus* family member EE444 (NRRL No. B-50977),
(bb) *Bacillus subtilis* EE405 (NRRL No. B-50978),
(cc) *Bacillus cereus* family member EE439 (NRRL No. B-50979),
(dd) *Bacillus megaterium* EE385 (NRRL No. B-50980),
(ee) *Bacillus cereus* family member EE387 (NRRL No. B-50981),
(ff)*Bacillus circulans* EE388 (NRRL No. B-50982),
(gg) *Bacillus thuringiensis* EE319 (NRRL No. B-50983),
(hh) *Bacillus cereus* family member EE377 (NRRL No. B-67119),
(ii) *Bacillus mycoides* EE363 (NRRL No. B-67121),
(jj) *Bacillus pseudomycoides* EE366 (NRRL No. B-67120);
(kk) *Bacillus thuringiensis* BT013A (NRRL No. B-50924);
or a combination of any thereof.

Each of these strains has been deposited with the United States Department of Agriculture (USDA) Agricultural Research Service (ARS), having the address 1815 North University Street, Peoria, Ill. 61604 U.S.A., and are identified by the NRRL deposit numbers provided in parentheses. Strains (a)-(d), (f), and (g) were deposited on Mar. 11, 2013. Strains (e), (h)-(q), (w), and (kk) were deposited on Mar. 10, 2014. Strains (x)-(ff) were deposited on Sep. 10, 2014. Strain (gg) was deposited on Sep. 17, 2014. Strains (r)-(v), (hh), (ii), and (jj) were deposited on Aug. 19, 2015. *Bacillus thuringiensis* BT013A is also known as *Bacillus thuringiensis* 4Q7.

The isolation and characterization of these strains is described hereinbelow in the Examples. Partial 16S ribosomal RNA sequences for each of these strains are provided in the sequence listing and summarized below in Table 17, together with their SEQ ID NOs.

TABLE 17

Partial 16S ribosomal RNA sequences

| Strain | SEQ ID NO. for partial 16S ribosomal RNA sequence |
|---|---|
| *Bacillus mycoides* EE118 | 75 |
| *Bacillus mycoides* EE141 | 76 |
| *Bacillus mycoides* BT46-3 | 77 |
| *Bacillus cereus* family member EE128 | 78 |
| *Bacillus cereus* family member EE349 | 79 |
| *Bacillus mycoides* BT155 | 80 |
| *Bacillus cereus* family member EE439 | 81 |
| *Bacillus thuringiensis* EE417 | 82 |
| *Bacillus cereus* EE444 | 83 |
| *Bacillus thuringiensis* EE319 | 84 |

TABLE 17-continued

| Partial 16S ribosomal RNA sequences | |
|---|---|
| Strain | SEQ ID NO. for partial 16S ribosomal RNA sequence |
| *Bacillus megaterium* EE385 | 85 |
| *Bacillus* sp. EE387 | 86 |
| *Bacillus circulans* EE388 | 87 |
| *Bacillus subtilis* EE405 | 88 |
| *Lysinibacillus fusiformis* EE442 | 89 |
| *Lysinibacillus sphaericus* EE443 | 90 |
| *Bacillus aryabhattai* CAP53 | 91 |
| *Bacillus aryabhattai* CAP56 | 92 |
| *Bacillus flexus* BT054 | 93 |
| *Paracoccus kondratievae* NC35 | 94 |
| *Enterobacter cloacae* CAP12 | 95 |
| *Bacillus nealsonii* BOBA57 | 96 |
| *Bacillus subtilis* EE148 | 97 |
| *Alcaligenes faecalis* EE107 | 98 |
| *Paenibacillus massiliensis* | 99 |
| *Bacillus subtilis* EE218 | 100 |
| *Bacillus megaterium* EE281 | 101 |
| *Bacillus thuringiensis* EE184 | 102 |
| *Bacillus mycoides* EE363 | 103 |
| *Bacillus pseudomycoides* EE366 | 104 |
| *Bacillus cereus* family member EE377 | 105 |
| *Bacillus pumulis* EE143 | 106 |
| *Bacillus mycoides* EE116 | 107 |
| *Bacillus thuringiensis* BT013A | 136 |

An endophytic microorganism can be used for expression of the enzymes. While many microorganism of the rhizosphere have a symbiotic relationship with the plant, only a small subset of these microorganisms are capable of being internalized into the plant and growing endophytically. Several *Bacillus cereus* family member strains and several non-*Bacillus cereus* family member bacterial strains have been isolated from corn seedlings and found to have the ability to grow endophytically in plants. Other endophytic microorganisms would also be useful including, but not limited to, bacterial endophytes from genera: *Cellulomonas, Clavibacter, Curtobacterium, Pseudomonas, Paenibacilllus, Enterobacter, Bacillus, Klebsiella, Arthrobacter, Lysinibacillus, Pantoea, Actinomyces, Streptomyces, Alcaligenes*, and *Microbacterium*. Fungal endophytes can also be used, including fungal endophytes from the genera: *Neotyphodium, Gliocadium, Acremonium lolii, Clavicipitaceae, Ascomycetes, Idriella, Xylariaceous, Ascomycotina, Deuteromycotina, Aspergillus, Phomopsis, Wardomyces, Fusarium, Dreschrella, Pestalotia, Curvularia, Humicola, Nodulisporium*, and *Penicillium*.

Many microorganisms can colonize, live next to, live on, or become endophytic to a plant. These microorganisms would provide a useful delivery mechanism of target enzymes to the plant, the seed, the vicinity of the plant, or the plant growth medium. Microorganisms selected that can colonize the roots or become endophytic can be screened, recombinantly modified to express or overexpress an enzyme, and produced commercially and applied on the seed, to the plant, or the vicinity around the plant in order to have the strain produce the target enzymes in situ (at or near the plant). These microorganisms can also be enhanced through point mutations or through genetic engineering to express higher or novel target enzymes to benefit the plants. Point mutations can be screened by mutating the host microorganism, and selecting for mutants with higher enzyme expression levels through enzyme assays, or using selective media that identifies high enzyme expressing strains. Common strains that are beneficial producers of enzymes as well as colonizers/endophytic species include: *Bacillus argri, Bacillus aizawai, Bacillus albolactis, Bacillus amyloliquefaciens, Bacillus cereus, Bacillus coagulans, Bacillus endoparasiticus, Bacillus endorhythmos, Bacillus kurstaki, Bacillus lacticola, Bacillus lactimorbus, Bacillus firmus, Bacillus lactis, Bacillus laterosporus, Bacillus lentimorbus, Bacillus licheniformis, Bacillus megaterium, Bacillus medusa, Bacillus metiens, Bacillus natto, Bacillus nigrificans, Bacillus popillae, Bacillus pumilus, Bacillus siamensis, Bacillus sphearicus, Bacillus subtilis, Bacillus thuringiensis, Bacillus unifagellatu*, other *Bacillus* species or a combination thereof plus those listed in the category of *Bacillus* Genus in Bergey's Manual of Systematic Bacteriology, First Ed. (1986), hereby incorporated in full by reference. Other potential strains could include, but are not limited to: *Cellulomonas, Clavibacter, Curtobacterium, Pseudomonas, Paenibacilllus, Enterobacter, Bacillus, Klebsiella, Arthrobacter, Lysinibacillus, Pantoea, Actinomyces, Saccharomyces, Rhizobium, Bradyrhizobium, Candida, Streptomyces, Alcaligenes, Chromatiales, Rhizobium, Bradyrhizobium, Rhodospiralles, Rhizobiales, Rhizobacteracae*, and *Microbacterium*.

For any of the methods or seeds described herein, the recombinant microorganism can comprise a mixture of two or more of any of the recombinant microorganisms described herein.

For any of the recombinant microorganisms, formulations, methods, or seeds described herein, the recombinant microorganism can be inactivated. Inactivation results in microorganisms that are unable to reproduce. Inactivation of microorganisms can be advantageous, for example because it allows for delivery of the microorganism to a plant or a plant growth medium while reducing or eliminating any detrimental effects that the live microorganism may have on a plant or on the environment. The recombinant microorganism can be inactivated by any physical or chemical means, e.g., by heat treatment, gamma irradiation, x-ray irradiation, UV-A irradiation, UV-B irradiation, or treatment with a solvent such as gluteraldehyde, formaldehyde, hydrogen peroxide, acetic acid, bleach, chloroform, or phenol, or combination of any thereof.

XIV. Methods for Making Recombinant Microorganisms

The recombinant microorganisms can be made using standard molecular biology methods known in the art. For example, a gene encoding an enzyme can be amplified by polymerase chain reaction (PCR). Where a signal sequence is used, the gene coding for the enzyme can be ligated to DNA coding for the signal sequence. The gene can then be cloned into any suitable vector, for example a plasmid vector. The vector suitably comprises a multiple cloning site into which the DNA molecule encoding the fusion protein can be easily inserted. The vector also suitably contains a selectable marker, such as an antibiotic resistance gene, such that bacteria transformed, transfected, or mated with the vector can be readily identified and isolated. Where the vector is a plasmid, the plasmid suitably also comprises an origin of replication. Alternatively, DNA coding for the enzyme or expansin protein can be integrated into the chromosomal DNA of the microorganism host.

XV. Effects on Plants

In any of the methods described herein, plants grown in the presence of the enzyme, the expansin protein, or the microorganism can exhibit increased growth as compared to plants grown in the absence of the enzyme, the expansin protein, or the microorganism, under the same conditions.

For any of the seeds described herein, plants grown from seeds treated with the free enzyme, the expansin protein, or the microorganism can exhibit increased growth as compared to plants grown from seeds not treated with the free enzyme, the expansin protein, or the microorganism, under the same conditions.

For any of the methods or seeds described herein, seeds to which the enzyme or the microorganism has been applied can exhibit increased germination rates as compared to seeds to which the enzyme or microorganism has not been applied, under the same conditions.

In any of the methods described herein, plants grown in the presence of the enzyme, the expansin protein, or the microorganism can exhibit increased nutrient uptake as compared to plants grown in the absence of the enzyme, the expansin protein, or the microorganism, under the same conditions.

For any of the seeds described herein, plants grown from seeds treated with the free enzyme, the expansin protein, or the microorganism can exhibit increased nutrient uptake as compared to plants grown from seeds not treated with the free enzyme, the expansin protein, or the microorganism, under the same conditions.

In any of the methods described herein, plants grown in the presence of the enzyme or the microorganism can exhibit decreased susceptibility to a pathogen as compared to plants grown in the absence of the enzyme or the microorganism, under the same conditions.

For any of the seeds described herein, plants grown from seeds treated with the free enzyme or the microorganism can exhibit decreased susceptibility to a pathogen as compared to plants grown from seeds not treated with the free enzyme or the microorganism, under the same conditions.

In any of the methods described herein, plants grown in the presence of the enzyme or the microorganism can exhibit decreased susceptibility to an environmental stress as compared to plants grown in the absence of the enzyme or the microorganism, under the same conditions.

For any of the seeds described herein, plants grown from seeds treated with the free enzyme or the microorganism can exhibit decreased susceptibility to an environmental stress as compared to plants grown from seeds not treated with the free enzyme or the microorganism, under the same conditions.

For example, the plants can exhibit decreased susceptibility to drought, flood, heat, freezing, salt, heavy metals, low pH, high pH, or a combination of any thereof.

In any of the methods described herein, plants grown in the presence of the enzyme, the expansin protein, or the microorganism can exhibit increased nutrient content as compared to plants grown in the absence of the enzyme, the expansin protein, or the microorganism, under the same conditions.

For any of the seeds described herein, seeds treated with the free enzyme, the expansin protein, or the microorganism or plants grown from seeds treated with the free enzyme, the expansin protein, or the microorganism can exhibit increased nutrient content as compared to seeds not treated with the free enzyme, the expansin protein, or the microorganism or plants grown from seeds not treated with the free enzyme, the expansin protein, or the microorganism, under the same conditions.

For example, the nutrient can comprise a polysaccharide, a protein, phytic acid, a phosphatate, a phospholipid, or a combination of any thereof.

In any of the methods described herein, plants grown in the presence of the enzyme or the microorganism can exhibit increased root nodulation as compared to plants grown in the absence of the enzyme or the microorganism, under the same conditions.

For any of the seeds described herein, plants grown from seeds treated with the free enzyme or the microorganism can exhibit increased root nodulation as compared to plants grown from seeds not treated with the free enzyme or the microorganism, under the same conditions.

In any of the methods described herein, plants grown in the presence of the enzyme or the microorganism can exhibit slower fruit ripening as compared to plants grown in the absence of the enzyme or the microorganism, under the same conditions.

For any of the seeds described herein, plants grown from seeds treated with the free enzyme or the microorganism can exhibit slower fruit ripening as compared to plants grown from seeds not treated with the free enzyme or the microorganism, under the same conditions.

In any of the methods described herein, plants grown in the presence of the enzyme, the expansin protein, or the microorganism can exhibit greater crop yield as compared to plants grown in the absence of the enzyme, the expansin protein, or the microorganism, under the same conditions.

For any of the seeds described herein, plants grown from seeds treated with the free enzyme, the expansin protein, or the microorganism can exhibit greater crop yield as compared to plants grown from seeds not treated with the free enzyme, the expansin protein, or the microorganism, under the same conditions.

In any of the methods described herein, plants grown in the presence of the enzyme or the microorganism can exhibit altered leaf senescence as compared to plants grown in the absence of the enzyme or the microorganism, under the same conditions.

For any of the seeds described herein, plants grown from seeds treated with the free enzyme or the microorganism can exhibit altered leaf senescence as compared to plants grown from seeds not treated with the enzyme or the microorganism, under the same conditions.

Slower leaf senescence can lead to a greater level of photosynthesis late in the season, which in turn leads to more photosynthates, more grain fill, and a larger grain and/or increased yield.

XVI. Formulations, Compositions, and Co-Application of Agrochemicals

In any of the methods described herein, the method can comprise applying the enzyme, the expansin protein, or the microorganism in a formulation comprising an agriculturally acceptable carrier.

For any of the seeds described herein, the seed can be coated with a formulation comprising the free enzyme, the expansin protein, or the recombinant microorganism and an agriculturally acceptable carrier.

Any of the compositions described herein can comprise an agriculturally acceptable carrier.

The agriculturally acceptable carrier can comprise a dispersant, a surfactant, an additive, water, a thickener, an anti-caking agent, residue breakdown product, a composting formulation, a granular application, diatomaceous earth, an oil, a coloring agent, a stabilizer, a preservative, a polymer, a coating, or a combination thereof.

The additive can comprises an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutane dioate, a benzene acetonitrile derivative, a proteinaceous material (e.g., a milk product, wheat flour, soybean meal, blood, albumin, gelatin, alfalfa meal, yeast extract, or a combination of any thereof), or a combination of any thereof.

The thickener can comprise a long chain alkylsulfonate of polyethylene glycol, a polyoxyethylene oleate, or a combination of any thereof.

The surfactant can comprise a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination of any thereof.

The surfactant can comprise a non-ionic surfactant.

The anti-caking agent can comprise a sodium salt (e.g., a sodium salt of monomethyl naphthalene sulfonate, a sodium salt of dimethyl naphthalene sulfonate, a sodium sulfite, a sodium sulfate, or a combination of any thereof), a calcium carbonate, diatomaceous earth, or a combination of any thereof.

The agriculturally acceptable carrier can comprise vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination of any thereof.

The formulation or composition can comprise a seed coating formulation or composition, a liquid formulation or composition for application to plants or to a plant growth medium, or a solid formulation or composition for application to plants or to a plant growth medium.

The seed coating formulation or composition can comprise an aqueous or oil-based solution for application to seeds or a powder or granular formulation for application to seeds.

The liquid formulation or composition for application to plants or to a plant growth medium can comprise a concentrated formulation or composition or a ready-to-use formulation or composition.

The solid formulation or composition for application to plants or to a plant growth medium can comprise a granular formulation or composition or a powder agent.

The formulation or composition can further comprise an agrochemical.

Alternatively or in addition, any of the methods described herein can further comprise applying an agrochemical to the plant growth medium, the plant, the plant seed, or the area surrounding the plant or the plant seed.

Any of the plant seeds described herein can be further treated or coated with an agrochemical.

The agrochemical can comprise a fertilizer, a micronutrient fertilizer material, an insecticide, a nematicide, an herbicide, a plant growth amendment, a fungicide, an insecticide, a molluscicide, an algicide, a bacterial inoculant, a fungal inoculant, a plant hormone, or a combination of any thereof.

The bacterial inoculant can comprise a plant-growth promoting strain of bacteria, an endophytic strain of bacteria, or a strain of bacteria that is both plant-growth promoting and endophytic.

The plant-growth promoting strain of bacteria can produce an insecticidal toxin (e.g., a Cry toxin), produce a fungicidal compound (e.g., a β-1,3-glucanase, a chitosanase, a lyticase, or a combination thereof), produce a nematicidal compound (e.g., a Cry toxin), produce a bacteriocidal compound, be resistant to one or more antibiotics, comprise one or more freely replicating plasmids, bind to plant roots, colonize plant roots, form biofilms, solubilize nutrients, secrete organic acids, or combinations thereof.

The plant-growth promoting strain of bacteria can comprise *Bacillus aryabhattai* CAP53 (NRRL No. B-50819), *Bacillus aryabhattai* CAP56 (NRRL No. B-50817), *Bacillus flexus* BT054 (NRRL No. B-50816), *Paracoccus kondratievae* NC35 (NRRL No. B-50820), *Bacillus mycoides* BT155 (NRRL No. B-50921), *Enterobacter cloacae* CAP12 (NRRL No. B-50822), *Bacillus nealsonii* BOBA57 (NRRL No. NRRL B-50821), *Bacillus mycoides* EE118 (NRRL No. B-50918), *Bacillus subtilis* EE148 (NRRL No. B-50927), *Alcaligenes faecalis* EE107 (NRRL No. B-50920), *Bacillus mycoides* EE141 (NRRL NO. B-50916), *Bacillus mycoides* BT46-3 (NRRL No. B-50922), *Bacillus cereus* family member EE128 (NRRL No. B-50917), *Paenibacillus massiliensis* BT23 (NRRL No. B-50923), *Bacillus cereus* family member EE349 (NRRL No. B-50928), *Bacillus subtilis* EE218 (NRRL No. B-50926), *Bacillus megaterium* EE281 (NRRL No. B-50925), *Bacillus cereus* family member EE-B00377 (NRRL B-67119); *Bacillus pseudomycoides* EE-B00366 (NRRL B-67120), *Bacillus mycoides* EE-B00363 (NRRL B-67121), *Bacillus pumilus* EE-B00143 (NRRL B-67123), or *Bacillus thuringiensis* EE-B00184 (NRRL B-67122), *Bacillus mycoides* EE116 (NRRL No. B-50919), *Bacillus cereus* family member EE417 (NRRL No. B-50974), *Bacillus subtilis* EE442 (NRRL No. B-50975), *Bacillus subtilis* EE443 (NRRL No. B-50976), *Bacillus cereus* family member EE444 (NRRL No. B-50977), *Bacillus subtilis* EE405 (NRRL No. B-50978), *Bacillus cereus* family member EE439 (NRRL No. B-50979), *Bacillus megaterium* EE385 (NRRL No. B-50980), *Bacillus cereus* family member EE387 (NRRL No. B-50981), *Bacillus circulans* EE388 (NRRL No. B-50982), *Bacillus thuringiensis* EE319 (NRRL No. B-50983), *Bacillus cereus* family member EE377 (NRRL No. B-67119), *Bacillus mycoides* EE363 (NRRL No. B-67121), *Bacillus pseudomycoides* EE366 (NRRL No. B-67120), *Bacillus thuringiensis* BT013A (NRRL No. B-50924), or a combination of any thereof.

The agrochemical can comprise a fertilizer.

The fertilizer can comprise a liquid fertilizer or a dry fertilizer.

The agrochemical can comprise a micronutrient fertilizer material, the micronutrient fertilizer material comprising boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination of any thereof.

The agrochemical can comprise an insecticide, the insecticide comprising an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination of any thereof.

The agrochemical can comprise an herbicide, the herbicide comprising a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carbamate, a carbanilate, chloropyridinyl, a cyclohexenone derivative, a dinitroaminobenzene derivative, a fluorodinitrotoluidine compound, isoxazolidinone, nicotinic acid, isopropylamine, an isopropylamine derivative, oxadiazolinone, a phosphate, a phthalate, a picolinic acid compound, a triazine, a triazole, a uracil, a urea derivative, endothall, sodium chlorate, or a combination of any thereof.

The agrochemical can comprise a fungicide, the fungicide comprising a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metalaxyl, thiamimefon, triforine, or a combination of any thereof.

The agrochemical can comprise a fungal inoculant, the fungal inoculant comprising a fungal inoculant of the family Glomeraceae, a fungal inoculant of the family Claroidoglomeraceae, a fungal inoculant of the family Gigasporaceae, a fungal inoculant of the family Acaulosporaceae, a fungal inoculant of the family Sacculosporaceae, a fungal inoculant of the family Entrophosporaceae, a fungal inoculant of the family Pacidsporaceae, a fungal inoculant of the family Diversisporaceae, a fungal inoculant of the family Paraglomeraceae, a fungal inoculant of the family Archaeosporaceae, a fungal inoculant of the family Geosiphonaceae, a fungal inoculant of the family Ambisporaceae, a fungal inoculant of the family Scutellosporaceae, a fungal inoculant of the family Dentiscultataceae, a fungal inoculant of the family Racocetraceae, a fungal inoculant of the phylum Basidiomycota, a fungal inoculant of the phylum Ascomycota, a fungal inoculant of the phylum Zygomycota, or a combination of any thereof.

The agrochemical can comprise a bacterial inoculant, the bacterial inoculant comprising a bacterial inoculant of the genus *Rhizobium*, a bacterial inoculant of the genus *Bradyrhizobium*, a bacterial inoculant of the genus *Mesorhizobium*, a bacterial inoculant of the genus *Azorhizobium*, a bacterial inoculant of the genus *Allorhizobium*, a bacterial inoculant of the genus *Sinorhizobium*, a bacterial inoculant of the genus *Kluyvera*, a bacterial inoculant of the genus *Azotobacter*, a bacterial inoculant of the genus *Pseudomonas*, a bacterial inoculant of the genus *Azospirillium*, a bacterial inoculant of the genus *Bacillus*, a bacterial inoculant of the genus *Streptomyces*, a bacterial inoculant of the genus *Paenibacillus*, a bacterial inoculant of the genus *Paracoccus*, a bacterial inoculant of the genus *Enterobacter*, a bacterial inoculant of the genus *Alcaligenes*, a bacterial inoculant of the genus *Mycobacterium*, a bacterial inoculant of the genus *Trichoderma*, a bacterial inoculant of the genus *Gliocladium*, a bacterial inoculant of the genus *Glomus*, a bacterial inoculant of the genus *Klebsiella*, or a combination of any thereof.

The agrochemical can comprise an effective amount of a rhizobacteria. The rhizobacteria can comprise *Bradyrhizobium* genus bacteria (e.g., *Bradyrhizobium japonicum*), *Rhizobium* genus bacteria (e.g., *Rhizobium phaseoli, Rhizobium leguminosarum*, or a combination thereof), or a combination thereof.

The agrochemical can comprise a fungicide, the fungicide comprises aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, boscalid, bromuconazole, bupirimate, buthiobate, calcium polysulphide, capsimycin, captafol, captan, carbendazim, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, dimethirimol, dimethomorph, dimoxystrobin, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, prothiocinazole, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, tioxymid, tolclofos-methyl, tolylfluanid, triadimefon, triadimenol, triazbutil, triazoxide, trichlamide, tricyclazole, tridemorph, trifloxystrobin, triflumizole, triforine, uniconazole, validamycin A, vinclozolin, viniconazole, zarilamide, zineb, ziram and also Dagger G, OK-8705, OK-8801, a-(1,1-dimethylethyl)-(3-(2-phenoxyethyl)-1H-1,2,4-triazole-1-ethanol, a-(2,4-dichlorophenyl)-[3-fluoro-3-propyl-1H-1,2,4-triazole-1-ethanol, a-(2,4-dichlorophenyl)-[3-methoxy-a-methyl-1H-1,2,4-triazole-1-ethanol, a-(5-methyl-1,3-dioxan-5-yl)-[3-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, 1-isopropyl{2-methyl-1-[[[1-(4-methylphenyl)-ethyl]-amino]-carbonyl]-propyl}carbamate, 1-(2,4-dichlorophenyl)-2-(1H-1,2,4-triazol-1-yl)-ethanone-O-(phenyl methyl)-oxime, 1-(2-methyl-1-naphthalenyl)-1H-pyrrole-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-(3-D-glycopyranosyl)-a-D-glucopyranos yl]-amino]-4-methoxy-1H-pyrrolo[2,3-d] pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4,5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium bicarbonate, methanetetrathiol-sodium salt, methyl 1-(2,3-dihydro-2,2-dimethyl-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethyl phenyl)-2-methoxy-N-(tetra hydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine-sodium salt, 0,0-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, and spiro [2H]-1-benzopyrane-2,1'(3'H)-isobenzofuran]-3'-one, N-trichloromethyl)thio-4-cyclohexane-1,2-dicarboximide, tetramethylthioperoxydicarbonic diamide, methyl N-(2,6-dimethylphenyl)-N-(methoxyacetyl)-DL-alaninate, 4-(2,2-difluoro-1,3-benzodioxol-4-yl)-1-H-pyrrol-3-carbonitril, or a combination of any thereof.

The agrochemical can comprise a bacterial inoculant of the genus *Bacillus*, the bacterial inoculant of the genus *Bacillus* comprising *Bacillus* argri, *Bacillus aizawai, Bacillus* albolactis, *Bacillus amyloliquefaciens, Bacillus cereus, Bacillus coagulans, Bacillus endoparasiticus, Bacillus endorhythmos, Bacillus kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus natto, Bacillus nigrificans, Bacillus popillae, Bacillus pumilus, Bacillus siamensis, Bacillus sphearicus, Bacillus* spp., *Bacillus subtilis, Bacillus thuringiensis, Bacillus unifagellatu*, or a combination of any thereof.

The agrochemical can comprise an herbicide, the herbicide comprising 2,4-D, 2,4-DB, acetochlor, acifluorfen, alachlor, ametryn, atrazine, aminopyralid, benefin, bensulfuron, bensulide, bentazon, bromacil, bromoxynil, butylate, carfentrazone, chlorimuron, chlorsulfuron, clethodim, clomazone, clopyralid, cloransulam, cycloate, DCPA, desmedipham, dicamba, dichlobenil, diclofop, diclosulam, diflufenzopyr, dimethenamid, diquat, diuron, DSMA, endothall, EPTC, ethalfluralin, ethofumesate, fenoxaprop, fluazifop-P, flucarbazone, flufenacet, flumetsulam, flumiclorac, flumioxazin, fluometuron, fluroxypyr, fomesafen, foramsulfuron, glufosinate, glyphosate, halosulfuron, hexazinone, imazamethabenz, imazamox, imazapic, imazaquin, imazethapyr, isoxaben, isoxaflutole, lactofen, linuron, MCPA, MCPB, mesotrione, metolachlor-s, metribuzin, metsulfuron, molinate, MSMA, napropamide, naptalam, nicosulfuron, norflurazon, oryzalin, oxadiazon, oxyfluorfen, paraquat, pelargonic acid, pendimethalin, phenmedipham, picloram, primisulfuron, prodiamine, prometryn, pronamide, propanil, prosulfuron, pyrazon, pyrithiobac, quinclorac, quizalofop, rimsulfuron, sethoxydim, siduron, simazine, sulfentrazone, sulfometuron, sulfosulfuron, tebuthiuron, terbacil, thiazopyr, thifensulfuron, thiobencarb, tralkoxydim, triallate, triasulfuron, tribenuron, triclopyr, trifluralin, triflusulfuron, or a combination of any thereof.

The agrochemical can comprise a fertilizer, the fertilizer comprising ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, sulfur-coated urea, polymer-coated urea, isobutylidene diurea, $K_2SO_4$-$2MgSO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, humic acid, or a combination of any thereof.

The agrochemical can comprise a plant hormone, the plant hormone comprising a gibberellin, an auxin, a kinetin, or a combination of any thereof.

Enzymes can be formulated in many ways. Common goals for formulation enzyme products include enhancing shelf life, preserving the product from microorganisms, and enhancing enzyme activity. Enzyme products can be lyophilized to extend the shelf life of most enzymes by freeze drying, spray drying, or otherwise removing the liquid aspect of the enzyme product. Liquid and lyophilized products are often bulked out with additives, such as buffers, stabilizers, antimicrobial agents, and volume additives. Enzymes can often be encapsulated or granulated to make the final product safer and easier to use. Granulated products can have enhanced shelf life and have little enzyme activity exposed to the outside surface of the granules. Enzymes may also be attached to organic or inorganic platforms, such as plastic beads, dolomite, clays, charcoals, biochar, nanoparticles, alginates, silica beads help bind them and keep them in an easy to use form. Often, enzymes are immobilized on matrices to allow for longer activity and shelf life of the enzyme products. Common matrices include carbon, nanocarbons, agarose, alginates, cellulose and cellulosic material, silica, plastic, stainless steel, glass, polystyrene, and ceramics.

Many formulations of the enzymes can be used to prolong enzymatic activity or shelf life of the products. These include but are not limited to preservatives, biocides, stabilizers, color enhancers, odor reduction, surfactants, detergents, buffers, cofactors, ions, and other modification to the formulation to enhance the performance of the enzymes.

XVII. Plant Growth Media

In any of the methods described herein involving the use of a plant growth medium, the plant growth medium can comprise soil, water, an aqueous solution, sand, gravel, a polysaccharide, mulch, compost, peat moss, straw, logs, clay, soybean meal, yeast extract, or a combination thereof.

The plant growth medium can comprise or consist essentially of a fertilizer.

Furthermore, the plant growth medium can be supplemented with a substrate for an enzyme.

The substrate can comprise tryptophan, an adenosine monophosphate, an adenosine diphosphate, an adenosine triphosphate (e.g., adenosine-3-triphosphate), a polyphosphate, a protein meal, a trimetaphosphate, a cellulose, a methylcellulose, a chitin, a chitosan, a cellulose derivative, a phosphate, a fat, a wax, a phospholipid, a phytic acid, or a combination of any thereof.

XVIII. Plants

In any of the above methods relating to plants, the plant can be a dicotyledon, a monocotyledon, or a gymnosperm.

Likewise, for any of the seeds described herein the seed can be a seed of a dicotyledon, a monocotyledon, or a gymnosperm.

For example, where the plant is a dicotyledon or the seed is a seed of a dicotyledon, the dicotyledon can be selected from the group consisting of bean, pea, tomato, pepper, squash, alfalfa, almond, aniseseed, apple, apricot, arracha, artichoke, avocado, bambara groundnut, beet, bergamot, black pepper, black wattle, blackberry, blueberry, bitter orange, bok-choi, Brazil nut, breadfruit, broccoli, broad bean, Brussels sprouts, buckwheat, cabbage, camelina, Chinese cabbage, cacao, cantaloupe, caraway seeds, cardoon, carob, carrot, cashew nuts, cassava, castor bean, cauliflower, celeriac, celery, cherry, chestnut, chickpea, chicory, chili pepper, *chrysanthemum*, cinnamon, citron, clementine, clove, clover, coffee, cola nut, colza, corn, cotton, cottonseed, cowpea, *crambe*, cranberry, cress, cucumber, currant, custard apple, drumstick tree, earth pea, eggplant, endive, fennel, fenugreek, fig, filbert, flax, geranium, gooseberry, gourd, grape, grapefruit, guava, hemp, hempseed, henna, hop, horse bean, horseradish, indigo, jasmine, Jerusalem artichoke, jute, kale, kapok, kenaf, kohlrabi, kumquat, lavender, lemon, lentil, *lespedeza*, lettuce, lime, liquorice, litchi, loquat, lupine, macadamia nut, mace, mandarin, mangel, mango, medlar, melon, mint, mulberry, mustard, nectarine, *niger* seed, nutmeg, okra, olive, opium, orange, *papaya*, parsnip, pea, peach, peanut, pear, pecan nut, persimmon, pigeon pea, pistachio nut, plantain, plum, pomegranate, pomelo, poppy seed, potato, sweet potato, prune, pumpkin, quebracho, quince, trees of the genus Cinchona, *quinoa*, radish, ramie, rapeseed, raspberry, rhea, rhubarb, rose, rubber, rutabaga, safflower, sainfoin, salsify, sapodilla, Satsuma, scorzonera, sesame, shea tree, soybean, spinach, squash, strawberry, sugar beet, sugarcane, sunflower, swede, sweet pepper, tangerine, tea, teff, tobacco, tomato, trefoil, tung tree, turnip, urena, vetch, walnut, watermelon, yerba mate, wintercress, shepherd's purse, garden cress, peppercress, watercress, pennycress, star anise, laurel, bay laurel, *cassia*, jamun, dill, tamarind, peppermint, oregano, rosemary, sage, soursop, pennywort, calophyllum, balsam pear, kukui nut, Tahitian chestnut, basil, huckleberry, hibiscus, passionfruit, star apple, *sassafras*, cactus, St. John's wort, loosestrife, hawthorn, cilantro, curry plant, kiwi, thyme, zucchini, ulluco, jicama, waterleaf, spiny monkey orange, yellow mombin, starfruit, amaranth, wasabi, Japanese pepper, yellow plum, mashua, Chinese toon, New Zealand spinach, bower spinach, ugu, tansy, chickweed, jocote, Malay apple, paracress, sowthistle, Chinese potato, horse parsley, hedge mustard, campion, agate, cassod tree, thistle, burnet, star gooseberry, saltwort, glasswort, sorrel, silver lace fern, collard greens, primrose, cowslip, purslane, knotgrass, terebinth, tree lettuce, wild *betel*, West African pepper, yerba santa, tarragon, parsley, chervil, land cress, burnet saxifrage, honeyherb, butterbur, shiso, water pepper, *perilla*, bitter bean, oca, kampong, Chinese celery, lemon basil, Thai basil, water *mimosa*, cicely, cabbage-tree, moringa, mauka, ostrich fern, rice paddy herb, yellow sawah lettuce, lovage, pepper grass, maca, bottle gourd, hyacinth bean, water spinach, catsear, fishwort, Okinawan spinach, lotus sweetjuice, gallant soldier, culantro, arugula, cardoon, caigua, mitsuba, chipilin, samphire, mampat, ebolo, ivy gourd, cabbage thistle, sea kale, chaya, huauzontle, Ethiopian mustard, magenta spreen, good king henry, epazole, lamb's quarters, centella plumed cockscomb, caper, rapini, napa cabbage, mizuna, Chinese savoy, kai-lan, mustard greens, Malabar spinach, chard, marshmallow, climbing wattle, China jute, paprika, annatto seed, spearmint, savory, marjoram, cumin, chamomile, lemon balm, allspice, bilberry, cherimoya, cloudberry, damson, pitaya, durian, elderberry, feijoa, jackfruit, jambul, jujube, physalis, purple mangosteen, rambutan, redcurrant, blackcurrant, salal berry, satsuma, ugli fruit, azuki bean, black bean, black-eyed pea, borlotti bean, common bean, green bean, kidney bean, lima bean, mung bean, navy bean, pinto bean, runner bean, mangetout, snap pea, broccoflower, calabrese, nettle, bell pepper, raddichio, daikon, white radish, skirret, tat soi, broccolini, black radish, burdock root, fava bean, broccoli raab, lablab, lupin, sterculia, velvet beans, winged beans, yam beans, mulga, ironweed, umbrella bush, tjuntjula, wakalpulka, witchetty bush, wiry wattle, chia, beech nut, candlenut, colocynth, mamoncillo, Maya nut, mongongo, ogbono nut, paradise nut, and cempedak.

Where the plant is a monocotyledon or the seed is a seed of a monocotyledon, the monocotyledon can be selected from the group consisting of corn, wheat, oat, rice, barley, millet, banana, onion, garlic, asparagus, ryegrass, millet, fonio, raishan, nipa grass, turmeric, saffron, galangal, chive, cardamom, date palm, pineapple, shallot, leek, scallion, water chestnut, ramp, Job's tears, bamboo, ragi, spotless watermeal, arrowleaf elephant ear, Tahitian spinach, abaca, *areca*, bajra, *betel* nut, broom millet, broom sorghum, citronella, coconut, cocoyam, maize, dasheen, durra, durum wheat, edo, Pique, formio, ginger, orchard grass, esparto grass, Sudan grass, guinea corn, Manila hemp, henequen, hybrid maize, jowar, lemon grass, maguey, bulrush millet, finger millet, foxtail millet, Japanese millet, proso millet, New Zealand flax, oats, oil palm, palm palmyra, sago palm, redtop, sisal, sorghum, spelt wheat, sweet corn, sweet sorghum, taro, teff, timothy grass, triticale, vanilla, wheat, and yam.

Where the plant is a gymnosperm or the seed is a seed of a gymnosperm, the gymnosperm can be from a family selected from the group consisting of Araucariaceae, Boweniaceae, Cephalotaxaceae, Cupressaceae, Cycadaceae, Ephedraceae, Ginkgoaceae, Gnetaceae, Pinaceae, Podocarpaceae, Taxaceae, Taxodiaceae, Welwitschiaceae, and Zamiaceae.

The plants and plant seeds described herein may include transgenic plants or plant seeds, such as transgenic cereals (wheat, rice), maize, soybean, potato, cotton, tobacco, oilseed rape and fruit plants (fruit of apples, pears, citrus fruits and grapes. Preferred transgenic plants include corn, soybeans, potatoes, cotton, tobacco and oilseed rape.

Suitable transgenic plants and seeds can be characterized by the plant's formation of toxins, especially from the *Bacillus thuringiensis* genetic material (e.g., by gene CryIA (a), CryIA (b), CryIA (c), CryIIA, CryIIIA, CryIIIB2 Cry9c, Ciy2Ab, Cry3Bb, CryIF or a combination thereof). The formation of toxins in plants increases the plant's resistance to insects, arachnids, nematodes and slugs and snails (hereinafter referred to as "Bt plants"). Bt plants, for example, are commercially available under the tradename YIELD GARB® (for example maize, cotton, soybeans), KnockOut® (for example maize), StarLink® (for example maize), Bollgard® (cotton), Nucotn® (cotton) and NewLeaf® (potato) maize varieties, cotton varieties, soybean varieties and potato varieties. Herbicide tolerance plants include plants under the trade names Roundup Ready® (a glyphosate tolerance, such as corn, cotton, soybeans), Clearfield® (for example maize), Liberty Link® (tolerance with glufosinate, for example oilseed rape), IMI® (with imidazolinone tolerance) and STS® (tolerance to a sulfonylurea, such as maize).

Plant seeds as described herein can be genetically modified (e.g., any seed that results in a genetically modified plant or plant part that expresses herbicide tolerance, tolerance to environmental factors such as water stress, drought; viruses, and nitrogen production; or resistance to bacterial, fungi or insect toxins). Suitable genetically modified seeds include those of cole crops, vegetables, fruits, trees, fiber crops, oil crops, tuber crops, coffee, flowers, legume, cereals, as well as other plants of the monocotyledonous and dicotyledonous species. Preferably, the genetically modified seeds include peanut, tobacco, grasses, wheat, barley, rye, sorghum, rice, rapeseed, sugarbeet, sunflower, tomato, pepper, bean, lettuce, potato, and carrot. Most preferably, the genetically modified seeds include cotton, soybean, and corn (sweet, field, seed, or popcorn).

Particularly useful transgenic plants which may be treated according to the invention are plants containing transformation events, or a combination of transformation events, that are listed for example in the databases from various national or regional regulatory agencies (see for example http://gmoinfo.jrc.it/gmp_browse.aspx and http://www.agbios.com/dbase.php). Having described the invention in detail, it will be apparent that modifications and variations are possible without departing from the scope of the invention defined in the appended claims.

EXAMPLES

The following non-limiting examples are provided to further illustrate the present invention.

Example 1: Free Endoglucanase on Corn, Greenhouse

*Acidothermus cellulolyticus* β-1,4 endoglucanase (SEQ ID NO: 30; commercially available from Sigma-Aldrich, St. Louis Mo., as product E2164) was diluted in citrate enzyme dilution buffer to concentrations of 12.5 through 1600 mU/mL. The U (units or international units) of endoglucanase activity was determined by the amount of enzyme that is required to breakdown 1 μMol/min/mL of substrate at ideal temperature and conditions. For each treatment group, 18 seeds of commercial hybrid BECK'S 6626RR corn, which contains a glyphosate tolerance trait, without seed treatment, were placed in 50 mL conical tubes. Each conical tube was vortexed, and 18 μL of enzyme solution was added to each tube for a final enzyme concentration of 0, 12.5 μU, 25 μU, 50 μU, 100 μU, 200 μU, 400 μU, 800 μU, or 1600 μU per seed of endoglucanase. The conical tubes were vortexed again for 20 seconds to gain an even coating on each seed. Seeds were allowed to dry for 5 minutes and then planted into 39.7 $cm^3$ pots containing commercial top soil at a depth of 2.54 cm, with 2 seeds per pot. After planting, 50 mL of room temperature water was added to each pot to allow for germination. The pots were kept in an artificial light plant growth room with a 13/11 hour light/day cycle, and at 21° C. day/15° C. night temperature range. Plants were watered as needed, and randomized on a 3 day cycle to avoid any cool spots within the room. At the end of 14 days, the height of the corn plants for each treatment was measured, and normalized to the height of the control plants that were seed coated with only water.

This experiment was repeated three times, and the values averaged across the experiments. As can be seen in Table 18, the major effect of endoglucanase as a seed treatment on BECK'S 6626RR (a corn hybrid with glyphosate resistance) is in the range of 100-1600 μU/seed of enzyme activity. At these values, there is a noticeable and reproducible effect on corn growth. Values below 50 μU per seed had a much lower effect on the corn growth rate for this hybrid. These enzyme treatments work well as a standalone treatment on crops.

TABLE 18

Height effects of β-1,4 endoglucanase treatment as a seed treatment

| Seed Treatment | Enzyme Activity/Seed | Height (Normalized to Control) |
|---|---|---|
| Water (Control) | 0 | 100% |
| *Acidothermus* β-1,4 Endoglucanase | 12.5 μU | 102.8% |
| *Acidothermus* β-1,4 Endoglucanase | 25 μU | 101.6% |
| *Acidothermus* β-1,4 Endoglucanase | 50 μU | 98.6% |
| *Acidothermus* β-1,4 Endoglucanase | 100 μU | 101.8% |
| *Acidothermus* β-1,4 Endoglucanase | 200 μU | 105% |
| *Acidothermus* β-1,4 Endoglucanase | 400 μU | 107.8% |
| *Acidothermus* β-1,4 Endoglucanase | 800 μU | 108.1% |
| *Acidothermus* β-1,4 Endoglucanase | 1600 μU | 101.2% |

Example 2: Free Endoglucanase on Corn, Greenhouse

*Acidothermus cellulolyticus* β-1,4 endoglucanase (SEQ ID NO: 30; commercially available from Sigma-Aldrich, St. Louis, Mo., as product E2164) was diluted in citrate enzyme dilution buffer to concentrations of 50 through 1200 mU/mL. The U of endoglucanase activity was determined by as the amount of enzyme that is required to breakdown 1 μMol/min/mL of substrate at ideal temperature and conditions. Eighteen seeds of a commercial hybrid BECK'S 5140HR corn, which contains HERCULEX corn borer (an insect protection trait) and a glyphosate tolerance trait, without seed treatment were placed in 50 mL conical tubes. Each conical tube was vortexed and 18 μL of enzyme solution was added to each tube for a final enzyme concentration of 0, 50 μU, 100 μU, 200 μU, 400 μU, 600 μU, 800 μU, or 1200 μU per seed of endoglucanase. The conical tubes were vortexed again for 20 seconds to gain an even coating on each seed. Seeds were allowed to dry for 5 minutes and then planted into 39.7 $cm^3$ pots containing commercial top soil at a depth of 2.54 cm, with 2 seeds per pot. After planting, 50 mL of room temperature water was added to each pot to allow for germination. The pots were kept in an artificial light plant growth room with a 13/11 hour light/day cycle, and at 21° C. day/15° C. night temperature range. Plants were watered as needed, and randomized on a 3 day cycle to avoid any cool spots within the room. At the end of 14 days, the height of the corn plants for each treatment was measured, and normalized to the height of the control plants that were seed coated with only water. Each trial was replicated 3 times.

As can be seen in Table 19, the major effect of endoglucanase as a seed treatment on BECK'S 5140HR is in the range of 600-1200 μU/seed of enzyme activity. At these values, there is a noticeable and reproducible effect on corn growth. Values below 400 μU per seed had a lower effect on the corn growth rate on this hybrid. These enzyme treatments work well as a standalone treatment on crops.

TABLE 19

Height effects of β-1,4 endoglucanase treatment as a seed treatment

| Seed Treatment | Enzyme Activity/Seed | Height (Normalized to Control) |
|---|---|---|
| Water (Control) | 0 | 100% |
| *Acidothermus* β-1,4 Endoglucanase | 50μ | 100.5% |
| *Acidothermus* β-1,4 Endoglucanase | 100 μU | 97.34% |
| *Acidothermus* β-1,4 Endoglucanase | 200 μU | 94.69% |
| *Acidothermus* β-1,4 Endoglucanase | 400 μU | 98.5% |
| *Acidothermus* β-1,4 Endoglucanase | 600 μU | 102.3% |
| *Acidothermus* β-1,4 Endoglucanase | 800 μU | 103.8% |
| *Acidothermus* β-1,4 Endoglucanase | 1200 μU | 103.2% |

Example 3: Glucanases and Phospholipases on Corn, Field

*Acidothermus cellulolyticus* β-1,4 endoglucanase (SEQ ID NO: 30; commercially available from Sigma-Aldrich, St. Louis, Mo., as product E2164), *Helix pomatia* β-1,3-D-glucanase (SEQ ID NO: 126; commercially available from Sigma-Aldrich, St. Louis, Mo., as product 67138), *Trichoderma reesi* β-1,4 endoglucanase "cellulase" (SEQ ID NO: 36; commercially available from Worthington Biochemical Corp., Lakewood, N.J., as product ATCC26921), and *Aspergillus oryzae* exo-β-1,3-glucanase (SEQ ID NO 41; commercially available from Megazyme, Chicago, Ill., as product E-EXG5AO) were diluted in citrate enzyme dilution buffer to concentrations of 600 mU/mL (for the *Acidothermus* β-1,4-endoglucanase and the *Trichoderma* β-1,4-endoglucanase) or 252 mU/mL (for the *Helix* β-1,3-D-glucanase) of activity. This grouping contained several cellulase (cellulolytic glucanase) and non-cellulolytic glucanase activities, including β-1,4-endoglucanase and β-1,3-D-glucanase activities, respectively. The U of enzyme activity was determined by as the amount of enzymes that is required to breakdown 1 μMol/min/mL of substrate at ideal temperature and conditions. *Bacillus cereus* phosphatidylinositol-specific phospholipase C (SEQ ID NO: 116; commercially available from Sigma-Aldrich, St. Louis, Mo., as product P5524), *Bacillus cereus* phosphatidylcholine-specific phospholipase C (SEQ ID NO: 115; commercially available from Sigma-Aldrich, St. Louis, Mo. as product P6621), *Clostridium perfringens* phospholipase C (SEQ ID NO: 18; commercially available from Sigma-Aldrich, St. Louis, Mo., as product P7633), and *Streptomyces chromofuscus* phospholipase D (SEQ ID NO: 19; commercially available from Sigma-Aldrich, St. Louis, Mo., as product P0065) were diluted in citrate enzyme dilution buffer to a final concentration of 2.5 U/mL (for the *Bacillus* phosphatidylcholine Phospholipase C, the *Clostridium* Phospholipase C, and the *Streptomyces* Phospholipase D) or 100 U/mL (for the *Bacillus* phosphatidylinositol Phospholipase C). Each of these phospholipases have different specific activities to phospholipids and to different cleavage sites for phospholipids. Seeds of commercial hybrid BECK'S 6175YE corn, which contains HERCULEX (rootworm and corn borer protection traits), MON810 (comprising a corn borer resistance trait), a glufosinate resistance trait, and a glyphosate tolerance trait were used, without seed treatment. Seeds were placed into a batch treater at 400 seeds for each treatment. 400 μL of solution was added to each batch for a final enzyme concentration of 600 μU/seed for the *Acidothermus* β-1,4-endoglucanase and the *Trichoderma* β-1,4-endoglucanase, 252 μU/seed for the *Helix* β-1,3-D-glucanase, 100 mU/seed for the phosphatidylinositol-specific phospholipase C, or 2.5 mU/seed for the *Bacillus* phosphatidylcholine-specific Phospholipase C and the phospholipase C and D coated seeds. Each batch was allowed to mix for 20 seconds to gain an even coating on each seed. Additionally, these seeds were coated with commercial packages of prothioconazole, penflufen, metalaxyl, and clothianidin (EVERGOL Energy/PONCHO Seed Treatment, commercially available from Bayer CropScience) ("Base"). Each trial was replicated 3 times. Seeds were allowed to dry for 3 weeks, and then planted into native soil in 9.14 m rows at 10.16 cm apart, at a depth of 3.81 cm. The plants were measured for height at 2 weeks post-planting, and normalized to the height of the control plants that were seed coated with only water with Base. Results are shown in Table 16 below.

TABLE 20

Height effects of glucanases and phospholipase treatments as a seed treatment

| Seed Treatment | Enzyme Activity/Seed | Height (Normalized to Control) |
|---|---|---|
| Water + Base | 0 | 100% |
| *Acidothermus* β-1,4 Endoglucanase + Base | 600 μU | 117.6% |
| *Helix* β-1,3-D-glucanase + Base | 252 μU | 101.5% |
| *Trichoderma* β-1,4 Endoglucanase + Base | 600 μU | 114.0% |
| *Bacillus phosphatidylinositol* Phospholipase C + Base | 100 mU | 95.9% |
| *Bacillus phosphatidylcholine* Phospholipase C + Base | 2.5 mU | 100.7% |
| *Clostridium Phospholipase* C + Base | 2.5 mU | 109.2% |
| *Streptomyces Phospholipase* D + Base | 2.5 mU | 121.3% |

β-1,3-exoglucanase (*Aspergillus oryzae*; SEQ ID NO 41; commercially available from Megazyme, Chicago, Ill., as product E-EXG5AO), phosphatidylinositol-specific phospholipase C (*Bacillus cereus*; SEQ ID NO: 116; commercially available from Sigma-Aldrich, St. Louis, Mo. as product P6621), phosphatidylcholine-specific phospholipase C (*Bacillus cereus*; SED ID NO: 115; commercially available from Sigma-Aldrich, St. Louis, Mo., as product P5542), and phospholipase D (*Streptomyces chromofuscus*; SEQ ID NO: 19; commercially available from Sigma-Aldrich as product P8023) were diluted in water to 182 mU/mL (for β-1,3-exoglucanase), 100 U/mL (for the phosphatidylinositol-specific phospholipase C) or 2.5 U/mL (for the phosphatidylcholine-specific phospholipase C and the phospholipase D). The enzymes were applied as seed treatments to corn (BECK'S 5828 YH) which contains HERCULEX traits (a rootworm protection trait and corn borer resistance trait), a glufosinate resistance trait, and a glyphosate resistance trait), using the same methods described above, planted, and allowed to grow to harvest. The seed treatments were made on top of a base seed treatment containing prothioconazole, penflufen, metalaxyl, and clothianidin ("Base") and treated as described in the above section of this Example. The yield of treated crops (quantified as bushels/acre (Bu/Ac) or metric tonnes per hectare (MT/ha)) was compared to and normalized to crops grown from water treated seeds. Each treatment was independently performed at least 4 times. Corn seed treatments using these free enzymes resulted in increased corn yield compared to control corn plants that received no seed treatment. β-1,3-exoglucanase increased crop yield by approximately 4%, phosphatidylinositol-specific phospholipase C increased crop yield by approximately 3% and phospholipase D increased crop yield by approximately 2%. Average weight per ear also increased for corn plants grown from seeds treated with these three free enzymes. Results are shown in Table 21 below.

TABLE 21

Glucanases and phospholipases applied as a seed treatment to increase yield in corn

| Seed Treatment (5828 AM) | Enzyme Activity/Seed | Average Ear count per ear row | Average Weight per ear (lbs) [kg] | Absolute Change in bushels/acre (Bu/Ac) over control (+/−) [MT/ha] | Yield (Normalized to Control) |
|---|---|---|---|---|---|
| Water + Base | 0 μU/seed | 93 | 0.2694 [0.1222 kg] | 0.00 | 100% |
| β-1,3-Exoglucanase (*Aspergillus oryzae*) + Base | 182 μU/seed | 94 | 0.2769 [0.1256 kg] | +5.49 [0.34 MT/ha] | 104% |
| Phosphatidylinositol Phospholipase C (*Bacillus cereus*) + Base | 100 mU/seed | 94 | 0.2764 [0.1254 kg] | +4.02 [0.25 MT/ha] | 103% |
| Phosphatidylcholine Phospholipase C (*Bacillus cereus*) + Base | 2.5 mU/seed | 98 | 0.2477 [0.1124 kg] | −4.71 [−0.30 MT/ha] | 97% |
| Phospholipase D (*Streptomyces chromofuscus*) + Base | 2.5 mU/seed | 92 | 0.2943 [0.1335 kg] | +3.3 [0.21 MT/ha] | 102% |

Out of the phospholipases and glucanases that were tested in this trial, the β-1,3-exoglucanase, and the *Bacillus cereus* phosphatidylinositol-specific phospholipase C and *Streptomyces* phospholipase D had the best plant responses. These enzyme treatments worked on multiple hybrids and trait packages.

Example 4: Glucanases on Corn, Field

*Acidothermus cellulolyticus* β-1,4 endoglucanase (SEQ ID NO: 30; commercially available from Sigma-Aldrich, St. Louis, Mo., as product E2164) was diluted in citrate enzyme dilution buffer to concentrations of 200 mU/ml and 450 mU/mL of activity. The U of endoglucanase activity was determined by as the amount of enzymes that is required to breakdown 1 μMol/min/mL of substrate at ideal temperature and conditions. 150 seeds of commercial hybrid BECK'S 6175YE, which contains, HERCULEX (rootworm and corn borer protection traits), MON810 (a corn borer resistance trait), a glufosinate resistance trait, and a glyphosate tolerance trait, without seed treatment was placed into 50 mL conical tubes at 50 seeds each. 50 μL of enzyme was added to each of the tubes with 250 μL of slurry containing prothioconazole, penflufen, metalaxyl, and clothianidin (EVERGOL Energy/PONCHO Seed Treatment) ("Base"). This led to a final enzyme concentration of 200 μU/seed and 450 μU/seed. The tubes were vortexed for 20 seconds to gain an even coating on each seed. Seeds were allowed to dry for 3 weeks, and then planted into native soil in 9.14 m rows at 10.16 cm apart, at a depth of 3.81 cm. The plants were measured for height at 2 weeks post-planting, and results were normalized to the height of the control plants that were seed coated with only water with Base (prothioconazole, penflufen, metalaxyl, and clothianidin) treatment.

The trials were repeated three times, and the values averaged across the experiments. The data in Table 22 below show that the growth rate of the corn for both concentrations of β-1,4-endoglucanase was increased at 2 weeks post-planting. At these concentrations, there is a noticeable and reproducible effect on corn growth. These enzyme treatments work well as a package on top of Base treatment on crops and on multiple hybrids and trait packages.

TABLE 22

Height effects of endoglucanase treatment as a seed treatment

| Seed Treatment | Enzyme Activity/Seed | Height (Normalized to Control) |
|---|---|---|
| Water (Control) + Base | 0 | 100% |
| *Acidothermus* β-1,4 Endoglucanase + Base | 200 μU | 115.5% |
| *Acidothermus* β-1,4 Endoglucanase + Base | 450 μU | 114.3% |

Example 5: Phospholipases on Corn, Greenhouse, High Range

*Bacillus cereus* phosphatidylcholine-specific phospholipase C (SEQ ID NO: 115; commercially available from Sigma-Aldrich, St. Louis, Mo., as product P6621), *Clostridium perfringens* phospholipase C (SEQ ID NO: 18;

commercially available from Sigma-Aldrich, St. Louis, Mo., as product P7633), and *Streptomyces chromofuscus* phospholipase D (SEQ ID NO: 19; commercially available from Sigma-Aldrich, St. Louis, Mo., as product P0065) were diluted in 100 mM tris buffer, pH 7.0 to concentrations between of 100 U/ml to 450 U/mL. For each treatment group, 18 seeds of commercial hybrid BECK'S 6626RR corn, which contains a glyphosate tolerance trait, without seed treatment were placed in 50 mL conical tubes. Each conical tube was vortexed, and 18 μL of enzyme solution was added to each tube for a final enzyme concentration of 100 mU/mL, 200 mU/mL, or 450 mU/mL per seed of phospholipase, and vortexed again for 20 seconds to gain an even coating on each seed. Seeds were allowed to dry for 5 minutes, and the seeds were then planted into 42.24 $in^3$ (692.19 $cm^3$) pots of commercial top soil at a depth of 2.54 cm, with 2 seeds per pot. After planting, 50 mL of room temperature water was added to each pot to allow for germination. The pots were kept in an artificial light plant growth room with a 13/11 hour light/day cycle, and at 21° C. day/15° C. night temperature range. Plants were watered as needed, and rotated on a 3 day cycle to avoid any cool spots within the room. At the end of 14 days, the height of the corn plants for each treatment was measured, and normalized to the height of the control plants that were seed coated with only water. Experiments were done in triplicate.

Predominantly, it can be seen, in Table 23, that the effect of phospholipases C and D enzymes is best at values at or below 100 mU/seed. At these values, there is a noticeable and reproducible effect on corn growth. Values at or above 200 mU/seed are detrimental to corn growth. This held true for both phospholipase C and D enzymes.

TABLE 23

Height effects of phospholipases treatment as a seed treatment

| Seed Treatment | Enzyme activity/Seed | Height (Normalized to Control) |
|---|---|---|
| Water (Control) | 0 | 100% |
| Phospholipase C, *B. cereus* | 100 mU | 102.4% |
| Phospholipase C, *B. cereus* | 200 mU | 94.5% |
| Phospholipase C, *B. cereus* | 450 mU | 99.7% |
| Phospholipase C, *C. perfringens* | 200 mU | 97.4% |
| Phospholipase D, *Streptomyces* | 100 mU | 108.1% |
| Phospholipase D, *Streptomyces* | 250 mU | 98.4% |

Example 6: 2015 Soy Yield, Endoglucanases and Phospholipases

*Acidothermus cellulolyticus* β-1,4 endoglucanase (SEQ ID NO: 30; commercially available from Sigma-Aldrich, St. Louis, Mo., as product E2164), *Helix pomatia* β-1,3-D-glucanase (SEQ ID NO: 126; commercially available from Sigma-Aldrich, St. Louis, Mo., as product 67138), and *Trichoderma* reesi β-1,4 endoglucanase "cellulase" (SEQ ID NO: 36; commercially available from, Worthington Biochemical Corp., Lakewood, N.J.) were diluted in water to concentrations of 600 mU/ml activity for the two β-1,4 endoglucanases and 252 mU/ml for the β-1,3-D-glucanase. This grouping contained several cellulolytic and non-cellulolytic glucanase activities, including both β-1,4-endoglucanase and β-1,3-D-glucanase activities. *Bacillus cereus* phosphatidylcholine-specific phospholipase C (SEQ ID NO: 115; commercially available from Sigma-Aldrich, St. Louis, Mo., as product P6621), *Clostridium perfringens* phospholipase C (SEQ ID NO: 18; commercially available from Sigma-Aldrich, St. Louis, Mo., as product P7633), and *Bacillus cereus* phosphatidylinositol-specific phospholipase C (SEQ ID NO: 116; commercially available from Sigma-Aldrich, St. Louis, Mo., as product P5524) were diluted in water to a final concentration of 2.5 U/ml (for the *Bacillus* phosphatidylcholine-specific phospholipase C and the *Clostridium* Phospholipase C) or 100 U/ml (for the *Bacillus* phosphatidylinositol-specific phospholipase C). Each of these phospholipases has different specific activities to phospholipids and to different cleavage sites for phospholipids. 720 seeds of commercial hybrid BECK'S 294NR soybeans, which contain a nematode resistance trait (SCN-SB) and a glyphosate resistance trait (ROUNDUP READY 1), with the metalaxyl and clothianidin Base seed treatment package ("Base") were placed into paint cans and coated with commercial seed treatment (Base). Each batch was mixed, and 720 μL of solution was added to each batch to obtain the final enzyme concentrations listed in Table 24 below. Seeds were allowed to dry for 3 weeks, and then planted into native soil in 9.14 m rows at 6.35 cm apart, at a depth of 3.81 cm. The plants were harvested and yield measured at harvest. Each treatment was replicated 4 times and planted 4 times in the field. Results are shown below in Table 24 as a percentage of weight over the control (Base) treatment.

TABLE 24

Yield Increases as a Percentage of Control

| Seed Treatment | Enzyme Activity/Seed | Yield (Normalized to Control) |
|---|---|---|
| Water + Base | 0 | 100% |
| *Acidothermus* β-1,4 Endoglucanase + Base | 600 μU | 123% |
| *Helix* β-1,3-D-glucanase + Base | 252 μU | 123% |
| *Trichoderma* β-1,4 Endoglucanase + Base | 600 μU | 123% |
| *Bacillus* phosphatidylinositol Phospholipase C + Base | 100 mU | 115% |
| *Bacillus* phosphatidylcholine Phospholipase C + Base | 2.5 mU | 145% |
| *Clostridium* Phospholipase C + Base | 2.5 mU | 92% |

As can be seen in Table 24, all three glucanases lead to a noticeable increase in yield in the soybean plants, as well as the PC-PLC and PI-PLC from *Bacillus cereus.*

Example 7: 2015 Corn Yield, Endoglucanase

*Acidothermus cellulolyticus* β-1,4 endoglucanase (SEQ ID NO: 30 commercially available from Sigma-Aldrich, St. Louis, Mo., as product E2164) was diluted in citrate enzyme dilution buffer to concentrations of 250 and 600 mU/ml of activity. Seeds of commercial hybrid BECK'S 5828YH corn with a prothioconazole, penflufen, metalaxyl, and clothianidin (EVERGOL Energy/PONCHO) Base seed treatment package ("Base") were placed into seed treater at 250 seeds each. Each batch was mixed, and 250 μL of solution was added to each tube for a final enzyme concentration of 200 or 600 μU/seed for the endoglucanases coated seeds. Each batch was mixed again for 20 seconds to gain an even coating on each seed. Seeds were allowed to dry for 3 weeks, and then planted into native soil in 9.14 m rows at 6.35 cm apart, at a depth of 3.81 cm. The plants were harvested and yield measured at harvest. Each treatment was replicate 4 times. Results are shown below in Table 25 as a harvest weight as a percentage over control treatment harvest weigh (normalized).

TABLE 25

| Yield Increases as a Percentage of Control | | |
|---|---|---|
| Seed Treatment | Enzyme Activity/Seed | Yield (Normalized to Control) |
| Water + Base | 0 | 100% |
| *Acidothermus* β-1,4 Endoglucanase + Base | 200 μU | 104.8% |
| *Acidothermus* β-1,4 Endoglucanase + Base | 600 μU | 102.4% |

As can be seen in Table 25, both rates of *Acidothermus* β-1,4 endoglucanase lead to an increase in the yield of the corn.

Example 8: Isolation and Identification of Plant-Growth Promoting Bacterial Strains Soil samples from rhizospheres of the healthiest and most resistant potato (*Solanum tuberosum*), yellow summer squash (*Cucurbita pepo*), tomato (*Solanum lycopersicum*), and pole bean (*Phaseolus coccineus*) plants were collected, diluted in sterile water, and spread onto nutrient agar plates. Bacterial isolates that demonstrated high growth rates and were able to be passaged and propagated were selected for further study. The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten butterhead lettuce seeds per treatment were planted at a depth of 1 cm in loam top soil (Columbia, Mo.) that was sieved to remove large debris. Seeds were inoculated at planting in 4 cm pots with 0.5 μl of resuspended bacteria in water mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75° F. (18-24° C.) with 11 hours of light/day, and 5 ml of watering every 3 days. After one week, plant heights and leaf diameters, as well as overall health of the plants were collected. Initial screening of rhizosphere isolates resulted in obtaining greater than 200 distinct species of bacteria and fungi from the rhizosphere of the four plants. Some of the bacterial species are described in Table 26. Identified strains are indicated by their proper bacterial identifications. Other strains are indicated by their unknown identification number. Inoculants giving results near control (+/−2%) were not included in the table.

TABLE 26

| Bacterial Inoculant | Avg. Height (cm) | Comparison | SEM |
|---|---|---|---|
| Uninoculated | 1.8 | Control | .07 |
| *Paracoccus kondratiavae* NC35 | 2 | 111.1% | .05 |
| *B. aryabhattai* CAP53 | 3.65 | 202.8% | .45 |
| *B. flexus* BT054 | 2.45 | 136.1% | .11 |
| *Bacillus mycoides* strain BT155 | 2.17 | 120.4% | .21 |
| *B. aryabhattai* CAP56 | 2.1 | 116.7% | .20 |
| *B. nealsonii* BOBA57 | 2.8 | 155.6% | .03 |
| *E. cloacae* CAP12 | 2.4 | 133.3% | .41 |
| Unknown 8 | 1.77 | 77.8% | .65 |
| Unknown 122 | 1.9 | 105.6% | .11 |
| Unknown 15 | 1.4 | 77.8% | .41 |
| Unknown 39 | 1.8 | 100.0% | .20 |
| Unknown 401 | 2 | 111.1% | .21 |
| Unknown 402 | 1.53 | 85.2% | .27 |
| Unknown 41 | 1.45 | 80.6% | .31 |
| Unknown 42 | 1.4 | 77.8% | .15 |
| Unknown 44 | 2.2 | 133.3% | .08 |
| Unknown 51 | 1.83 | 102.9% | .21 |

Bacterial strains that produced the greatest effect on the overall plant health and plant height in the initial lettuce trial were subjected to further identification. Bacterial strains were grown overnight in Luria Bertani broth at 37° C., and overnight cultures were spun down in a centrifuge. Media was decanted and the remaining bacterial pellet was subjected to chromosomal DNA isolation using the Qiagen Bacterial Chromosomal DNA Isolation kit. Chromosomal DNA was subjected to PCR amplification of the 16S rRNA coding regions using the primers E338F 5'-ACT CCT ACG GGA GGC AGC AGT-3' (SEQ ID NO: 108), E1099R A 5'-GGG TTG CGC TCG TTG C-3' (SEQ ID NO: 109), and E1099R B 5'-GGG TTG CGC TCG TTA C-3' (SEQ ID NO: 110). PCR amplicons were purified using a Promega PCR purification kit, and the resultant amplicons were diluted and sent to the University of Missouri DNA Core for DNA sequencing. DNA sequences were compared to the NCBI BLAST database of bacterial isolates, and genus and species were identified by direct comparison to known strains. Top identified species are indicated in Table 26. In many cases, 16S rRNA DNA sequences were only able to delineate the genus of the selected bacterial strain. In cases where a direct identification was not forthcoming, additional biochemistry analyses, using methods standard in the field, were performed to differentiate strains at the species and strain levels, and are listed in Table 27.

TABLE 27

| Test | *E. cloacae* CAP12 | *P. kondratiavae* NC35 | *B. aryabhattai* CAP53 | *B. flexus* BT054 | *B. mycoides* BT155 | *B. aryabhattai* CAP56 | *B. nealsonii* BOBA57 |
|---|---|---|---|---|---|---|---|
| Urease | − | − | − | − | − | − | + |
| Catalase | + | + | + | + | + | + | + |
| Oxidase | − | + | + | + | − | − | − |
| Nitrate | + | + | − | + | + | − | + |
| Growth, 5% NaCl | + | − | + | + | − | + | + |
| Growth, 7.5% NaCl | − | − | + | + | − | + | − |
| Growth, 42° C. | + | + | + | + | + | + | + |
| Growth, 50° C. | − | − | + | + | − | + | − |
| Growth, pH 5 | + | − | + | + | − | + | − |
| Growth, pH 9 | + | + | + | + | + | + | + |
| Acid, Cellobiose | + | − | + | + | + | + | − |
| Acid, Lactose | + | − | + | + | + | − | + |
| Acid, Starch | − | − | − | + | − | + | − |

Example 9: Isolation and Identification of Additional Plant-Growth Promoting Bacterial Strains Soil samples from agricultural fields near Gas, Kans. were collected, diluted in sterile water, and spread onto nutrient agar plates. Bacterial isolates that demonstrated high growth rates and were able to be passaged and propagated were selected for further study. The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Corn seeds were coated with commercial seed polymer mixed with water alone (1.6 μl per seed total) or commercial seed polymer containing selected bacterial strains (1.6 μl per seed total). Coated seeds were planted in 3 inch (7.62 cm) diameter pots at a depth of 1 inch (2.54 cm) in loam top soil (Columbia, Mo.) that was sieved to remove large debris. Plants were grown at temperatures between 18-24° C. (65-75° F.) with 11 hours of light/day, and 50 ml of watering at planting and every 3 days. After two weeks, plant heights and leaf diameters, as well as overall health of the plants were collected. For germination assays and determining 3 day root length, seeds were coated as indicated above and evenly dispersed at 10 seeds per paper towel. The paper towels were wetted with 10 ml of water, rolled up, placed in a small plastic bag and incubated at 30° C. or placed on a germination heat mat at 27-30° C. (80-85° F.). Root measurements were recorded after 3 days. Initial screening of rhizosphere isolates resulted in obtaining greater than 100 distinct species of bacteria and fungi from the rhizosphere. Some of the bacterial species are described in Table 28. Identified strains are indicated by their proper bacterial identifications.

TABLE 28

| Bacterial Inoculant | Avg. Height (2 weeks), normalized to polymer control (%) | Avg. Root Length (3 days), normalized to polymer control (%) |
|---|---|---|
| Polymer control | 100 | 100 |
| *B. mycoides* EE118 | 111.1 | 189.1 |
| *B. subtilis* EE148 | 99.4 | 172.8 |
| *Alcaligenes faecalis* EE107 | 111.5 | 129.2 |
| *B. mycoides* EE141 | 109.2 | 143.5 |
| *B. mycoides* BT46-3 | 105.6 | 141.3 |
| *B. cereus* family member EE128 | 105.6 | — |
| *B. thuringiensis* BT013A | 101.8 | 103.8 |
| *Paenibacillus massiliensis* BT23 | 104.2 | 139.4 |
| *B. cereus* family member EE349 | 105.2 | — |
| *B. subtilis* EE218 | 106.6 | — |
| *B. megaterium* EE281 | 107.8 | — |

Bacterial strains that produced the greatest effect on plant health are described in Table 28. Bacterial strains were grown overnight in Luria Bertani broth at 37° C., and overnight cultures were spun down in a centrifuge. Media was decanted and the remaining bacterial pellet was subjected to chromosomal DNA isolation using the Qiagen Bacterial Chromosomal DNA Isolation kit. Chromosomal DNA was subjected to PCR amplification of the 16S rRNA coding regions using the primers E338F 5'-ACT CCT ACG GGA GGC AGC AGT-3' (SEQ ID NO: 108), E1099R A 5'-GGG TTG CGC TCG TTG C-3' (SEQ ID NO: 109), and E1099R B 5'-GGG TTG CGC TCG TTA C-3' (SEQ ID NO: 110). PCR amplicons were purified using a Promega PCR purification kit, and the resultant amplicons were diluted and sent to the University of Missouri DNA Core for DNA sequencing. DNA sequences were compared to the NCBI BLAST database of bacterial isolates, and genus and species were identified by direct comparison to known strains. Top identified species are indicated in Table 28. In many cases, 16S rRNA DNA sequences were only able to delineate the genus of the selected bacterial strain. In cases where a direct identification was not forthcoming, additional biochemistry analyses, using methods standard in the field, were performed to differentiate strains at the species and strain levels, and the differentiated strains are listed in Table 29.

TABLE 29

| Test | *B. thuringiensis* BT013A | *B. cereus* family member EE349 | *B. subtilis* EE148 | *B. subtilis* EE218 | *B. megaterium* EE281 | *Paenibacillus massiliensis* BT23 |
|---|---|---|---|---|---|---|
| Motility | + | + | + | + | + | + |
| Rhizoid Colony | − | − | − | − | − | + |
| Catalase | + | + | + | + | + | + |
| Oxidase | + | − | − | − | − | − |
| Nitrate | + | + | wk | − | − | − |
| Growth, 5% NaCl | + | wk | − | + | + | − |
| Growth, 7.5% NaCl | wk | − | − | + | + | − |
| Growth, 42° C. | − | + | + | + | + | + |
| Growth, 50° C. | − | − | − | − | − | − |
| Growth, pH 5 | wk | − | + | + | + | − |
| Growth, pH 9 | + | + | − | + | + | − |
| Acid, Cellobiose | − | − | wk | + | − | + |
| Acid, Lactose | − | + | + | + | + | − |
| Acid, Starch | − | + | − | + | + | − |

TABLE 29-continued

| Test | *B. mycoides* BT46-3 | *Alcaligenes faecalis* EE107 | *B. mycoides* EE118 | *B. cereus* family member EE128 | *B. mycoides* EE141 |
|---|---|---|---|---|---|
| Motility | − | + | − | − | − |
| Rhizoid Colony | + | − | + | − | + |
| Catalase | + | + | + | + | + |
| Oxidase | − | + | − | − | − |
| Nitrate | + | + | + | + | + |
| Growth, 5% NaCl | + | + | − | + | − |
| Growth, 7.5% NaCl | − | − | − | − | − |
| Growth, 42° C. | + | + | − | + | − |
| Growth, 50° C. | − | − | − | − | − |
| Growth, pH 5 | wk | + | − | + | − |
| Growth, pH 9 | wk | + | + | + | − |
| Acid, Cellobiose | + | wk | + | − | wk |
| Acid, Lactose | + | + | − | + | wk |
| Acid, Starch | + | wk | + | + | − |

wk = weak growth or low growth

Example 10: Testing of Plant-Growth Promoting Bacterial Strains on Alfalfa

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and bacteria resuspended in an equal amount of distilled water. Ten ZEBA-coated alfalfa seeds were planted for each treatment at a depth of 0.6 cm in loam top soil (Columbia, Mo.) that was sieved to remove large debris. ZEBA is a superabsorbent cornstarch based polymer used as a moisture-retention seed coating. Seeds were inoculated at planting with 0.5 μl of resuspended bacteria in water mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75° F. (18-24° C.) with 11 hours of light/day, and 5 ml of watering every 3 days. Alfalfa was allowed to grow for 1 week to analyze emergence and initial outgrowth of plants under described conditions. Identified strains indicated by their proper bacterial identifications and final height data are listed in Table 30.

TABLE 30

| Bacterial Inoculant | Avg. Height (cm) | Comparison | SEM |
|---|---|---|---|
| Uninoculated | 4.82 | — | .008 |
| *B. aryabhattai* CAP56 | 4.85 | 101.20% | .016 |
| *B. nealsonii* BOBA57 | 4.86 | 101.70% | .021 |
| *E. cloacae* CAP12 | 5.6 | 116.23% | .020 |

Example 11: Testing of Plant-Growth Promoting Bacterial Strains on Cucumbers

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in equal amount of distilled water. Ten cucumber seeds were planted for each treatment at a depth of 1 cm in loam top soil (Columbia, Mo.) that was sieved to remove large debris. Seeds were inoculated at planting with 0.5 μl of resuspended bacteria in water mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75° F. (18-24° C.) with 11 hours of light/day, and 5 ml of watering every 3 days. Cucumbers were allowed to grow for 2 weeks to analyze emergence and initial outgrowth of plants under described conditions. Identified strains indicated by their proper bacterial identifications and final height data are listed in Table 31.

TABLE 31

| Bacterial Inoculant | Avg. Height (cm) | Comparison | SEM |
|---|---|---|---|
| Uninoculated | 11.23 | — | .067 |
| *B. aryabhattai* CAP53 | 11.5 | 102.00% | .023 |
| *B. aryabhattai* CAP56 | 11.35 | 101.20% | .035 |
| *B. nealsonii* BOBA57 | 11.33 | 101.10% | .014 |

Example 12: Testing of Plant-Growth Promoting Bacterial Strains on Yellow Squash The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten yellow squash seeds were planted for each treatment at a depth of 1 cm in loam top soil (Columbia, Mo.) that was sieved to remove large debris. Seeds were inoculated at planting with 0.5 μl of resuspended bacteria in water mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75° F. (18-24° C.) with 11 hours of light/day, and 5 ml of watering every 3 days. Squash was allowed to grow for 2 weeks to analyze emergence and initial outgrowth of plants under described conditions. Identified strains indicated by their proper bacterial identifications, final height data, and final leaf diameter (by span of the two leaves) data are listed in Table 32.

TABLE 32

| Bacterial Inoculant | Avg. Height (cm) | Comparison | SEM | Leaf Diameter (cm) | Comparison |
|---|---|---|---|---|---|
| Uninoculated | 10.16 | — | .028 | 5.08 | — |
| *B. aryabhattai* CAP53 | 11.75 | 115.60% | .055 | 7.25 | 142.60% |
| *B. flexus* BT054 | 11.88 | 116.90% | .017 | 6.36 | 125.20% |
| *Bacillus mycoides* BT155 | 11.92 | 117.20% | .051 | 6.33 | 124.60% |
| *B. aryabhattai* CAP56 | 11.95 | 117.60% | .027 | 6.33 | 124.60% |
| *B. nealsonii* BOBA57 | 11.89 | 117.00% | .118 | 6.42 | 126.40% |
| *E. cloacae* CAP12 | 11.42 | 112.30% | .039 | 6.83 | 134.40% |

Example 13: Testing of Plant-Growth Promoting Bacterial Strains on Ryegrass

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Thirty ryegrass seeds were planted for each treatment at a depth of 0.3 cm in loam top soil (Columbia, Mo.) that was sieved to remove large debris. Seeds were inoculated at planting with 0.5 μl of resuspended bacteria in water mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75° F. (18-24° C.) with 11 hours of light/day, and 5 ml of watering every 3 days. Ryegrass was allowed to grow for 1.5 weeks to analyze emergence and initial outgrowth of plants under described conditions. Identified strains indicated by their proper bacterial identifications and height data are listed in Table 33.

TABLE 33

| Bacterial Inoculant | Avg. Height (cm) | Comparison | SEM |
|---|---|---|---|
| Uninoculated | 1.61 | — | .023 |
| *B. aryabhattai* CAP53 | 2.01 | 124.70% | .012 |
| *B. flexus* BT054 | 2.21 | 137.30% | .034 |
| *Bacillus mycoides* BT155 | 2.29 | 142.20% | .049 |
| *B. aryabhattai* CAP56 | 2.19 | 136.00% | .009 |
| *B. nealsonii* BOBA57 | 2.29 | 142.40% | .045 |
| *E. cloacae* CAP12 | 1.98 | 122.50% | .015 |

Example 14: Testing of Plant-Growth Promoting Bacterial Strains on Corn

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten corn seeds were planted for each treatment at a depth of 2.5 cm in loam top soil (Columbia, Mo.) that was sieved to remove large debris. Seeds were inoculated at planting with 0.5 μl of resuspended bacteria in water mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75° F. (18-24° C.) with 11 hours of light/day, and 5 ml of watering every 3 days. Corn was allowed to grow for 2 weeks to analyze emergence and initial outgrowth of plants under described conditions. Identified strains indicated by their proper bacterial identifications and final height data are listed in Table 34.

TABLE 34

| Bacterial Inoculant | Avg. Height (cm) | Comparison | SEM |
|---|---|---|---|
| Uninoculated | 8.9 | — | .039 |
| *B. aryabhattai* CAP53 | 11.01 | 123.60% | .081 |
| *B. flexus* BT054 | 9.96 | 112.00% | .095 |
| *Bacillus mycoides* strain BT155 | 9.6 | 107.90% | .041 |
| *B. aryabhattai* CAP56 | 9.54 | 107.10% | .088 |
| *B. nealsonii* BOBA57 | 9.23 | 103.70% | .077 |

Example 15: Testing of Plant-Growth Promoting Bacterial Strains on Soybeans

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight, or for *Bradyrhizobium* or *Rhizobium* on yeast mannitol media). Overnight cultures (30° C.) of selected strains were spun down, media decanted off, and resuspended in equal amount of distilled water. Ten soybean seeds were planted for each treatment at a depth of 2.5 cm in loam top soil (Columbia, Mo.) that was sieved to remove large debris. Seeds were inoculated at planting with 0.5 μl of resuspended bacteria in water mixed into 10 ml of $H_2O$. When testing two bacterial strains, 0.5 μl of each resuspended bacteria was mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75° F. (18-24° C.) with 11 hours of light/day, and 5 ml of watering every 3 days. Soybeans were allowed to grow for 2 weeks to analyze emergence and initial outgrowth of plants under described conditions. Identified strains indicated by their proper bacterial identifications and final height data are listed in Table 35. Co-inoculation of bacteria strains in the present invention with members of the *Bradyrhizobium* sp. or *Rhizobium* sp. lead to an increase in plant growth compared to either inoculant alone.

TABLE 35

| Bacterial Inoculant | Avg. Height (cm) | Comparison | SEM |
|---|---|---|---|
| Uninoculated | 13.94 | — | .089 |
| *B. aryabhattai* CAP53 | 16.32 | 117.1% | .146 |
| *B. flexus* BT054 | 17.85 | 128.0% | .177 |
| *Bacillus mycoides* strain BT155 | 18.93 | 135.8% | .117 |
| *B. aryabhattai* CAP56 | 17.23 | 123.6% | .133 |
| *B. aryabhattai* CAP53 | 16.32 | 117.1% | .077 |
| *B. aryabhattai* CAP53 and *Bradyrhizobium* sp. | 16.72 | 119.9% | .182 |
| *B. aryabhattai* CAP53 and *Rhizobium* sp. | 17.32 | 124.2% | .086 |
| *Bradyrhizobium* sp. | 14.25 | 102.2% | |
| *Rhizobium* sp. | 14.75 | 105.8% | |

Example 16: *Bacillus cereus* Family Members with Plant Growth Promoting Attributes

*Bacillus mycoides* strain BT155, *Bacillus mycoides* strain EE118, *Bacillus mycoides* strain EE141, *Bacillus mycoides* strain BT46-3, *Bacillus cereus* family member strain EE349, *Bacillus thuringiensis* strain BT013A, and *Bacillus megaterium* strain EE281 were grown in Luria Bertani broth at 37° C. and overnight cultures were spun down, media decanted off, and resuspended in equal amount of distilled water. Twenty corn seeds were planted for each treatment at a depth of 2.5 cm in loam top soil (Columbia, Mo.) that was sieved to remove large debris. Seeds were inoculated at planting with 0.5 μl of resuspended bacteria in water mixed into 50 ml of $H_2O$. Fifty ml of $H_2O$ was sufficient to deliver the bacteria into the 29 $in^3$ (475.22 $cm^3$) of soil as well as saturate the soil for proper germination of seeds. Plants were grown at temperatures between 65-72° F. with 13 hours of light/day, and 5 ml of watering every 3 days. Seedlings were allowed to grow for 2 weeks to analyze emergence and initial outgrowth of plants under described conditions. Identified strains indicated by their proper bacterial identifications and final height data are listed in Table 36.

TABLE 36

| Bacterial Inoculant | Avg. Height, cm, Corn | Percentage | SEM, |
|---|---|---|---|
| $H_2O$ Control | 11.41 | 100% | .123 |
| *B. mycoides* EE118 | 12.43 | 108.9% | .207 |
| *B. mycoides* EE141 | 12.84 | 112.5% | .231 |
| *B. mycoides* BT46-3 | 11.81 | 103.5% | .089 |
| *Bacillus thuringiensis* BT013A | 12.05 | 105.6% | .148 |
| *Bacillus cereus* family member EE128 | 13.12 | 114.9% | .159 |
| *Bacillus mycoides* BT155 | 12.85 | 112.6% | .163 |
| *Bacillus megaterium* EE281 | 11.99 | 105.1% | .098 |

All plant-growth promoting bacteria tested had a beneficial effect on corn height at two weeks under the described conditions. The *Bacillus cereus* family member EE128 strain had the greatest effect in this trial, giving a greater than at 14% boost in corn height.

Example 17: Isolation, Identification, and Characterization of Endophytic *Bacillus cereus* Family Bacterial Strains

*Bacillus cereus* family member 349, discussed above in the immediately preceding example, was found to have the ability to grow endophytically. Several other *Bacillus cereus* family members that have the ability to grow endophytically were also identified: *Bacillus cereus* family member EE439, *Bacillus thuringiensis* EE417, *Bacillus cereus* EE444, *Bacillus thuringiensis* EE319, *Bacillus thuringiensis* EE-B00184, *Bacillus mycoides* EE-B00363, *Bacillus pseudomycoides* EE-B00366, and *Bacillus cereus* family member EE-B00377.

To obtain these additional *Bacillus cereus* family members, commercial hybrid corn seed was planted in potting soil and allowed to grow. The corn seeds were coated with a fungicide and a biological inoculant. Plants were grown under artificial light for 14 hours a day and plant growth over a 14 day period was determined. Plants were watered every three days over the course of the experiment. After 14 days, the plants were extracted from the soil and washed to remove excess debris. The plants were then inverted, exposed to 5% bleach for ten minutes, washed in water, exposed to hydrogen peroxide (10%) for ten minutes, washed again in water, and the stalks split with a sterile razor blade. The split halves of the stalks were placed face down onto nutrient agar plates for two hours. After two hours, the stalks were removed, and the agar plates incubated at 30° C. for 48 hours. After 48 hours, the plates were examined for colony morphology, and *Bacillus cereus* family member colonies found internal to the plant were toothpicked onto nutrient agar. These were then were grown overnight at 30° C. in brain heart infusion broth, and spun down at 10,000×g for 5 minutes. The supernatant was removed, and the pellet frozen overnight at −20° C. Chromosomal DNA was then extracted from each clone, and the identity of each colony verified by PCR using 16S rRNA primers and amplicons were sent for DNA sequencing and identification. The 16S rRNA sequences for these strains are provided above in Table 17.

Example 18: Isolation, Identification, and Characterization of Additional Endophytic Bacterial Strains (Non-*Bacillus cereus* Family Members)

The endophytic bacterial strains *Bacillus megaterium* EE385, *Bacillus* sp. EE387, *Bacillus circulans* EE388, *Bacillus subtilis* EE405, *Lysinibacillus* fusiformis EE442, *Lysinibacillus* spp. EE443, and *Bacillus pumilus* EE-B00143 were isolated from corn seedlings. Two week old corn seedlings were first sterilized. The plants were extracted them from the soil and washed to remove excess debris. The plants were then inverted, exposed to 5% bleach for ten minutes, washed in water, exposed to hydrogen peroxide (10%) for ten minutes, and washed again in water. The stalks were then split with a sterile razor blade. The split halves of the stalks were placed face down onto nutrient agar plates for two hours. After two hours, the plant stems were removed from the plates, and the plates were then incubated at 30° C. for 48 hours. Bacilli colonies that were endophytic were selected for further analysis. These strains were grown up in brain heart infusion broth overnight at 30° C., and the cultures subjected to extraction of DNA using a Qiagen Chromosomal DNA Kit. The DNA was PCR amplified to obtain the 16S rRNA gene, which was sent for DNA sequencing. The resultant sequences were BLAST searched using the NCBI databases to establish the identity of the Bacilli species. The 16S rRNA sequences are provided above in Table 17.

Example 19: Free ACC Deaminase on Corn, Greenhouse 1-aminocyclopropane-1-carboxylate deaminase (ACC deaminase) was applied in a foliar application as a spray to corn plants. Two amino acids of D-cysteine desulfhydrase of *Bacillus thuringiensis* strain IS5056 (SEQ ID NO: 113) were mutated, resulting in a modest increase in ACC deaminase (1-aminocyclopropane-1-carboxylate) activity. In addition to its D-cysteine desulfhydrase activity, the native D-cysteine desulfhydrase from *Bacillus thuringiensis* strain IS5056 has ample inherent ACC deaminase activity. However, for purposes of the present Example and Example 20 below, the native D-cysteine desulfhydrase from *Bacillus thuringiensis* strain IS5056 (SEQ ID NO: 113) will be referred to as a "D-cysteine desulfhydrase." Since the mutated version of the enzyme (SEQ ID NO: 114) has increased ACC deaminase activity, for purposes of the present examples, the mutated enzyme will be referred to as an "ACC deaminase." The sequences with the mutations are provided as SEQ ID NO: 112 (nucleic acid) and SEQ ID NO: 114 (protein). In Table 2, the two amino acid substitutions shown are in bold and underlined text. The threonine at position 290 of SEQ ID NO: 113 was substituted with a glutamic acid residue and serine residue at position 317 of SEQ ID NO: 113 was substituted with a leucine residue using PCR mutagenesis techniques standard in the art. The genes encoding the D-cysteine deaminase (SEQ ID NO: 111) and ACC deaminase (SEQ ID NO: 112) were then cloned into the Gram positive pBC vector (a miniaturized version of the naturally occurring plasmid pBC16) under the control of a Bc1A sporulation promoter. The vectors were then transformed into *Bacillus thuringiensis*. After sporulation in minimal media, which releases cellular content, including the enzymes, all cells were removed through filtration and the remaining active enzyme fractions were applied to plants. ACC deaminase activity was quantified using a standard dinitrophenol hydrazine assay (Li et al., *A colorimetric assay of* 1-*aminocyclopropane*-1-*carboxylate* (*ACC*) *based on ninhydrin reaction for rapid screening of bacteria containing ACC deaminase*, LETT APPL. MICROBIOL. 53(2):178-85 (2011).

The wild-type enzyme (SEQ ID NO: 113) and the enzyme with the two point mutations (SEQ ID NO: 114) were provided as free enzymes using foliar delivery to 2-week-old corn (BECK'S 5828 YH, V2 to V3 stage of development) and 4-week old soybean plants (BECK'S 297NR, V2 to V3 stage of development). BECK's 5828 YH corn contains HERCULEX (rootworm resistance and corn borer resistance traits), a glufosinate resistance trait, and a glyphosate resistance trait. BECK'S 297NR soy contains a nematode resistance trait (SCN-SB) and a glyphosate resistance trait.

Sixteen replicate plants per trial were individually treated using foliar applications of the D-cysteine desulfhydrase and the ACC deaminase enzymes and compared to a surfactant-alone control (Control). Activities of the foliar applied D-cysteine desulfhydrase (SEQ ID NO: 113) and the ACC deaminase (SEQ ID NO: 114) enzymes were standardized to the same protein content and applied using consistent use rates as foliar spray containing 0.1% non-ionic surfactant (NIS) (ALLIGARE SURFACE, Alligare LLC), which was used for delivery of the enzymes to corn and soy plants at a rate of 10 ml/plant. Activity of ACC deaminase activity is described herein as 1 mU equals 1 nmol product/mg protein/hour at 30° C. The initial activity of the D-cysteine desulfhydrase for this assay is 500 mU/ml, and the activity of the ACC deaminase is 2,124 mU/ml. After dilution in to 10 ml/plant, the delivery of the enzyme is at 2.5% volume with a final concentration of 12.5 mU/ml final activity per plant for D-cysteine desulfhydrase and 53.1 mU/ml for ACC deaminase. The ALLIGARE SURFACE surfactant contains a blend of alkylpolyoxethylene, glycol derivatives, humectant, and formulation aids.

Two weeks after the foliar application, roots were harvested from the corn or soybean plants, rinsed with water, gently blotted dry to remove any excess water and the fresh root weight (grams) was determined. The fresh root weight for each treatment was normalized to control plants treated only with the vehicle containing only minimal media and the 0.1% non-ionic surfactant. Results are shown in Tables 37 and 38 below.

As is shown in Table 37, foliar application of ACC deaminase in corn resulted in a significant (approximately 12%) increase in fresh root mass as compared to plants treated with non-ionic surfactant treatment alone (*p value=0.015). By contrast, average fresh root mass from corn plants that received the D-cysteine desulfhydrase was comparable to that of the control plants that received the surfactant only treatment.

In soybean plants (Table 38) treated with the D-cysteine desulfhydrase, there was a slight trend towards an increase in root mass 2 weeks after foliar application. By contrast, ACC deaminase-treated soybean plants exhibited an average of a 12% increase in root mass over the control.

This study, looking at both the monocot corn and the dicot soybean, demonstrates that foliar application of ACC deaminase (and to a lesser extent, D-cysteine desulfhydrase) can directly lead to increases in root mass of the foliar-treated plants over the control treatments.

TABLE 37

Average root mass for corn plants treated with a foliar application of ACC deaminase compared to control plants

| Corn Treatment | Average Root Mass (grams fresh weight) | Standard deviation | Percent (%) Change in Root Mass Normalized to Control |
|---|---|---|---|
| Control | 2.7 | 0.36 | — |
| D-cysteine desulfhydrase (wild-type) (SEQ ID NO: 113) | 2.54 | 0.43 | 94.1% |
| ACC deaminase (with mutations) (SEQ ID NO: 114) | 3.02* | 0.33 | 111.9% |

TABLE 38

Average root mass for soybean plants treated with a foliar application of ACC deaminase compared to control plants

| Soybean Treatment | Average Root Mass (grams fresh weight) | Standard deviation | Percent (%) Change in Root Mass Normalized to Control |
|---|---|---|---|
| Control | 4.03 | 0.86 | — |
| D-cysteine desulfhydrase (wild-type) (SEQ ID NO: 113) | 4.06 | 0.78 | 100.7% |
| ACC deaminase (with mutations) (SEQ ID NO: 114) | 4.50 | 1.11 | 111.7% |

The ACC deaminase (SEQ ID NO: 114) was also applied as an in-furrow (soil-applied) treatment on rice to the area surrounding hybrid rice seed, which also resulted in increased plant growth. ACC deaminase (SEQ ID NO: 114) was were created and purified as described above, at the above initial concentrations, and delivered at a rate of 8 fl oz/Ac (584.2 ml/hectare) of enzyme for every 2.5 gallons of water/Ac (23.4 liters/hectare). 6.25 mU/ml final activity was created after dilution in water for the D-cysteine desulfhydrase, and 52.1 mU/ml final activity for ACC deaminase. Product was applied directly on top of the seed at a rate of 1 ml per seed, and allowed to dry in the soil before the seed was covered with loose soil. Results are shown in Table 39 below. An average increased height for 2 trials (36 plants each) of approximately 131%, normalized to the control, was observed for the in-furrow treatment using the rice hybrid. This study demonstrates that exogenous in-furrow application of free enzyme ACC deaminase enzyme directly impacts plant growth and vigor by increasing plant height.

TABLE 39

ACC deaminase provided growth promoting properties to rice when applied as an in-furrow treatment

| Treatment | Average Percent (%) Change Plant Height (cm) Normalized to Control, Trial 1 | Average Percent (%) Change Plant Height (cm) Normalized to Control, Trial 2 | Average Percent (%) Change Plant Height (cm) Normalized to Control, Trial 1 & 2 |
|---|---|---|---|
| ACC deaminase (with mutations) (SEQ ID NO: 114) *Bacillus thuringiensis* | 151.7% | 110.0% | 130.9% |

Example 20: ACC Deaminase Free Enzyme Delays Fruit Ripening 1-aminocyclopropane-1-carboxylate deaminase (ACC deaminase) degrades 1-aminocyclopropane-1-carboxylate (ACC), the natural precursor to ethylene ($C_2H_4$), which stimulates and regulates fruit ripening. Ethylene acts at trace levels throughout the life of a plant by stimulating or regulating the ripening of fruit, the opening of flowers, and the abscission or shredding of fruits and leaves. Ethylene is an important natural plant hormone, used in agriculture to force the ripening of fruits (Lin et al., *Recent advances in ethylene research*, JOURNAL OF EXPERIMENTAL BOTANY 60: 3311-3336 (2009)). Ethylene-induced ripening is characterized by an accelerated color shift (accumulation of pigments) and is accompanied by a softening of both the outer skin or peel and the flesh area internal to the outer fruit layer. To determine whether application of free ACC deaminase or D-cysteine sulfhydrase to fruit can delay fruit ripening, both enzymes were applied to unripened mango fruits.

ACC deaminase and D-cysteine sulfhydrase were characterized and had the activities described in Example 19 above. The ACC deaminase sequence having two amino acid mutations described above in Example 19 (SEQ ID NO: 114) and the native the D-cysteine desulfhydrase enzyme (SEQ ID NO: 113) were expressed and provided as free enzymes using the methods described above in Example 19. As noted above in Example 19, the native D-cysteine desulfhydrase enzyme (SEQ ID NO: 113) has both D-cysteine desulfhydrase and ACC deaminase activity.

Unripened mango fruits (commercially available variety, Keitt) were treated with the ACC deaminase or D-cysteine desulfhydrase enzymes and compared to mango fruits that were treated with a water (control) or a filtrate-alone control without enzymes (expression strain without any expressed enzyme). Four fruits were used per treatment group. The outer layer(s) of the mango fruit was completely wetted using 1 mL of the free enzymes (equal to a final protein concentration of 10 μg/mL in filtrate). The estimated ACC deaminase enzyme activity for application to fruit at application for D-cysteine desulfhydrase for this assay was 500 mU/ml, and the activity of the ACC deaminase was 2,124 mU/ml. The two control treatments (filtrate or water alone) were also applied to mango fruits using 1 mL volumes. The mango fruits were then placed in sealed plastic bags overnight. The next day, excess liquid was removed with a paper towel and fruit was blotted dry. Dried mango fruits were then placed in a sealed brown bag (separate bags used for different treatments) to enhance the ripening response for a period of 4 days. The ripening response was scored for softening and color change on a scale of 1-5 with 1 being the least ripened (firm, green or no color change/shift) and 5 being the most ripened (softened, color shift from green to yellow/pink in coloration) with varying degrees of ripening in between these low and high scores (2-4). The ripening responses for both softening and color shift were then combined to result in a "total ripening response" on a scale of 1-10, which was used to judge the effectiveness of the treatment.

Data are provided in Table 40 below and represent average scores for the fruits in each treatment group. Both ACC deaminase and D-cysteine desulfhydrase applied as free enzyme treatments to mango fruit resulted in delayed ripening as compared to the water or filtrate alone control treatments after 4 days. Free enzyme treatments of ACC deaminase or *D*-cysteine desulfhydrase resulted in similar effects in the overall ripening response based on softening and color change when applied to mango. These results demonstrate that both types of enzymes may be used as fruit wash/drench treatments to delay fruit ripening and may be useful for application to other economically important fruits to prevent accelerated ripening or fruit losses from other stresses.

TABLE 40

ACC deaminase and D-cysteine desulfhydrase free enzymes resulted in delayed ripening in mango fruits

| Treatment | Softening | Color Shift | Total Ripening |
|---|---|---|---|
| Water (Control) | 2 | 3 | 5 |
| Filtrate (Control) | 3 | 4 | 7 |
| ACC deaminase | 2 | 2 | 4 |
| D-cysteine desulfhydrase | 2 | 2 | 4 |

Example 21: Glucanases and Phospholipases on Soybean Seed, Field

β-1,4-endoglucanase (*Acidothermus*; SEQ ID NO: 30), β-1,3-D-glucanase (*Helix pomatia*; SEQ ID NO: 126), phosphatidylinositol-specific phospholipase C (*Bacillus cereus*; SEQ ID NO:116), and phosphatidylcholine-specific phospholipase C (*Bacillus cereus*; SEQ ID NO: 115) were applied as free enzymes to soybean seed (BECK'S 294 NR). Free enzymes were diluted in water to the concentrations (μU/seed or mU/seed) listed in Table 41 below. The unit (U) of the endoglucanase or phospholipase enzyme activity was determined by the amount of enzyme that is required to breakdown 1 μmol/min/mL of substrate (1 U=1 μmol substrate/min) at ideal temperature and conditions. Each seed received the amount of enzyme solution required for the final activity for the treatments (1 μL/seed) and was mixed with seed treatments metalaxyl and clothianidin. Seed was dried completely and then planted in the field to approximate standard practices for planting depth and row spacing (1.5 to 2 inches (3.8 cm to 5 cm) deep to ensure normal root development and on average 150,000 plants per acre (370, 658 plants per hectare) with row widths of 30 inches (76.2 cm) and seed spacing of approximately 7 to 8 seeds per foot (26 seeds per meter)). Fertilizer was applied as recommended by soil tests. Herbicides were applied for weed control and supplemented with cultivation when necessary.

Three replicate trials consisting of 600 seeds each were conducted. Soybean yield was measured at approximately six months after sowing and is reported in Table 41 below as the absolute change in bushels/acre (Bu/Ac) or metric tonnes/hectare (MT/ha) over control (water only) and as a percentage of yield normalized to the control. Applications of endoglucanases or phospholipases (β-1,4-endoglucanase (*Acidothermus*), β-1,3-D-glucanase (*Helix pomatia*), phosphatidylinositol-specific phospholipase C (*Bacillus cereus*), and phosphatidylcholine-specific phospholipase C (*Bacillus cereus*)) as seed treatments all resulted in increased yield compared to the control (water-treated) seed. Of the enzymes tested, phosphatidylcholine-specific phospholipase C (*Bacillus cereus*) provided the greatest increase in yield over the control, resulting in a more than 8 Bu/Ac (more than 0.5 MT/ha) increase or a 145% yield gain over the non-treated control seed (See Table 41).

TABLE 41

Glucanases and phospholipases applied as a seed treatment to increase yield in soybean

| Seed Treatment | Enzyme Activity/Seed | Absolute change in bushels/acre (Bu/Ac) [MT/ha] over control (+/−) | Yield (Normalized to Control) |
|---|---|---|---|
| Water Control | 0 μU/seed | 0.00 | 100.00% |
| β-1,4-Endoglucanase (*Acidothermus*) | 600 μU/seed | +1.44 [+0.10 MT/ha] | 123% |
| β-1,3-D-glucanase (*Helix pomatia*) | 600 μU/seed | +5.22 [0.35 MT/ha] | 123% |
| Phosphatidylinositol Phospholipase C (*Bacillus cereus*) | 100 mU/seed | +3.25 [0.22 MT/ha] | 115% |
| Phosphatidylcholine Phospholipase C (*Bacillus cereus*) | 2.5 mU/seed | +8.11 [0.55 MT/ha] | 145% |

Example 22: Free Phospholipases on Corn Seed, Greenhouse

Phosphatidylcholine-specific phospholipase C (PLC) from *Bacillus cereus* (SEQ ID NO: 115) was diluted in water to concentrations of 20 mU/seed to 800 mU/seed activity (as listed in Table 42 below). The unit of PLC enzyme activity was determined by the amount of enzyme that is required to breakdown 1 μmol/min/mL of substrate (1 U=1 μmol substrate/min) at ideal temperature and conditions.

Two replicate trials consisting of eighteen seeds each of a commercial hybrid (BECK'S 5828 YH corn were placed in 50 mL conical tubes. Each conical tube was vortexed and 18 μL of enzyme solution was added to each tube to achieve a final enzyme concentration of 20, 50, 100, 200, 400, 600, or 800 mU activity of PLC applied per seed. The conical tubes were vortexed again for 20 seconds to gain an even coating on each seed. Seeds were dried for 5 minutes and then planted into 39.7 $cm^3$ pots containing top soil at a depth of 2.54 cm, with 2 seeds per pot. After planting, 50 mL of room temperature water was added to each pot to allow for germination. The pots were kept in an artificial lighted growth room receiving a light level of approximately 300 μmol $m^{-2}$ $s^{-1}$ for a 13/11 light/day cycle and a 21° C. day/15° C. night temperature range.

Plant height was averaged over 2 replicated trials using 18 plants per trial per treatment group. The difference in plant height after seed treatment using the PLC enzyme was normalized to the control plants that received only a water treatment. Changes in plant height are represented in Table 42 as a percentage of the average plant height normalized to the control and reported with the standard deviations (STDEV) for the 2 trials. As can be seen in Table 42, PLC enzyme activities of 50 mU/seed to 600 mU/seed resulted in significant increases in height (cm) of corn plants when compared and normalized to the water (non-enzyme) treated control plants.

TABLE 42

Phospholipase C (PLC) applied as a seed treatment to corn to promote growth

| Seed Treatment | Percent Plant height (Normalized to Control) Trial 1 | Percent Plant height (Normalized to Control) Trial 2 | Percent Plant height (Normalized to Control) Average (STDEV) |
|---|---|---|---|
| Control | 100.0% | 100.0% | 100% (2.07) |
| PLC 20 mU/seed | 98.9% | 96.6% | 97.8% (1.70) |
| PLC 50 mU/seed | 113.7% | 106.2% | 110% (1.83) |
| PLC 100 mU/seed | 116.0% | 100.5% | 108.3% (1.59) |
| PLC 200 mU/seed | 112.1% | 112.5% | 112.3% (1.83) |
| PLC 400 mU/seed | 106.2% | 108.3% | 107.3% (1.60) |
| PLC 600 mU/seed | 98.6% | 106.7% | 103.7% (1.80) |
| PLC 800 mU/seed | 99.7 | 89.4 | 94.6% (1.71) |

In a second experiment, titrations of Phospholipase D required to achieve optimal growth were determined. Phospholipase D (PLD) from *Acidovorax avenae* (SEQ ID NO: 117) was diluted in water to concentrations of 20 mU/seed to 800 mU/seed. The unit of PLD enzyme activity was determined by the amount of enzyme that is required to breakdown 1 μmol/min/mL of substrate (1 U=1 μmol substrate/min) at ideal temperature and conditions. Two replicate trials were conducted using 18 plants per trial per enzyme activity level. For each treatment group in both trials, 18 seeds of a commercial corn hybrid (BECK'S 5828 YH) were placed in 50 mL conical tubes. Each conical tube was vortexed and 18 μL of enzyme solution was added to each tube to achieve a final enzyme concentration of 20, 50, 100, 200, 400, 600, or 800 mU per seed of PLD. The titrations of PLD ranging from 20 mU/seed to 800 mU/seed were applied to the corn seed using 1 μl volumes to determine the optimal PLD seed treatment to promote growth. The conical tubes were vortexed again for 20 seconds to gain an even coating on each seed. Seeds were dried for 5 minutes and then plated into 39.7 $cm^3$ pots containing top soil at a depth of 2.54 cm, with 2 seeds per pot. After planting, 50 mL of room temperature water was added to each pot to allow for germination. The pots were kept in an artificial lighted growth room receiving a light level of approximately 300 μmol $m^{-2}$ $s^{-1}$ for a 13/11 light/day cycle and a 21° C. day/15° C. night temperature range.

Plant height (in cm) was averaged over 2 replicated trials using 18 plants per trial per treatment. The height of plants generated from PLD treated seeds was normalized to control and represented as a percentage of the average plant height normalized to non-enzyme treated (water) control plants and is reported in Table 43 below with the standard deviations (STDEV) for the 2 trials.

As can be seen in Table 43, phospholipase D applied to corn seed had a positive effect on plant growth at every enzyme activity level tested. In each instance, plants treated with PLD as a seed had an increased height compared to control plants.

TABLE 43

Phospholipase D (PLD) applied as a seed treatment to corn to promote growth

| Seed Treatment | Percent Plant height (Normalized to Control) Trial 1 | Percent Plant height (Normalized to Control) Trial 2 | Percent Plant height (Normalized to Control) Average (STDEV) |
|---|---|---|---|
| Control | 100.0% | 100.0% | 100% (1.40) |
| PLD 20 mU/seed | 97.5% | 110.6% | 104.1% (1.18) |
| PLD 50 mU/seed | 101.7% | 104.4% | 103.1% (0.92) |
| PLD 100 mU/seed | 99.6% | 103.0% | 101.3% (1.05) |
| PLD 200 mU/seed | 101.5% | 104.1% | 102.8% (1.03) |
| PLD 400 mU/seed | 99.6.2% | 106.2% | 102.9% (1.14) |
| PLD 600 mU/seed | 103.1% | 98.0% | 100.6% (1.16) |
| PLD 800 mU/seed | 101.5% | 102.0% | 101.8% (0.89) |

Example 23: Free Phospholipases and Xyloglucanases on Corn and Soybean, Foliar, Greenhouse Free xyloglucanase (SEQ ID NO: 125; *Paenibacillus* sp.) and phospholipase D (SEQ ID NO: 117*; Acidovorax avenae*) were applied as foliar treatments using the enzyme concentrations as described in Table 44 (below) to 2 week old hybrid corn (BECK'S 5828 YH) with 0.1% non-ionic surfactant (ALLIGARE SURFACE) using a spray bottle and delivering 10 ml/plant. The average plant height was normalized to the control plants that received a foliar application of water plus surfactant alone. Both the xyloglucanase and phospholipase D treatments applied as a foliar spray to corn plants resulted in increased plant height compared to the control plants (Table 44). Xyloglucanase applied at a foliar use rate providing 600 μU/ml and phospholipase D applied at a foliar use rate providing 200 μU/ml to corn plants exhibited the greatest increases in plant growth resulting in increases of 106.5% and 111.1%, respectively, over the control plants.

TABLE 44

Foliar treatment of corn using xyloglucanase and phospholipase D as free enzymes to promote growth in corn plants

| Foliar Treatment | Enzyme Activity Applied | Average Percent (%) Change in Plant Height as Normalized to Control |
|---|---|---|
| Water + Surfactant (control) | | 100% |
| Xyloglucanase (*Paenibacillus* sp.) + Surfactant | 600 μU/ml | 106.5% |
| Xyloglucanase (*Paenibacillus* sp.) + Surfactant | 3000 μU/ml | 103.1% |
| Phospholipase D (*Acidovorax*) + Surfactant | 200 μU/ml | 111.1% |
| Phospholipase D (*Acidovorax*) + Surfactant | 1000 μU/ml | 107.3% |

In another experiment, phospholipase D (PLD) from *Acidovorax* was applied as a seed treatment to soybean seed (BECK'S 297NR) using 1 μL volumes equivalent to 600 mU/seed and 800 mU/seed final activities provided per each seed (these activities were selected for testing in soy based on the titrations described above in Example 22 for corn). The PLD activities of 600 mU/seed and 800 mU/seed were applied as a seed treatment to soybean seed and resulted in positive impacts on plant growth rate.

Treated seeds were planted in and allowed to grow in a greenhouse. When plants had reached the V2 to V3 stage of development, their total biomass, root biomass, and nodulation counts were measured. The V2 to V3 stage is the earliest stage of development for nodule formation. Nodule initiation begins in soybean seedlings as soon as root hairs are present on primary or branch roots. Nitrogen fixation begins about 2 to 3 weeks after initial rhizobial infection. Soybean plants had fully formed first trifoliate leaves at the V1 to V2 stage and were measured in the peak estimated for nitrogen fixation. Effective nodulation of soybean roots result in higher yields and higher quality seed production, protein, and oil per acre.

Two independent experiments were run (18 replicate plants per trial per treatment group). Data from PLD-treated plants were normalized to control plants grown from water-treated control seeds.

PLD applied as a seed treatment using 800 mU per soybean seed resulted in significant increases in both total biomass and root biomass as compared to the plants grown from water-treated control seeds that did not receive the PLD free enzyme (Table 45).

PLD treatment also increased nodulation counts on plant roots. Both of the seed treatments, with either 600 mU or 800 mU of PLD activity, resulted in nodulation increases compared to untreated controls, with the 800 mU treatment almost doubling the number of nodules on the roots of soybean plants.

TABLE 45

Biomass effects of phospholipase D treatment as a soybean seed treatment

| Seed Treatment | Enzyme Activity/ Seed | Total Biomass (Normalized to control) | Root Biomass (Normalized to Control) | Nodulation (Normalized to Control) |
|---|---|---|---|---|
| Phospholipase D *Acidovorax* | 600 mU/seed | 101.7% | 99.0% | 121.4% |
| Phospholipase D *Acidovorax* | 800 mU/seed | 115.7% | 125.2% | 201.9% |

Example 24: Free Enzymes on Corn, Field

Free xyloglucanase, xylanase, chitosanase, lichenase, xylosidase, protease, and lipase enzymes were diluted in water to the activity levels listed in Table 46 below. Hybrid corn (BECK'S 5828 YH) seeds were treated with 1 μL free enzyme solution per seed to achieve the activities per seed (1 U=1 μmol substrate/min) as shown in Table 46 below. Seeds were dried completely and planted in 4 replicate 24' (7.3 m) rows per treatment with seed spacing of 1.72 seeds/foot/row (5.64 seeds/meter/row). Field seedbeds at each location were prepared using conventional or conservation tillage methods for corn plantings. Herbicides were applied for weed control and supplemented with cultivation when necessary. Each trial was repeated 4 times. Seed treatment was applied to all treatments, which included prothioconazole, penflufen, metalaxyl, and clothianidin.

After harvest, the absolute change in bushels per acre (Bu/Ac) or metric tonnes per hectare was measured for each free enzyme treatment and normalized to the yield of the non-treated control (water) plants (Table 46, below). Control corn seed averaged 162 Bu/Ac (10.17 MT/ha). Seed treatments with lichenase, protease, or lipase resulted in the greatest increases in corn yield over the control plants.

Treatment with lichenase showed the greatest yield increases compared to control plants with an average increase of 22 Bu/Ac (1.39 MT/ha), which equates to a 114% increase when normalized to corn control plants.

TABLE 46

Yield increase using free enzymes applied on corn

| Seed Treatment: Corn | Enzyme Activity/Seed | Absolute Change in bushels/ acre (Bu/Ac) [MT/ha] over control (+/−) | Yield (Normalized to Control) |
|---|---|---|---|
| Water | 0 µU/seed | — | 100.00% |
| Xyloglucanase (*Paenibacillus* sp.) SEQ ID NO: 125 | 600 µU/seed | +1.09 [+0.07 MT/ha] | 100.67% |
| β-xylanase (*Bacillus stearothermophilus*) SEQ ID NO: 25 | 500 µU/seed | −6.84 [−0.43 MT/ha] | 95.78% |
| Chitosanase (*Streptomyces* species N174) SEQ ID NO: 124_ | 150 µU/seed | +7.57 [+0.48 MT/ha] | 104.67% |
| Lichenase (*Bacillus subtillis*) SEQ ID NO: 43 | 600 µU/seed | +22.17 [+1.39 MT/ha] | 113.67% |
| Protease A (*Aspergillus saitoi*) SEQ ID NO: 127 | 360 µU/seed | +14.64 [+0.92 MT/ha] | 109.02% |
| Lipase (*Burkholderia cepacia*) SEQ ID NO: 118 | 20 µU/seed | +9.50 [+0.60 MT/ha] | 105.85% |

In a second experiment, free enzymes (endoglucanase, exoglucanase, chitosanase, protease, and phytase) were applied via foliar application to corn (BECK'S Hybrid 5140 HR) at 4 locations across the Midwest at the V5-V8 stage of development, which has the HERCULEX rootworm trait and glyphosate resistance traits. To allow for even coating of plant leaves, all enzyme treatments and the control were additionally treated with a non-ionic surfactant (ALLIGARE SURFACE) provided at a final concentration of 0.1%. Absolute change in bushels/acre (Bu/Ac) (and equivalent values in MT/ha) is reported over the control plants and also reported in yield as normalized to the control plants ("water/surfactant control") (Table 47). Results from the foliar treatments using free enzymes are reported as the absolute yield Bu/Ac (or MT/ha) and the absolute change in yield for the adjusted yields (Bu/Ac or MT/ha) normalized to the control plants comparison across the 4 replications (Table 47). There were positive yield increases in the enzyme-treated as compared to the control (plants treated with water and surfactant only) plants. Phytase applied as a foliar treatment resulted in the greatest overall increase in yield (~24 Bu/Ac (~1.51 MT/ha) absolute yield change over control).

TABLE 47

Yield increase using free enzymes applied as a foliar treatment on corn

| Treatment | Absolute Yield Bu/Ac [MT/ha] | Absolute Yield Change (Bu/Ac) [MT/ha] Normalized to Control |
|---|---|---|
| Water/Surfactant Control | 177.42 [11.14 MT/ha] | — |
| β-1,4-endoglucanase (*Acidothermus*) SEQ ID NO: 30 | 190.35 [11.95 MT/ha] | 12.93 [0.81 MT/ha] |
| β-1,3-exoglucanase (*Aspergillis oryzae*) SEQ ID NO: 41 | 186.36 [11.70 MT/ha] | 8.94 [0.56 MT/ha] |
| Chitosanase (*Streptomyces* species N174) SEQ ID NO: 124 | 204.77 [12.85 MT/ha] | 27.34 [1.72 MT/ha] |
| Protease A (*Aspergillus saitoi*) SEQ ID NO: 127 | 189.35 [11.89 MT/ha] | 12.29 [0.77 MT/ha] |
| Phytase (*Triticum aestivum*) SEQ ID NOs: 132, 133, 134 | 201.08 [12.62 MT/ha] | 23.66 [1.49 MT/ha] |

Example 25: Lipases on Corn Seed, Greenhouse

An experiment was conducted to determine if lipases applied as a seed treatment to corn also promoted plant growth. Lipase (*Pseudomonas fluorescens*; SEQ ID NO: 119) was diluted in water to concentrations which provided an activity of 3000 µU and 6000 µU lipase per seed. Lipase was applied using 3000 µU/seed and 6000 µU/seed of activity to corn seed (BECK'S Corn Variety 5828 YH) using 1 µL of enzyme per seed to achieve the activities as reported per seed. Seeds were dried for 5 minutes and then planted in 39.7 $cm^3$ pots containing top soil at a depth of 2.54 cm, with 2 seeds per pot. After planting, 50 mL of room temperature water was added to each pot to allow for germination. The pots were kept in an artificial lighted growth room receiving a light level of approximately 300 µmol $m^{-2}$ $s^{-1}$ for a 13/11 light/day cycle and a 21° C. day/15° C. night temperature range. At the end of 2 weeks, when the plants had all reached the V2 to V3 stage of development, the height of the corn plants treated with lipase were measured and normalized to the height of the control plants that were seed treated with water only.

The experiment was replicated twice with 18 plants per treatment group (and 3 replicates per treatment group) and the values averaged across experiments and are reported in Table 48 together with standard deviations (STDEV). Lipase applied as a free enzyme using 3000 µU and 6000 µU of activity per seed resulted in an average increase in plant height of approximately 106% and 103% respectively.

TABLE 48

| Height effects of lipase treatment as a corn seed treatment | | | |
|---|---|---|---|
| Seed Treatment | Percent Plant height (Normalized to Control) Trial 1 | Percent Plant height (Normalized to Control) Trial 2 | Percent Plant height (Normalized to Control) Average (STDEV) |
| Control (water) | 100.0% | 100.0% | 100% (1.80) |
| Lipase (*Pseudomonas*) 3000 μU/seed | 107.6% | 103.6% | 105.6% (1.67) |
| Lipase (*Pseudomonas*) 6000 μU/seed | 103.0% | 101.8% | 102.4% (1.54) |

Example 26: Lipase or Phospholipase on Corn, Greenhouse in-Furrow

Lipase (*Burkholderia cepacia*) applied as an in-furrow treatment was used to determine if application of lipase as a free enzyme to the area surrounding a corn seed would result in early stage positive growth benefits to a corn plant. Lipase enzyme (*Burkholderia cepacia*, SEQ ID NO:118) was diluted in water to the activity levels listed in Table 49 below. Corn seeds (BECK'S 6626 RR) were planted into 39.7 $cm^3$ pots containing top soil at a depth of 2.54 cm, with 2 seeds per pot. After planting but prior to covering the seed, 1 μL volumes of lipase enzyme with activities ranging from 2 μU to 200 μU were applied per in-furrow area surrounding a seed. A subset of seeds were treated instead with β-1,4-endoglucanase (*Acidothermus cellulolyticus*; SEQ ID NO: 30) applied at an activity of 1000 μU in furrow to the area surrounding the seed. The pots were kept in an artificial lighted growth room receiving a light level of approximately 300 μmol $m^{-2}$ $s^{-1}$ for a 13/11 light/day cycle and a 21° C. day/15° C. night temperature range. After approximately two weeks, when the plants had reached the V2 to V3 stage of development, their height was measured and normalized to control plants that received only water. Plants treated with lipase were further compared to those receiving β-1,4-endoglucanase (*Acidothermus*).

The experiment was repeated for a total of two trials (18 plants per trial per treatment group). The average plant height for the treatments across both trials, normalized to control is reported with standard deviations (STDEV) (Table 49). Lipase applied using 20 μU per seed as an in-furrow treatment to corn resulted in the greatest increase in plant height compared to the other lipase activities applied as in-furrow treatments. The β-1,4-endoglucanase applied as a free enzyme treatment in-furrow also resulted in positive changes in plant height and had growth promoting effects reported on corn plants. Lipase applied at 20 μU per area (per ml of volume in water) surrounding a seed was comparable to the in-furrow treated seed that received the β-1,4-endoglucanase.

TABLE 49

| Titration of lipase and effect of β-1,4-Endoglucanase as applied as an in-furrow treatment to the area surrounding a corn seed to promote growth | |
|---|---|
| Seed Treatment | Percent Plant height (Normalized to Control) Average (STDEV) |
| Control (Water) | 100% (1.15) |
| Lipase 2 μU/seed area | 100.5% (1.05) |
| Lipase 5 μU/seed area | 98.9% (1.35) |
| Lipase 10 μU/seed area | 100.4% (1.15) |
| Lipase 20 μU/seed area | 103.9% (1.36) |
| Lipase 50 μU/seed area | 100.1% (0.97) |
| Lipase 200 μU/seed area | 101.0% (1.14) |
| β-1,4-Endoglucanase 1000 μU/seed area | 103.8% (1.25) |

In a second experiment, phosphatidylcholine-specific phospholipase C from *Bacillus cereus* (SEQ ID NO: 115) was applied with a fertilizer (SF) containing 12% ammoniacal nitrogen and 58% available phosphate (derived from monoammonium phosphate) using direct in-furrow methods as described above to corn seed (BECK'S 5828 YH). The enzyme was applied at an application rate of 8 Fl oz/Ac (584.2 ml/hectare) or approximately 1200 mU to the area surrounding a seed. This treatment resulted in an average increase in plant height averaged over 3 replicated trials of 105% as normalized to the control which used water and the fertilizer treatment alone. Results are shown in Table 50 below.

TABLE 50

| Plant height using an in-furrow treatment using free enzyme phospholipase C for corn | |
|---|---|
| Treatment | Average percent change in plant height as normalized to the control |
| Water Control + SF | 100% |
| Phospholipase CF (*Bacillus cereus*) + SF | 105% |

Example 27: Acid Phosphatase on Squash and Corn, in Furrow

The effects of acid phosphatase (alone or in combination with lipase, β-xylanase, pectoylase, mannanase, lichenase, or xylanase) on plant growth was tested. Free enzymes comprising acid phosphatase (*Triticum aestivum*, a mixture of two different isoforms with the sequences provided herein by SEQ ID NOs. 130 and 131, commercially available from Sigma-Aldrich, St. Louis Mo., as product number P3627), alone or in combination with lipase (*Pseudomonas fluorescens*, SEQ ID NO: 119), β-xylanase (*Neocallimastix patriciarum*, SEQ ID NO: 122), pectolyase (*Aspergillus*, SEQ ID NO: 129), mannanase (*Bacillus* sp., SEQ ID NO: 128), lichenase (*Bacillus subtilis*, SEQ ID NO: 43) or xylanase (*Thermomyces lanuginosus*, SEQ ID NO: 121) were applied at the activity levels listed in Table 51 using direct in-furrow applications to the area surrounding squash seeds using the same methods as described above in Example 26 (Ambassador hybrid squash, commercially available from Park Seed as product 05298). The enzyme treatments were provided to squash seeds containing a seed treatment (Thiram) and provided together with fertilizer (SF) containing 12% ammoniacal nitrogen and 58% available phosphate. The in-furrow enzyme and fertilizer alone treatments were applied using the application use rates listed as units of activity per ml of volume in Table 51 below, and delivered at 1 ml per seed to the soil around the seed. Plant height was determined for 2 trials with 18 plants measured per each trial per treatment. Data are reported in Table 51, below and provide the percent change in plant height for squash seeds receiving the in-furrow free enzyme treatment compared to the control seed (fertilizer alone control). The acid phosphatase free enzyme treatment alone exhibited on average a 49.6% increase in plant height as compared to the control plants. Squash seed that received the free enzyme in-furrow treatment comprising acid phosphatase combined with enzymes lipase, β-xylanase, pectolyase, mannanase, lichenase or xylanase had increased plant height compared to the water and fertilizer treated squash. In-furrow treatment using the acid phosphatase enzyme alone resulted in the greatest average percent increase in overall growth as represented by the increase in plant height compared to combining acid phosphatase with other enzymes (lipase, β-xylanase, pectolyase, mannanase, lichenase, or xylanase).

In another experiment, free enzymes comprising acid phosphatase (*Triticum aestivum*, a mixture of two isoforms with the sequences provided herein by SEQ ID NOs. 130 and 131), phosphatidylcholine-specific phospholipase C (*Bacillus cereus*; SEQ ID NO: 115), or β-1,4-endoglucanase (*Acidothermus cellulolyticus*; SEQ ID NO: 30) were applied using direct in-furrow treatment to the area surrounding hybrid corn seed (BECK'S 5828 YH) at the rates listed in Table 52 below. The in-furrow treatments were provided together with a hormone biostimulant (CYTOPLEX, commercially available from Miller Chemical & Fertilizer, LLC) that contains a sea plant extract, kinetin, gibberellic acid and indole-3-butyric acid at 2 fl oz/Ac (146.2 ml/hectare). Plant height was determined for 2 trials with 18 plants measured in each trial per treatment group. The data, in Table 52 below, are reported as the percent change in plant height for corn seeds receiving the in-furrow treatment using the free enzymes compared to the control seeds (hormone biostimulant alone). The acid phosphatase free enzyme treatment exhibited on average a 16% and 8% increase in plant height as compared to the control plants for the 300 mU/ml and 600 mU/ml use rates, respectively, applied in-furrow per seed area. Plant height in corn grown from in-furrow treated seed with phospholipase C and β-1,4-endoglucanase also resulted in increases in plant height over the seed treated with the hormone biostimulant alone. The 300 mU/ml use rate applied for each of the free enzymes: acid phosphatase, phospholipase C and β-1,4-endoglucanase resulted in approximately 2-fold increases in plant height over the 600 mU/ml use rate applied in-furrow per seed area. Each of the three enzymes combined with the hormone biostimulant treatments had increased plant height over the hormone biostimulant alone controls.

TABLE 51

Change in plant height with an in-furrow treatment for squash applied using an application of acid phosphatase and free enzymes

| In-Furrow Treatment (seed area = 1 ml/seed) | Enzyme Activity | Average: Percent Change in Plant Height compared to Control Squash (water & SF alone) |
|---|---|---|
| Fertilizer (SF)/seed area | — | — |
| Acid Phosphatase (AP) *Triticum* + SF | 35 μU (AP)/seed area | +49.6% |
| Acid Phosphatase (AP) *Triticum* + Lipase (LP) *Pseudomonas* + SF | 35 μU (AP) + 10 mU (LP)/seed area | +28.1% |
| Acid Phosphatase (AP) *Triticum* + β-Xylanase (XL) *Neocallimastix* + SF | 35 μU (AP) + 1500 mU (XL)/seed area | +17.0% |
| Acid Phosphatase (AP) *Triticum* + Pectolyase (PL) *Aspergillus* + SF | 35 μU (AP) + 30 mU (XL)/seed area | +21.9% |
| Acid Phosphatase (AP) *Triticum* + Mannanase (MN) *Bacillus* + SF | 35 μU (AP) + 300 mU (MN)/seed area | +18.3% |
| Acid Phosphatase (AP) *Triticum* + Lichenase (LN) *Bacillus* + SF | 35 μU (AP) + 600 mU (LN)/seed area | +14.1% |
| Acid Phosphatase (AP) *Triticum* + Xylanase (XL) *Thermomyces* + SF | 35 μU (AP) + 1500 mU (XL)/seed area | +40% |

TABLE 52

Changes in plant height using an in-furrow treatment for corn applied using an application of acid phosphatase, phospholipase C and β-1,4-endoglucanase in combination with a biostimulant

| In-Furrow Treatment | Use rate (seed area = 1 ml volume per seed) | Average: Percent Change in Plant Height compared to Control Corn with no enzyme application |
|---|---|---|
| Acid Phosphatase (*Triticum aestivum*) + Biostimulant | 300 mU/seed area | +16% |
| Acid Phosphatase (*Triticum aestivum*) + Biostimulant | 600 mU/seed area | +8% |
| Phospholipase C (*Bacillus cereus*) + Biostimulant | 300 mU/seed area | +17% |
| Phospholipase C (*Bacillus cereus*) + Biostimulant | 600 mU/seed area | +9.5% |
| β-1,4-Endoglucanase (*Acidothermus*) + Biostimulant | 300 mU/seed area | +16% |
| β-1,4-Endoglucanase (*Acidothermus*) + Biostimulant | 600 mU/seed area | +7% |

Free enzymes comprising acid phosphatase (*Triticum aestivum*, a mixture of two different isoforms with the sequences provided herein by SEQ ID NOs. 130 and 131) or phosphatidylcholine-specific phospholipase C (*Bacillus cereus*; SEQ ID NO: 115) were applied using direct in-furrow applications to the area surrounding hybrid corn seed (BECK'S 5828 YH). In-furrow treatment with the enzymes was combined with a hormone biostimulant (CYTOPLEX, commercially available from Miller Chemical & Fertilizer, LLC) treatment containing a sea plant extract, kinetin, gibberellic acid and indole-3-butyric acid. The in-furrow enzyme treatments were applied using application use rates of 2, 4 and 8 Fl. oz per seed area (59.14, 118.29, and 236.59 ml per seed area). Plant height was determined for 2 trials with 18 plants measured per each trial. The data are reported in Table 53 below as the percent change in plant height for corn seeds receiving the in-furrow treatment using the acid phosphatase or phospholipase C enzymes compared to the control seeds (biostimulant alone). The acid phosphatase free enzyme treatment increased plant height as compared to the control plants for the use rates of 2, 4 and 8 Fl. oz (59.14, 118.29, and 236.59 ml) applied per seed area (approximately 150 mU/ml, 300 mU/ml and 600 mU/ml per seed area), with 4 Fl. oz (118.29 ml) resulting in an increase of 8.3% over the control plants for the 300 mU/ml use rate. In furrow treatment of corn grown with phospholipase C resulted in increased plant height compared to corn grown using the biostimulant alone control when applied using 2 and 4 Fl. oz (59.14 and 118.29 ml) use rate per seed area (approximately equal to 150 and 300 mU per seed area, respectively). The 4 Fl. oz (118.29 ml) use rate was preferable for plant growth, resulting in an 11.4% increase in plant height over the biostimulant alone control. The biostimulant only control resulted in corn plants with slower growth rates as compared to treatment with water only.

TABLE 53

Changes in plant height using an in-furrow treatment for corn applied using an application of acid phosphatase or phospholipase C, combined with a biostimulant

| In-Furrow Treatment | Use rate (seed area = 1 ml volume per seed) | Average: Percent Change in Plant Height as over Control Corn (water & BS alone) |
|---|---|---|
| Water Control | — | — |
| Biostimulant (BS) | 2 Fl. oz/seed area (59.14 ml/seed area) | −4.9% |
| Acid Phosphatase (*Triticum aestivum*) + Biostimulant | 2 Fl. oz/seed area (59.14 ml/seed area) | +2.3% |
| Acid Phosphatase (*Triticum aestivum*) + Biostimulant | 4 Fl. oz/seed area (118.29 ml/seed area) | +8.3% |
| Acid Phosphatase (*Triticum aestivum*) + Biostimulant | 8 Fl. oz/seed area (236.59 ml/seed area) | +5.5% |
| Phospholipase C (*Bacillus cereus*) + Biostimulant | 2 Fl. oz/seed area (59.14 ml/seed area) | +5.5% |
| Phospholipase C (*Bacillus cereus*) + Biostimulant | 4 Fl. oz/seed area (118.29 ml/seed area) | +11.4% |
| Phospholipase C (*Bacillus cereus*) + Biostimulant | 8 Fl. oz/seed area (236.59 ml/seed area) | −0.1% |

Example 28: Protease or Xylosidase on Corn, in Furrow

Protease A (*Aspergillus saitoi*; SEQ ID NO: 127) and xylosidase (*Bacillus pumilus*; SEQ ID NO: 123) were applied to corn as an in-furrow free enzyme treatments, and effects on plant height and growth were examined. For both the protease A and xylosidase enzymes, similar methods were used as described above in Example 26 for the lipase in-furrow treatments with corn. In-furrow treatments (1 ml per seed) were applied to the area surrounding the corn seed (BECK'S 5828 YH) after planting of the corn but before covering the seed with loose soil. In-furrow treatments using protease A and xylosidase were delivered in 1 µL volumes equivalent to 428 µU/seed area of activity for protease and 714 µU/seed area (per ml) of activity for xylosidase. Both Protease A and xylosidase resulted in increased plant height when normalized to control plants (water only treatment). Results are shown in Table 54 below.

TABLE 54

Plant height using an in-furrow treatment for corn treated with protease A or xylosidase

| Treatment | Enzyme Activity/ml | Percent change in plant height (Normalized to Control) Average |
|---|---|---|
| Protease A (*Aspergillus saitoi*) | 714 µU | 108.4% |
| Xylosidase (*Bacillus pumilus*) | 428 µU | 112.3% |

Example 29: Xylanase or Xylosidase on Corn and Soybean Seed, Greenhouse

Free enzymes were applied as seed treatments to corn and soybean. Xylanases derived from *Thermomyces lanuginosus* (SEQ ID NO: 121) or *Neocallimastix patriciarum* (SEQ ID NO: 122) and xylosidase derived from *Bacillus pumilus* (SEQ ID NO: 123) were applied to corn (BECK'S 5828 NR) and soybean (BECK'S 297 NR) seeds in conical tubes using 2 µL volumes equivalent to activities of 600 µU per seed for the xylanases (*Thermomyces lanuginosus; Neocallimastix patriciarum*) and 714 µU per seed for the xylosidase (*Bacillus pumilus*). Two separate sets of corn and soybean seeds were treated with β-1,4-endoglucanase (*Acidothermus cellulolyticus*; SEQ ID NO: 30) at 1000 µU activity/seed. Seeds were allowed to dry after coating and planted in commercial topsoil as described above in Example 1. At the end of 14 days, the average percent change in plant height compared to water controls was determined for two replicated trials for corn and one trial for soybean with 12 plants per trial. Changes in average plant height (cm) were compared to the control plants as well as corn and soybean plants grown from seeds treated with β-1,4-endoglucanase (*Acidothermus*) which resulted in an increase in plant growth when applied as a seed treatment to both corn and soybean. Average percent change in plant height as normalized to water control treatments are reported in Table 55 below with the standard deviation from mean average (STDEV) for the 2 trials conducted in corn and soybean.

Xylanases (*Thermomyces lanuginosus; Neocallimastix patriciarum*) applied as a seed treatment to both corn and soybean seed at activities of 600 µU/seed resulted in increased height in plants as compared to the control plants. Xylanase (*Thermomyces lanuginosus*) treatment applied to corn seed resulted in, on average, a 9% increase in plant height for corn and an average 12% increase for soybean. β-xylanase (*Neocallimastix patriciarum*) treatment applied to corn seed resulted in on average a 4% increase in plant height for corn. Xylosidase (*Bacillus pumilus*) applied as a seed treatment to corn and soybean seed at 714 µU/seed resulted in an approximate 9-11% increase for both corn and soybean plants compared to the control plants. Positive impact on plant height for the xylanase and xylosidase treatments applied as free enzyme treatments to corn and soybean seed was comparable or better than β-1,4-endoglucanase (*Acidothermus*) for both the corn and soybean plants. After two weeks, plant height was measured and normalized to plants that received only fertilizer treatment.

TABLE 55

Corn and soybean treated with endo-1,4-β-xylanase, endoglucanase, and xylosidase as seed treatments

| Seed Treatment | Corn: Average Percent change in Plant height (Normalized to Control) (STDEV) | Soybean: Average Percent change in plant height (Normalized to Control) (STDEV) |
|---|---|---|
| Water Control | 100% | 100% |
| Xylanase (*Thermomyces lanuginosus*) | 108.8% (1.39) | 112.0% (1.31) |
| β-xylanase (*Neocallimastix patriciarum*) | 104.3% (1.42) | 100.3% (0.37) |
| Xylosidase (*Bacillus pumilus*) | 108.7% (1.18) | 111.1% (1.32) |
| β-1,4-Endoglucanase (*Acidothennus*) | 109.6% (1.46) | 104.0% (1.39) |

Example 30: Free Enzymes and Titration of Activities for Seed Treatment and in-Furrow Treatment on Corn and Soybean Lichenase (*Bacillus subtilis*, commercially available from Megazyme as product E-LICHN; SEQ ID NO: 43), xyloglucanase (*Paenibacillus* species, commercially available from Megazyme, as product E-XEGP; SEQ ID NO: 125), β-xylanase (*Bacillus stearothermophilus*, commercially available from Megazyme as product E-XYNBS; SEQ ID NO: 25), mannanase (*Bacillus* species, commercially available from Megazyme as product E-BMABS; SEQ ID NO: 128), lipase (*Burkholderia stearothermophilus*, commercially available from Sigma-Aldrich, as product 534641; SEQ ID NO: 120), pectolyase (*Aspergillus japonicus*, commercially available from Sigma-Aldrich, as product P3026; SEQ ID NO: 129) and β-1,4-endoglucanase (*Acidothermus cellulolyticus*, commercially available from Sigma-Aldrich, as product E2164; SEQ ID NO: 30) were each diluted in water to achieve the activity levels as listed below in Table 56. Aliquots (1 µL) of these preparations were used to treat seeds in the experiments described below in this example and in Example 31.

TABLE 56

Titrations of enzymes used to determine the optimal enzyme activities as a seed treatment to corn and soybean seeds to promote growth in plants

| Enzyme | Organism derived from | Titration Use Rate (μU Activity) |
|---|---|---|
| Water Control | — | 0 μU |
| Lichenase | *Bacillus subtilis* | 400 μU |
| Lichenase | *Bacillus subtilis* | 500 μU |
| Lichenase | *Bacillus subtilis* | 600 μU |
| Lichenase | *Bacillus subtilis* | 700 μU |
| Lichenase | *Bacillus subtilis* | 800 μU |
| Lichenase | *Bacillus subtilis* | 900 μU |
| Xyloglucanase | *Paenibacillus* species | 500 μU |
| Xyloglucanase | *Paenibacillus* species | 600 μU |
| Xyloglucanase | *Paenibacillus* species | 1500 μU |
| Xyloglucanase | *Paenibacillus* species | 3000 μU |
| Xyloglucanase | *Paenibacillus* species | 4000 μU |
| β-Xylanase | *Bacillus stearothermophilus* | 50 μU |
| β-Xylanase | *Bacillus stearothermophilus* | 300 μU |
| β-Xylanase | *Bacillus stearothermophilus* | 500 μU |
| β-Xylanase | *Bacillus stearothermophilus* | 1500 μU |
| β-Xylanase | *Bacillus stearothermophilus* | 3000 μU |
| β-Xylanase | *Bacillus stearothermophilus* | 5000 μU |
| Mannanase | *Bacillus* species | 60 μU |
| Mannanase | *Bacillus* species | 300 μU |
| Mannanase | *Bacillus* species | 600 μU |
| Mannanase | *Bacillus* species | 1200 μU |
| Mannanase | *Bacillus* species | 3000 μU |
| Mannanase | *Bacillus* species | 6000 μU |
| Lipase | *Burkholderia stearothermophilus* | 2 μU |
| Lipase | *Burkholderia stearothermophilus* | 5 μU |
| Lipase | *Burkholderia stearothermophilus* | 10 μU |
| Lipase | *Burkholderia stearothermophilus* | 20 μU |
| Lipase | *Burkholderia stearothermophilus* | 50 μU |
| Lipase | *Burkholderia stearothermophilus* | 200 μU |
| Pectolyase | *Aspergillus japonicus* | 60 μU |
| Pectolyase | *Aspergillus japonicus* | 300 μU |
| Pectolyase | *Aspergillus japonicus* | 600 μU |
| Pectolyase | *Aspergillus japonicus* | 1200 μU |
| Pectolyase | *Aspergillus japonicus* | 3000 μU |
| Pectolyase | *Aspergillus japonicus* | 6000 μU |
| β-1,4-endoglucanase | *Acidothermus cellulolyticus* | 1000 μU |

Titrations of the six free enzymes (lichenase, xyloglucanase, xylanase, mannanase, lipase, and pectolyase) were tested to determine optimal activities that promote growth when used as a seed treatment on corn (BECK'S 5828 YH) and soybean (BECK'S 297 NR). Titration activities that were determined to be optimal for use as a seed treatment for the six enzymes are listed in Table 57 below (listed as free enzyme activity per seed). Experiments were conducted under the same environmental conditions in a controlled growth environment as described in Example 29. Percent changes in average plant height were determined for the six enzymes used as a seed treatment applied to corn or soybean seed (Table 57, below). Average plant height for each of the six enzymes was normalized to that of plants grown from seed that received a water control treatment and recorded as a percent change (Table 57). Additionally, the free enzymes treatments applied to corn seed included and were compared to treatment with β-1,4-endoglucanase free enzyme because this enzyme had previously been shown to promote growth when applied as a seed treatment on corn plants (see Examples 1-4, 7, 26, and 29, above).

All six free enzymes (lichenase, xyloglucanase, β-xylanase, mannanase, lipase, and pectolyase), when used as a seed treatment at their optimized activity levels on corn and soybean, increased plant height as compared to control plants grown from non-enzyme-treated seeds. Results are shown in Table 57 below. β-1,4-endoglucanase free enzyme applied to corn seed resulted in an increase in plant height for corn as normalized to the control plants. When both corn and soybean plant varieties were considered, mannanase resulted in the largest increases in plant height as normalized to the control plants (107% increase in corn and 110% increase in soybean).

TABLE 57

Height effects of free enzymes applied as a seed treatment to corn and soybean plants

| Seed Treatment: Corn | Percent change in average corn plant height (Normalized to Control) |
|---|---|
| Water Control | 100% |
| Lichenase 600 μU | 102% |
| Xyloglucanase 600 μU | 101% |
| β-xylanase 5000 μU | 100% |
| Mannanase 300 μU | 107% |
| Lipase 20 μU | 100% |
| Pectolyase 3000 μU | 107% |
| β-1,4-Endoglucanase 1000 μU | 102% |
| **Seed Treatment: Soybean** | **Percent change in average soybean plant height (Normalized to Control)** |
| Water Control | 100% |
| Lichenase 400 μU | 103% |
| Xyloglucanase 600 μU | 113.2% |
| β-xylanase 5000 μU | 105.5% |
| Mannanase 6000 μU | 110.1% |
| Lipase 200 μU | 105.4% |
| Pectolyase 300 μU | 105.8% |

Titrations of four of the same enzymes (lichenase, xyloglucanase, mannanase, and pectolyase, listed in Table 56 above) were performed to determine optimal activities for use as an in-furrow treatment on corn (BECK'S 5828 YH) for promoting plant growth. Each enzyme titration was optimized for growth potential (Table 58) and was directly applied to the area surrounding a seed using 1 ml of water per seed just prior to the completion of planting and covering the seed with soil. Two weeks after planting, plant height was measured and normalized to the height of plants that received no enzyme treatment but instead received only a water control. This experiment was repeated in three trials with 18 plants per trial and measurements were averaged across trials to generate a percent change in average corn plant height (compared to control). Data are reported in Table 58 for the four free enzymes: lichenase, xyloglucanase, mannanase, and pectolyase. Free enzymes lichenase, xyloglucanase, and pectoylase all increased corn as height compared to the water-only control when applied as in-furrow treatments to the area surrounding corn seeds.

TABLE 58

Height effects of free enzymes applied as an in-furrow treatment surrounding corn seeds

| In Furrow: Corn | Percent change in average corn plant height (Normalized to Control) |
|---|---|
| Water Control | 100% |
| Lichenase 900 μU/seed area | 101% |
| Xyloglucanase 500 μU/seed area | 104% |
| Mannanase 6000 μU/seed area | 98% |
| Pectolyase 300 μU/seed area | 103% |

Titrations of the same six free enzymes (lichenase, xyloglucanase, xylanase, mannanase, lipase, and pectolyase, listed above in Table 56) were performed to determine optimal activities for application as seed treatments on soybean (BECK'S 297 NR). The activities (μU/seed) are reported for each enzyme in Table 59 below. Three trials with 18 plants per trial were conducted and measured for changes in total biomass, shoot biomass, root biomass and nodulation. Experiments were conducted under the same environmental conditions in a controlled growth environment as described in Example 6 above. In some experiments, an additional group of seeds was treated with β-1,4-endoglucanase (1000 μU/seed). Changes in total biomass, shoot biomass, root biomass and nodulation are reported in Table 59 below as percent (%) changes as normalized to soybean seed that did not receive a treatment with free enzyme (water-treated control).

TABLE 59

Free enzymes applied as a seed treatment for promoting growth in soybean plants

| Seed Treatment: Optimized Enzyme Activity | |
|---|---|
| | Total Biomass (Normalized to Control) |
| Lichenase 800 μU | 112% |
| Xyloglucanase 3000 μU | 103% |
| P-xylanase 3000 μU | 104% |
| Mannanase 3000 μU | 116% |
| Lipase 2 μU | 111% |
| Pectolyase 6000 μU | 104% |
| β-1,4-Endoglucanase 1000 μU | 106% |
| | Shoot Biomass (Normalized to Control) |
| Lichenase 400 μU | 117% |
| Xyloglucanase 1500 μU | 98% |
| β-xylanase 5000 μU | 101% |
| Mannanase 3000 μU | 121% |
| Lipase 2 μU | 117% |
| Pectolyase 300 μU | 111% |
| β-1,4-Endoglucanase 1000 μU | 109% |
| | Root Biomass (Normalized to Control) |
| Lichenase 800 μU | 123% |
| Xyloglucanase 1500 μU | 137% |
| β-xylanase 3000 μU | 107% |
| Mannanase 600 μU | 121% |
| Lipase 2 μU | 98% |
| Pectolyase 1200 μU | 102% |
| β-1,4-Endoglucanase 1000 μU | 127% |
| | Nodulation (Normalized to Control) |
| Lichenase 700 μU | 469% |
| Xyloglucanase 3000 μU | 123% |
| β-xylanase 300 μU | 121% |
| Lipase 50 μU | 114% |

Example 31: Free Enzymes Used as a Seed Treatment to Increase Yield of Zucchini The lichenase, xyloglucanase, xylanase, lipase free enzymes described above in Example 30 and β-1,4-endoglucanase (*Acidothermus cellulolyticus*, SEQ ID NO: 30) were applied as seed treatments at an optimal rate as determined by a titration series and applied to zucchini seeds (Spineless Beauty, commercially available from Park Seed) using 1 μL volumes of the enzymes with the activities as reported in μU/seed (Table 60). Total yield of the free enzyme-treated seed with lichenase, xyloglucanase, xylanase, lipase and β-1,4-endoglucanase is reported in Table 60 as the total weight of zucchini fruit harvested, normalized to the control, and is averaged for two harvests completed in the month of August (Columbia, Mo.). Free enzyme treatments applied to zucchini seed using lichenase (700 μU/seed), xylanase (3000 μU/seed), and lipase (50 μU/seed) all showed positive yield increases compared to control treatment. The increases in total harvestable yield for zucchini plants using the free enzyme seed treatments for lichenase, xylanase and lipase showed similar total yield advantages as β-1,4-Endoglucanase (1000 μU/seed).

TABLE 60

Table: Zucchini yield after treatment of zucchini seeds with free enzymes

| Treatment | Total Yield as a percentage of Control |
|---|---|
| Lichenase 700 μU | 113% |
| Xyloglucanase 3000 μU | 89% |
| β-xylanase 300 μU | 118% |
| Lipase 50 μU | 130% |
| β-1,4-Endoglucanase 1000 μU | 132% |

Example 32: Synergy of Multiple Enzymes on Corn, in Furrow

Mannanase (*Bacillus* sp.; SEQ ID NO: 128), xyloglucanase (*Paenibacillus* sp., SEQ ID NO: 125), phosphatidylcholine-specific phospholipase C (*Bacillus cereus*, SEQ ID NO: 115) and xylosidase (*Bacillus pumilus*; SEQ ID NO: 123) were applied to corn (BECK'S 5828 YH) as in-furrow free enzyme treatments, and effects on plant height and growth were examined. Enzyme treatments, including combinations of enzymes, are described in Table 61. For all the free enzymes, similar methods were used as described above in Example 26 for the lipase in-furrow treatments with corn. Briefly, in-furrow treatments were applied to the area surrounding the corn seed after planting of the corn but before covering the seed with loose soil. Each treatment was applied in a volume of 1 ml per seed, which included both the enzyme(s) and a fertilizer containing orthopolyphosphate and potassium acetate. In-furrow treatments using each enzyme were delivered at rates of 300 mU/seed area of activity for mannanase and phosphatidylcholine-specific phospholipase C, 500 mU/seed area for xyloglucanase, and 714 mU/seed area (per ml) of activity for xylosidase. The enzymes were delivered to seeds in volumes of 1 ml per seed area, containing both the enzyme(s) and the fertilizer. 54 seeds were used per treatment, divided among 3 replicates of 18 plants each. After about two weeks, plant heights were measured and normalized to control plants treated with only fertilizer.

Results are shown in Table 61 below. Mannanase or xyloglucanase alone did not result in significant height increases. Both phospholipase C and xylosidase applied alone led to an increase in plant height. Surprisingly, combinations of phospholipase C and either mannanase or xyloglucanase led to synergistic increases in plant height as compared to either treatment alone. The combination of mannanase and xyloglucanase was also more efficacious than either enzyme alone.

TABLE 61

Plant height using an in-furrow treatment for corn treated with free mannanase, xyloglucanase, xylosidase, phospholipase C, or combinations thereof

| Treatment | Enzyme Activity/ml | Average percent change in plant height (Normalized to Control) |
|---|---|---|
| Fertilizer, 8 fl oz/Ac (584.622 ml/hectare) | N/A | 100% |
| Fertilizer + Xylosidase (*Bacillus*) | 714 mU/seed area | 105.1% |
| Fertilizer + Mannanase (*Bacillus*) | 300 mU/seed area | 100.4% |
| Fertilizer + Xyloglucanase (*Paenibacillus*) | 500 mU/seed area | 93.9% |
| Fertilizer + Phospholipase C (*Bacillus*) | 300 mU/seed area | 108.8% |
| Fertilizer + Phospholipase C (PLC) + Xyloglucanase | 300 mU/seed area (PLC) + 500 mU/seed area (xyloglucanase) | 110.9% |
| Fertilizer + Phospholipase C + Mannanase | 300 mU/seed area (PLC) + 300 mU/seed area (mannanase) | 110.6% |
| Fertilizer + Xyloglucanase + Mannanase | 500 mU/seed area (xyloglucanase) + 300 mU/seed area (mannanase) | 101.1% |

Example 33: Additive Effects of Multiple Enzymes on Squash, in Furrow

Mannanase (*Bacillus* sp.; SEQ ID NO: 128), lichenase (*Bacillus subtilis*, SEQ ID NO: 43), acid phosphatase (*Triticum aestivum*, a mixture of two different isoforms with the sequences provided herein by SEQ ID NOs. 130 and 131), pectolyase (*Aspergillus japonicus*, SEQ ID NO:129), β-xylanase (*Neocallismastix patriciarum*, SEQ ID NO: 122), and β-xylanase (*Bacillus stearothermophilius*, SEQ ID NO: 25) were applied to Ambassador hybrid squash (commercially available from Park Seed as product 05298) as in-furrow free enzyme treatments, and effects on plant height and growth were examined. For all the free enzymes, similar methods were used as described above in Example 26 for the lipase in-furrow treatments with corn. Briefly, in-furrow treatments were applied to the area surrounding the squash seed after planting of the squash but before covering the seed with loose soil. Each treatment was applied in a volume of 1 ml per seed, which included both the enzyme(s) and a fertilizer containing monoammonium phosphate). In-furrow treatments using each enzyme were delivered at rates of 300 mU/seed area of activity for mannanase, 600 mU/seed area for lichenase, 30 mU/seed area for pectolyase, 35 μU/seed area for acid phosphatase, and 1500 mU/seed area for both β-xylanases. The enzymes were delivered to seeds in volumes of 1 ml per seed area, containing both the enzyme(s) and the fertilizer. After two weeks, plant height was measured and normalized to plants that received only fertilizer treatment Results are shown in Table 62 below. Acid phosphatase alone resulted in increased height over the fertilizer alone control, and this effect was slightly better when lichenase was applied together with the acid phosphatase. A large increase was seen when the fertilizer/acid phosphatase combination was further augmented with the pectolyase, the mannanase, or either of the xylanases. These non-cellulolytic carbohydrate hydrolases add significant plant height in combination with acid phosphatase as a soil delivered mechanism.

TABLE 62

Plant height using an in-furrow treatment for squash treated with free mannanase, xylanase, acid phosphatase, pectolyase, lichenase, or combinations thereof

| Treatment | Enzyme Activity/ml | Average percent change in plant height (Normalized to Control) |
|---|---|---|
| Fertilizer, 8 fl oz/Ac (584.622 ml/hectare) | N/A | 100% |
| Fertilizer + acid phosphatase (ACP) | 35 μU/seed area | 103.4% |
| Fertilizer + acid phosphatase + pectolyase | 35 μU/seed area (ACP) + 30 mU/seed area (pectolyase) | 113.6% |
| Fertilizer + acid phosphatase + mannanase | 35 μU/seed area (ACP) + 300 mU/seed area (mannanase) | 114.5% |
| Fertilizer + acid phosphatase + lichenase | 35 μU/seed area (ACP) + 600 mU/seed area (lichenase) | 103.7% |
| Fertilizer + acid phosphatase + β-xylanase (*Neocallismastix patriciarum*) | 35 μU/seed area (ACP) + 1500 mU/seed area (xylanase) | 110.5% |
| Fertilizer + acid phosphatase + β-xylanase (*Bacillus stearothermophilus*) | 35 μU/seed area (ACP) + 1500 mU/seed area (xylanase) | 115.1% |

In view of the above, it will be seen that the several objects of the invention are achieved and other advantageous results attained.

As various changes could be made in the above enzymes, recombinant organisms, methods, and seeds, without departing from the scope of the invention, it is intended that all matter contained in the above description shall be interpreted as illustrative and not in a limiting sense.

What is claimed is:

1. A composition comprising a fertilizer and a free enzyme or expansin protein, wherein the enzyme is selected from a phospholipase, a lipase, a xylosidase, a lactonase, a mannanase, a pectinase, a chitosanase, a protease, a glucanase, an ACC deaminase, and combinations of any thereof, wherein:

when the enzyme comprises a glucanase, the glucanase does not comprise a beta-1,3-glucanase, a xyloglucanase, or a lichenase; and when the enzyme comprises a mannanase: (i) the composition further comprises a phospholipase or an acid phosphatase; (ii) the composition is a granular composition; or (iii) the composition further comprises a phospholipase or an acid phosphatase and is a granular composition.

2. The composition of claim 1, wherein the composition further comprises a biostimulant.

3. The composition of claim 1, wherein the fertilizer comprises nitrogen, phosphate, potassium, zinc, iron, selenium, boron, copper, or a combination of any thereof.

4. The composition of claim 1, wherein the enzyme or expansin protein comprises a crude cell extract containing the enzyme or expansin protein.

5. The composition of claim 1, wherein the enzyme or expansin protein comprises a partially purified enzyme or expansin protein.

6. The composition of claim 1, wherein the enzyme or expansin protein comprises a substantially purified enzyme or expansin protein.

7. The composition of claim 1, wherein the enzyme or expansin protein comprises enzyme or expansin protein that is immobilized on a matrix or support.

8. The composition of claim 7, wherein the matrix or support comprises charcoal, biochar, nanocarbon, agarose, an alginate, cellulose, a cellulose derivative, silica, plastic, stainless steel, glass, polystyrene, a ceramic, dolomite, a clay, diatomaceous earth, talc, a polymer, a gum, a water-dispersable material, or a combination of any thereof.

9. The composition of claim 1, wherein the composition further comprises an agriculturally acceptable carrier, an additional agrochemical, or a combination thereof.

10. The composition of claim 1, wherein the enzyme comprises the phospholipase.

11. The composition of claim 10, wherein the phospholipase comprises a phospholipase C, a phospholipase D, or a combination thereof.

12. The composition of claim 10, wherein the phospholipase comprises an amino acid sequence having at least 80% identity to any one of SEQ ID NOs. 13-19 and 115-117.

13. The composition of claim 12, wherein the phospholipase comprises an amino acid sequence having at least 80% identity to SEQ ID NO: 14, 19, or 116.

14. The composition of claim 1, wherein the enzyme comprises the glucanase.

15. The composition of claim 14, wherein the glucanase comprises a non-cellulolytic glucanase.

16. The composition of claim 15, wherein the non-cellulolytic glucanase comprises an amylase, an amyloglucanase, amyloglucosidase, a laminarinase, a beta-1,6-glucanase, an alpha-1,4-glucanase, an alpha 1,6-glucanase, or a combination of any thereof.

17. The composition of claim 14, wherein the glucanase comprises an amino acid sequence having at least 80% identity to any one of SEQ ID NOs. 30-40 and 42.

18. The composition of claim 1, wherein the enzyme comprises the mannanase.

19. The composition of claim 18, wherein the mannanase comprises an amino acid sequence having at least 80% identity to SEQ ID NO: 128.

20. The composition of claim 1, wherein the enzyme comprises the ACC deaminase.

21. The composition of claim 20, wherein the ACC deaminase comprises an amino acid sequence having at least 80% identity to any one of SEQ ID NOs. 7-12, 113, and 114.

22. The composition of claim 21, wherein the ACC deaminase comprises an amino acid sequence having at least 80% identity to SEQ ID NO: 113, wherein the amino acid sequence comprises a substitution of the threonine residue at position 290 of SEQ ID NO: 113 with a glutamic acid residue and a substitution of the serine residue at position 317 of SEQ ID NO: 113 with a leucine residue.

23. The composition of claim 1, wherein the enzyme comprises the xylosidase, the lactonase, the pectinase, or a combination of any thereof.

24. The composition of claim 23, wherein:

the xylosidase comprises an amino acid sequence having at least 80% identity to SEQ ID NO: 26 or 123;

the lactonase comprises an amino acid sequence having at least 80% identity to SEQ ID NO: 27 or 28; and/or the pectinase comprises an amino acid sequence having at least 80% identity to SEQ ID NO: 129.

25. The composition of claim 24, wherein:

the xylosidase comprises an amino acid sequence having at least 80% identity to SEQ ID NO: 123; and/or the lactonase comprises an amino acid sequence having at least 80% identity to SEQ ID NO: 27.

26. The composition of claim 3, wherein the phosphate comprises monoammonium phosphate, diammonium phosphate, orthophosphate, orthopolyphosphate, or a combination of any thereof; or wherein the potassium comprises potassium acetate.

27. The composition of claim 1, wherein the fertilizer comprises a micronutrient fertilizer material, the micronutrient fertilizer material comprising boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination of any thereof.

28. The composition of claim 1, wherein the fertilizer comprises ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, sulfur-coated urea, polymer-coated urea, isobutylidene diurea, $K_2SO_4$—$2MgSO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, humic acid, or a combination of any thereof.

29. The composition of claim 9, wherein the agriculturally acceptable carrier comprises a dispersant, a surfactant, an additive, water, a thickener, an anti-caking agent, residue breakdown product, a composting formulation, a granular application, diatomaceous earth, an oil, a coloring agent, a stabilizer, a preservative, a polymer, a coating, or a combination of any thereof.

30. The composition of claim 29, wherein the agriculturally acceptable carrier comprises an additive, and the additive comprises an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutane dioate, a benzene acetonitrile derivative, a proteinaceous material, or a combination of any thereof; the agriculturally acceptable carrier comprises a thickener, and the thickener comprises a long chain alkylsulfonate of polyethylene glycol, a polyoxyethylene oleate, or a combination of any thereof; the agriculturally acceptable carrier comprises a surfactant, and the surfactant comprises a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination of any thereof; or the agriculturally acceptable carrier comprises an anti-caking agent, and the anti-caking agent comprises a sodium salt, a calcium carbonate, diatomaceous earth, or a combination of any thereof.

31. The composition of claim 9, wherein the additional agrochemical comprises an insecticide, a nematicide, an herbicide, a plant growth amendment, a fungicide, an insecticide, a molluscicide, an algicide, a bacterial inoculant, a fungal inoculant, a plant hormone, or a combination of any thereof.

32. The composition of claim 3, wherein the fertilizer comprises 12% ammoniacal nitrogen and 58% available phosphate.

33. A method for stimulating plant growth and/or promoting plant health, comprising applying the composition of claim 1 to a plant growth medium, a plant, a plant seed, or an area surrounding a plant or a plant seed.

34. A plant seed treated with the composition of claim 1.

35. The plant seed of claim 34, wherein the plant seed is coated with the composition.

36. The composition of claim 1, wherein the composition comprises the mannanase and the acid phosphatase, and the acid phosphatase comprises an amino acid sequence having at least 90% identity to SEQ ID NO: 131 or 132.

37. The composition of claim 18, wherein the mannanase comprises an amino acid sequence having at least 90% identity to SEQ ID NO: 128.

38. The composition of claim 10, wherein the phospholipase comprises an amino acid sequence having at least 90% identity to SEQ ID NO: 14.

39. The composition of claim 1, wherein the enzyme comprises the phospholipase, the lipase, the xylosidase, the lactonase, the pectinase, the chitosanase, the protease, the glucanase, or the ACC deaminase, and the composition is a granular composition.

40. The composition of claim 1, wherein the enzyme or expansin protein does not comprise enzyme or expansin protein bound to exosporium of a recombinant *Bacillus cereus* family member.

41. The composition of claim 40, wherein the enzyme or expansin protein is not bound to exosporium of an intact *Bacillus cereus* family member spore.

42. The composition of claim 9, wherein the agriculturally acceptable carrier comprises vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination of any thereof.

* * * * *